(12) United States Patent
He et al.

(10) Patent No.: US 11,401,272 B2
(45) Date of Patent: Aug. 2, 2022

(54) HETEROCYCLIC COMPOUNDS AS LSD1 INHIBITORS

(71) Applicant: Incyte Corporation, Wilmington, DE (US)

(72) Inventors: Chunhong He, Chadds Ford, PA (US); Zhenwu Li, Wilmington, DE (US); Liangxing Wu, Wilmington, DE (US); Wenqing Yao, Chadds Ford, PA (US); Fenglei Zhang, Berwyn, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/006,072

(22) Filed: Aug. 28, 2020

(65) Prior Publication Data

US 2020/0392143 A1 Dec. 17, 2020

Related U.S. Application Data

(60) Division of application No. 15/914,047, filed on Mar. 7, 2018, now Pat. No. 10,800,779, which is a continuation of application No. 15/088,259, filed on Apr. 1, 2016, now Pat. No. 9,944,647.

(60) Provisional application No. 62/183,906, filed on Jun. 24, 2015, provisional application No. 62/142,717, filed on Apr. 3, 2015.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ... C07D 487/04; C07D 519/00; C07D 417/14
See application file for complete search history.

(56) References Cited

U.S. PATENT DOCUMENTS

| | | | |
|---|---|---|---|
| 4,537,889 A | 8/1985 | Spitzer | |
| 4,625,040 A | 11/1986 | Georgiev et al. | |
| 5,658,857 A | 8/1997 | Andree et al. | |
| 5,932,223 A | 8/1999 | Burke et al. | |
| 7,759,386 B2 | 7/2010 | Benjain et al. | |
| 7,858,609 B2 | 12/2010 | Shaw et al. | |
| 8,115,000 B2 | 2/2012 | Rajagopalan et al. | |
| 8,349,210 B2 | 1/2013 | Xu et al. | |
| 8,383,154 B2 | 2/2013 | Bar-Shalom et al. | |
| 8,546,394 B2 | 10/2013 | Li | |
| 8,558,008 B2 | 10/2013 | Statler et al. | |
| 8,568,782 B2 | 10/2013 | Viscomi et al. | |
| 8,614,315 B2 | 12/2013 | Bilgic | |
| 8,648,077 B2 | 2/2014 | Tomesch et al. | |
| 8,853,408 B2 | 10/2014 | Johnson | |
| 9,493,442 B2 | 11/2016 | Wu et al. | |
| 9,493,450 B2 | 11/2016 | Wu et al. | |
| 9,527,835 B2 | 12/2016 | Wu et al. | |
| 9,670,210 B2 | 6/2017 | Wu et al. | |
| 9,695,167 B2 | 7/2017 | Wu et al. | |
| 9,695,168 B2 | 7/2017 | Wu et al. | |
| 9,695,180 B2 | 7/2017 | Wu et al. | |
| 9,758,523 B2 | 9/2017 | Wu et al. | |
| 9,790,169 B2 | 10/2017 | Balog et al. | |
| 9,809,541 B2 | 11/2017 | Marx et al. | |
| 9,944,647 B2 | 4/2018 | He et al. | |
| 9,994,546 B2 | 6/2018 | Wu et al. | |
| 10,112,950 B2 | 10/2018 | Wu et al. | |
| 10,125,133 B2 | 11/2018 | Wu et al. | |
| 10,138,249 B2 | 11/2018 | Wu et al. | |
| 10,166,221 B2 | 1/2019 | Rocco et al. | |
| 10,174,030 B2 | 1/2019 | Wu et al. | |
| 10,300,051 B2 | 5/2019 | Wu et al. | |
| 10,329,255 B2 | 6/2019 | Pan et al. | |
| 10,556,908 B2 * | 2/2020 | Wu ........................ A61P 35/00 |
| 10,640,503 B2 | 5/2020 | Wu et al. | |
| 10,676,457 B2 | 6/2020 | Wu et al. | |
| 10,717,737 B2 | 7/2020 | Wu et al. | |

(Continued)

FOREIGN PATENT DOCUMENTS

| | | |
|---|---|---|
| BR | 2011-01013 | 6/2013 |
| CA | 2831143 | 10/2012 |

(Continued)

OTHER PUBLICATIONS

Amente et al., "The histone LSD1 demethylase in stemness and cancer transcription programs," Biochimica et Biophysica Acta., 2013, 1829(10):981-986.
Bloxam, "Chemistry Inorganic and Organic with Experiments," P. Blakiston's Son & Co: Philadelphia, 1913, 10th Edition, pp. 562-568.
Colombian Office Action in Colombian Application No. NC2018/0012482, dated Jul. 14, 2021, 21 pages.

(Continued)

*Primary Examiner* — Pancham Bakshi
(74) *Attorney, Agent, or Firm* — Fish & Richardson P.C.

(57) ABSTRACT

The present invention is directed to compounds of Formula I which are LSD1 inhibitors useful in the treatment of diseases such as cancer.

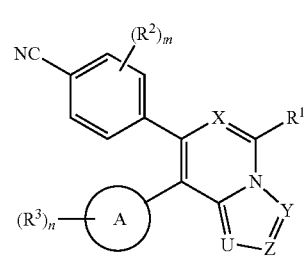

31 Claims, No Drawings
Specification includes a Sequence Listing.

(56) References Cited

U.S. PATENT DOCUMENTS

| | | |
|---|---|---|
| 10,723,700 B2 | 7/2020 | Pan et al. |
| 10,800,779 B2 | 10/2020 | He et al. |
| 10,968,200 B2 | 4/2021 | Jia et al. |
| 10,968,221 B2 | 4/2021 | Wu et al. |
| 11,155,532 B2 | 10/2021 | Wu et al. |
| 11,247,992 B2 | 2/2022 | Wu et al. |
| 2002/0151549 A1 | 10/2002 | Hayakawa et al. |
| 2004/0023972 A1 | 2/2004 | Sundermann et al. |
| 2004/0058938 A1 | 3/2004 | Cullmann et al. |
| 2004/0082635 A1 | 4/2004 | Hashimoto et al. |
| 2004/0082781 A1 | 4/2004 | Hibi et al. |
| 2004/0220189 A1 | 11/2004 | Sun et al. |
| 2005/0009832 A1 | 1/2005 | Sun et al. |
| 2005/0113283 A1 | 5/2005 | Solow-Cordero et al. |
| 2006/0178399 A1 | 8/2006 | Nishizawa et al. |
| 2006/0194842 A1 | 8/2006 | Uchida et al. |
| 2006/0276339 A1 | 12/2006 | Windsor et al. |
| 2007/0004772 A1 | 1/2007 | Sun et al. |
| 2007/0128276 A1 | 6/2007 | Jain et al. |
| 2007/0191395 A1 | 8/2007 | Kawakami |
| 2007/0191421 A1 | 8/2007 | Buettelmann et al. |
| 2008/0167337 A1 | 7/2008 | Gano |
| 2008/0249154 A1 | 10/2008 | Ohmoto et al. |
| 2009/0004281 A1 | 1/2009 | Nghiem et al. |
| 2009/0047336 A1 | 2/2009 | Yang et al. |
| 2009/0203690 A1 | 8/2009 | Akritopoulou-Zanze et al. |
| 2009/0318436 A1 | 12/2009 | Albrecht et al. |
| 2010/0113441 A1 | 5/2010 | Siegel et al. |
| 2010/0143481 A1 | 6/2010 | Shenoy et al. |
| 2010/0209489 A1 | 8/2010 | Liang et al. |
| 2010/0316712 A1 | 12/2010 | Nangia et al. |
| 2011/0105457 A1 | 5/2011 | Taniyama et al. |
| 2011/0112067 A1 | 5/2011 | Hartmann et al. |
| 2012/0004262 A1 | 1/2012 | Guibourt et al. |
| 2012/0108500 A1 | 5/2012 | Sakane et al. |
| 2012/0220582 A1 | 8/2012 | Mitchell et al. |
| 2012/0283266 A1 | 11/2012 | Ortega Munoz et al. |
| 2012/0322877 A1 | 12/2012 | Casero et al. |
| 2013/0035377 A1 | 2/2013 | Minucci et al. |
| 2013/0040946 A1 | 2/2013 | Siegel et al. |
| 2013/0090386 A1 | 4/2013 | Ortega Munoz et al. |
| 2013/0095067 A1 | 4/2013 | Baker et al. |
| 2013/0109751 A1 | 5/2013 | Salvatore |
| 2013/0197013 A1 | 8/2013 | Fyfe et al. |
| 2013/0203754 A1 | 8/2013 | Yang et al. |
| 2013/0217878 A1 | 8/2013 | Lizuka et al. |
| 2013/0231342 A1 | 9/2013 | Munoz et al. |
| 2013/0303545 A1 | 11/2013 | Maes et al. |
| 2014/0011857 A1 | 1/2014 | Casero et al. |
| 2014/0018393 A1 | 1/2014 | Johnson et al. |
| 2014/0094445 A1 | 4/2014 | Vakayalapati et al. |
| 2014/0206757 A1 | 7/2014 | Shi et al. |
| 2014/0213657 A1 | 7/2014 | Munoz et al. |
| 2014/0228405 A1 | 8/2014 | Tomita et al. |
| 2014/0256742 A1 | 9/2014 | Baker et al. |
| 2014/0296255 A1 | 10/2014 | Maes et al. |
| 2014/0329833 A1 | 11/2014 | Maes et al. |
| 2014/0343118 A1 | 11/2014 | McCafferty et al. |
| 2015/0064250 A1 | 3/2015 | Ghebre-Sellassie et al. |
| 2015/0065434 A1 | 3/2015 | Woster et al. |
| 2015/0065495 A1 | 3/2015 | Vankayalapati et al. |
| 2015/0133564 A1 | 5/2015 | Oh et al. |
| 2015/0225375 A1 | 8/2015 | Wu et al. |
| 2015/0225379 A1 | 8/2015 | Wu et al. |
| 2015/0225394 A1 | 8/2015 | Wu et al. |
| 2015/0225401 A1 | 8/2015 | Wu et al. |
| 2015/0232436 A1 | 8/2015 | Baker et al. |
| 2015/0265683 A1 | 9/2015 | Sahib et al. |
| 2015/0296852 A1 | 10/2015 | Penhasi et al. |
| 2016/0009711 A1 | 1/2016 | Wu et al. |
| 2016/0009712 A1 | 1/2016 | Wu et al. |
| 2016/0009720 A1 | 1/2016 | Wu et al. |
| 2016/0009721 A1 | 1/2016 | Wu et al. |
| 2016/0289238 A1 | 4/2016 | He et al. |
| 2017/0044101 A1 | 2/2017 | Pan et al. |
| 2017/0112816 A1 | 4/2017 | Wu et al. |
| 2017/0121302 A1 | 5/2017 | Wu et al. |
| 2017/0158633 A1 | 6/2017 | Wu et al. |
| 2017/0304282 A1 | 10/2017 | Rocco et al. |
| 2017/0342070 A1 | 11/2017 | Wu et al. |
| 2017/0362245 A1 | 12/2017 | Wu et al. |
| 2017/0369487 A1 | 12/2017 | Wu et al. |
| 2017/0369488 A1 | 12/2017 | Wu et al. |
| 2017/0369497 A1 | 12/2017 | Wu et al. |
| 2018/0118765 A1 | 5/2018 | Brias et al. |
| 2019/0040058 A1 | 2/2019 | Wu et al. |
| 2019/0055250 A1 | 2/2019 | He et al. |
| 2019/0062301 A1 | 2/2019 | Wu et al. |
| 2019/0106426 A1 | 4/2019 | Wu et al. |
| 2019/0119272 A1 | 4/2019 | Wu et al. |
| 2019/0152976 A1 | 5/2019 | Wu et al. |
| 2019/0211014 A1 | 7/2019 | Wu et al. |
| 2019/0307736 A1 | 10/2019 | Rocco et al. |
| 2019/0345106 A1 | 11/2019 | Pan et al. |
| 2020/0024277 A1 | 1/2020 | Wu et al. |
| 2020/0031835 A1 | 1/2020 | Wang et al. |
| 2020/0071289 A1 | 3/2020 | Jia et al. |
| 2020/0181077 A1 | 6/2020 | Wu et al. |
| 2020/0316041 A1 | 10/2020 | Rocco et al. |
| 2021/0024487 A1 | 1/2021 | Wu et al. |
| 2021/0032203 A1 | 2/2021 | Pan et al. |
| 2021/0032244 A1 | 2/2021 | Wu et al. |
| 2021/0300891 A1 | 9/2021 | Jia et al. |

FOREIGN PATENT DOCUMENTS

| | | |
|---|---|---|
| CA | 2844525 | 2/2013 |
| CA | 2849564 | 4/2013 |
| CA | 2887598 | 4/2014 |
| CL | 201400314 | 8/2014 |
| CL | 201400988 | 11/2014 |
| CL | 201702482 | 4/2018 |
| CL | 201702494 | 5/2018 |
| CL | 201800374 | 7/2019 |
| CN | 101848713 | 9/2010 |
| CN | 101987082 | 3/2011 |
| CN | 102247321 | 11/2011 |
| CN | 102397552 | 4/2012 |
| CN | 102579381 | 7/2012 |
| CN | 102772444 | 11/2012 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| CN | 104173313 | 12/2014 |
| CN | 105232488 | 1/2016 |
| DE | 102006041292 | 3/2008 |
| EP | 0179254 | 4/1986 |
| EP | 0404190 | 12/1990 |
| EP | 0430385 | 6/1991 |
| EP | 2168579 | 3/2010 |
| EP | 2524918 | 11/2012 |
| EP | 2740474 | 6/2014 |
| EP | 2743256 | 6/2014 |
| EP | 3105218 | 12/2016 |
| EP | 3277689 | 2/2018 |
| FR | 2662163 | 11/1991 |
| FR | 2920090 | 2/2009 |
| FR | 2920091 | 2/2009 |
| GB | 1277393 | 6/1972 |
| IN | 2007MU01698 | 3/2009 |
| JP | S 6178778 | 4/1986 |
| JP | H06-116146 | 4/1994 |
| JP | 2844351 | 1/1999 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |

(56) References Cited

FOREIGN PATENT DOCUMENTS

| | | |
|---|---|---|
| JP | 2008511668 | 4/2008 |
| JP | 2008531543 | 8/2008 |
| JP | 2009507843 | 2/2009 |
| JP | 2010070503 | 4/2010 |
| JP | 2010524953 | 7/2010 |
| JP | 2011500547 | 1/2011 |
| JP | 2011514363 | 5/2011 |
| JP | 2013530968 | 8/2013 |
| JP | 2014515013 | 6/2014 |
| JP | 2016044170 | 4/2016 |
| JP | 6602778 | 11/2019 |
| KR | 20090069703 | 7/2009 |
| WO | WO 1988/004298 | 6/1988 |
| WO | WO 1993/025553 | 12/1993 |
| WO | WO 1994/018198 | 8/1994 |
| WO | WO 1995/012594 | 5/1995 |
| WO | WO 1999/024434 | 5/1999 |
| WO | WO 01/25237 | 4/2001 |
| WO | WO 2001/27119 | 4/2001 |
| WO | WO 2001/83481 | 8/2001 |
| WO | WO 2002/000196 | 1/2002 |
| WO | WO 2002/06286 | 1/2002 |
| WO | WO 2002/034748 | 5/2002 |
| WO | WO 2002/38562 | 5/2002 |
| WO | WO 2002/038568 | 5/2002 |
| WO | WO 2002/051831 | 7/2002 |
| WO | WO 2002/072549 | 9/2002 |
| WO | WO 2003/006471 | 1/2003 |
| WO | WO 2003/044021 | 5/2003 |
| WO | WO 2003/062392 | 7/2003 |
| WO | WO 2004/017950 | 3/2004 |
| WO | WO 2004/021989 | 3/2004 |
| WO | WO 2004/058762 | 7/2004 |
| WO | WO 2004/072081 | 8/2004 |
| WO | WO 2004/074290 | 9/2004 |
| WO | WO 2004/089380 | 10/2004 |
| WO | WO 2004/089416 | 10/2004 |
| WO | WO 2004/096131 | 11/2004 |
| WO | WO 2004/108692 | 12/2004 |
| WO | WO 2005/007658 | 1/2005 |
| WO | WO 2005/025558 | 3/2005 |
| WO | WO 2005/035532 | 4/2005 |
| WO | WO 2005/042537 | 5/2005 |
| WO | WO 2005/044793 | 5/2005 |
| WO | WO 2005/097052 | 10/2005 |
| WO | WO 2006/015263 | 2/2006 |
| WO | WO 2006/018727 | 2/2006 |
| WO | WO 2006/038116 | 4/2006 |
| WO | WO 2006/057946 | 6/2006 |
| WO | WO 2006/058752 | 6/2006 |
| WO | WO 2006/073938 | 7/2006 |
| WO | WO 2006/074041 | 7/2006 |
| WO | WO 2006/113704 | 10/2006 |
| WO | WO 2006/131003 | 12/2006 |
| WO | WO 2006/135667 | 12/2006 |
| WO | WO 2006/135795 | 12/2006 |
| WO | WO 2006/138695 | 12/2006 |
| WO | WO 2006/138734 | 12/2006 |
| WO | WO 2007/022529 | 2/2007 |
| WO | WO 2007/028051 | 3/2007 |
| WO | WO 2007/058942 | 5/2007 |
| WO | WO 2007/074491 | 7/2007 |
| WO | WO 2007/095588 | 8/2007 |
| WO | WO 2007/113226 | 10/2007 |
| WO | WO 2007/145921 | 12/2007 |
| WO | WO 2007/149478 | 12/2007 |
| WO | WO 2008/005262 | 1/2008 |
| WO | WO 2008/005423 | 1/2008 |
| WO | WO 2008/005908 | 1/2008 |
| WO | WO 2008/008539 | 1/2008 |
| WO | WO 2008/11560 | 1/2008 |
| WO | WO 2008/027812 | 3/2008 |
| WO | WO 2008/037607 | 4/2008 |
| WO | WO 2008/045393 | 4/2008 |
| WO | WO 2008/056176 | 5/2008 |
| WO | WO 2008/064157 | 5/2008 |
| WO | WO 2008/065198 | 6/2008 |
| WO | WO 2008/110523 | 9/2008 |
| WO | WO 2008/113559 | 9/2008 |
| WO | WO 2008/125111 | 10/2008 |
| WO | WO 2008/130951 | 10/2008 |
| WO | WO 2008/141239 | 11/2008 |
| WO | WO 2008/154241 | 12/2008 |
| WO | WO 2008/156614 | 12/2008 |
| WO | WO 2008/157752 | 12/2008 |
| WO | WO 2009/010530 | 1/2009 |
| WO | WO 2009/017701 | 2/2009 |
| WO | WO 2009/017954 | 2/2009 |
| WO | WO 2009/023179 | 2/2009 |
| WO | WO 2009/028900 | 3/2009 |
| WO | WO 2009/045753 | 4/2009 |
| WO | WO 2009/047514 | 4/2009 |
| WO | WO 2009/047563 | 4/2009 |
| WO | WO 2009/048993 | 4/2009 |
| WO | WO 2009/085230 | 7/2009 |
| WO | WO 2009/085980 | 7/2009 |
| WO | WO 2009/091374 | 7/2009 |
| WO | WO 2009/114180 | 9/2009 |
| WO | WO 2009/114512 | 9/2009 |
| WO | WO 2009/128520 | 10/2009 |
| WO | WO 2009/138176 | 11/2009 |
| WO | WO 2010/010184 | 1/2010 |
| WO | WO 2010/010187 | 1/2010 |
| WO | WO 2010/010188 | 1/2010 |
| WO | WO 2010/010189 | 1/2010 |
| WO | WO 2010/019899 | 2/2010 |
| WO | WO 2010/021607 | 2/2010 |
| WO | WO 2010/033906 | 3/2010 |
| WO | WO 2010/036380 | 4/2010 |
| WO | WO 2010/043721 | 4/2010 |
| WO | WO 2010/048149 | 4/2010 |
| WO | WO 2010/064020 | 6/2010 |
| WO | WO 2010/084160 | 7/2010 |
| WO | WO 2010/088368 | 8/2010 |
| WO | WO 2010/090614 | 8/2010 |
| WO | WO 2010/091067 | 8/2010 |
| WO | WO 2010/091824 | 8/2010 |
| WO | WO 2010/101537 | 9/2010 |
| WO | WO 2010/104306 | 9/2010 |
| WO | WO 2010/107404 | 9/2010 |
| WO | WO 2010/108059 | 9/2010 |
| WO | WO 2010/113942 | 10/2010 |
| WO | WO 2010/119264 | 10/2010 |
| WO | WO 2010/136438 | 12/2010 |
| WO | WO 2010/144571 | 12/2010 |
| WO | WO 2010/151711 | 12/2010 |
| WO | WO 2011/022439 | 2/2011 |
| WO | WO 2011/033265 | 3/2011 |
| WO | WO 2011/035941 | 3/2011 |
| WO | WO 2011/042217 | 4/2011 |
| WO | WO 2011/050245 | 4/2011 |
| WO | WO 2011/089400 | 7/2011 |
| WO | WO 2011/097607 | 8/2011 |
| WO | WO 2011/106105 | 9/2011 |
| WO | WO 2011/106106 | 9/2011 |
| WO | WO 2011/112766 | 9/2011 |
| WO | WO 2011/113606 | 9/2011 |
| WO | WO 2011/113862 | 9/2011 |
| WO | WO 2011/121137 | 10/2011 |
| WO | WO 2011/131576 | 10/2011 |
| WO | WO 2011/131697 | 10/2011 |
| WO | WO 2011/141713 | 11/2011 |
| WO | WO 2011/143365 | 11/2011 |
| WO | WO 2011/149438 | 12/2011 |
| WO | WO 2011/160548 | 12/2011 |
| WO | WO 2012/003392 | 1/2012 |
| WO | WO 2012/006959 | 1/2012 |
| WO | WO 2012/007345 | 1/2012 |
| WO | WO 2012/009475 | 1/2012 |
| WO | WO 2012/013727 | 2/2012 |
| WO | WO 2012/013728 | 2/2012 |
| WO | WO 2012/016133 | 2/2012 |
| WO | WO 2012/034116 | 3/2012 |
| WO | WO 2012/042042 | 4/2012 |

(56) References Cited

FOREIGN PATENT DOCUMENTS

| | | |
|---|---|---|
| WO | WO 2012/047852 | 4/2012 |
| WO | WO 2012/052730 | 4/2012 |
| WO | WO 2012/052745 | 4/2012 |
| WO | WO 2012/054233 | 4/2012 |
| WO | WO 2012/054698 | 4/2012 |
| WO | WO 2012/071469 | 5/2012 |
| WO | WO 2012/072713 | 6/2012 |
| WO | WO 2012/080230 | 6/2012 |
| WO | WO 2012/080232 | 6/2012 |
| WO | WO 2012/080234 | 6/2012 |
| WO | WO 2012/080236 | 6/2012 |
| WO | WO 2012/080476 | 6/2012 |
| WO | WO 2012/080729 | 6/2012 |
| WO | WO 2012/088411 | 6/2012 |
| WO | WO 2012/088438 | 6/2012 |
| WO | WO 2012/100229 | 7/2012 |
| WO | WO 2012/107498 | 8/2012 |
| WO | WO 2012/107499 | 8/2012 |
| WO | WO 2012/116237 | 8/2012 |
| WO | WO 2012/129562 | 9/2012 |
| WO | WO 2012/135113 | 10/2012 |
| WO | WO 2012/147890 | 11/2012 |
| WO | WO 2012/156531 | 11/2012 |
| WO | WO 2012/156537 | 11/2012 |
| WO | WO 2012/176856 | 12/2012 |
| WO | WO 2012/177606 | 12/2012 |
| WO | WO 2013/010380 | 1/2013 |
| WO | WO 2013/025805 | 2/2013 |
| WO | WO 2013/033515 | 3/2013 |
| WO | WO 2013/033688 | 3/2013 |
| WO | WO 2013/053690 | 4/2013 |
| WO | WO 2013/057320 | 4/2013 |
| WO | WO 2013/057322 | 4/2013 |
| WO | WO 2013/074390 | 5/2013 |
| WO | WO 2013/085877 | 6/2013 |
| WO | WO 2011/136264 | 7/2013 |
| WO | WO 2013/131609 | 9/2013 |
| WO | WO 2013/147711 | 10/2013 |
| WO | WO 2014/002051 | 1/2014 |
| WO | WO 2014/009296 | 1/2014 |
| WO | WO 2014/051698 | 3/2014 |
| WO | WO 2014/055955 | 4/2014 |
| WO | WO 2014/058071 | 4/2014 |
| WO | WO 2014/078479 | 5/2014 |
| WO | WO 2014/084298 | 6/2014 |
| WO | WO 2014/085613 | 6/2014 |
| WO | WO 2014/086790 | 6/2014 |
| WO | WO 2014/127350 | 8/2014 |
| WO | WO 2014/138791 | 9/2014 |
| WO | WO 2014/153001 | 9/2014 |
| WO | WO 2014/164867 | 10/2014 |
| WO | WO 2014/194280 | 12/2014 |
| WO | WO 2014/205213 | 12/2014 |
| WO | WO 2014/205223 | 12/2014 |
| WO | WO 2013/022047 | 3/2015 |
| WO | WO 2015/031564 | 3/2015 |
| WO | WO 2015/036512 | 3/2015 |
| WO | WO 2015/089192 | 6/2015 |
| WO | WO 2015/122187 | 8/2015 |
| WO | WO 2015/122188 | 8/2015 |
| WO | WO 2015/123424 | 8/2015 |
| WO | WO 2015/123465 | 8/2015 |
| WO | WO 2015/145145 | 10/2015 |
| WO | WO 2015/153720 | 10/2015 |
| WO | WO 2015/155281 | 10/2015 |
| WO | WO 2015/155297 | 10/2015 |
| WO | WO 2015/156417 | 10/2015 |
| WO | WO 2015/181380 | 12/2015 |
| WO | WO 2016/007722 | 1/2016 |
| WO | WO 2016/007727 | 1/2016 |
| WO | WO 2016/007731 | 1/2016 |
| WO | WO 2016/007736 | 1/2016 |
| WO | WO 2016/055394 | 4/2016 |
| WO | WO 2016/055797 | 6/2016 |
| WO | WO 2016/161282 | 10/2016 |
| WO | WO 2017/027678 | 2/2017 |
| WO | WO 2017/130933 | 8/2017 |
| WO | WO 2017/184934 | 10/2017 |
| WO | WO 2018/136634 | 7/2018 |
| WO | WO 2018/166493 | 9/2018 |

OTHER PUBLICATIONS

International Preliminary Report on Patentability in International Application No. PCT/US2019/048725, dated Mar. 2, 2021, 12 pages.

Kohne, "Hemoglobinopathies," Deutsches Arzteblatt International, 2011, 108(31-32):532-540.

Morrison, "Physical Science Level 3," Pearson Education, 2008, pp. 15-19.

Rivers et al., "RN-1, a Potent and Selective LSD1 Inhibitor, Induces High Levels of Fetal Hemoglobin (HbF) in Anemic Baboons (*P. anubis*)," Blood, 2014, 124(21):336.

Stahl and Wermuth, "Handbook of Pharmaceutical Salts: Properties, Selection and Use," Supplementary Material—list of pharmaceutically acceptable acids, Weinheinn/Zurich Wiley—VCH/VHCA, 2002, retrieved from URL <http://www.google.com/url?sa=t&rct=j&q=&esrc=s&source=web&cd=&ved=2ahUKEwiw7tKn-tHyAhU7EFkFHXeGCWoQFnoECAMQAQ&url=http%3A%2F%2Fwww.rsc.org%2Fsuppdata%2Fce%2Fb5%2Fb503309h%2Fb503309h.doc&usg=AOvVaw1BxiTGQwJeLRsoglOnEbf_ ("Stahl"))>, 1 page.

Suzuki et al., "Fetal globin gene repressors as drug targets for molecular therapies to treat the b-globinopathies." Mol Cell Biol., 2014, 34:3560-3569.

Wislicenus et al., "Adolf Strecker's Short Textbook of Organic Chemistry," 1881, Spottiswoode, London, pp. 38-39.

Canadian Office Action in Canadian Application No. 2,939,082, dated Mar. 24, 2021, 4 pages.

Japanese Office Action in Japanese Application No. 2018-555256, dated Mar. 16, 2021, 8 pages.

Taiwan Office Action in Taiwan Application No. 106113499, dated Mar. 15, 2021, 9 pages.

"LSD1 inhibitors of Lysine specific demethylase 1, a novel target in neurodegenerative disease," Powerpoint presentation, Oryzon, Feb. 2011, 42 pages.

Abdulla et al., "Natural Polyphenols Inhibit Lysine-Specific Demethylase-1 in vitro," Journal of Biochemical and Pharmacological Research, Mar. 2013, 1: 56-63.

Adamo et al., "LSD1 and pluripotency: a new player in the network," Cell Cycle, Oct. 2011, 10(19): 3215-6.

Adamo et al., "LSD1 regulates the balance between self-renewal and differentiation in human embryonic stem cells," Nat. Cell Biol, Jun. 2011, 13(6): 652-9.

Anand and Marmorstein, "Structure and mechanism of lysine-specific demethylase enzymes," J Biol Chem, Dec. 2007, 282(49): 35425-9.

Atzrodt et al., "The Renaissance of H/D Exchange," Angew. Chem. Int. Ed., Sep. 21, 2007, 46:7744-7765.

Balamuth, "Ewings sarcoma" Lancet Oncology (2010), 11(2), 184-192.

Baron et al., "Molecular Mimicry and Ligand Recognition in Binding and Catalysis by the Histone Demethylase LSD1-CoREST Complex," Structure, Feb. 2011, 19: 212-220.

Bauer et al., "Reawakening fetal hemoglobin: prospects for new therapies for the β-globin disorders," Blood, Oct. 2012, 120(15): 3945-53.

Beck and Blanpain, "Unravelling cancer stem cell potential," Nat Rev Cancer, Oct. 2013, 13(10): 727-38.

Benelkebir et al., "Enantioselective synthesis of tranylcypromine analogues as lysine demethylase (LSD1) inhibitors," Bioorganic & Medicinal Chemistry, 2011, 19: 3709-3716.

Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.

(56) References Cited

OTHER PUBLICATIONS

Berge and Robiette, "Development of a Regioselective N-Methylation of (Benz)imidazoles Providing the More Sterically Hindered Isomer," The Journal of Organic Chemistry, 2013, 78(23):12220-12223.
Berge et al., "Pharmaceutical salts," J Pharm Sci, 1977, 66(1): 1-19.
Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.
Binda et al., "Molecular Insights into Human Monoamine Oxidase B Inhibition by the Glitazone Antidiabetes Drugs," ACS Med. Chem. Letter, 2012, 3: 39-42.
Blom et al., "Optimizing Preparative LC/MS Configurations and Methods for Parallel Synthesis Purification," J. Comb. Chem., 2003, 5(5): 670-683.
Blom et al., "Preparative LC-MS Purification: Improved Compound-Specific Method Optimization," J. Comb. Chem., 2004, 6(6): 874-883.
Blom, "Two-Pump at-Column-Dilution Configuration for Preparative Liquid Chromatography—Mass Spectrometry," J. Comb. Chem, 2002, 4(4): 295-301.
Cain, "AML takes LSD1," SciBX, Apr. 2012, pp. 1-3.
Carey, "Structure Determines Properties," Organic Chemistry, 6th Ed. McGraw Hill. 2006, chapter 1, pp. 9 and 10.
Cao et al., "One-Pot Regiospecific Synthesis of Imidazo[1,2-a]pyridines: A Novel, Metal-Free, Three-Component Reaction for the Formation of C—N, C—O, and C—S Bonds," Org Lett., 2014, 16(1):146-149.
Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.
Chen et al., "Lysine-specific histone demethylase 1 (LSD1): A potential molecular target for tumor therapy," Crit Rev Eukaryot Gene Expre, 2012, 22(1): 53-9.
Chilean Opposition in Chilean Application No. 2021-2016, dated Dec. 23, 2016, 3 pages (English Translation).
Chilean Office Action in Chilean Application No. 2021-2016, dated Apr. 10, 2018, 13 pages (English Translation).
Chilean Office Action in Chilean Application No. 2021-2016, dated Oct. 19, 2018, 16 pages (English Translation).
Chilean Office Action in Chilean Application No. 3040-2017, dated Jun. 15, 2020, 33 pages (English Translation).
Chinese Office Action in Chinese Application No. 201580017095, dated Mar. 30, 2018, 11 pages (English Translation).
Chinese Office Action in Chinese Application No. 201580017095, dated Dec. 17, 2018, 11 pages (English Translation).
Chinese Office Action in Chinese Application No. 201580019205.7, dated Nov. 27, 2019, 10 pages.
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
ClinicalTrials.Gov, "An Open-Label, Dose-Escalation/Dose-Expansion Safety Study of INCB059872 in Subjects with Advanced Malignancies," [retrieved on Nov. 5, 2018] retrieved from <https://clinicaltrials.gov/ct2/show/NCT02712905> 7 pages.
ClinicalTrials.Gov, "IMG-7289, with and without ATRA, in patients with advanced myeloid malignancies," Jul. 25, 2016, [last update Feb. 26, 2019] retrieved from URL <https://clinicaltrials.gov/ct2/show/NCT02842827>, 6 pages.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, Jun. 1, 2015, 1-31.
Cui, Shuaiying, "Nuclear Receptors TR2 and TR4 Recruit Multiple Epigenetic Transcriptional Corepressors That Associate Specifically with the Embryonic-Type Globin Promoters in Differentiated Adult Erythroid Cells," Molecular and Cellular Biology, Aug. 31, 2011, 31(16): 3298-3311.
Culhane and Cole, "LSD1 and the chemistry of histone demethylation," Current Opinion in Chemical Biology, 2007, 11: 561-568.
Culhane et al., "A Mechanism-Based Inactivator for Histone Demethylase LSD1," J. Am. Chem. Soc., 2006, 128: 4536-4537.
Culhane et al., "Comparative Analysis of Small Molecules and Histone Substrate Analogues as LSD1 Lysine Demethylase Inhibitors," J. Am. Chem. Soc., 2010, 132: 3164-3176.
Colombian Office Action in Colombian Application No. NC20160001817, dated Mar. 20, 2018, 9 pages.
Dancy et al., "Azalysine Analogues as Probes for Protein Lysine Deacetylation and Demethylation," J. Am. Chem. Soc., 2012, 5138-5148.
Dawson and Kouzarides, "Cancer epigenetics: from mechanism to therapy," Cell, Jul. 2012, 150(1): 12-27.
Dhanak, "Cracking the Code: The Promise of Epigenetics," ACS Med. Chem. Letter, 2012, 3: 521-523.
Dhudshia and Thadani, "Diastereoselective allylation and crotylation of N-unsubstituted imines derived from ketones," Chem. Commun., 2005, 33 pages.
Dhudshia et al., "Diastereoselective allylation and crotylation of N-unsubstituted imines derived from ketones," Chem Commun, 2005, 5551-5553.
Ding et al., "LSD1-mediated epigenetic modification contributes to proliferation and metastasis of colon cancer," Br J Cancer, Aug. 2013, 109(4): 994-1003.
Dulla et al., "Synthesis and evaluation of 3-amino/guanidine substituted phenyl oxazoles as a novel class of LSD1 inhibitors with anti-proliferative properties," The Royal Society of Chemistry, Jan. 25, 2013.
Eurasian Office Action in Eurasian Application No. 201691620, dated Mar. 16, 2017, 6 pages (English Translation).
Eurasian Office Action in Eurasian Application No. 201691594, dated Sep. 27, 2017, 4 pages (English Translation).
Eurasian Office Action in Eurasian Application No. 201792205, dated Apr. 4, 2018, 6 pages (English Translation).
European Search Report from European Application No. 18160157, dated Sep. 3, 2018, 6 pages.
European Extended Search Report in European Application No. 19190014.1, dated Jan. 23, 2020, 7 pages.
European Extended Search Report in European Application No. 19190494.5 dated Jan. 29, 2020, 10 pages.
European Examination Report in European Application No. 15707007.9, dated Feb. 27, 2018, 3 pages.
Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.
Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.
Forneris et al., "LSD1: oxidative chemistry for multifaceted functions in chromatin regulation," Cell Press, Mar. 2008, 181-189.
Forneris, F., et al., "Structural basis of LSD1-CoREST selectivity in histone H3 recognition," J Biol Chem, 2007. 282(28): p. 20070-4.
Ganesan, "Targeting Epigenetic Demethylation," University of East Anglia (School of Pharmacy), PowerPoint presentation, Presented from the World Epigenetics Summit, London, Jul. 24, 2012, 26 pages.
Garson et al., "Models of ovarian cancer—are we there yet?," Mol Cell Endocrinol., Jul. 15, 2005, 239(1-2):15-26.
Ge et al., "Pd-Catalyzed α-Arylation of α,α-Difluoroketones with Aryl Bromides and Chlorides. A Route to Difluoromethylarenes," J Am Chem Soc., 2014, 136(11):4149-4152.
George et al., "Soft Tissue and Uterine Leiomyosarcoma," J Clin Oncol., Dec. 8, 2017, 36(2):144-150.

(56) References Cited

OTHER PUBLICATIONS

Ghosh and Barik, "Formulation and in vitro evaluation of once daily sustained release formulation of aceclofenac," Tropical Journal of Pharmaceutical Research, 2010, 9(3):265-273.

Gonzalez et al., "Selective and Potent Morpholinone Inhibitors of the MDM2-p53 Protein-Protein Interaction," J. Med. Chem., 2013, 57(6):2472-2488.

Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.

Greaves and Gribben, "The role of B7 family molecules in hematologic malignancy," Blood, Jan. 2013, 121(5): 734-44.

Gui et al., "C—H Methylation of Heteroarenes Inspired by Radical SAM Methyl Transferase," J Am Chem Soc., 2014, 136(13):4853-4856.

Guiles et al. "preparation of triazolopyrimidine derivatives as P2T receptor antagonists," CA130:168386 (1999).

Hackam et al., "Translation of research evidence from animals to humans," JAMA, Oct. 2006, 296(14), 1731-1732.

Hakimi et al., "A core-BRAF35 complex containing histone deacetylase mediates repression of neuronal-specific genes," Proc Natl Acad Sci USA, May 2002, 99(11): 7420-5.

Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.

Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.

Han et al., "Synergistic re-activation of epigenetically silenced genes by combinatorial inhibition of DNMTs and LSD1 in cancer cells," pLoS One, Sep. 2013, 8(9): e75136.

Harris et al., "The histone demethylase KDM1A sustains the oncogenic potential of MLL-AF9 leukemia stem cells," Cancer Cell, Apr. 2012, 21(4): 473-87.

Hayami et al., "Overexpression of LSD1 contributes to human carcinogenesis through chromatin regulation in various cancers," Int J Cancer, Feb. 2011, 128(3): 574-86.

Hazeldine et al., "Low Molecular Weight Amidoximes that Act as Potent Inhibitors of Lysine-Specific Demethylase 1," J. Med. Chem., 2012, 55: 7378-7391.

Hesp et al., "Expedient Synthesis of α-Heteroaryl Piperidines Using a Pd-Catalyzed Suzuki Cross-Coupling—Reduction Sequence," Org. Lett., 2013, 16(2):413-415.

Hicken et al., "Discovery of a Novel Class of Imidazo[1,2-a]Pyridines with Potent PDGFR Activity and Oral Bioavailability," ACS Med. Chem. Lett., 2013, 5(1):78-83.

Hitchin et al., "Development and evaluation of selective, reversible LSD1 inhibitors derived from fragments," Med. Chem. Commun., 2013, 4: 1513-1522.

Hoffmann et al., "The role of histone demethylases in cancer therapy," Molecular Oncology, 2012, 6: 683-703.

Hou and Yu, "Structural insights into histone lysine demethylation," Current Opinion in Structural Biology, 2010, 20:739-748.

Hruschka et al., "Fluorinated phenylcyclopropylamines. Part 5: Effects of electron-withdrawing or -donating aryl substituents on the inhibition of monoamine oxidases A and B by 2-aryl-2-fluoro-cyclopropylamines," Bioorganic & Medicinal Chemistry, 2008, 16: 7148-7166.

Huang et al., "p53 is regulated by the lysine demethylase LSD1," Nature, Sep. 2007, 449(7158): 105-8.

Huang et al., "Rhodium(III)-Catalyzed Direct Selective C(5)—H Oxidative Annulations of 2-Substituted Imidazoles and Alkynes by Double C—H Activation," Organic Letters, Feb. 2013, 15(8): 1878-1881.

Improper Markush Fed. Reg. 76(27) p. 7612-75, slide 1, 64-67 (2011).

International Preliminary Report on Patentability in International Application No. PCT/US2015/015600, dated Aug. 25, 2016, 7 pages.

International Preliminary Report on Patentability in International Application No. PCT/US2015/015635, dated Aug. 16, 2016, 8 pages.

International Preliminary Report on Patentability in International Application No. PCT/US2015/015663, dated Aug. 16, 2016, 7 pages.

International Preliminary Report on Patentability in International Application No. PCT/US2015/015706, dated Aug. 16, 2016, 10 pages.

International Preliminary Report on Patentability in International Application No. PCT/US2015/039734, dated Jan. 10, 2017, 10 pages.

International Preliminary Report on Patentability in International Application No. PCT/US2015/039706, dated Jan. 10, 2017, 10 pages.

International Preliminary Report on Patentability in International Application No. PCT/US2015/039724, dated Jan. 10, 2017, 10 pages.

International Preliminary Report on Patentability in International Application No. PCT/US2015/039718, dated Jan. 10, 2017, 9 pages.

International Preliminary Report on Patentability in International Application No. PCT/US2016/025550, dated Oct. 2, 2017, 8 pages.

International Preliminary Report on Patentability in International Application No. PCT/US2016/046497, dated Feb. 22, 2018, 8 pages.

International Preliminary Report on Patentability in International Application No. PCT/US2017/028756, dated Oct. 23, 2018, 8 pages.

International Search Report and Written Opinion in International Application No. PCT/US2015/015600, dated May 18, 2015, 9 pages.

International Search Report and Written Opinion in International Application No. PCT/US2015/015635, dated May 8, 2015, 10 pages.

International Search Report and Written Opinion in International Application No. PCT/US2015/015663, dated May 6, 2015, 10 pages.

International Search Report and Written Opinion in International Application No. PCT/US2015/015706, dated May 6, 2015, 16 pages.

International Search Report and Written Opinion in International Application No. PCT/US2015/039718, dated Sep. 15, 2015, 13 pages.

International Search Report and Written Opinion in International Application No. PCT/US2015/039724, dated Sep. 15, 2015, 14 pages.

International Search Report and Written Opinion in International Application No. PCT/US2015/039734, dated Sep. 18, 2015, 14 pages.

International Search Report and Written Opinion in International Application No. PCT/US2016/025550, dated Aug. 30, 2016, 12 pages.

International Search Report and Written Opinion in International Application No. PCT/US2016/046497, dated Oct. 21, 2016, 13 pages.

International Search Report and Written Opinion in International Application No. PCT/US2015/039706, dated Sep. 16, 2015, 12 pages.

International Search Report and Written Opinion in International Application No. PCT/US2017/028756, dated Jul. 3, 2017, 23 pages.

International Search Report and Written Opinion in International Application No. PCT/US2019/048725, dated Jan. 3, 2020, 19 pages.

Invitation to Pay Fees in International Application No. PCT/US2019/048725, dated Oct. 30, 2019, 12 pages.

Jalluri, Drug Analysis Table, LSD1 KDM1a Cortellis Update, retrieved on May 6, 2013, 3 pages.

Jordan, "Tamoxifen: A Most Unlikely Pioneering Medicine," Nature Reviews: Drug Discovery, Mar. 2003, 2:205-213.

(56) References Cited

OTHER PUBLICATIONS

Kahl et al., "Androgen Receptor Coactivators Lysine-Specific Histone Demethylase 1 and Four and a Half LIM Domain Protein 2 Predict Risk of Prostate Cancer Recurrence," Cancer Res., Dec. 2006, 66(23): 11341-11347.
Kakizawa et al., "Histone H3 peptide based LSD1-selective inhibitors," Bioorganic & Medicinal Chemistry Letters, 2015, 25: 1925-1928.
Karytinos et al., "A novel mammalian flavin-dependent histone demethylase," J Biol Chem, Jan. 2009, 284(26): 17775-82.
Kelly and Lipshutz, "Chemoselective Reductions of Nitroaromatics in Water at Room Temperature," Org. Lett., 2013, 16(1):98-101.
Kerekes et al., "Aurora Kinase Inhibitors Based on the Imidazo[1,2-a]pyrazine Core: Fluorine and Deuterium Incorporation Improve Oral Absorption and Exposure," J. Med. Chem. Dec. 3, 2011, 54:201-210.
Kettle et al., "Diverse Heterocyclic Scaffolds as Allosteric Inhibitors of AKT," Journal of Medicinal Chemistry, Mar. 2012, 55(3): 1261-1273.
Khan et al., "An Overview of Phenylcyclopropylamine Derivatives: Biochemical and Biological Significance and Recent Developments," Medicinal Research Reviews, 2012, 874-910.
Khoury et al., "Efficient Assembly of Iminodicarboxamides by a "Truly" Four-Component Reaction," Angew. Chem. Int. Ed., 2012, 51: 10280-10283.
Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.
Kjer-Nielsen et al., "MR1 presents microbial vitamin B metabolites to MAIT cells," Nature, Nov. 2012, 491: 717-725.
Kocienski et al., "Carbonyl Protecting Groups," Protecting Groups, Thieme, 2005, Chapter 2, p. 52.
Kong et al., "Immunohistochemical expression of RBP2 and LSD1 in papillary thyroid carcinoma," Rom J Morphol Embryol, 2013, 54(3): 499-503.
Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.
Kontaki and Talianidis, "Lysine methylation regulates E2F1-induced cell death," Mol Cell, Jul. 2010, 39(1): 152-60.
Kooistra and Helin, "Molecular mechanisms and potential functions of histone demethylases," Nat Rev Mol Cell Biol, Apr. 2012, 13(5): 297-311.
Kuroyanagi et al., "Novel anti fungal agents: Triazolopyridines as inhibitors of beta-1,6-glucan synthesis," Bioorganic & Medicinal Chemistry, Aug. 2010, 18(16):5845-5854.
Kuroyanagi et al., "1,3-Benzoxazole-4-carbonitrile as a novel antifungal scaffold of beta-1,6-glucan synthesis inhibitors," Bioorganic & Medicinal Chemistry, Nov. 2010, 18(21):7593-7606.
Kutz et al., "3,5-Diamino-1,2,4-triazoles as a novel scaffold for potent, reversible LSD1 (KDM1A) inhibitors," Med. Chem. Commun., 2014, 5: 1863-1870.
Lan et al., "Recognition of unmethylated histone H3 lysine 4 links BHC80 to LSD1-mediated gene repression," Nature, 2007, 718-723.
Larsen and Hartwig, "Iridium-Catalyzed C—H Borylation of Heteroarenes: Scope, Regioselectivity, Application to Late-Stage Functionalization, and Mechanism," J. Am. Chem. Soc., 2013, 136(11):4287-4299.
Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.

Liang et al., "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS ONE, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Lynch et al., "LSD1 Inhibition: A therapeutic strategy in cancer?," Expert Opinion on Therapeutic Targets, 2012, 16(12): 1239-1249.
Masakatu et al., Medicinal Chemistry, 1995, 1:98-99.
Merck KGaA, "Product comparison—EMD4Biosciences," Comparison of LSD1 inhibitors, EMD Millipore USA, retrieved on May 6, 2013, 3 pages.
Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistiy, 2010, 49: 6494-6503.
Moon et al., "Copper-Catalyzed Chan-Lam Coupling between Sulfonyl Azides and Boronic Acids at Room Temperature," Org. Lett., 2013, 16(2):338-341.
Moormann et al., "Potential Antisecretory Antidiarrheals. 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Muntean and Hess, "Biological Perspectives: Epigenetic Dysregulation in Cancer," Am J of Pathol., Oct. 2009, 175(4):1353-1361.
Neelamegam et al., "Brain-penetrant LSD1 inhibitors can block memory consolidation," Supplementary Data, 2012, 24 pages.
Neelamegam et al., "Brain-Penetrant LSD1 Inhibitors Can Block Memory Consolidation," ACS Chem. Neurosci., 2012, 3:120-128.
No Author, "FS14 Myelofibrosis Facts," Leukemia & Lymphoma Society, [last updated Apr. 2012] retrieved from URL <http://www.lls.org/sites/default/files/file_assets/FS14_Myelofibrosis_Fact%20Sheet_Final9.12.pdf>, 9 pages.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery Mechanism," Supporting Information, Angew. Chem. Int. Ed., 2013, 52: 8620-8624.
Patani et al., "Bioisosterism: A Rational Approach in Drug Design," Chemical Reviews, 1996, 96: 3147-3176.
Petursson et al., "Protecting Groups in Carbohydrate Chemistry," J. Chem. Educ., Nov. 1, 1997, 74:1297.
Pitt "Heteroaromatic Rings of the Future" J. Med. Chem. 2009, 52, 2952-2963.
Portela and Esteller, "Epigenetic modifications and human disease," Nat Biotechnol, Oct. 2010, 28(10): 1057-68.
Potts et al., "The mass spectra of some s-triazolo[4,3-a]pyrazines," Organic Mass Spectrometry, Jun. 1971, 5(6): 663-674.
Pozharskii et al., "Molecular Rings Studded with Jewels," Heterocycles in Life and Society, John Wiley & Sons Ltd., 1997, pp. 1-6.

(56) References Cited

OTHER PUBLICATIONS

Rambaldi et al., "From Palliation to Epigenetic Therapy in Myelofibrosis," Hematology Am Soc Hematol Educ Program., 2008, 83-91.
*Remington's Pharmaceutical Sciences*, 17th Ed., (Mack Publishing Company, Easton, 1985), p. 1418.
Robertson et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Rotilli and Mai, "Targeting Histone Demethylases: A New Avenue for the Fight against Cancer," Genes and Cancer, Aug. 9, 2011, 2(6): 663-679.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.
Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Sale "Models of ovarian cancer metastasis: Murine models," Drug Discov Today Dis Models., Jun. 1, 2006, 3(2):149-154.
Samann et al., "Full Functionalization of the Imidazole Scaffold by Selective Metalation and Sulfoxide/Magnesium Exchange," Angew. Chem. Int. Ed., 2013, 52: 1-6.
Sankar et al., "Reversible LSD1 inhibition interferes with global EWS/ETS transcriptional activity and impedes Ewing sarcoma tumor growth," Clin Cancer Res., Sep. 1, 2014, 20(17):4584-4597.
Sankaran, "Anemia: progress in molecular mechanisms and therapies," Nature Medicine, 2015, 21(3): 221-230.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-111.
Schmitt et al., "Nonpeptidic Propargylamines as Inhibitors of Lysine Specific Demethylase 1 (LSD1) with Cellular Activity," J. Med. Chem., 2013, 56(18):7334-7342.
Schulte et al., "Lysine-Specific Demethylase 1 Is Strongly Expressed in Poorly Differentiated Neuroblastoma: Implications for Therapy," Cancer Res, 2009, 69(5): 2065-71.
Search Report, dated Jun. 3, 2014, 7 pages.
Search Report, dated May 30, 2014, 109 pages.
Search Report, dated May 30, 2014, 6 pages.
Search Report, dated Feb. 12, 2016, 84 pages.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elevated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.
Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Shih et al., "The role of mutations in epigenetic regulators in myeloid malignancies," Nat Rev Cancer., Sep. 2012, 12(9):599-612.

Singh et al., "Inhibition of LSD1 sensitizes glioblastoma cells to histone deacetylase inhibitors," Neuro Oncol, Aug. 2011, 13(8): 894-903.
Son et al., "Structure of human monoamine oxidase A at 2.2—A resolution: The control of opening the entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primary, Secondary, Tertiary) to Alcohols using $SmI_2$/Amine/$H_2O$ under Mild Conditions," J. Am. Chem. Soc., 2013, 136(6):2268-2271.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, 8(8): 1677-1682.
Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.
Ueda et al., "Identification of Cell-Active Lysine Specific Demethylase 1-Selective Inhibitors," J. Am. Chem. Soc., 2009, 131: 17536-17537.
Ungerstedt, "Epigenetic Modifiers in Myeloid Malignancies: The Role of Histone Deacetylase Inhibitors," Int J Mol Sci., 2018, 19:3091, 18 pages.
Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.
Wakefield, Basil "Fluorinated Pharmaceuticals" Innovations in Pharmaceutical Technology 2003, 74: 76-78, Online "http://web.archive.org/web/20030905122408/http://www.iptonline.com/articles/public/IPTFOUR74NP.pdf". (accessed via Wayback machine Nov. 20, 2009 showing web availability as of Sep. 2003).
Waldmann and Schneider, "Targeting histone modifications—epigenetics in cancer," Curr Opin Cell Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.
Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.
Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Xu et al., "Design, synthesis and biological evaluation of deuterated nintedanib for improving pharmacokinetic properties," J. Label Compd. Radiopharm, May 26, 2015, 58:308-312.
Yang et al., "Reversible methylation of promoter-bound STAT3 by histone-modifying enzymes," Proc Natl Acad Sci USA, Dec. 2010, 107(50): 21499-504.

(56) References Cited

OTHER PUBLICATIONS

Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yuan et al., "6-Thioguanine Reactivates Epigenetically Silenced Genes in Acute Lymphoblastic Leukemia Cells by Facilitating Proteasome-Mediated Degradation of DNMT1," Cancer Res., Jan. 14, 2011, 71:1904-1911.
Yu et al., "Energetic factors determining the binding of type I inhibitors to c-Met kinase: experimental studies and quantum mechanical calculations," Acta Pharmacologica Sinica, Nov. 2013, 34(11): 1475-1783.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," Medicinal Research Reviews, 2015, pp. 1-40.
Zhu et al., "Preparation of imidazolidin-2-imines and their analogs as aspartyl protease inhibitors for treating various diseases," CA149: 307842 (2008).
Cancer, definition by Medical Dictionary, retrieved from URL<http://medical-dictionary.thefreedictionary.com/Cancer+(disease), p. 1 (2017).
SEER Training Modules, "Cancer Classification," [retrieved on Dec. 26, 2005], retrieved from URL<http://training.seer.cancer.gov/module_...ase/unit3_categories2_by_histology.html>, p. 1-3 (2005).
No Author, "Beta Thalassemia," Wikipedia, 2017 [retrieved on May 18, 2017], retrieved from URL<https://en.wikipedia.org/wiki/Beta_thalassemia>, 5 pages.
Pringle, "Overview of viruses" Merck Manual, Aug. 2013 [retrieved on May 18, 2017], retrieved from URL <http://merkmanuals.com/professional/infections-diseases/viruses/overview-of-viruses>, 5 pages.
Simone, Oncology: Introduction, Cecil Textbook of Medicine, 20th Edition, 1996 vol. 1, 1004-1010.
Vardiman, "The World Health Organization (WHO) classification of the myeloid neoplasms," Blood, 2002, 100(7): 2292-2302.
Estey, "New drug approvals in acute myeloid leukemia: what's the best end point?" Leukemia, 2016, 30: 521-525.
Pui, "Treatment of Acute Lymphoblastic Leukemia," New England Journal of Medicine, 2006, 354: 166-78.
Krishnan, "Multiple myeloma and persistence of drug resistance in the age of novel drugs (Review)," International Journal of Oncology, 2016, 49: 33-50.
Stewart, "Novel therapeutics in multiple myeloma," Hematology, 2012, 17(S1): s105-s108.
Howington, "Treatment of Stage I and II Non-Small Cell Lung Cancer Diagnosis and Management of Lung Cancer 3rd Ed: American College of Chest Physicians Evidence-Based Clinical Practice Guidelines," CHEST 2013, 143(5)(Suppl): e278S-e313S.
Socinski, "Treatment of Stage IV Non-small Cell Lung Cancer Diagnosis and Management of Lung Cancer, 3rd ed: American College of Chest Physicians Evidence-Based Clinical Practice Guideline," CHEST 2013, 143(5)(Suppl): e341S-e368S.
Sanz-Garcia, "Current and advancing treatments for metastatic colorectal cancer," Expert Opinion on Biological Therapy, 2016, 16:1, 93-110.
Boniface, "Multidisciplinary management for esophageal and gastric cancer," Cancer Management and Research, 2016, 39-44.
Yoo, "New drugs in prostate cancer," Prostate Int., 2016, 4: 37-42.
Jett, "Treatment of Small Cell Lung Cancer Diagnosis and Management of Lung Cancer, 3rd ed: American College of Chest Physicians Evidence-Based Clinical Practice Guidelines," CHEST 2013, 143(5)(Suppl): e400S-e419S.
Fattaneh and Devilee, "World Health Organization Classification of Tumours: Pathology and Genetics of Tumours of the Breast and Female Genital Organs," Online http://www.iarc.fr/en/publications/pdfs-online/pat-gen/bb4/BB4.pdf, accessed Nov. 4, 2016 IARCPress Lyon, 2003, 430 pages.
Hudis, "Triple-Negative Breast Cancer: An Unmet Medical Need," The Oncologist, 2011, 16(suppl 1): 1-11.
Gerratana, "Do platinum salts fit all triple negative breast cancers?" Cancer Treatment Reviews, 2016, 48:34-41.
Gyawali, "Chemotherapy in locally advanced head and neck squamous cell carcinoma," Cancer Treatment Reviews, 2016, 44: 10-16.
Damia, "Contemporary pre-clinical development of anticancer agents—What are the optimal preclinical models?" European Journal of Cancer, 2009, 45: 2768-2781.
Sharma, "Cell-line based platforms to evaluate the therapeutic efficacy of candidate anticancer agents," Nature Reviews Cancer, Apr. 2010, 10: 241-253.
Ocana, "Preclinical development of molecular targeted agents for cancer," Nat. Rev. Clin. Oncol., 2011, 8: 200-209.
Ledford, "US cancer institute overhauls cell lines," Nature, Feb. 2016, 530: 391.
Johnson et al., "Relationships between drug activity in NCI preclinical in vitro and in vivo models and early clinical trials," British Journal of Cancer, 2001, 84: 1424-1431.
Rotili, "Targeting Histone Demethylases: A New Avenue for the Fight Against Cancer," J. Genes & Cancer, Aug. 9, 2011, 2(6): 663-679.
Muller and Krausslich, "Antiviral Strategies," Handbook of Experimental Pharmacology, 2009, 189(1): 1-24.
Wada et al., "Overexpression of the shortest isoform of histone demethylase LSD1 primes hematopoietic stem cells for malignant transformation," Blood, Jun. 2015, 125(24): 3731-3746.
Wermuth, The Practice of Medicinal Chemistry, 1998, p. 241-243, 253, 254 (with English Translation).
Yatim et al., "NOTCH1 Nuclear Interactome Reveals Key Regulators of Its Transcriptional Activity and Oncogenic Function," Molecular Cell, 2012, 48: 1-14.
Goossens et al., "Oncogenic ZEB2 activation drives sensitivity toward KDM1A inhibition in T-cell acute lymphoblastic leukemia," Blood, Feb. 2017, 129(8): 981-990.
Hu et al., "LSD1-mediated epigenetic modification is required for TAL1 function and hematopoiesis," PNAS, Jun. 2009, 106(25): 10141-10146.
Niebel et al., "Lysine-specific demethylase 1 (LSD1) in hematopoietic and lymphoid neoplasms," Blood, 2014, 124: 151-152.
Australian Examination Report in Australian Application No. 2015217073, dated Aug. 6, 2018, 4 pages.
Australian Examination Report in Australian Application No. 2015217119, dated Jun. 22, 2018, 4 pages.
Australian Office Action in Australian Application No. 2016306555, dated Jan. 17, 2020, 4 pages.
Australian Office Action in Australian Application No. 2019204244, dated Mar. 27, 2020, 4 pages.
Argentina Office Action in Argentina Application No. 20150100415, dated Jan. 27, 2020, 18 pages.
Argentina Office Action in Argentina Application No. 20150102198, dated Feb. 26, 2020, 6 pages.
Chilean Office Action in Chilean Application No. 2991-2018, dated Oct. 11, 2019, 15 pages (English Translation).
Chinese Office Action in Chinese Application No. 201580019205 dated May 22, 2018, 14 pages (English Translation).
Chinese Office Action in Chinese Application No. 201580019205.7, dated Mar. 15, 2019, 9 pages (English Translation).
Chinese Office Action in Chinese Application No. 201580021455.9, dated Oct. 17, 2019, 13 pages.

(56) References Cited

OTHER PUBLICATIONS

Colombian Office Action in Colombian Application No. NC2016/0001337, dated Jan. 9, 2019, 8 pages.
Colombian Office Action in Colombian Application No. NC2016/0001337, dated Jul. 10, 2018, 8 pages.
Colombian Office Action in Colombian Application No. NC2017/0011216, dated May 3, 2019, 9 pages.
Colombian Office Action in Colombian Application No. NC2019/0009689, dated Jan. 22, 2020, 10 pages.
Colombian Office Action in Colombian Application No. NC20180002354, dated Apr. 1, 2020, 14 pages.
Colombian Office Action in Colombian Application No. NC 2018/0012482, dated Jun. 23, 2020, 20 pages.
Chilean Opposition in Chilean Application No. 3040-2017, dated Sep. 25, 2019, 20 pages.
Chilean Office Action in Chilean Application No. 2991-2018, dated Apr. 15, 2020, 14 pages.
Ecuador Opposition in Ecuador Application No. IEPI-2018-18869, dated Feb. 8, 2019, 34 pages (English Translation).
Eurasian Office Action in Eurasian Application No. 201691620, dated Jan. 18, 2019, 4 pages.
Eurasian Office Action in Eurasian Application No. 201892395, dated Oct. 28, 2019, 12 pages.
European Search Report in European Application No. 19190056.2 dated Feb. 7, 2020, 8 pages.
Indian Office Action in Indian Application No. 201627028454, dated Jun. 26, 2019, 6 pages.
Indian Office Action in Indian Application No. 201817043771, dated Jul. 15, 2020, 6 pages.
Indian Office Action in Indian Application No. 201627030320, dated Aug. 21, 2020, 5 pages.
Indian Office Action in Indian Application No. 201717036403, dated Oct. 22, 2020, 6 pages.
Israeli Office Action in Israeli Application No. 257,290, dated May 17, 2020, 10 pages.
Japanese Office Action in Japanese Application No. 2016-551815, dated Oct. 2, 2018, 6 pages.
Japanese Office Action in Japanese Application No. 2016-551710, dated Oct. 2, 2018, 7 pages.
Japanese Office Action in Japanese Application No. 2017-551636, dated Mar. 20, 2020, 8 pages.
New Zealand Office Action in New Zealand Application No. 723203, dated Jan. 15, 2020, 4 pages.
New Zealand Office Action in New Zealand Application No. 723817, dated Jan. 13, 2020, 4 pages.
Peruvian Office Action in Peruvian Application No. 1466, dated Feb. 13, 2020, 16 pages.
Philippine Office Action in Philippine Application No. 1/2017/501817, dated Mar. 12, 2020, 3 pages.
Taiwanese Office Action in Taiwan Application No. 104104830, dated Jul. 30, 2018, 8 pages (English Search Report).
Taiwanese Office Action in Taiwan Application No. 104104827, dated Dec. 18, 2018 11 pages (English Translation).
Taiwan Office Action in Taiwan Application No. 104122393, dated May 3, 2019, 6 pages (English Translation).
Taiwan Office Action in Taiwan Application No. 108112023, dated Mar. 25, 2020, 7 pages (English Translation).
Ukrainian Office Action in Ukraine Application No. a 2016 09399, dated Sep. 26, 2019, 6 pages (English Translation).
Elder et al., "The utility of sulfonate salts in drug development," J Pharm Sci., Jul. 2010, 99(7):2948-2961.
Mangilal et al., "Formulation and Evaluation of Sorafenib Tosylate Immediate Release Film Coated Tablets for Renal Cancer," World Journal of Pharmacy and Pharmaceutical Sciences, May 12, 2015, 4(6):841-858.
Peruvian Office Action in Peruvian Application No. 1467, dated Oct. 14, 2020, 11 pages.
Taiwan Office Action in Taiwan Application No. 109101686, dated Sep. 25, 2020, 7 pages.
Jhon et al., "Conformational Preferences of Proline Analogues with Different Ring Size," J Phys Chem., 2007, 111:3496-3507.
Radic et al., "Ring Strain and Other Factors Governing the Basicity of Nitrogen Heterocycles—An Interpretation by Triadic Analysis," Croat Chem Acta., 2012, 85(4):495-504.
Korean Notice of Allowance in Korean Application No. 10-2016-7025066, dated Nov. 16, 2021, 3 pages.

* cited by examiner

HETEROCYCLIC COMPOUNDS AS LSD1 INHIBITORS

CLAIM OF PRIORITY

This application is a divisional of U.S. patent application Ser. No. 15/914,047, filed on Mar. 7, 2018; which is a continuation of U.S. patent application Ser. No. 15/088,259, filed on Apr. 1, 2016; now U.S. Pat. No. 9,944,647, issued on Apr. 17, 2018; which claims the benefit of U.S. Provisional Application No. 62/183,906, filed on Jun. 24, 2015; and U.S. Provisional Application No. 62/142,717, filed on Apr. 3, 2015, each of which is incorporated herein by reference in its entirety.

FIELD OF THE INVENTION

The present invention is directed to heterocyclic compounds and compostions thereof which are LSD1 inhibitors useful in the treatment of diseases such as cancer.

BACKGROUND OF THE INVENTION

Epigenetic modifications can impact genetic variation but, when dysregulated, can also contribute to the development of various diseases (Portela, A. and M. Esteller, *Epigenetic modifications and human disease*. Nat Biotechnol, 2010. 28(10): p. 1057-68; Lund, A. H. and M. van Lohuizen, *Epigenetics and cancer*. Genes Dev, 2004. 18(19): p. 2315-35). Recently, in depth cancer genomics studies have discovered many epigenetic regulatory genes are often mutated or their own expression is abnormal in a variety of cancers (Dawson, M. A. and T. Kouzarides, *Cancer epigenetics: from mechanism to therapy*. Cell, 2012. 150(1): p. 12-27; Waldmann, T. and R. Schneider, *Targeting histone modifications—epigenetics in cancer*. Curr Opin Cell Biol, 2013. 25(2): p. 184-9; Shen, H. and P. W. Laird, *Interplay between the cancer genome and epigenome*. Cell, 2013. 153(1): p. 38-55). This implies epigenetic regulators function as cancer drivers or are permissive for tumorigenesis or disease progression. Therefore, deregulated epigenetic regulators are attractive therapeutic targets.

One particular enzyme which is associated with human diseases is lysine specific demethylase-1 (LSD1), the first discovered histone demethylase (Shi, Y., et al., *Histone demethylation mediated by the nuclear amine oxidase homolog LSD1*. Cell, 2004. 119(7): p. 941-53). It consists of three major domains: the N-terminal SWIRM which functions in nucleosome targeting, the tower domain which is involved in protein-protein interaction, such as transcriptional co-repressor, co-repressor of RE1-silencing transcription factor (CoREST), and lastly the C terminal catalytic domain whose sequence and structure share homology with the flavin adenine dinucleotide (FAD)-dependent monoamine oxidases (i.e., MAO-A and MAO-B) (Forneris, F., et al., *Structural basis of LSD1-CoREST selectivity in histone H3 recognition*. J Biol Chem, 2007. 282(28): p. 20070-4; Anand, R. and R. Marmorstein, *Structure and mechanism of lysine-specific demethylase enzymes*. J Biol Chem, 2007. 282(49): p. 35425-9; Stavropoulos, P., G. Blobel, and A. Hoelz, *Crystal structure and mechanism of human lysine-specific demethylase-1*. Nat Struct Mol Biol, 2006. 13(7): p. 626-32; Chen, Y., et al., *Crystal structure of human histone lysine-specific demethylase 1 (LSD1)*. Proc Natl Acad Sci USA, 2006. 103(38): p. 13956-61). LSD1 also shares a fair degree of homology with another lysine specific demethylase (LSD2) (Karytinos, A., et al., *A novel mammalian flavin-dependent histone demethylase*. J Biol Chem, 2009. 284(26): p. 17775-82). Although the biochemical mechanism of action is conserved in two isoforms, the substrate specificities are thought to be distinct with relatively small overlap. The enzymatic reactions of LSD1 and LSD2 are dependent on the redox process of FAD and the requirement of a protonated nitrogen in the methylated lysine is thought to limit the activity of LSD1/2 to mono- and di-methylated lysines at the position of 4 or 9 of histone 3 (H3K4 or H3K9). These mechanisms make LSD1/2 distinct from other histone demethylase families (i.e. Jumonji domain containing family) that can demethylate mono-, di-, and tri-methylated lysines through alpha-ketoglutarate dependent reactions (Kooistra, S. M. and K. Helin, *Molecular mechanisms and potential functions of histone demethylases*. Nat Rev Mol Cell Biol, 2012. 13(5): p. 297-311; Mosammaparast, N. and Y. Shi, *Reversal of histone methylation: biochemical and molecular mechanisms of histone demethylases*. Annu Rev Biochem, 2010. 79: p. 155-79).

Methylated histone marks on H3K4 and H3K9 are generally coupled with transcriptional activation and repression, respectively. As part of corepressor complexes (e.g., CoREST), LSD1 has been reported to demethylate H3K4 and repress transcription, whereas LSD1, in nuclear hormone receptor complex (e.g., androgen receptor), may demethylate H3K9 to activate gene expression (Metzger, E., et al., *LSD1 demethylates repressive histone marks to promote androgen-receptor-dependent transcription*. Nature, 2005. 437(7057): p. 436-9; Kahl, P., et al., *Androgen receptor coactivators lysine-specific histone demethylase 1 and four and a half LIM domain protein 2 predict risk of prostate cancer recurrence*. Cancer Res, 2006. 66(23): p. 11341-7). This suggests the substrate specificity of LSD1 can be determined by associated factors, thereby regulating alternative gene expressions in a context dependent manner. In addition to histone proteins, LSD1 may demethylate non-histone proteins. These include p53 (Huang, J., et al., *p53 is regulated by the lysine demethylase LSD1*. Nature, 2007. 449(7158): p. 105-8), E2F (Kontaki, H. and I. Talianidis, *Lysine methylation regulates E2F1-induced cell death*. Mol Cell, 2010. 39(1): p. 152-60), STAT3 (Yang, J., et al., *Reversible methylation of promoter-bound STAT3 by histone-modifying enzymes*. Proc Natl Acad Sci USA, 2010. 107(50): p. 21499-504), Tat (Sakane, N., et al., *Activation of HIV transcription by the viral Tat protein requires a demethylation step mediated by lysine-specific demethylase 1 (LSD1/KDM1)*. PLoS Pathog, 2011. 7(8): p. e1002184), and myosin phosphatase target subunit 1 (MYPT1) (Cho, H. S., et al., *Demethylation of RB regulator MYPT1 by histone demethylase LSD1 promotes cell cycle progression in cancer cells*. Cancer Res, 2011. 71(3): p. 655-60). The lists of non-histone substrates are growing with technical advances in functional proteomics studies. These suggest additional oncogenic roles of LSD1 beyond regulating chromatin remodeling. LSD1 also associates with other epigenetic regulators, such as DNA methyltransferase 1 (DNMT1) (Wang, J., et al., *The lysine demethylase LSD1 (KDM1) is required for maintenance of global DNA methylation*. Nat Genet, 2009. 41(1): p. 125-9) and histone deacetylases (HDACs) complexes (Hakimi, M. A., et al., *A core-BRAF35 complex containing histone deacetylase mediates repression of neuronal-specific genes*. Proc Natl Acad Sci USA, 2002. 99(11): p. 7420-5; Lee, M. G., et al., *Functional interplay between histone demethylase and deacetylase enzymes*. Mol Cell Biol, 2006. 26(17): p. 6395-402; You, A., et al., *CoREST is an integral component of the CoREST-human histone deacetylase complex*. Proc Natl Acad Sci USA, 2001. 98(4): p. 1454-8). These associations augment the activities of DNMT or HDACs. LSD1 inhibitors may therefore potentiate the effects of HDAC or DNMT inhibitors. Indeed, preclinical studies have shown such potential already (Singh, M. M., et al., *Inhibition of LSD1 sensitizes glioblastoma cells to histone deacetylase inhibitors*. Neuro Oncol, 2011. 13(8): p. 894-903; Han, H., et al., *Synergistic re-activation of epigenetically silenced genes by combinatorial inhibition of DNMTs and LSD1 in cancer cells*. PLoS One, 2013. 8(9): p. e75136).

LSD1 has been reported to contribute to a variety of biological processes, including cell proliferation, epithelial-mesenchymal transition (EMT), and stem cell biology (both embryonic stem cells and cancer stem cells) or self-renewal and cellular transformation of somatic cells (Chen, Y., et al., *Lysine-specific histone demethylase 1 (LSD1): A potential molecular target for tumor therapy*. Crit Rev Eukaryot Gene Expr, 2012. 22(1): p. 53-9; Sun, G., et al., *Histone demethylase LSD1 regulates neural stem cell proliferation*. Mol Cell Biol, 2010. 30(8): p. 1997-2005; Adamo, A., M. J. Barrero, and J. C. Izpisua Belmonte, *LSD1 and pluripotency: a new player in the network*. Cell Cycle, 2011. 10(19): p. 3215-6; Adamo, A., et al., *LSD1 regulates the balance between self-renewal and differentiation in human embryonic stem cells*. Nat Cell Biol, 2011. 13(6): p. 652-9). In particular, cancer stem cells or cancer initiating cells have some pluripotent stem cell properties that contribute to the heterogeneity of cancer cells. This feature may render cancer cells more resistant to conventional therapies, such as chemotherapy or radiotherapy, and then develop recurrence after treatment (Clevers, H., *The cancer stem cell: premises, promises and challenges*. Nat Med, 2011. 17(3): p. 313-9; Beck, B. and C. Blanpain, *Unravelling cancer stem cell potential*. Nat Rev Cancer, 2013. 13(10): p. 727-38). LSD1 was reported to maintain an undifferentiated tumor initiating or cancer stem cell phenotype in a spectrum of cancers (Zhang, X., et al., *Pluripotent Stem Cell Protein Sox2 Confers Sensitivity to LSD1 Inhibition in Cancer Cells*. Cell Rep, 2013. 5(2): p. 445-57; Wang, J., et al., *Novel histone demethylase LSD1 inhibitors selectively target cancer cells with pluripotent stem cell properties*. Cancer Res, 2011. 71(23): p. 7238-49). Acute myeloid leukemias (AMLs) are an example of neoplastic cells that retain some of their less differentiated stem cell like phenotype or leukemia stem cell (LSC) potential. Analysis of AML cells including gene expression arrays and chromatin immunoprecipitation with next generation sequencing (ChIP-Seq) revealed that LSD1 may regulate a subset of genes involved in multiple oncogenic programs to maintain LSC (Harris, W. J., et al., *The histone demethylase KDM1A sustains the oncogenic potential of MLL-AF9 leukemia stem cells*. Cancer Cell, 2012. 21(4): p. 473-87; Schenk, T., et al., *Inhibition of the LSD1 (KDM1A) demethylase reactivates the all-trans-retinoic acid differentiation pathway in acute myeloid leukemia*. Nat Med, 2012. 18(4): p. 605-11). These findings suggest potential therapeutic benefit of LSD1 inhibitors targeting cancers having stem cell properties, such as AMLs.

Overexpression of LSD1 is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Over-expression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6(1): p. 75; Sareddy, G. R., et al., *KDM1 is a novel therapeutic target for the treatment of gliomas*. Oncotarget, 2013. 4(1): p. 18-28; Ding, J., et al., *LSD1-mediated epigenetic modification contributes to proliferation and metastasis of colon cancer*. Br J Cancer, 2013. 109(4): p. 994-1003; Bennani-Baiti, I. M., et al., *Lysine-specific demethylase 1 (LSD1/KDM1A/AOF2/BHC110) is expressed and is an epigen5etic drug target in chondrosarcoma, Ewing's sarcoma, osteosarcoma, and rhabdomyosarcoma*. Hum Pathol, 2012. 43(8): p. 1300-7; Schulte, J. H., et al., *Lysine-specific demethylase 1 is strongly expressed in poorly differentiated neuroblastoma: implications for therapy*. Cancer Res, 2009. 69(5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70(8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54(3): p. 499-503.

Recently, the induction of CD86 expression by inhibiting LSD1 activity was reported (Lynch, J. T., et al., *CD86 expression as a surrogate cellular biomarker for pharmacological inhibition of the histone demethylase lysine-specific demethylase 1*. Anal Biochem, 2013. 442(1): p. 104-6). CD86 expression is a marker of maturation of dendritic cells (DCs) which are involved in antitumor immune response. Notably, CD86 functions as a co-stimulatory factor to activate T cell proliferation (Greaves, P. and J. G. Gribben, *The role of B7 family molecules in hematologic malignancy*. Blood, 2013. 121(5): p. 734-44; Chen, L. and D. B. Flies, *Molecular mechanisms of T cell co-stimulation and co-inhibition*. Nat Rev Immunol, 2013. 13(4): p. 227-42).

In addition to playing a role in cancer, LSD1 activity has also been associated with viral pathogenesis. Particularly, LSD1 activity appears to be linked with viral replications and expressions of viral genes. For example, LSD1 functions as a co-activator to induce gene expression from the viral immediate early genes of various type of herpes virus including herpes simplex virus (HSV), varicella zoster virus (VZV), and β-herpesvirus human cytomegalovirus (Liang, Y., et al., *Targeting the JMJD2 histone demethylases to epigenetically control herpesvirus infection and reactivation* from latency. Sci Transl Med, 2013. 5(167): p. 167ra5; Liang, Y., et al., *Inhibition of the histone demethylase LSD1 blocks alpha-herpesvirus lytic replication and reactivation from latency*. Nat Med, 2009. 15(11): p. 1312-7). In this setting, a LSD1 inhibitor showed antiviral activity by blocking viral replication and altering virus associated gene expression.

Recent studies have also shown that the inhibition of LSD1 by either genetic depletion or pharmacological intervention increased fetal globin gene expression in erythroid cells (Shi, L., et al., *Lysine-specific demethylase 1 is a therapeutic target for fetal hemoglobin induction*. Nat Med, 2013. 19(3): p. 291-4; Xu, J., et al., *Corepressor-dependent silencing of fetal hemoglobin expression by BCL11A*. Proc Natl Acad Sci USA, 2013. 110(16): p. 6518-23). Inducing fetal globin gene would be potentially therapeutically beneficial for the disease of β-globinopathies, including β-thalassemia and sickle cell disease where the production of normal β-globin, a component of adult hemoglobin, is impaired (Sankaran, V. G. and S. H. Orkin, *The switch from fetal to adult hemoglobin*. Cold Spring Harb Perspect Med, 2013. 3(1): p. a011643; Bauer, D. E., S. C. Kamran, and S. H. Orkin, *Reawakening fetal hemoglobin: prospects for new therapies for the beta-globin disorders*. Blood, 2012. 120 (15): p. 2945-53). Moreover, LSD1 inhibition may potentiate other clinically used therapies, such as hydroxyurea or azacitidine. These agents may act, at least in part, by increasing γ-globin gene expression through different mechanisms.

In summary, LSD1 contributes to tumor development by altering epigenetic marks on histones and non-histone proteins. Accumulating data have validated that either genetic depletion or pharmacological intervention of LSD1 normalizes altered gene expressions, thereby inducing differentiation programs into mature cell types, decreasing cell proliferation, and promoting apoptosis in cancer cells. Therefore, LSD1 inhibitors alone or in combination with established therapeutic drugs would be effective to treat the diseases associated with LSD1 activity.

SUMMARY OF THE INVENTION

The present invention is directed to, inter alia, a compound of Formula I:

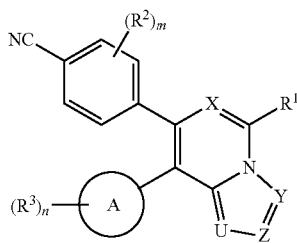

or a pharmaceutically acceptable salt thereof, wherein constituent variables are defined herein.

The present invention is further directed to a pharmaceutical composition comprising a compound of Formula I and at least one pharmaceutically acceptable carrier.

The present invention is further directed to a method of inhibiting LSD1 comprising contacting the LSD1 with a compound of Formula I.

The present invention is further directed to a method of modulating LSD1 comprising contacting the LSD1 with a compound of Formula I. The present invention is further directed to a method of mediating LSD1 comprising contacting the LSD1 with a compound of Formula I. The present invention is further directed to a method of modulating LSD1 signaling comprising contacting the LSD1 with a compound of Formula I.

The present invention is further directed to a method of treating an LSD1-mediated disease in a patient comprising administering to the patient a therapeutically effective amount of a compound of Formula I.

DETAILED DESCRIPTION

The present invention provides, inter alia, LSD1-inhibiting compounds such as a compound of Formula I:

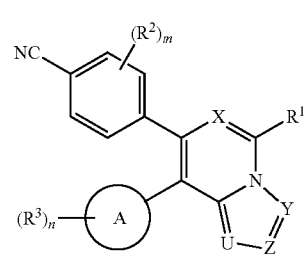

or a pharmaceutically acceptable salt thereof, wherein:

ring A is $C_{6-10}$ aryl, $C_{3-10}$ cycloalkyl, 5-10 membered heteroaryl, or 4-10 membered heterocycloalkyl, wherein the 5-10 membered heteroaryl or 4-10 membered heterocycloalkyl of ring A each has at least one ring-forming carbon atom and 1, 2, 3, or 4 ring-forming heteroatoms selected from N, O, and S, wherein N or S is optionally oxidized; and wherein a ring-forming carbon atom of the $C_{3-10}$ cycloalkyl or 4-10 membered heterocycloalkyl is optionally substituted by oxo to form a carbonyl group;

X is N or $CR^X$, wherein $R^X$ is H, OH, CN, halo, $NH_2$, $C_{1-4}$ alkyl, $C_{1-4}$ alkoxy, $C_{1-4}$ haloalkyl, $C_{1-4}$ haloalkoxy, $NHC_{1-4}$ alkyl, $N(C_{1-4}$ alkyl$)_2$ or $C_{1-4}$ alkylthio;

U is N or $CR^U$, wherein $R^U$ is H, OH, CN, halo, $NH_2$, $C_{1-4}$ alkyl, $C_{1-4}$ alkoxy, $C_{1-4}$ haloalkyl, $C_{1-4}$ haloalkoxy, $NHC_{1-4}$ alkyl, $N(C_{1-4}$ alkyl$)_2$ or $C_{1-4}$ alkylthio;

Y is N or $CR^4$;

Z is N or $CR^5$;

with the proviso that at least one of U, Y, and Z is N;

$R^1$ is H, halo, $C_{1-6}$ alkyl, $C_{2-6}$ alkenyl, $C_{2-6}$ alkynyl, $C_{1-6}$ haloalkyl, $C_{1-6}$haloalkoxy, NHOH, $NHOC_{1-6}$ alkyl, $Cy^1$, CN, $OR^{a1}$, $SR^{a1}$, $C(O)R^{b1}$, $C(O)NR^{c1}N^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $-L^1-R^6$, or $-L^2-NR^7R^8$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}N^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$L^1$ is a bond, —O—, —$NR^9$—, —C(O)NH—, —NHC(O)—, $C_{1-4}$ alkylene; wherein $R^9$ is H, $C_{1-6}$ alkyl, —C(O)$C_{1-6}$ alkyl or —C(O)O$C_{1-6}$ alkyl;

$L^2$ is a bond, —C(O)—, $C_{1-4}$ alkylene, —O—$C_{1-4}$ alkylene-, —$C_{1-4}$ alkylene-O—, —$C_{1-4}$ alkylene-$NR^9$—, or —$NR^9$—$C_{1-4}$ alkylene-;

$R^2$, at each occurrence, is independently selected from H, OH, CN, halo, $NH_2$, $C_{1-4}$ alkyl, $C_{1-4}$ alkoxy, $C_{1-4}$ haloalkyl, $C_{1-4}$ haloalkoxy, NH$C_{1-4}$ alkyl, N($C_{1-4}$ alkyl)$_2$, and $C_{1-4}$ alkylthio;

$R^3$, at each occurrence, is independently selected from H, $Cy^2$, halo, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{e2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

or two adjacent $R^3$ substituents on ring A taken together with the atoms to which they are attached form a fused 5- or 6-membered heterocycloalkyl ring, a fused $C_{3-6}$ cycloalkyl ring, or a fused 5- or 6-membered heteroaryl ring, each of which is optionally substituted with 1 or 2 independently selected $R^A$ substituents, wherein a ring carbon of the fused 5- or 6-membered heterocycloalkyl ring or fused $C_{3-6}$ cycloalkyl ring is optionally replaced by a carbonyl group;

alternatively, two $R^A$ substituents attached to the same carbon of the fused 5- or 6-membered heterocycloalkyl ring or fused $C_{3-6}$ cycloalkyl ring taken together form a $C_{3-6}$ cycloalkyl ring or 4- to 7-membered heterocycloalkyl ring;

$R^4$ and $R^5$ are each independently selected from H, $Cy^3$, halo, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{e3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^6$ is 5- to 10-membered heteroaryl, 5- to 10-membered heteroaryl-$C_{1-4}$ alkyl, 4- to 10-membered heterocycloalkyl, or 4- to 10-membered heterocycloalkyl-$C_{1-4}$ alkyl, each of which is optionally substituted with 1, 2, 3 or 4 independently selected $R^A$ substituents;

$R^7$ and $R^8$ together with the nitrogen atom to which they are attached form 4- to 10-membered heterocycloalkyl ring having 0, 1 or 2 heteroatoms selected from N and S in addition to the nitrogen atom connected to $R^7$ and $R^8$, wherein a ring-forming carbon atom of the heterocycloalkyl group is optionally substituted by an oxo group, and wherein the heterocycloalkyl is optionally substituted with 1, 2, 3 or 4 independently selected $R^B$ substituents;

each $R^A$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $Cy^2$, $C_{3-10}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $Cy^3$, $C_{3-10}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted by 1, 2, or 3 substituents independently selected from halo, $C_{1-6}$ haloalkyl, $C_{1-6}$ haloalkoxy, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^B$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $Cy^3$, $C_{3-10}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, $Cy^4$, $C_{3-10}$ cycloalkyl-$C_{1-4}$ alkyl, 5-10 membered heteroaryl-$C_{1-4}$ alkyl and 4-10 membered heterocycloalkyl-$C_{1-4}$ alkyl are each optionally substituted by 1, 2, or 3 substituents independently selected from halo, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $Cy^1$, $Cy^2$, $Cy^3$, and $Cy^4$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy}$;

each $R^{Cy}$ is independently selected from H, halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl-, oxo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-6}$ alkyl, $C_{1-4}$ haloalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a3}$, $R^{b3}$, $R^{c3}$ and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C$ (=NR$^{e5}$)NR$^{c5}$R$^{d5}$, NR$^{c5}$S(O)R$^{b5}$, NR$^{c5}$S(O)$_2$R$^{b5}$NR$^{c5}$ S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^{a4}$, R$^{b4}$, R$^{c4}$ and R$^{d4}$ is independently selected from H, C$_{1-6}$ alkyl, C$_{1-4}$ haloalkyl, C$_{2-6}$ alkenyl, and C$_{2-6}$ alkynyl, wherein said C$_{1-6}$ alkyl, C$_{2-6}$ alkenyl, and C$_{2-6}$ alkynyl are each optionally substituted with 1, 2, 3, 4, or 5 substituents independently selected from C$_{1-4}$ alkyl, C$_{1-4}$ haloalkyl, C$_{1-4}$ cyanoalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from C$_{1-6}$ alkyl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^{a5}$, R$^{b5}$, R$^{c5}$, and R$^{d5}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl are each optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy;

each R$^{e1}$, R$^{e2}$, R$^{e3}$, R$^{e4}$, and R$^{e5}$ is independently selected from H, C$_{1-4}$ alkyl, and CN;

the subscript m is 1 or 2; and the subscript n is 1, 2, 3 or 4.

In some embodiments, the compounds of the invention have Formula II:

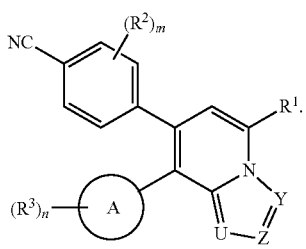

II

In some embodiments, the compounds of the invention have Formula III:

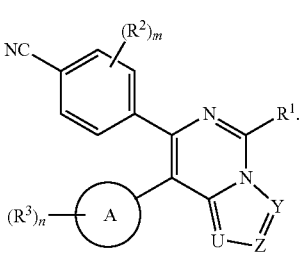

III

In some embodiments, U is CR$^U$.

In some embodiments, the compounds of the invention have Formula IIIb:

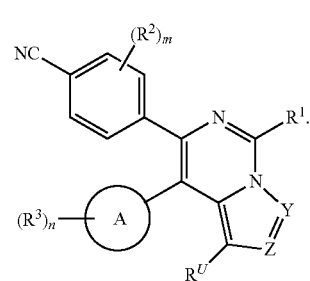

IIIb

In some embodiments, U is N.

In some embodiments, the compounds of the invention have Formula IIIa:

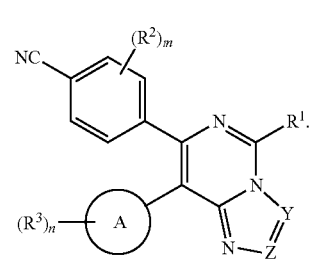

IIIa

In some embodiments, Y is N.
In some embodiments, Y is CR$^4$.
In some embodiments, Z is N.
In some embodiments, Z is CR$^5$.
In some embodiments, Y and Z are each CH.
In some embodiments, (i) U, Y and Z are each N; (ii) U and Z are N and Y is CR$^4$; (iii) U and Y are N and Z is CR$^5$; (iv) U is N, Y is CR$^4$, and Z is CR$^5$; (v) U is CR$^U$ and both Y and Z are N; (vi) U is CR$^U$, Y is N, and Z is CR$^5$; or (vii) U is CR$^U$, Y is CR$^4$, and Z is N.
In some embodiments, U, Y and Z are each N.
In some embodiments, U and Z are N and Y is CR$^4$.
In some embodiments, U and Y are N and Z is CR$^5$.
In some embodiments, U is N, Y is CR$^4$, and Z is CR$^5$.
In some embodiments, U is CR$^U$ and both Y and Z are N.
In some embodiments, U is CR$^U$, Y is N, and Z is CR$^5$.
In some embodiments, U is CR$^U$, Y is CR$^4$, and Z is N.
In some embodiments, two of U, Y, and Z are N.
In some embodiments, one of U, Y, and Z are N.
In some embodiments, ring A is C$_{6-10}$ aryl, 5-10 membered heteroaryl, or 4-10 membered heterocycloalkyl, wherein the 5-10 membered heteroaryl or 4-10 membered heterocycloalkyl of ring A each has at least one ring-forming carbon atom and 1, 2, 3, or 4 ring-forming heteroatoms selected from N, O, and S, wherein N or S is optionally oxidized; and wherein a ring-forming carbon atom of the 4-10 membered heterocycloalkyl is optionally substituted by oxo to form a carbonyl group.

In some embodiments, ring A is phenyl, 5-6 membered heteroaryl, or 4-7 membered heterocycloalkyl, wherein the 5-6 membered heteroaryl or 4-7 membered heterocycloalkyl of ring A each has at least one ring-forming carbon atom and 1, 2, 3, or 4 ring-forming heteroatoms selected from N, O, and S, wherein N or S is optionally oxidized; and wherein a ring-forming carbon atom of the 4-10 membered heterocycloalkyl is optionally substituted by oxo to form a carbonyl group.

In some embodiments, ring A is $C_{6-10}$ aryl.

In some embodiments, ring A is phenyl.

In some embodiments, ring A is 5-10 membered heteroaryl. In some embodiments, ring A is 5-6 membered heteroaryl. In some embodiments, ring A is 6 membered heteroaryl. In some embodiments, ring A is 5 membered heteroaryl.

In some embodiments, ring A is pyridyl, 1H-indazolyl, 1H-pyrrolo[2,3-b]pyridinyl, or 1H-benzo[d]imidazolyl.

In some embodiments, ring A is pyridyl.

In some embodiments, ring A is 4-10 membered heterocycloalkyl having at least one ring-forming carbon atom and 1, 2, 3, or 4 ring-forming heteroatoms selected from N, O, and S, wherein N or S is optionally oxidized, and wherein a ring-forming carbon atom is optionally substituted by oxo to form a carbonyl group.

In some embodiments, ring A is 4-7 membered heterocycloalkyl having at least one ring-forming carbon atom and 1, 2, 3, or 4 ring-forming heteroatoms selected from N, O, and S, wherein N or S optionally oxidized, and wherein a ring-forming carbon atom is optionally substituted by oxo to form a carbonyl group.

In some embodiments, ring A is 2-oxo-2,3-dihydro-1H-indolyl; 2-oxo-2,3-dihydro-1,3-benzoxazolyl; 3,4-dihydro-2H-pyrido[3,2-b][1,4]oxazinyl; 3-oxo-3,4-dihydro-2H-1,4-benzoxazinyl; 1H-pyrazolo[3,4-b]pyridinyl; 3-methyl-2-oxo-3,4-dihydro-2H-1,3-benzoxazin-7-yl; 2-oxo-2,3-dihydro-1H-benzimidazolyl; 1H-benzimidazolyl; 2-oxo-2,3-dihydro[1,3]oxazolo[4,5-b]pyridinyl; or 2,3-dihydro-1-benzofuranyl.

In some embodiments, ring A is 2,3-dihydro-1H-indolyl; 2,3-dihydro-1,3-benzoxazolyl; 3,4-dihydro-2H-pyrido[3,2-b][1,4]oxazinyl; 3,4-dihydro-2H-1,4-benzoxazinyl; or 2,3-dihydro-1-benzofuran.

In some embodiments, ring A is 2-oxo-2,3-dihydro-1H-indolyl; 2-oxo-2,3-dihydro-1,3-benzoxazolyl; 3,4-dihydro-2H-pyrido[3,2-b][1,4]oxazinyl; 3-oxo-3,4-dihydro-2H-1,4-benzoxazinyl; or 2,3-dihydro-1-benzofuran.

In some embodiments, ring A is phenyl; 2,3-dihydro-1,4-benzodioxine; 2,3-dihydro-1H-pyrrolo[2,3-b]pyridin-5-yl; 5,6,7,8-tetrahydro-1,8-naphthyridin-3-yl; 2-oxo-1,2,3,4-tetrahydroquinolin-7-yl; pyridyl; 2-oxo-2,3-dihydro-1,3-benzoxazolyl; 1,3-benzothiazol-5-yl; 2, 3-dihydro-1H-inden-5-yl; 1H-pyrrolo[2,3-b]pyridinyl; 8-quinoxalin-6-yl; 2-oxo-1,2,3,4-tetrahydroquinolin-6-yl; or 1H-pyrazolo[3,4-b]pyridinyl.

In some embodiments, ring A is phenyl; pyridyl; 1H-indazolyl; 1H-pyrrolo[2,3-b]pyridinyl; 1H-benzo[d]imidazolyl; 2-oxo-2,3-dihydro-1H-indolyl; 2-oxo-2,3-dihydro-1,3-benzoxazolyl; 3,4-dihydro-2H-pyrido[3,2-b][1,4]oxazinyl; 3-oxo-3,4-dihydro-2H-1,4-benzoxazinyl; 1H-pyrazolo[3,4-b]pyridinyl; 3-methyl-2-oxo-3,4-dihydro-2H-1,3-benzoxazin-7-yl; 2-oxo-2,3-dihydro-1H-benzimidazolyl; 1H-benzimidazolyl; 2-oxo-2,3-dihydro[1,3]oxazolo[4,5-b]pyridinyl; 2,3-dihydro-1-benzofuranyl; 2,3-dihydro-1H-indolyl; 2,3-dihydro-1,3-benzoxazolyl; 3,4-dihydro-2H-1,4-benzoxazinyl; 2,3-dihydro-1,4-benzodioxine; 2,3-dihydro-1H-pyrrolo[2,3-b]pyridin-5-yl; 5,6,7,8-tetrahydro-1,8-naphthyridin-3-yl; 2-oxo-1,2,3,4-tetrahydroquinolin-7-yl; 1,3-benzothiazol-5-yl; 2,3-dihydro-1H-inden-5-yl; 8-quinoxalin-6-yl; or 2-oxo-1,2,3,4-tetrahydroquinolin-6-yl.

In some embodiments, $R^3$, at each occurrence, is independently selected from $Cy^2$, $C_{1-6}$ alkyl, CN, $OR^{a2}$, $C(O)NR^{c2}R^{d2}$, and $NR^{c2}R^{d2}$; wherein said $C_{1-6}$ alkyl is optionally substituted with 1, 2, or 3 substituents independently selected from $Cy^2$, $C(O)R^{b2}$, and $C(O)NR^{c2}R^{d2}$.

In some embodiments, $R^3$ is, at each occurrence, CN, methyl, methoxy, 1-pyrrolidinyl, 2-oxo-1-pyrrolidinyl, —C(O)N(CH$_3$)$_2$, dimethylamino, 4-methylpiperazinylmethyl, morpholinyl, 4-methylpiperazinylcarbonylmethyl, morpholinylmethyl, morpholinoethyl, or 3-cyano-1-pyrrolidinylmethyl.

In some embodiments, two adjacent $R^3$ substituents on ring A taken together with the atoms to which they are attached form a fused 5- or 6-membered heterocycloalkyl ring, a fused $C_{3-6}$ cycloalkyl ring, or a fused 5- or 6-membered heteroaryl ring, each of which is optionally substituted with 1 or 2 independently selected $R^4$ substituents; wherein a ring carbon of the fused 5- or 6-membered heterocycloalkyl ring or fused $C_{3-6}$ cycloalkyl ring is optionally replaced by a carbonyl group;

alternatively, two $R^4$ substituents attached to the same carbon of the fused 5- or 6-membered heterocycloalkyl or fused $C_{3-6}$ cycloalkyl taken together form a $C_{3-6}$ cycloalkyl or 4- to 7-membered heterocycloalkyl ring.

In some embodiments, two $R^4$ substituents attached to the same carbon of the fused 5- or 6-membered heterocycloalkyl or fused $C_{3-6}$ cycloalkyl taken together form a cyclopropyl group.

In some embodiments, two adjacent $R^3$ substituents on ring A taken together with the atoms to which they are attached form a fused ring selected from 1-methylpyrrolidine, 4-methyl-3-oxo-morpholine, 1-methylimidazole, 1-methylpiperidine, 1-methyl-2-oxopyrrolidine, and 1-methylpyrazole, each of which is optionally substituted with 1 or 2 $R^4$ substituents.

In some embodiments, two adjacent $R^3$ substituents on ring A taken together with the atoms to which they are attached form a fused ring selected from pyrrolidine, 3-oxo-morpholine, imidazole, piperidine, 2-oxopyrrolidine, and pyrazole, each of which is optionally substituted with 1 or 2 $R^4$ substituents.

In some embodiments, $R^3$ is $C_{1-6}$ alkyl, halo, $C_{1-6}$ hydroxyalkyl, $C_{1-6}$ haloalkyl, CN, $OR^{a2}$, 1-pyrrolidinyl, 2-oxo-1-pyrrolidinyl, $NR^{c2}C(O)OR^{a2}$, —(C$_{1-6}$ alkyl)-$NR^{c2}C(O)OR^{a2}$, $C(O)NR^{c2}R^{d2}$, $NR^{c2}R^{d2}$, piperazinylmethyl, 4-methylpiperazinylmethyl, piperidinyl, morpholinyl, 4-methylpiperazinylcarbonylmethyl, morpholinylmethyl, or 3-cyano-1-pyrrolidinyl.

In some embodiments, $R^3$ is $C_{1-6}$ alkyl, CN, $OR^{a2}$, 1-pyrrolidinyl, 2-oxo-1-pyrrolidinyl, $C(O)NR^{c2}R^{d2}$, $NR^{c2}R^{d2}$, piperazinylmethyl, 4-methylpiperazinylmethyl, piperidinyl, morpholinyl, 4-methylpiperazinylcarbonylmethyl, morpholinylmethyl or 3-cyano-1-pyrrolidinyl.

In some embodiments, $R^3$ is CN, F, hydroxymethyl, (CH$_3$O)C(O)N(CH$_3$)—, (CH$_3$O)C(O)N(CH$_3$)-methyl, difluoromethyl, amino, methyl, methoxy, 1-pyrrolidinyl, 2-oxo-1-pyrrolidinyl, —C(O)N(CH$_3$)$_2$, dimethylamino, 4-methylpiperazinylmethyl, morpholinyl, 4-methylpiperazinylcarbonylmethyl, morpholinylmethyl, morpholinoethyl, or 3-cyano-1-pyrrolidinylmethyl.

In some embodiments, $R^3$ is, at each occurrence, CN, F, hydroxymethyl, (CH$_3$O)C(O)N(CH$_3$)—, (CH$_3$O)C(O)N(CH$_3$)-methyl, difluoromethyl, methyl, methoxy, —C(O)N(CH$_3$)$_2$, dimethylamino, morpholinylmethyl, (CH$_3$)S(O$_2$)N(CH$_3$)-methyl, (CH$_3$)$_2$NC(O)N(CH$_3$)-methyl, Cl, 1-hydroxyethyl, methoxymethyl, isopropyl, ethyl, (CH$_3$)S(O$_2$)N(CH$_3$)—, or ethoxy.

In some embodiments, $R^3$ is CN, F, hydroxymethyl, (CH$_3$O)C(O)N(CH$_3$)—, (CH$_3$O)C(O)N(CH$_3$)-methyl, difluoromethyl, amino, methyl, methoxy, 1-pyrrolidinyl, 2-oxo-1-pyrrolidinyl, —C(O)N(CH$_3$)$_2$, dimethylamino, 4-methylpiperazinylmethyl, morpholinyl, 4-methylpiperazinylcarbonylmethyl, morpholinylmethyl, morpholinoethyl, or 3-cyano-1-pyrrolidinylmethyl, (CH$_3$)S(O$_2$)N(CH$_3$)-methyl, (CH$_3$)$_2$NC(O)N(CH$_3$)-methyl, Cl, 1-hydroxyethyl, methoxymethyl, isopropyl, ethyl, (CH$_3$)S(O$_2$)N(CH$_3$)—, or ethoxy.

In some embodiments, two adjacent R$^3$ substituents on ring A taken together with the atoms to which they are attached form fused 5- or 6-membered heterocycloalkyl, fused C$_{3-6}$ cycloalkyl or fused 5- or 6-membered heteroaryl, each of which is optionally substituted with 1-2 independently selected R$^A$ substituents, wherein a ring carbon of the fused 5- or 6-membered heterocycloalkyl or fused C$_{3-6}$ cycloalkyl is optionally replaced by a carbonyl group.

In some embodiments, two adjacent R$^3$ substituents on ring A taken together with the atoms to which they are attached form fused 5- or 6-membered heterocycloalkyl, which is optionally substituted with 1-2 independently selected R$^A$ substituents, wherein a ring carbon of the fused 5- or 6-membered heterocycloalkyl is optionally replaced by a carbonyl group.

In some embodiments, two adjacent R$^3$ substituents on ring A taken together with the atoms to which they are attached form a fused 2,3-dihydro-1H-pyrrolyl; 2-oxo-2,3-dihydro-1H-pyrrolyl; 2,3-dihydro-oxazolyl; 2-oxo-2,3-dihydro-oxazolyl; 3,4-dihydro-2H-1,4-oxazinyl; 3-oxo-3,4-dihydro-2H-1,4-oxazinyl; or 2,3-dihydro-furanyl group, each of which is optionally substituted with 1-2 independently selected R$^A$ substituents.

In some embodiments, two adjacent R$^3$ substituents on ring A taken together with the atoms to which they are attached form a fused 2,3-dihydro-1H-pyrrolyl group, which is optionally substituted with one R$^A$ substituent.

In some embodiments, two adjacent R$^3$ substituents on ring A taken together with the atoms to which they are attached form a 2-oxo-2,3-dihydro-1H-pyrrolyl group, which is optionally substituted with one R$^A$ substituent.

In some embodiments, two adjacent R$^3$ substituents on ring A taken together with the atoms to which they are attached form a fused 2,3-dihydro-oxazolyl group, which is optionally substituted with one R$^A$ substituent.

In some embodiments, two adjacent R$^3$ substituents on ring A taken together with the atoms to which they are attached form a fused 2-oxo-2,3-dihydro-oxazolyl group, which is optionally substituted with one R$^A$ substituent.

In some embodiments, two adjacent R$^3$ substituents on ring A taken together with the atoms to which they are attached form a fused 2,3-dihydro-furanyl group, which is optionally substituted with one R$^A$ substituent.

In some embodiments, R$^A$ is C$_{1-4}$ alkyl.

In some embodiments, R$^A$ is methyl.

In some embodiments, R$^A$ is —C(O)NR$^{c4}$R$^{d4}$ wherein R$^{c4}$ and R$^{d4}$ are each, independently selected from H and C$_{1-4}$ alkyl.

In some embodiments, R$^A$ is —C(O)N(CH$_3$)$_2$.

In some embodiments, R$^1$ is -L$^1$-R$^6$ or -L$^2$-NR$^7$R$^8$.

In some embodiments, R$^1$ is -L$^2$-NR$^7$R$^8$, wherein L$^2$ is a bond, —C(O)—, C$_{1-4}$ alkylene, —O—C$_{1-4}$ alkylene, —C$_{1-4}$ alkylene-O—, C$_{1-4}$ alkylene-NH— or —NH—C$_{1-4}$ alkylene.

In some embodiments, L$^2$ is a —O—C$_{1-4}$ alkylene.

In some embodiments, R$^7$ and R$^8$ together with the nitrogen atom to which they are attached form 4- to 6-membered heterocycloalkyl ring having 0, 1 or 2 heteroatoms selected from N and S in addition to the nitrogen atom connected to R$^7$ and R$^8$, wherein a ring-forming carbon atom of the heterocycloalkyl group is optionally substituted by an oxo group, and wherein the heterocycloalkyl is optionally substituted with 1, 2, 3 or 4 independently selected R$^B$ substituents.

In some embodiments, R$^1$ is -L$^1$-R$^6$.

In some embodiments, L$^1$ is —O—.

In some embodiments, R$^6$ is 5- to 10-membered heteroaryl-C$_{1-4}$ alkyl or 4- to 10-membered heterocycloalkyl-C$_{1-4}$ alkyl, each of which is optionally substituted with 1, 2, 3 or 4 independently selected R$^A$ substituents.

In some embodiments, R$^6$ is 4- to 10-membered heterocycloalkyl-C$_{1-4}$ alkyl which is optionally substituted with 1, 2, 3 or 4 independently selected R$^A$ substituents.

In some embodiments, R$^6$ is pyrrolidinyl-C$_{1-4}$ alkyl- which is optionally substituted with 1, 2 or 3 independently selected R$^A$ substituents. In some embodiments, R$^6$ is pyrrolidinyl-methylene- which is optionally substituted with 1, 2 or 3 independently selected R$^A$ substituents.

In some embodiments, R$^6$ is piperidinyl-C$_{1-4}$ alkyl- which is optionally substituted with 1, 2 or 3 independently selected R$^A$ substituents. In some embodiments, R$^6$ is piperidinyl-methylene- which is optionally substituted with 1, 2 or 3 independently selected R$^A$ substituents.

In some embodiments, R$^1$ is OR$^{a1}$.

In some embodiments, R$^1$ is OR$^{a1}$, wherein R$^{a1}$ is C$_{1-6}$ alkyl substituted with Cy$^4$.

In some embodiments, R$^1$ is OR$^{a1}$, wherein R$^{a1}$ is methylene substituted with Cy$^4$.

In some embodiments, R$^1$ is OR$^{a1}$, wherein R$^{a1}$ is methylene substituted with 4-10 membered heterocycloalkyl optionally substituted with 1, 2, 3, or 4 substituents independently selected from R$^{Cy}$.

In some embodiments, R$^1$ is OR$^{a1}$, wherein R$^{a1}$ is methylene substituted with 4-7 membered heterocycloalkyl optionally substituted with 1, 2, 3, or 4 substituents independently selected from R$^{Cy}$.

In some embodiments, Cy$^4$ is pyrrolidinyl or piperidinyl optionally substituted with 1 or 2 substituents independently selected from R$^{Cy}$.

In some embodiments, R$^1$ is (1-methylpiperidin-3-yl)methoxy, (1-ethylpiperidin-3-yl)methoxy, (2-cyanoethylpiperidin-3-yl)methoxy, (2-hydroxyethylpiperidin-3-yl)methoxy, (2-methoxyethylpiperidin-3-yl)methoxy, 4-dimethylaminopiperidin-1-yl, 3-dimethylaminopyrrolidin-1-yl, 7-methyl-2,7-diazaspiro[4.4]non-2-yl, or (1-methylpyrrolidin-3-yl)methoxy.

In some embodiments, R$^1$ is (1-methylpiperidin-3-yl)methoxy or (1-methylpyrrolidin-3-yl)methoxy.

In some embodiments, R$^1$ is (1-methylpiperidin-3-yl)methoxy, (1-ethylpiperidin-3-yl)methoxy, (2-cyanoethylpiperidin-3-yl)methoxy, 4-dimethylaminopiperidin-1-yl, 3-dimethylaminopyrrolidin-1-yl, (2-hydroxypropylpiperidin-3-yl)methoxy, or 2-hydroxy-2-methylpropyl)piperidin-3-yl]methoxy.

In some embodiments, R$^1$ is (1-methylpiperidin-3-yl)methoxy, (1-ethylpiperidin-3-yl)methoxy, (2-cyanoethylpiperidin-3-yl)methoxy, (2-hydroxyethylpiperidin-3-yl)methoxy, (2-methoxyethylpiperidin-3-yl)methoxy, 4-dimethylaminopiperidin-1-yl, 3-dimethylaminopyrrolidin-1-yl, 7-methyl-2,7-diazaspiro[4.4]non-2-yl, (1-methylpyrrolidin-3-yl)methoxy, or 2-hydroxy-2-methylpropyl)piperidin-3-yl]methoxy.

In some embodiments, R$^2$ is H.

In some embodiments, R$^4$ is H.

In some embodiments, R$^5$ is H.

In some embodiments, R$^U$ is H.

In some embodiments, R$^X$ is H.

In some embodiments, m is 1.

In some embodiments, n is 1.

In some embodiments, the compounds of the invention have Formula IVa, IVb, IVc, IVd, IVe, or IVf:

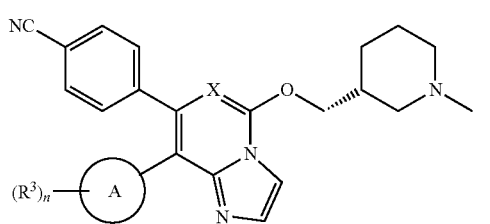

IVa

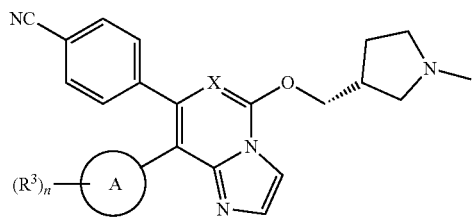

IVb

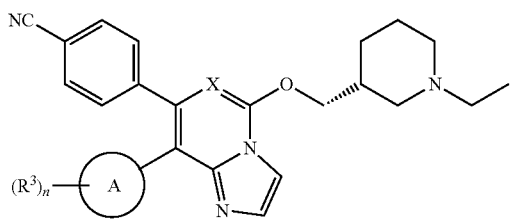

IVc

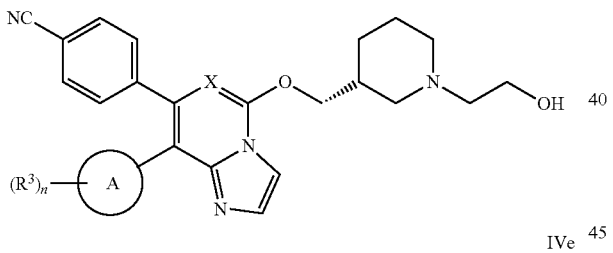

IVd

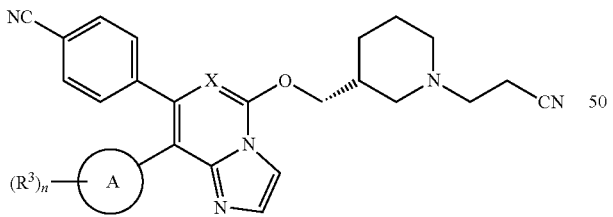

IVe

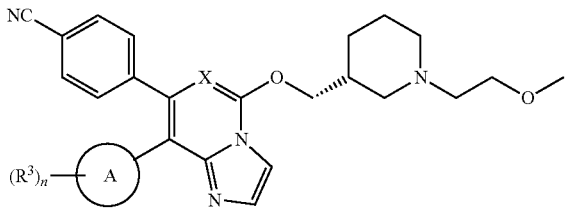

IVf or a pharmaceutically acceptable salt thereof.

In some embodiments, the compounds provided herein have Formula IVg, IVh, or IVi:

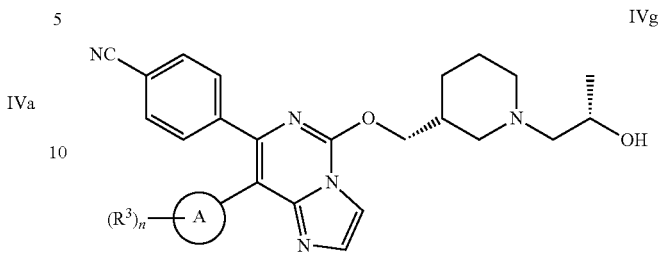

IVg

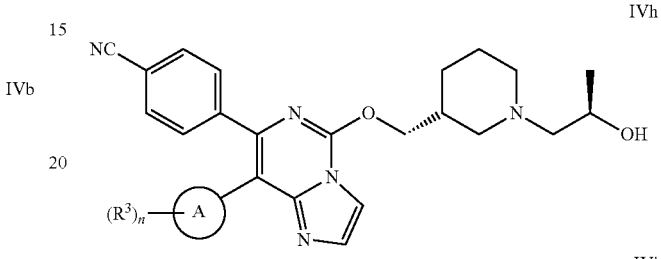

IVh

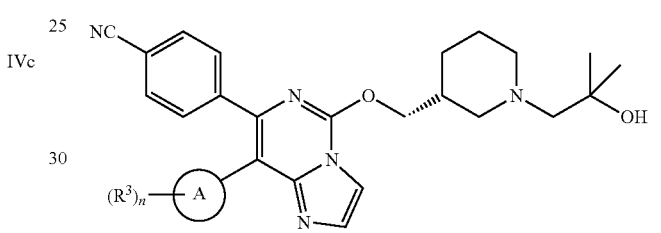

IVi or a pharmaceutically acceptable salt thereof.

In some embodiments, the compounds of the invention have Formula IVa or IVb:

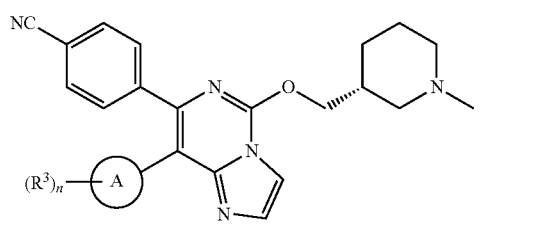

IVa

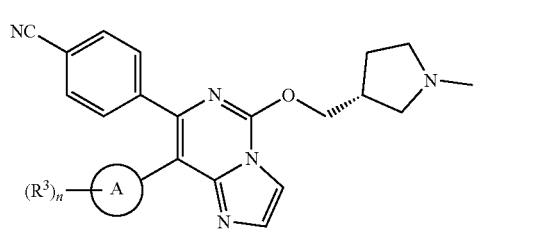

IVb or a pharmaceutically acceptable salt thereof.

In some embodiments, the compounds of the invention have Formula IVa.

In some embodiments, the compounds of the invention have Formula IVb.

In some embodiments, the compounds of the invention have Formula IVc.

In some embodiments, the compounds of the invention have Formula IVd.

In some embodiments, the compounds of the invention have Formula IVe.

In some embodiments, the compounds of the invention have Formula IVf.

In some embodiments, the compounds of the invention have Formula IVg.

In some embodiments, the compounds of the invention have Formula IVh.

In some embodiments, the compounds of the invention have Formula IVi.

In some embodiments of compounds of Formula I, the present disclosure provides compounds having Formula V:

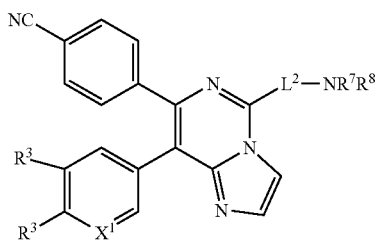

V wherein $X^1$ is CH or N.

In some embodiments of the compounds of Formula V:

two $R^3$ substituents taken together with the carbon atoms to which they are attached form a fused 5-membered heterocycloalkyl ring or a fused 5-membered heteroaryl ring, each of which is optionally substituted with 1 or 2 independently selected $R^4$ substituents, wherein a ring carbon of the fused 5-membered heterocycloalkyl ring is optionally replaced by a carbonyl group;

$X^1$ is N or CH;

$L^2$ is a bond or O—$C_{1-4}$ alkylene; and $R^7$ and $R^8$ together with the nitrogen atom to which they are attached form 4- to 7-membered heterocycloalkyl ring having 0, 1 or 2 heteroatoms selected from N and S in addition to the nitrogen atom connected to $R^7$ and $R^8$, wherein the heterocycloalkyl is optionally substituted with 1, 2, 3 or 4 independently selected $R^B$ substituents.

In some aspects of these embodiments, $X^1$ is CH. In other aspects of these embodiments $X^1$ is N. In some aspects of these embodiments, $L^2$ is a bond, —C(O)—, $C_{1-4}$ alkylene, —O—$C_{1-4}$ alkylene-, —$C_{1-4}$ alkylene-O—, —$C_{1-4}$ alkylene-$NR^9$—, or —$NR^9$—$C_{1-4}$ alkylene-. In some aspects of these embodiments, two $R^3$ substituents taken together with the carbon atoms to which they are attached form a fused 5-membered heterocycloalkyl ring or a fused 5-membered heteroaryl, each of which is optionally substituted with 1 or 2 independently selected $R^4$ substituents, wherein a ring carbon of the fused 5-membered heterocycloalkyl ring is optionally replaced by a carbonyl group. In some instances, a ring carbon of the fused 5-membered heterocycloalkyl ring is replaced by a carbonyl group. In some instances, $R^4$ is $C_{1-4}$ alkyl such as methyl. In some instances, the fused 5-membered heterocycloalkyl ring or fused 5-membered heteroaryl has 1 or 2 heteroatoms as ring members selected from O, N or S. In some aspects of these embodiments, $R^7$ and $R^8$ together with the nitrogen atom to which they are attached form 4- to 7-membered heterocycloalkyl ring having 0, 1 or 2 additional heteroatoms selected from N and S as ring members, wherein a ring-forming carbon atom of the heterocycloalkyl group is optionally substituted by an oxo group, and wherein the heterocycloalkyl is optionally substituted with 1, 2, 3 or 4 independently selected $R^B$ substituents. In some instances, $R^B$ is $C_{1-4}$ alkyl such as methyl.

In one embodiment of compounds of Formula V, $L^2$ is a bond. In another embodiment of compounds of Formula V, $L^2$ is —O—$C_{1-4}$ alkylene-. In yet another embodiment of compounds of Formula V, $L^2$ is —OCH$_2$—.

In some embodiments of compounds of Formula V, two $R^3$ substituents taken together with the carbon atoms to which they are attached form a fused pyrazole ring optionally substituted with 1 or 2 $R^4$ substituents. In some aspects of these embodiments, $R^4$ is $C_{1-4}$ alkyl such as methyl.

In some embodiments of compounds of Formula V, two $R^3$ substituents taken together with the carbon atoms to which they are attached form a fused 2-oxo-oxazolidine ring, which is optionally substituted with 1 or 2 $R^B$ substitutents. In some aspects of these embodiments, $R^B$ is $C_{1-4}$ alkyl such as methyl.

In some embodiments, moiety

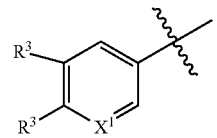

in Formula V is 1-methyl-1H-pyrazolo[3,4-b]pyridin-5-yl, 1-methyl-1H-indazol-5-yl, 3-methyl-2-oxo-3,4-dihydro-2H-1,3-benzoxazin-7-yl; 1,3-dimethyl-2-oxo-2,3-dihydro-1H-benzimidazol-5-yl; 3-methyl-2-oxo-2,3-dihydro-1,3-benzoxazol-6-yl; 5-fluoro-3-methyl-2-oxo-2,3-dihydro-1,3-benzoxazol-6-yl; 4-methyl-3-oxo-3,4-dihydro-2H-1,4-benzoxazin-7-yl; 2-(difluoromethyl)-1-methyl-1H-benzimidazol-5-yl; 1,2-dimethyl-1H-benzimidazol-5-yl, 6-methoxypyridin-3-yl, 5-fluoro-6-methoxypyridin-3-yl, 6-(2-oxopyrrolidin-1-yl)pyridin-3-yl, 1-methyl-1H-benzimidazol-5-yl, 6-methoxy-5-methylpyridin-3-yl, 4-fluoro-3-methyl-2-oxo-2,3-dihydro-1,3-benzoxazol-6-yl, 3-methyl-2-oxo-2,3-dihydro[1,3]oxazolo[4,5-b]pyridin-6-yl, 1-methyl-2-oxo-2,3-dihydro-1H-indol-5-yl, 2-methylnicotinonitrile, or 5,6-dimethylpyridin-3-yl.

In some embodiments, the compounds of the invention have Formula VIa, VIb, or VIc:

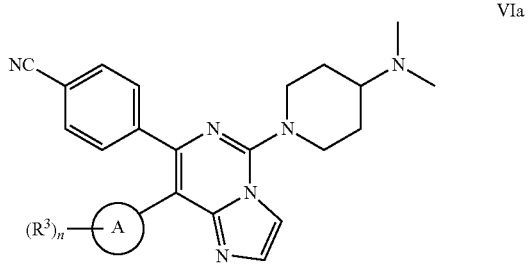

VIa

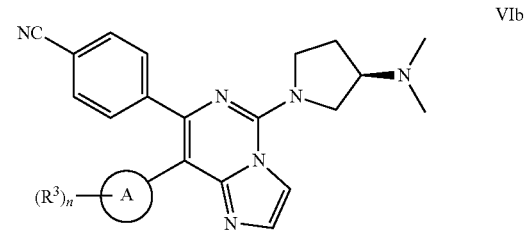

VIb

-continued

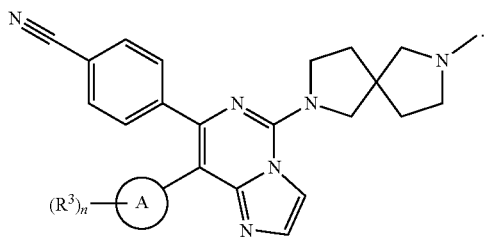

VIc

In some embodiments, the compounds of the invention have Formula VIa.

In some embodiments, the compounds of the invention have Formula VIb.

In some embodiments, the compounds of the invention have Formula VIc.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a monovalent substituent, or two hydrogen atoms are replaced with a divalent substituent like a terminal oxo group. It is to be understood that substitution at a given atom is limited by valency.

Throughout the definitions, the term "$C_{i-j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms. In some embodiments, the alkylamino group is —NH($C_{1-4}$ alkyl) such as, for example, methylamino, ethylamino, or propylamino.

As used herein, the term "di-$C_{1-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "aryl-$C_{i-j}$ alkyl," employed alone or in combination with other terms, refers to an alkyl group substituted by an aryl group. An example of an aryl-$C_{i-j}$ alkyl group is benzyl.

As used herein, the term "carbonyl", employed alone or in combination with other terms, refers to a —C(O)— group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group that includes a fused aromatic ring can be attached to the core or scaffold via any ring-forming atom, including a ring-forming atom of the fused aromatic group. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Examplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl.

As used herein, the term "$C_{i-j}$ cycloalkyl-$C_{i-j}$ alkyl," employed alone or in combination with other terms, refers to an alkyl group substituted by a cycloalkyl group. An example of a C cycloalkyl-$C_{i-j}$ alkyl group is cyclopropylmethyl.

As used herein, "$C_{i-j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. When the heteroaryl group contains more than one heteroatom ring member, the heteroatoms may be the same or different. The nitrogen atoms in the ring(s) of the heteroaryl group can be oxidized to form N-oxides. Examplary heteroaryl groups include, but are not limited to, pyridyl, pyrimidinyl, pyrazinyl, pyridazinyl, pyrrolyl, pyrazolyl, azolyl, oxazolyl, isoxazolyl, thiazolyl, isothiazolyl, imidazolyl, furanyl, thiophenyl, triazolyl, tetrazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, and the like. In some embodiments, the heteroaryl group is pyridyl, 1H-indazolyl, 1H-pyrrolo[2,3-b]pyridinyl, or 1H-benzo[d]imidazolyl.

A 5-membered heteroaryl is a heteroaryl group having five ring-forming atoms comprising wherein one or more of the ring-forming atoms are independently selected from N, O, and S. In some embodiments, the 5-membered heteroaryl group has 1, 2, 3, or 4 heteroatom ring members. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heteroaryl-$C_{i-j}$ alkyl," employed alone or in combination with other terms, refers to an alkyl group substituted by a heteroaryl group. An example of a heteroaryl-$C_{i-j}$ alkyl group is pyridylmethyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused to (i.e., having a bond in common with) the non-aromatic ring, for example, 1,2,3,4-tetrahydro-quinoline, dihydrobenzofuran, and the like. A heterocycloalkyl group including a fused aromatic ring can be attached to the core or scaffold via any ring-forming atom, including a ring-forming atom of the fused aromatic group. The S or N ring-forming atoms can be optionally "oxidized" to include one or two oxo groups as valency permits (e.g., sulfonyl or sulfinyl or N-oxide). One or more ring-forming carbon atoms of the heterocycloalkyl group can include an oxo moiety to form a ring-forming carbonyl. In some embodiments, a ring-forming nitrogen atom can be quaternized. In some embodiments, the heterocycloalkyl is 5- to 10-membered, 4- to 10-membered, 4- to 7-membered, 5-membered, or 6-membered. Examples of heterocycloalkyl groups include 1, 2, 3, 4-tetrahydro-quinolinyl, dihydrobenzofuranyl, azetidinyl, azepanyl, pyrrolidinyl, piperidinyl, piperazinyl, morpholinyl, thiomorpholinyl, dihydrofuranyl, tetrahydrofuranyl, 2-oxopyrrolidinyl, 3-oxomorpholinyl, 2-oxooxazolidinyl, and pyranyl. Further examples of heterocycloalkyl groups include 2,3-dihydro-1H-pyrrolyl; 2-oxo-2,3-dihydro-1H-pyrrolyl; 2,3-dihydro-oxazolyl; 2-oxo-2,3-dihydro-oxazolyl; 3,4-dihydro-2H-1,4-oxazinyl; 3-oxo-3,4-dihydro-2H-1,4-oxazinyl; or 2,3-dihydro-furanyl. In further embodiments, the heterocycloalkyl group is azetidinyl, piperidinyl, pyrrolidinyl, diazapanyl, or diazaspirononanyl. In yet further embodiments, the heterocycloalkyl group is 2,3-dihydro-1H-indolyl; 2,3-dihydro-1,3-benzoxazolyl; 3,4-dihydro-2H-pyrido[3,2-b][1,4]oxazinyl; 3,4-dihydro-2H-1,4-benzoxazinyl; or 2,3-dihydro-1-benzofuran.

As used herein, the term "heterocycloalkyl-$C_{i-j}$ alkyl," employed alone or in combination with other terms, refers to an alkyl group substituted by a heterocycloalkyl group. An example of a heterocycloalkyl-$C_{i-j}$ alkyl group is pyrrolidinylmethyl.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified. The compounds of the invention are not limited by the manner in which they are made or formed. For example, the present invention includes compounds which are prepared synthetically, formed through a biological process or transformation, or a combination thereof.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); IPA (isopropyl alcohol); J (coupling constant); LCMS (liquid chromatography-mass spectrometry); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. Protecting groups in the synthetic schemes are typically represented by "PG."

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

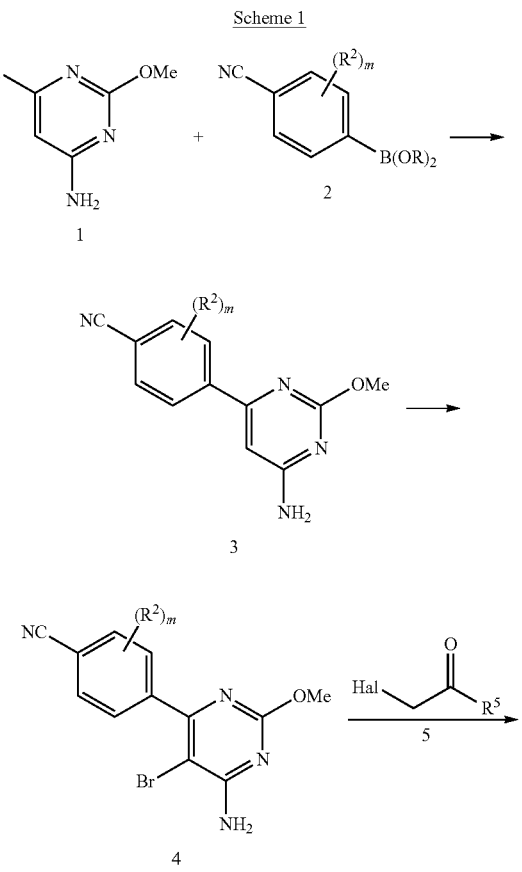

Scheme 1

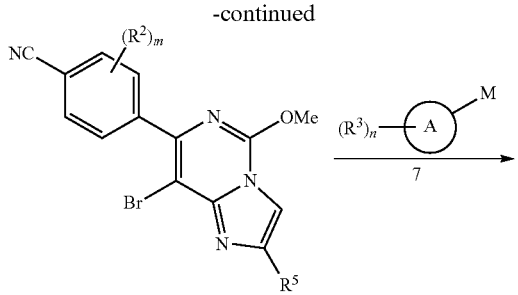

6

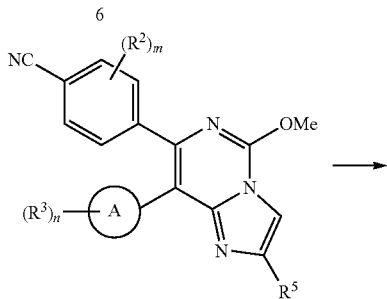

8

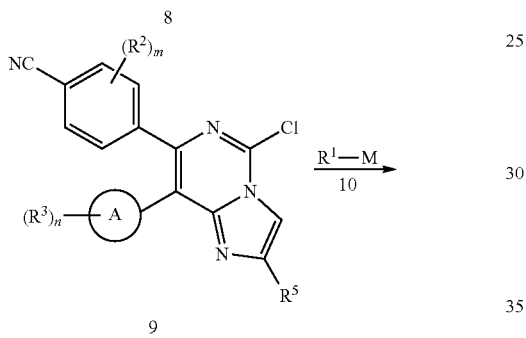

9

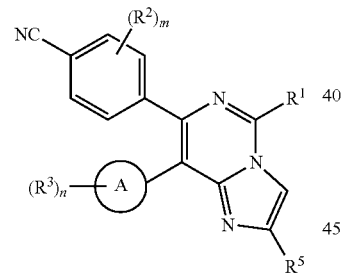

11

Compounds of the invention can be prepared via the synthetic route outlined in Scheme 1. The commercially available starting material 1 can undergo Suzuki coupling with the boronic acid or ester of formula 2 (R═H or alkyl) under standard Suzuki conditions (e.g., in the presence of a palladium catalyst and a base such as potassium carbonate) to afford compound 3. Bromination of compound 3 in the presence of N-bromosuccinimide (NBS) can give the compound of formula 4. Condensation of compound 4 with the carbonyl derivatives of formula 5 (Hal is a halide such as Cl or Br) at elevated temperature can generate the bicyclic compound of formula 6. The bromide in compound 6 can be coupled to a compound of formula 7, in which M is a boronic acid, boronic ester or an appropriately substituted metal [e.g., M is B(OR)$_2$, Sn(Alkyl)$_4$, or Zn-Hal], under standard Suzuki coupling conditions (e.g., in the presence of a palladium catalyst and a suitable base) or standard Stille coupling conditions (e.g., in the presence of a palladium catalyst), or standard Negishi coupling conditions (e.g., in the presence of a palladium catalyst) to give the derivative of formula 8. Alternatively, compound 7 can be a cyclic amine (where M is H and attached to an amine nitrogen) and the coupling of arylbromide 6 with the cyclic amine 7 can be performed under Buchwald amination conditions (e.g., in the presence of a palladium catalyst and a base such as sodium tert-butoxide). Conversion of the methoxy group in compound 8 to chloride can be achieved in the presence of phosphoryl chloride (POCl$_3$) at suitable temperature to give compound of formula 9. Displacement of the chloride in compound 9 with a nucleophile of formula 10 (wherein R$^1$-M is an alcohol or an amine, e.g., M is H which is attached to an alcohol oxygen or an amine nitrogen) in the presence of a suitable base such as sodium hydride, sodium hydroxide, potassium carbonate or diisopropylethylamine at elevated temperature can give compound of formula 11. Alternatively, the coupling of compound 9 with compound 10 can be performed under standard Suzuki conditions (when M is boronic acid or ester), or standard Stille coupling conditions [when M is Sn(Alkyl)$_4$], or standard Negishi coupling conditions (when M is Zn-Hal) to give compound 11.

Scheme 2

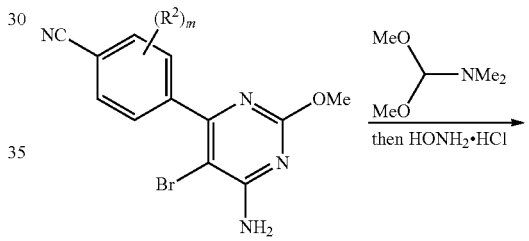

4

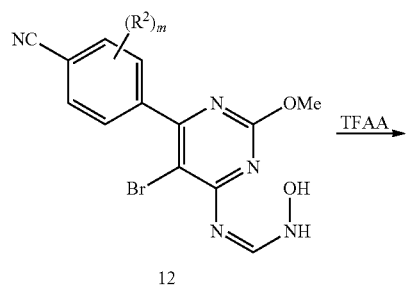

12

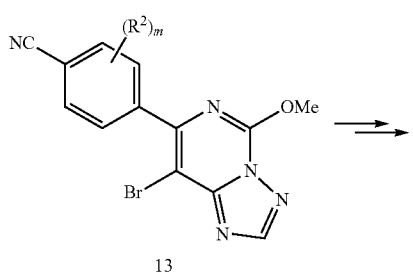

13

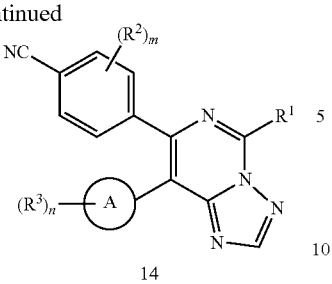

14

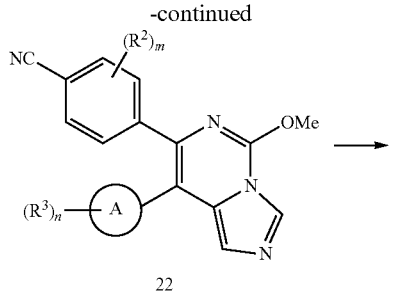

22

Compounds of the invention can be prepared via the synthetic route outlined in Scheme 2 starting from compound 4 which can be prepared as described in Scheme 1. Compound 4 can be converted to a formamidoxime derivative of formula 12 by reacting with N,N-dimethylformamide dimethyl acetal, followed by treatment with hydroxylamine. The formamidoxime derivative 12 can undergo cyclization upon treating with trifluoroacetic anhydride (TFAA) to afford the triazole compound of formula 13. The preparation of compound 14 from compound 13 can be achieved using similar conditions as described in Scheme 1 (i.e., conditions used for preparation of compound 11 from compound 8).

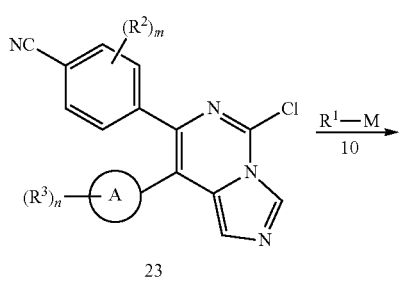

23

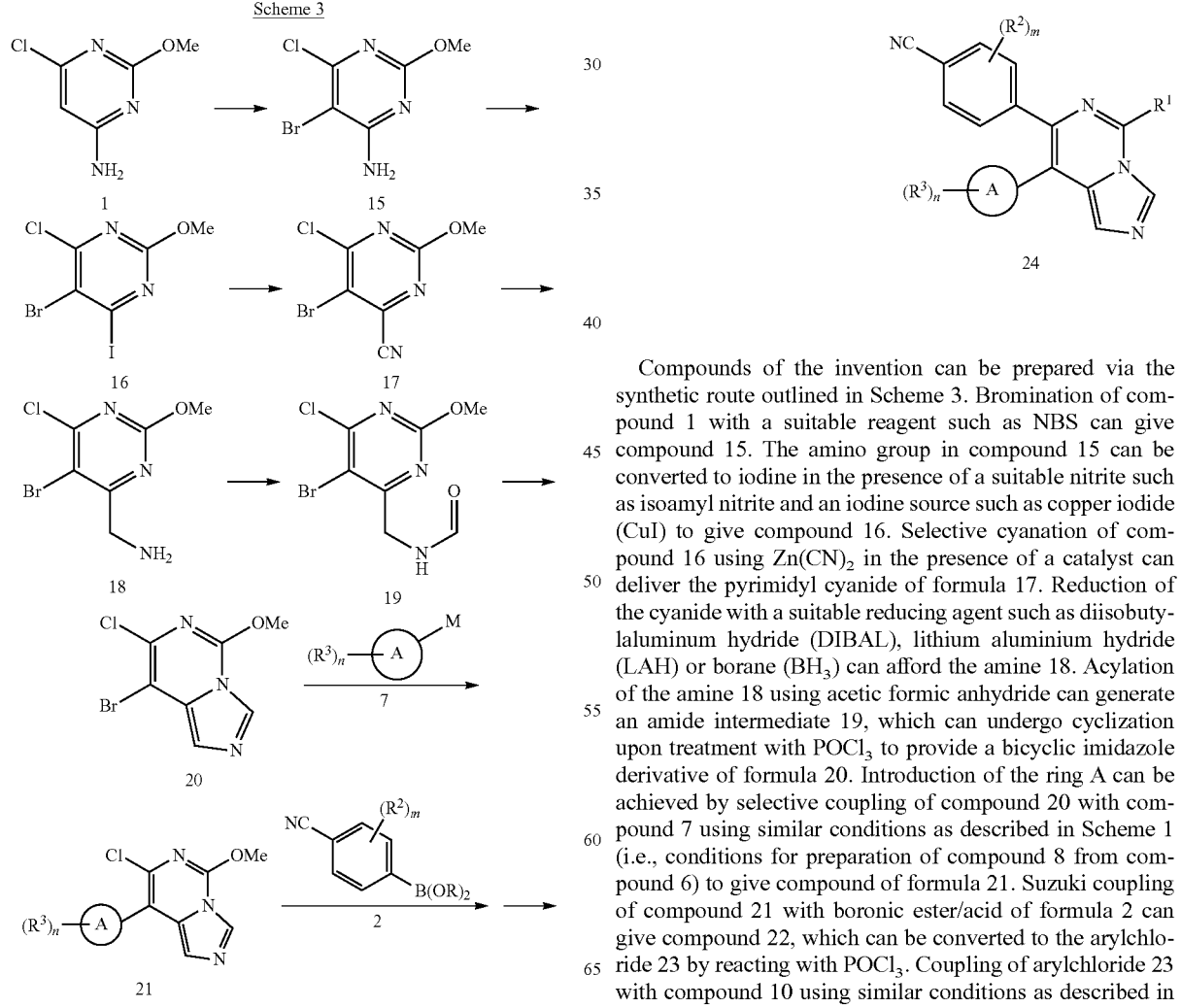

Compounds of the invention can be prepared via the synthetic route outlined in Scheme 3. Bromination of compound 1 with a suitable reagent such as NBS can give compound 15. The amino group in compound 15 can be converted to iodine in the presence of a suitable nitrite such as isoamyl nitrite and an iodine source such as copper iodide (CuI) to give compound 16. Selective cyanation of compound 16 using $Zn(CN)_2$ in the presence of a catalyst can deliver the pyrimidyl cyanide of formula 17. Reduction of the cyanide with a suitable reducing agent such as diisobutylaluminum hydride (DIBAL), lithium aluminium hydride (LAH) or borane ($BH_3$) can afford the amine 18. Acylation of the amine 18 using acetic formic anhydride can generate an amide intermediate 19, which can undergo cyclization upon treatment with $POCl_3$ to provide a bicyclic imidazole derivative of formula 20. Introduction of the ring A can be achieved by selective coupling of compound 20 with compound 7 using similar conditions as described in Scheme 1 (i.e., conditions for preparation of compound 8 from compound 6) to give compound of formula 21. Suzuki coupling of compound 21 with boronic ester/acid of formula 2 can give compound 22, which can be converted to the arylchloride 23 by reacting with $POCl_3$. Coupling of arylchloride 23 with compound 10 using similar conditions as described in Scheme 1 can generate compound of formula 24.

Scheme 4

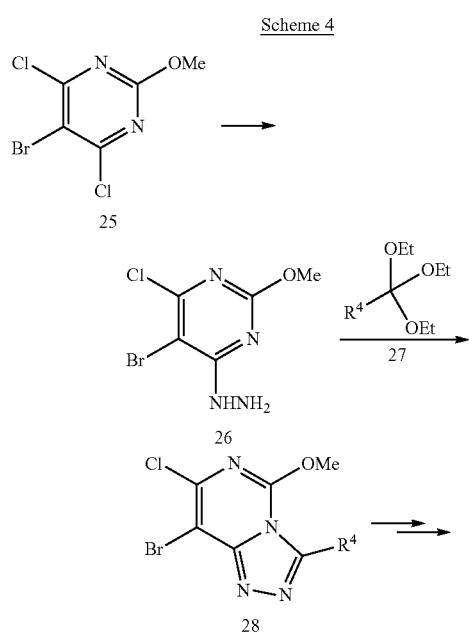

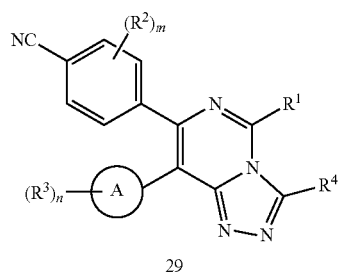

Compounds of the invention can be prepared via the synthetic route outlined in Scheme 4 starting from the commercially available compound 25. Introduction of the hydrazine moiety can be achieved via SNAr displacement of the chloride in compound 25 with hydrazine to give compound 26. A condensation reaction can be performed between compound 26 with compound of formula 27 at elevated temperature to produce compound 28. Preparation of compound 29 from compound 28 can be achieved using similar procedures as described in Scheme 3 (i.e., conditions used for preparation of compound 24 from compound 20).

Scheme 5

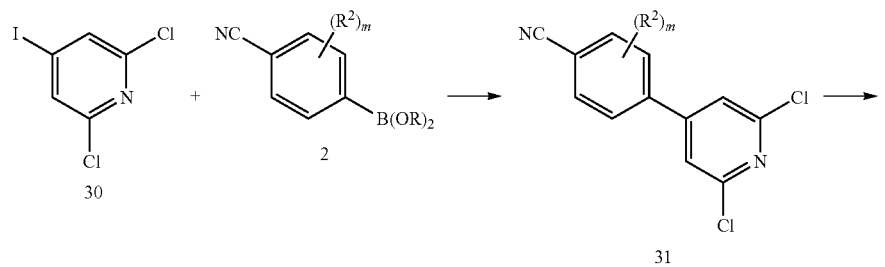

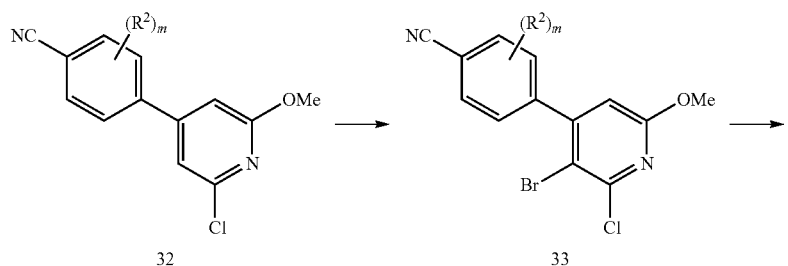

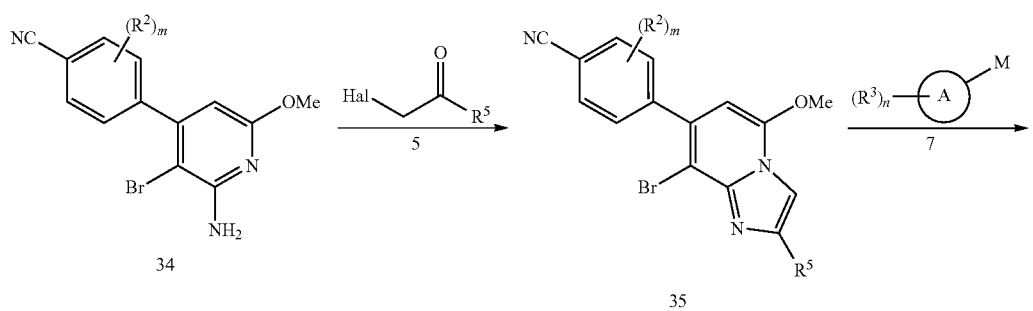

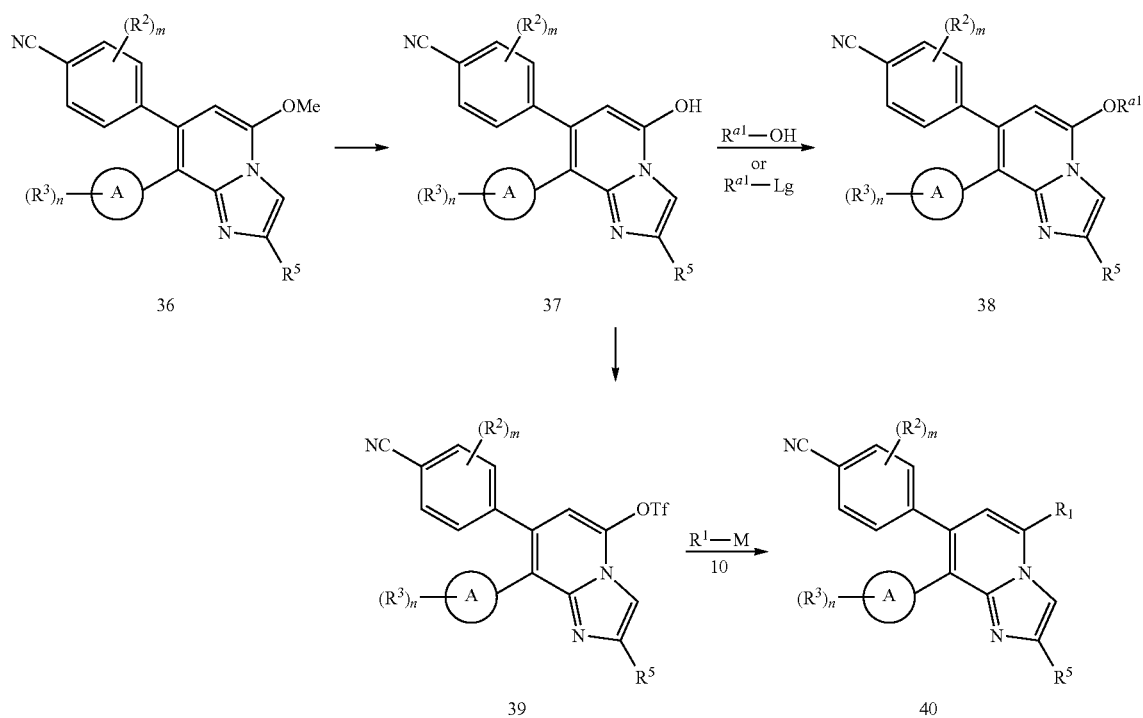

Compounds of the invention can be prepared via the synthetic route outlined in Scheme 5. Selective Suzuki coupling of iodo-derivative of formula 30 with boronic acid/ester 2 under standard Suzuki coupling conditions (i.e. in the presence of a palladium catalyst and a suitable base) can give dichloro-compound 31. Selective displacement of one of the chlorides in compound 31 with methoxy by reacting with sodium methoxide can give compound 32. Bromination of compound 32 under suitable conditions (i.e. in the presence of NBS) can give compound 33, which can react with ammonia to give the aminopyridine derivative 34. Condensation of compound 34 with compound 5 can give the bicyclic compound 35. Installation of Ring A can be achieved using similar conditions as described in Scheme 1 (i.e., conditions used for preparation of compound 8 from compound 6) to give compound 36. The phenol derivative 37 can be prepared by demethylation of compound 36 under a suitable condition [i.e., boron tribromide (BBr$_3$) or trimethylsilyl iodide (TMSI)]. Compound 38 can be prepared from compound 37 via Mitsunobu reaction with an alcohol (R$^{a1}$—OH) or alkylation with R$^{a1}$-Lg (Lg is a leaving group such as halide or OMs). Alternatively, the phenol 37 can be converted to triflate 39 under suitable conditions (i.e., in the presence of triflic anhydride and a base such as pyridine). The coupling of triflate 39 with compound 10 can be performed under standard Suzuki conditions (when M is boronic acid or ester), or standard Stille coupling conditions [when M is Sn(Alkyl)$_4$], or standard Negishi coupling conditions (when M is Zn-Hal) to give compound 40.

Scheme 6

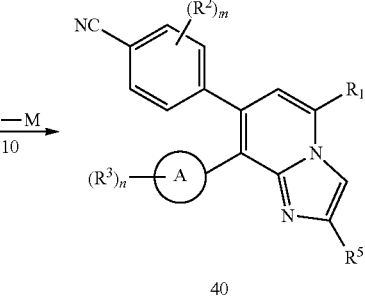

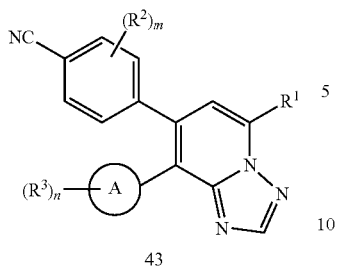

43

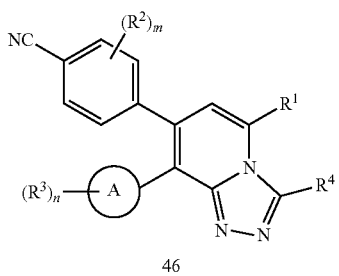

46

Compounds of the invention can be prepared using the synthetic route outlined in Scheme 6. Condensation of aminopyridine 34 with N,N-dimethylformamide dimethyl acetal, followed by treatment with hydroxylamine can give the formamidoxime derivative of formula 41, which can undergo cyclization upon treating with trifluoroacetic anhydride (TFAA) to afford the triazole compound of formula 42. The preparation of compound 43 from compound 42 can be achieved using similar synthetic conditions as described in Scheme 5 (i.e. procedures used for preparation of compound 40 or 38 from compound 35).

Compounds of the invention can be prepared using the synthetic route outlined in Scheme 7. Introduction of the hydrazine moiety can be achieved via SNAr displacement of the chloride in compound 33 with hydrazine to give compound 44. A condensation reaction can be performed between compound 44 with compound of formula 27 at elevated temperature to produce compound 45. Preparation of compound 46 from compound 45 can be achieved using similar procedures as described in Scheme 5 (i.e. procedures used for preparation of compound 40 or 38 from compound 35).

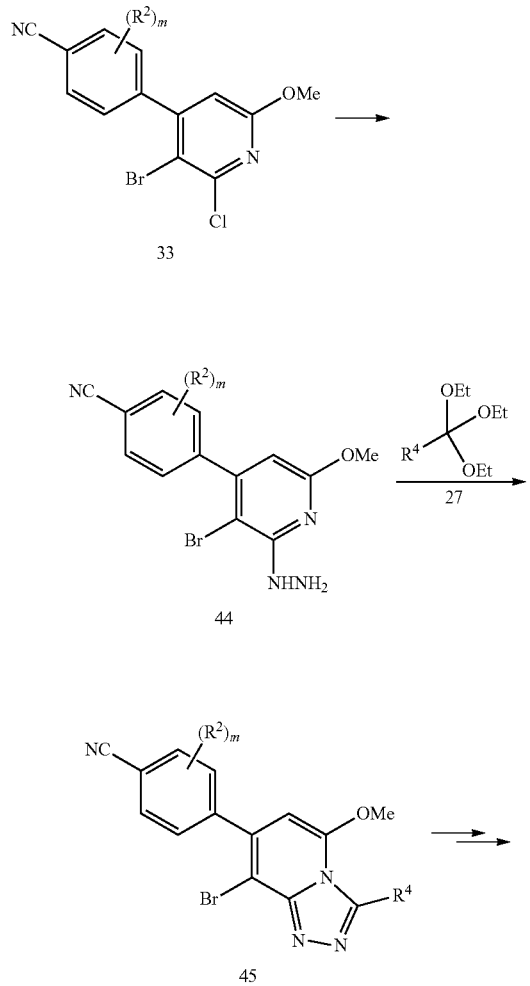

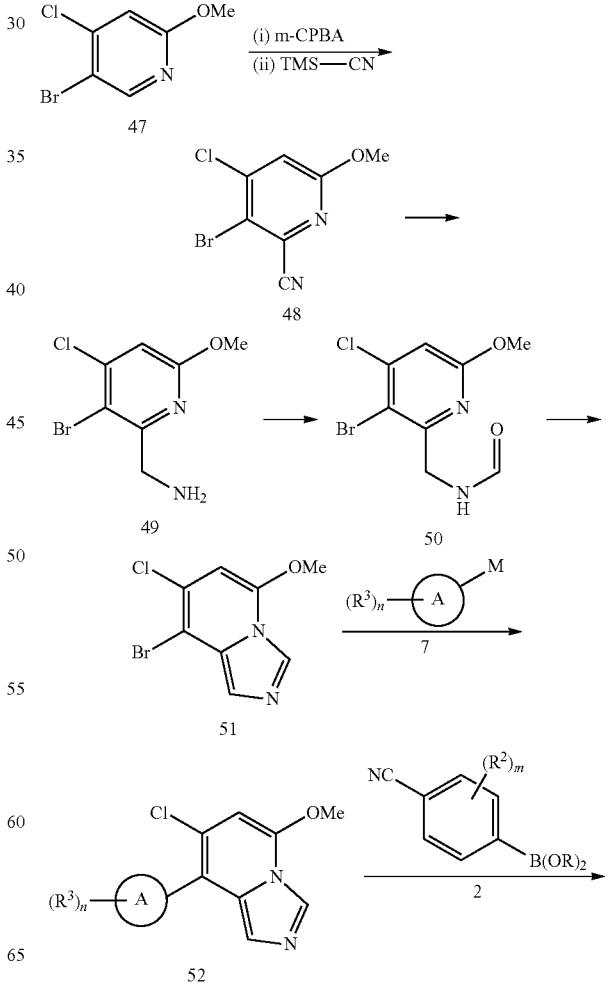

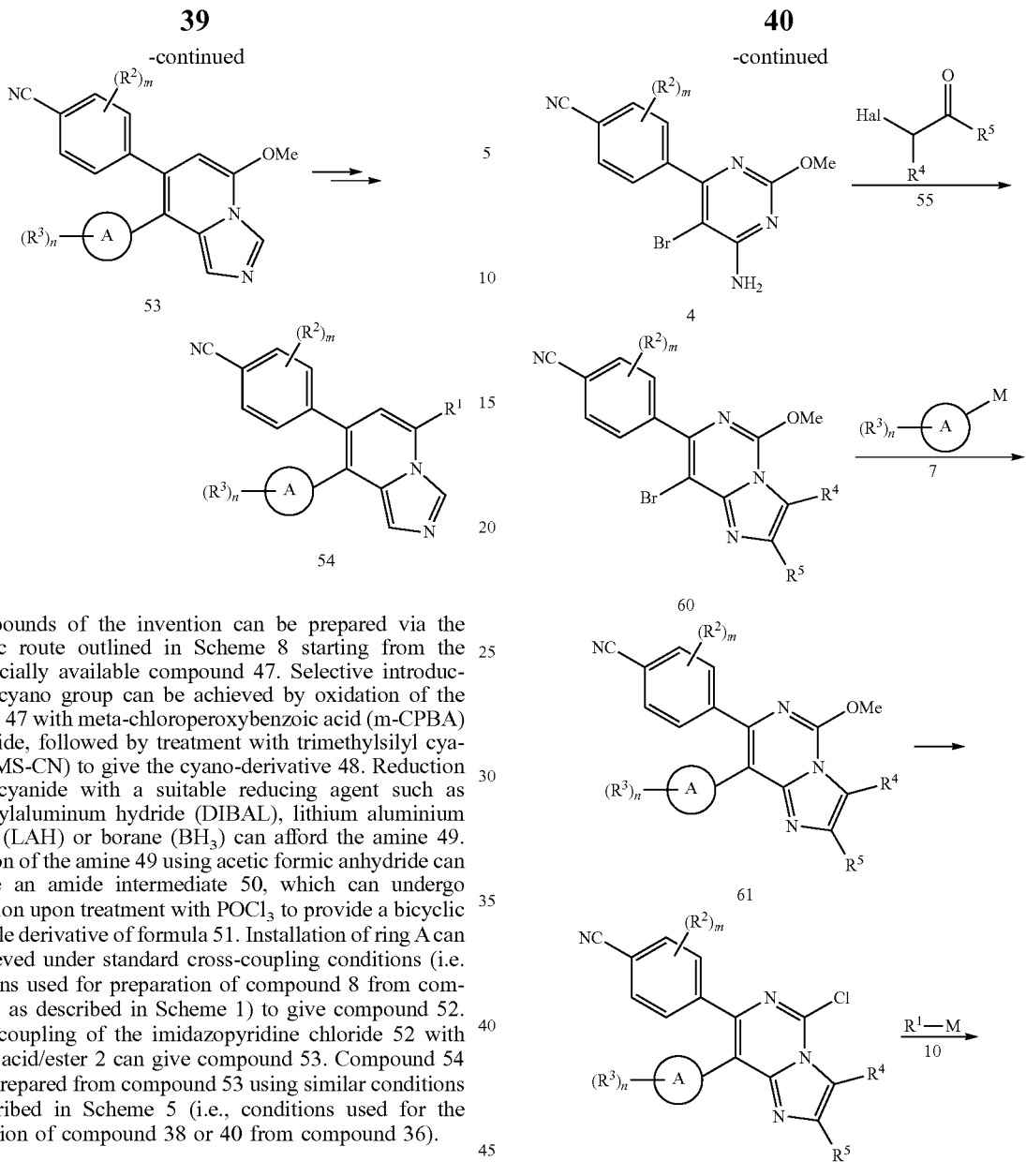

Compounds of the invention can be prepared via the synthetic route outlined in Scheme 8 starting from the commercially available compound 47. Selective introduction of cyano group can be achieved by oxidation of the pyridine 47 with meta-chloroperoxybenzoic acid (m-CPBA) to N-oxide, followed by treatment with trimethylsilyl cyanide (TMS-CN) to give the cyano-derivative 48. Reduction of the cyanide with a suitable reducing agent such as diisobutylaluminum hydride (DIBAL), lithium aluminium hydride (LAH) or borane ($BH_3$) can afford the amine 49. Acylation of the amine 49 using acetic formic anhydride can generate an amide intermediate 50, which can undergo cyclization upon treatment with $POCl_3$ to provide a bicyclic imidazole derivative of formula 51. Installation of ring A can be achieved under standard cross-coupling conditions (i.e. conditions used for preparation of compound 8 from compound 6 as described in Scheme 1) to give compound 52. Suzuki coupling of the imidazopyridine chloride 52 with boronic acid/ester 2 can give compound 53. Compound 54 can be prepared from compound 53 using similar conditions as described in Scheme 5 (i.e., conditions used for the preparation of compound 38 or 40 from compound 36).

Scheme 9

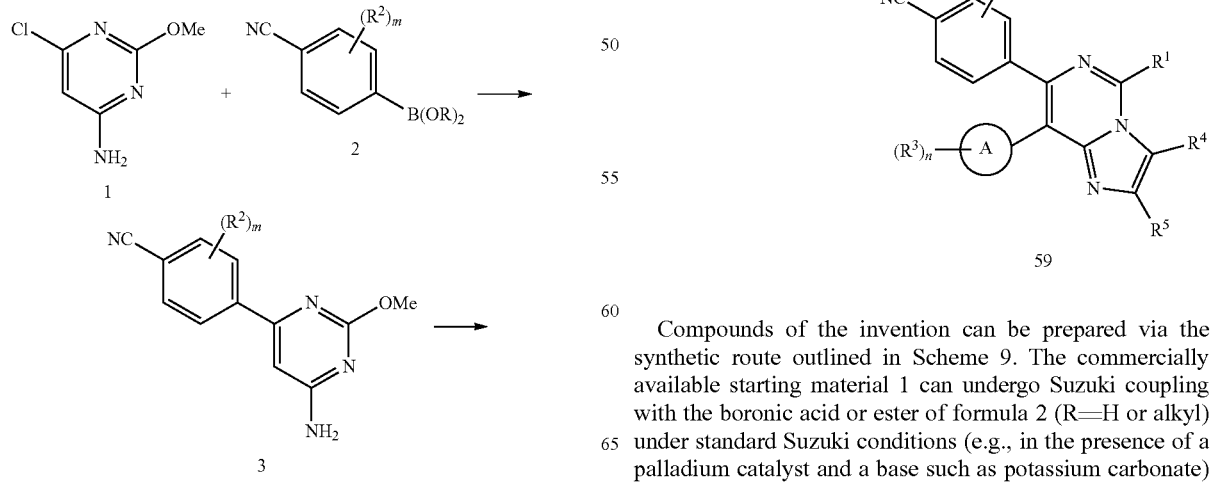

Compounds of the invention can be prepared via the synthetic route outlined in Scheme 9. The commercially available starting material 1 can undergo Suzuki coupling with the boronic acid or ester of formula 2 (R═H or alkyl) under standard Suzuki conditions (e.g., in the presence of a palladium catalyst and a base such as potassium carbonate) to afford compound 3. Bromination of compound 3 in the presence of N-bromosuccinimide (NBS) can give the compound of formula 4. Condensation of compound 4 with the carbonyl derivatives of formula 55 (Hal is a halide such as Cl or Br) at elevated temperature can generate the bicyclic compound of formula 60. The bromide in compound 60 can be coupled to a compound of formula 7, in which M is a boronic acid, boronic ester or an appropriately substituted metal [e.g., M is B(OR)$_2$, Sn(Alkyl)$_4$, or Zn-Hal], under standard Suzuki coupling conditions (e.g., in the presence of a palladium catalyst and a suitable base) or standard Stille coupling conditions (e.g., in the presence of a palladium catalyst), or standard Negishi coupling conditions (e.g., in the presence of a palladium catalyst) to give the derivative of formula 61. Alternatively, compound 7 can be a cyclic amine (where M is H and attached to an amine nitrogen) and the coupling of arylbromide 60 with the cyclic amine 7 can be performed under Buchwald amination conditions (e.g., in the presence of a palladium catalyst and a base such as sodium tert-butoxide) to yield a compound of formula 61. Conversion of the methoxy group in compound 61 to chloride can be achieved in the presence of phosphoryl chloride (POCl$_3$) at suitable temperature to give compound of formula 62. Displacement of the chloride in compound 62 with a nucleophile of formula 10 (wherein R$^1$-M' is an alcohol or an amine, e.g., M' is H which is attached to an alcohol oxygen or an amine nitrogen) in the presence of a suitable base such as sodium hydride, sodium hydroxide, potassium carbonate or diisopropylethylamine at elevated temperature can give compound of formula 59. Alternatively, the coupling of compound 62 with compound 10 can be performed under standard Suzuki conditions (when M is boronic acid or ester), or standard Stille coupling conditions [when M is Sn(Alkyl)$_4$], or standard Negishi coupling conditions (when M is Zn-Hal) to give compound 59.

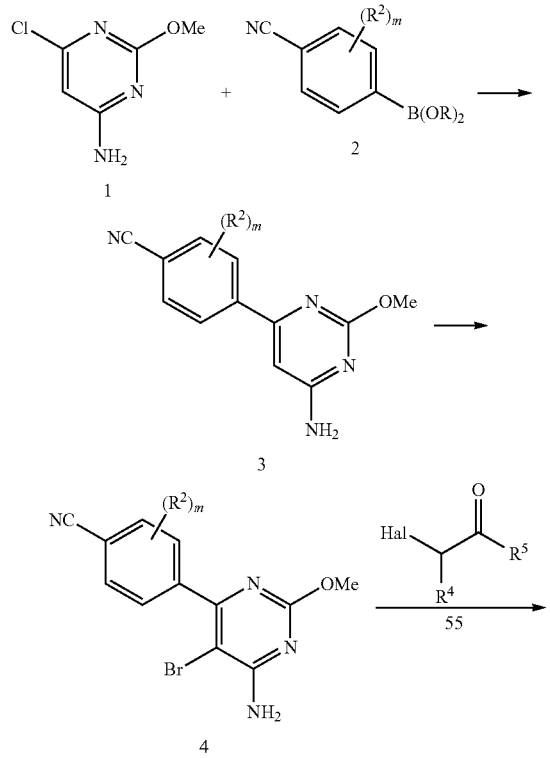

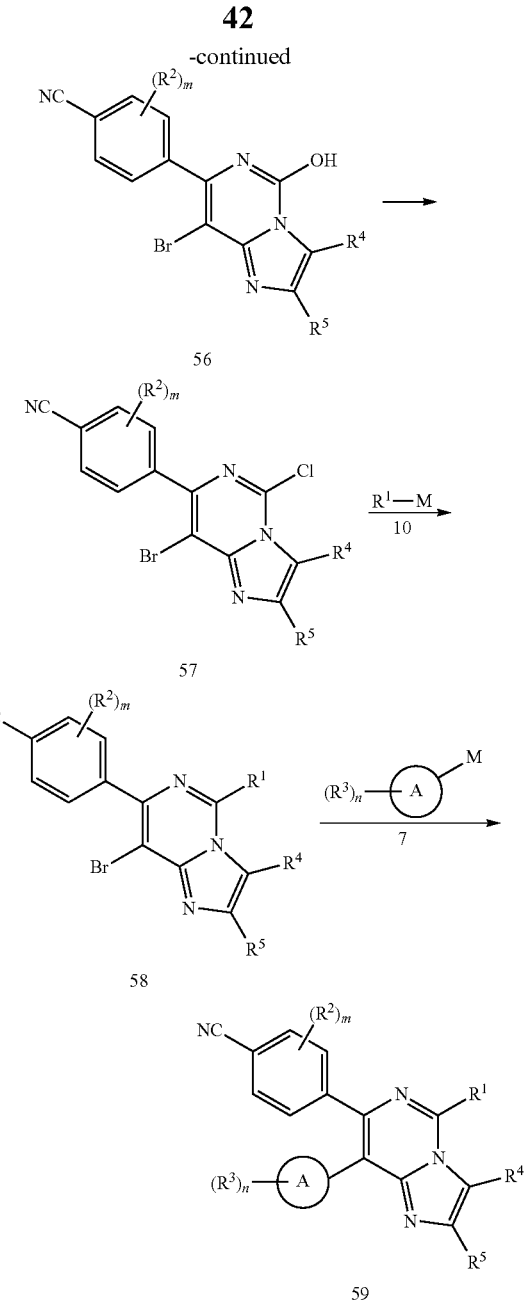

Compounds of the invention can be prepared via the synthetic route outlined in Scheme 10. The commercially available starting material 1 can undergo Suzuki coupling with the boronic acid or ester of formula 2 (R=H or alkyl) under standard Suzuki conditions (e.g., in the presence of a palladium catalyst and a base such as potassium carbonate) to afford compound 3. Bromination of compound 3 in the presence of N-bromosuccinimide (NBS) can give the compound of formula 4. Condensation of compound 4 with the carbonyl derivatives of formula 55 (Hal is a halide such as Cl or Br) at elevated temperature can generate the bicyclic compound of formula 56. The hydroxyl group in compound 56 can be replaced with a halide (such as e.g. Cl), by treating compound 56 with an acid halide (e.g. acid chloride, such as for example phosphorus trichloride or phosphoryl chloride (phosphorus oxychloride)) to yield a compound of formula 57. Displacement of the chloride in compound 57 with a nucleophile of formula 10 (wherein R¹-M' is an alcohol or an amine, e.g., M' is H which is attached to an alcohol oxygen or an amine nitrogen) in the presence of a suitable base such as sodium hydride, sodium hydroxide, potassium carbonate or diisopropylethylamine at elevated temperature can give compound of formula 58. Alternatively, the coupling of compound 57 with compound 10 can be performed under standard Suzuki conditions (when M is boronic acid or ester), or standard Stille coupling conditions [when M is Sn(Alkyl)$_4$], or standard Negishi coupling conditions (when M is Zn-Hal) to give compound 58. The bromide in compound 58 can be coupled to a compound of formula 7, in which M is a boronic acid, boronic ester or an appropriately substituted metal [e.g., M is B(OR)$_2$, Sn(Alkyl)$_4$, or Zn-Hal], under standard Suzuki coupling conditions (e.g., in the presence of a palladium catalyst and a suitable base) or standard Stille coupling conditions (e.g., in the presence of a palladium catalyst), or standard Negishi coupling conditions (e.g., in the presence of a palladium catalyst) to give the derivative of formula 59. Alternatively, compound 7 can be a cyclic amine (where M is H and attached to an amine nitrogen) and the coupling of arylbromide 58 with the cyclic amine 7 can be performed under Buchwald amination conditions (e.g., in the presence of a palladium catalyst and a base such as sodium tert-butoxide) to yield a compound of formula 59.

Methods of Use

Compounds of the invention are LSD1 inhibitors and, thus, are useful in treating diseases and disorders associated with activity of LSD1. For the uses described herein, any of the compounds of the invention, including any of the embodiments thereof, may be used.

The present invention is directed to a method of modulating LSD1 comprising contacting the LSD1 with a compound of Formula I. The present invention is further directed to a method of mediating LSD1 comprising contacting the LSD1 with a compound of Formula I. The present invention is further directed to a method of modulating LSD1 signaling comprising contacting the LSD1 with a compound of Formula I.

In some embodiments, the compounds of the invention are selective for LSD1 over LSD2, meaning that the compounds bind to or inhibit LSD1 with greater affinity or potency, compared to LSD2. In general, selectivity can be at least about 5-fold, at least about 10-fold, at least about 20-fold, at least about 50-fold, at least about 100-fold, at least about 200-fold, at least about 500-fold or at least about 1000-fold.

As inhibitors of LSD1, the compounds of the invention are useful in treating LSD1-mediated diseases and disorders. The term "LSD1-mediated disease" or "LSD1-mediated disorder" refers to any disease or condition in which LSD1 plays a role, or where the disease or condition is associated with expression or activity of LSD1. The compounds of the invention can therefore be used to treat or lessen the severity of diseases and conditions where LSD1 is known to play a role.

Diseases and conditions treatable using the compounds of the invention include, generally cancers, inflammation, autoimmune diseases, viral induced pathogenesis, beta-globinopathies, and other diseases linked to LSD1 activity.

Cancers treatable using compounds according to the present invention include, for example, hematological cancers, sarcomas, lung cancers, gastrointestinal cancers, genitourinary tract cancers, liver cancers, bone cancers, nervous system cancers, gynecological cancers, and skin cancers.

Examplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Examplary sarcomas include chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Examplary lung cancers include non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Examplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Examplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Examplary liver cancers include hepatoma (hepatocellular carcinoma), cholangiocarcinoma, hepatoblastoma, angiosarcoma, hepatocellular adenoma, and hemangioma.

Examplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Examplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Examplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Examplary skin cancers include melanoma, basal cell carcinoma, squamous cell carcinoma, Kaposi's sarcoma, moles dysplastic nevi, lipoma, angioma, dermatofibroma, and keloids.

The compounds of the invention can further be used to treat cancer types where LSD1 may be overexpressed including, for example, breast, prostate, head and neck, laryngeal, oral, and thyroid cancers (e.g., papillary thyroid carcinoma).

The compounds of the invention can further be used to treat genetic disorders such as Cowden syndrome and Bannayan-Zonana syndrome.

The compounds of the invention can further be used to treat viral diseases such as herpes simplex virus (HSV), varicella zoster virus (VZV), human cytomegalovirus, hepatitis B virus (HBV), and adenovirus.

The compounds of the invention can further be used to treat beta-globinopathies including, for example, beta-thalassemia and sickle cell anemia.

As used herein, the term "contacting" refers to the bringing together of indicated moieties in an in vitro system or an in vivo system. For example, "contacting" a LSD1 protein with a compound of the invention includes the administration of a compound of the present invention to an individual or patient, such as a human, having a LSD1 protein, as well as, for example, introducing a compound of the invention into a sample containing a cellular or purified preparation containing the LSD1 protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the onset and development of a disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, JAK, PIM, PI3K, PD-1, PD-L1, bromodomain, indoleamine 2,3-dioxygenase (IDO), TAM, FGFR inhibitors and other tumor directed therapies (small molecules or biologics in nature) for treatment of LSD1-mediated diseases, disorders or conditions. The one or more additional pharmaceutical agents can be administered to a patient simultaneously or sequentially. In some embodiments, the compounds of the present disclosure can be used in combination with a vaccine, an immunotherapy, such as LADD immunotherapy, CRS-207 or DPX-Survivac for the treatment of cancer.

In some embodiments, the compounds of the invention can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

In some embodiments, biological anticancer drugs, such as antibodies and cytokines, can be combined with the compounds of the present invention. In addition, drugs modulating microenvironment or immune responses can be combined with the compounds of the invention. Examples of such drugs include anti-Her2 antibodies, anti-CD20 antibodies, anti-CTLA1, anti-PD-1, anti-PDL1, and other immunotherapeutic drugs.

For treating cancer and other proliferative diseases, the compounds of the invention can be used in combination with targeted therapies, including JAK kinase inhibitors (Ruxolitinib, additional JAK1/2 and JAK1-selective), Pim kinase inhibitors, TAM kinase inhibitors, PI3 kinase inhibitors including PI3K-delta selective (e.g., INCB50797), PI3K-gamma selective and broad spectrum PI3K inhibitors, MEK inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors such as INCB54329 and INCB57643), FGFR inhibitors (e.g., INCB54828, INCB62079 and INCB63904) and indoleamine 2,3-dioxygenase inhibitors (e.g., epacadostat and GDC0919).

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S, 4R, 5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

For treating beta-thalassemia or sickle cell disease, the compound of the invention can be administered in combination with one or more additional agents such as Hydrea® (hydroxyurea).

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided LSD1 inhibitor compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Compounds of the present disclosure can be used in combination with one or more immune checkpoint inhibitors. Examplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating LSD1 in tissue samples, including human, and for identifying LSD1 ligands by inhibition binding of a labeled compound. Accordingly, the present invention includes LSD1 assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to 3H (also written as T for tritium), 11C, 13C, 14C, 13N, 15N, 15O, 17O, 18O, 18F, 35S, 36Cl, 82Br, 75Br, 76Br, 77Br, 123I, 124I, 125I and 131I. The radionuclide that is incorporated in the instant radio-labeled compounds will depend on the specific application of that radio-labeled compound.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind LSD1 by monitoring its concentration variation when contacting with LSD1, through tracking of the labeling. For example, a test compound (labeled) can be evaluated for its ability to reduce binding of another compound which is known to bind to LSD1 (i.e., standard compound). Accordingly, the ability of a test compound to compete with the standard compound for binding to LSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of LSD1 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

EXAMPLES

Example 1

4-(8-(4-methylphenyl)-5-{[(3R)-1-methylpiperidin-3-yl]methoxy}imidazo[1,2-c]pyrimidin-7-yl)benzonitrile

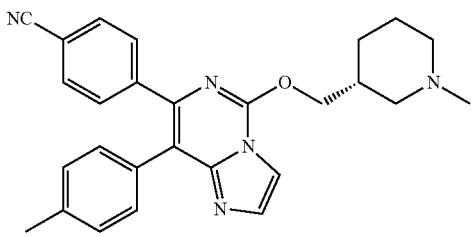

Step 1: 4-(6-amino-2-methoxypyrimidin-4-yl)benzonitrile

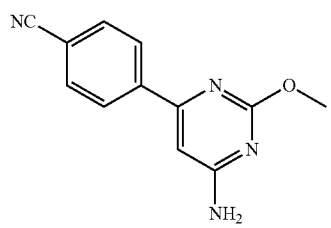 [SMILES: COc1nc(N)cc(-c2ccc(C#N)cc2)n1]

To a mixture of 6-chloro-2-methoxypyrimidin-4-amine (Ark Pharm, cat #AK-25131: 1.3 g, 8.0 mmol), (4-cyanophenyl)boronic acid (1.41 g, 9.60 mmol) and sodium carbonate (1.7 g, 16 mmol) in 1,4-dioxane (15 mL) and water (5 mL) was added dichloro(bis{di-tert-butyl[4-(dimethylamino)phenyl]phosphoranyl})palladium (170 mg, 0.24 mmol). The reaction mixture was purged with nitrogen then stirred at 95° C. overnight. The reaction mixture was cooled to room temperature then water (20 mL) was added. The resulting precipitate was collected via filtration then dried to give the desired product (1.7 g, 94%), which was used in the next step without further purification. LC-MS calculated for $C_{12}H_{11}N_4O$ $(M+H)^+$: m/z=227.1; found 227.1.

Step 2: 4-(6-amino-5-bromo-2-methoxypyrimidin-4-yl)benzonitrile

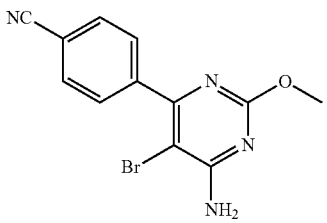 [SMILES: COc1nc(N)c(Br)c(-c2ccc(C#N)cc2)n1]

N-Bromosuccinimide (1.3 g, 7.5 mmol) was added to a solution of 4-(6-amino-2-methoxypyrimidin-4-yl)benzonitrile (1.7 g, 7.5 mmol) in dimethyl sulfoxide (15 mL)/acetonitrile (8 mL)/water (0.5 mL) at 0° C. The resulting mixture was stirred at 0° C. for 2 h then water (25 mL) was added. The resulting precipitate was collected via filtration then dried to give the desired product (2.1 g, 92%), which was used in the next step without further purification. LC-MS calculated for $C_{12}H_{10}BrN_4O$ $(M+H)^+$: m/z=305.0. found 305.0.

Step 3: 4-(8-bromo-5-hydroxyimidazo[1,2-c]pyrimidin-7-yl)benzonitrile

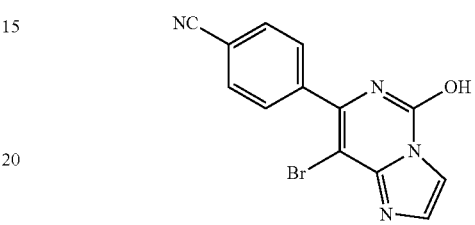

Chloroacetaldehyde (7 M in water, 6 mL, 42 mmol) was added to a mixture of 4-(6-amino-5-bromo-2-methoxypyrimidin-4-yl)benzonitrile (1.5 g, 4.9 mmol) in isopropyl alcohol (15 mL). The resulting mixture was stirred at 110° C. for 4 h then cooled to room temperature and concentrated. The residue was titurated with ethyl acetate to give desired product as the HCl salt (1.3 g, 84%), which was used in the next step without further purification. LC-MS calculated for $C_{13}H_8BrN_4O$ $(M+H)^+$: m/z=315.0. found 315.1.

Step 4: 4-(8-bromo-5-chloroimidazo[1,2-c]pyrimidin-7-yl)benzonitrile

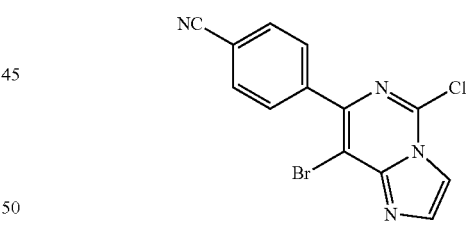

Phosphoryl chloride (12 mL, 130 mmol) was added to a mixture of 4-(8-bromo-5-hydroxyimidazo[1,2-c]pyrimidin-7-yl)benzonitrile (1.0 g, 3.2 mmol) in acetonitrile (12 mL). The resulting mixture was stirred at 110° C. overnight then cooled to room temperature and concentrated. The residue was dissolved in methylene chloride then washed with sat'd $NaHCO_3$ solution, water and brine. The organic layer was dried over $Na_2SO_4$, filtered and concentrated. The residue was purified by flash chromatography on a silica gel column eluting with 0 to 30% EtOAc/DCM to give the desired product (0.68 g, 64%). LC-MS calculated for $C_{13}H_7BrClN_4$ $(M+H)^+$: m/z=333.0. found 333.0.

Step 5: tert-butyl (3R)-3-({[8-bromo-7-(4-cyanophenyl)imidazo[1,2-c]pyrimidin-5-yl]oxy}methyl)piperidine-1-carboxylate

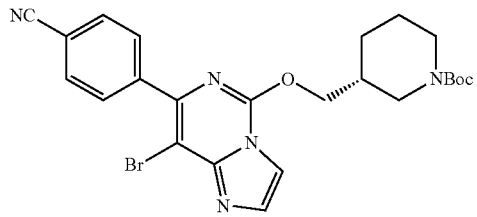 [SMILES: CC(C)(C)OC(=O)N1CCC[C@@H](COc2nc(-c3ccc(C#N)cc3)c(Br)c3nccn23)C1]

Sodium hydride (49 mg, 1.2 mmol) was added to a solution of tert-butyl (3R)-3-(hydroxymethyl)piperidine-1-carboxylate (D-L Chiral Chemicals, cat #LAC-B-393: 260 mg, 1.2 mmol) in N,N-dimethylformamide (3 mL) at 0° C. The resulting mixture was stirred at room temperature for 20 min then added to a suspension of 4-(8-bromo-5-chloroimidazo[1,2-c]pyrimidin-7-yl)benzonitrile (370 mg, 1.1 mmol) in N,N-dimethylformamide (3 mL) at 0° C. The resulting mixture was stirred at room temperature for 1 h then quenched with water and extracted with ethyl acetate. The combined extracts were washed with sat'd NaHCO$_3$, water and brine. The organic layer was dried over Na$_2$SO$_4$, filtered and concentrated. The residue was purified by flash chromatography on a silica gel column eluting with 0 to 40% EtOAc/DCM to give the desired product (0.52 g, 91%). LC-MS calculated for C$_{24}$H$_{27}$BrN$_5$O$_3$ (M+H)$^+$: m/z=512.1. found 512.1.

Step 6: 4-{8-bromo-5-[(3R)piperidin-3-ylmethoxy]imidazo[1,2-c]pyrimidin-7-yl}benzonitrile Hydrochloride

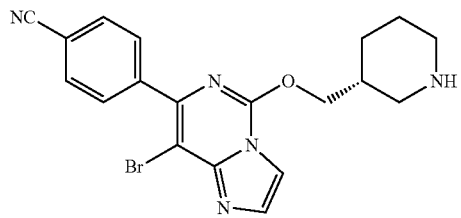 [SMILES: N#Cc1ccc(-c2nc(OC[C@@H]3CCCNC3)n3ccnc3c2Br)cc1]

4.0 M Hydrogen chloride in dioxane (3 mL, 12 mmol) was added to a solution of tert-butyl (3R)-3-({[8-bromo-7-(4-cyanophenyl)imidazo[1,2-c]pyrimidin-5-yl]oxy}methyl)piperidine-1-carboxylate (0.52 g, 1.0 mmol) in methylene chloride (2 mL). The resulting mixture was stirred at room temperature for 30 min then concentrated. The residue was used in the next step without further purification. LC-MS calculated for C$_{19}$H$_{19}$BrN$_5$O (M+H)$^+$: m/z=412.1. found 412.1.

Step 7: 4-(8-bromo-5-{[(3R)-1-methylpiperidin-3-yl]methoxy}imidazo[1,2-c]pyrimidin-7-yl)benzonitrile

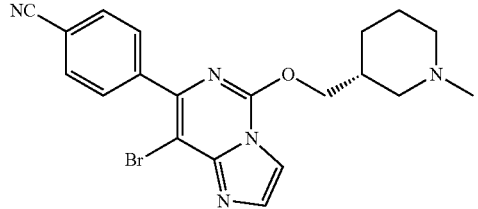 [SMILES: CN1CCC[C@@H](COc2nc(-c3ccc(C#N)cc3)c(Br)c3nccn23)C1]

7.0 M Formaldehyde in water (2 mL, 14 mmol) was added to a mixture of 4-{8-bromo-5-[(3R)-piperidin-3-ylmethoxy]imidazo[1,2-c]pyrimidin-7-yl}benzonitrile hydrochloride (400 mg, 0.89 mmol) and N,N-diisopropylethylamine (310 µL, 1.8 mmol) in methylene chloride (8 mL). The resulting mixture was stirred at room temperature for 30 min then sodium triacetoxyborohydride (380 mg, 1.8 mmol) was added. The reaction mixture was stirred at room temperature for 1 h then diluted with methylene chloride, washed with 1 N NaOH, water and brine. The organic layer was dried over Na$_2$SO$_4$, filtered and concentrated. The residue was purified by flash chromatography on a silica gel column eluting with 0 to 10% MeOH/DCM to give the desired product (0.35 g, 92%). LC-MS calculated for C$_{20}$H$_{21}$BrN$_5$O (M+H)$^+$: m/z=426.1. found 426.1.

Step 8: 4-(8-(4-methylphenyl)-5-{[(3R)-1-methylpiperidin-3-yl]methoxy}imidazo[1,2-c]pyrimidin-7-yl)benzonitrile A mixture of (4-methylphenyl)boronic acid (6.4 mg, 0.047 mmol), 4-(8-bromo-5-{[(3R)-1-methylpiperidin-3-yl]methoxy}imidazo[1,2-c]pyrimidin-7-yl)benzonitrile (10, mg, 0.023 mmol), sodium carbonate (7.5 mg, 0.070 mmol), and dichloro[1,1'-bis(dicyclohexylphosphino)ferrocene]palladium(II) (1.8 mg, 0.0023 mmol) in tert-butyl alcohol (0.1 mL) and water (0.2 mL) was first purged with nitrogen, then heated to 105° C. and stirred for 4 h. The reaction mixture was cooled to room temperature then purified by prep-HPLC (pH=2, acetonitrile/water+TFA) to give the desired product as the TFA salt. LC-MS calculated for C$_{27}$H$_{28}$N$_5$O (M+H)$^+$: m/z=438.2. found 438.2.

Example 2

4-(8-(4-methylphenyl)-5-{[(3R)-1-methylpyrrolidin-3-yl]methoxy}imidazo[1,2-c]pyrimidin-7-yl)benzonitrile

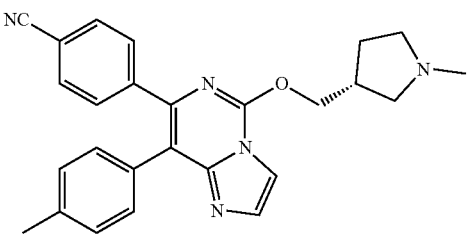

Step 1: 4-(8-bromo-5-{[(3R)-1-methylpyrrolidin-3-yl]methoxy}imidazo[1,2-c]pyrimidin-7-yl)benzonitrile

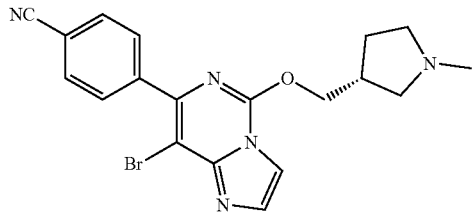 [SMILES: CN1CC[C@@H](COc2nc(-c3ccc(C#N)cc3)c(Br)c3nccn23)C1]

This compound was prepared using similar procedures as described for Example 1, Step 1-7, with tert-butyl (3R)-3-(hydroxymethyl)pyrrolidine-1-carboxylate (Synnovator, cat #PB00887) replacing tert-butyl (3R)-3-(hydroxymethyl)piperidine-1-carboxylate in Step 5. The crude product was purified by flash chromatography on a silica gel column eluting with 0 to 10% MeOH/DCM to give the desired product. LC-MS calculated for $C_{19}H_{19}BrN_5O$ (M+H)$^+$: m/z=412.1. found 412.1.

Step 2: 4-(8-(4-methylphenyl)-5-{[(3R)-1-methylpyrrolidin-3-yl]methoxy}imidazo[1,2-c]pyrimidin-7-yl)benzonitrile A mixture of (4-methylphenyl)boronic acid (23 mg, 0.17 mmol), 4-(8-bromo-5-{[(3R)-1-methylpyrrolidin-3-yl]methoxy}imidazo[1,2-c]pyrimidin-7-yl)benzonitrile (35 mg, 0.085 mmol), sodium carbonate (18 mg, 0.17 mmol), and dichloro[1,1'-bis(dicyclohexylphosphino)ferrocene]palladium(II) (6.4 mg, 0.0085 mmol) in tert-butyl alcohol (0.5 mL) and water (0.3 mL) was purged with nitrogen, then stirred at 105° C. for 4 h. The reaction mixture was cooled to room temperature then purified by prep-HPLC (pH=2, acetonitrile/water+TFA) to give the desired product as the TFA salt. LC-MS calculated for $C_{26}H_{26}N_5O$ (M+H)$^+$: m/z=424.2. found 424.2.

Example 3

4-(8-(6-methoxypyridin-3-yl)-5-{[(3R)-1-methylpiperidin-3-yl]methoxy}imidazo[1,2-c]pyrimidin-7-yl)benzonitrile

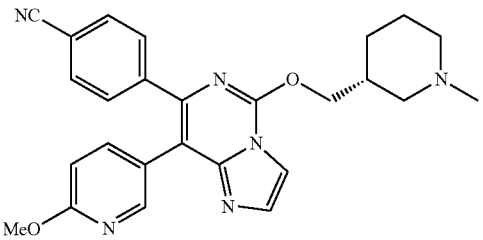

This compound was prepared using similar procedures as described for Example 1 with (6-methoxypyridin-3-yl)boronic acid (Aldrich, cat #637610) replacing (4-methylphenyl)boronic acid in Step 8. The product was purified by prep-HPLC (pH=2, acetonitrile/water+TFA) to give the desired product as the TFA salt. LC-MS calculated for $C_{26}H_{27}N_6O_2$ (M+H)$^+$: m/z=455.2; found 455.2. $^1$H NMR (500 MHz, DMSO) δ 8.09-8.04 (m, 2H), 7.83-7.78 (m, 2H), 7.73-7.71 (m, 1H), 7.66 (dd, J=8.6, 2.5 Hz, 1H), 7.60-7.54 (m, 2H), 6.88-6.83 (m, 1H), 4.68-4.62 (m, 1H), 4.59-4.52 (m, 1H), 3.86 (s, 3H), 3.71-3.63 (m, 1H), 3.49-3.41 (m, 1H), 3.00-2.78 (m, 5H), 2.46-2.36 (m, 1H), 1.97-1.85 (m, 2H), 1.81-1.65 (m, 1H), 1.46-1.32 (m, 1H).

Example 4

4-(8-[6-(dimethylamino)pyridin-3-yl]-5-{[(3R)-1-methylpiperidin-3-yl]methoxy}imidazo[1,2-c]pyrimidin-7-yl)benzonitrile

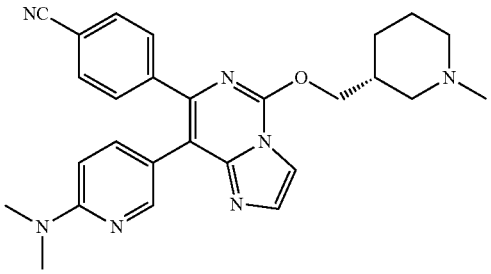

This compound was prepared using similar procedures as described for Example 1 with [6-(dimethylamino)pyridin-3-yl]boronic acid (Combi-Blocks, cat #FA-2296) replacing (4-methylphenyl)boronic acid in Step 8. The product was purified by prep-HPLC (pH=2, acetonitrile/water+TFA) to give the desired product as the TFA salt. LC-MS calculated for $C_{27}H_{30}N_7O$ (M+H)$^+$: m/z=468.3. found 468.2.

Example 5

4-[5-{[(3R)-1-methylpiperidin-3-yl]methoxy}-8-(6-pyrrolidin-1-ylpyridin-3-yl)imidazo[1,2-c]pyrimidin-7-yl]benzonitrile

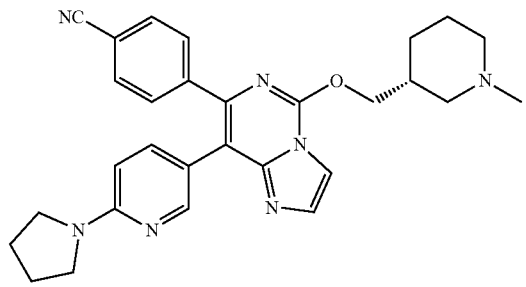 [SMILES: CN1CCC[C@@H](COc2nc(-c3ccc(C#N)cc3)c(-c3ccc(N4CCCC4)nc3)c3nccn23)C1]

This compound was prepared using similar procedures as described Example 1 with 2-pyrrolidin-1-yl-5-(4,4,5,5-tetramethyl-1,3,2-dioxaborolan-2-yl)pyridine (Combi Blocks, cat #PN-8695) replacing (4-methylphenyl)boronic acid in Step 8. The product was purified by prep-HPLC (pH=2, acetonitrile/water+TFA) to give the desired product as the TFA salt. LC-MS calculated for $C_{29}H_{32}N_7O$ (M+H)$^+$: m/z=494.3. found 494.3.

Example 6

4-(8-(1-methyl-2-oxo-2,3-dihydro-1H-indol-5-yl)-5-{[(3R)-1-methylpiperidin-3-yl]methoxy}imidazo[1,2-c]pyrimidin-7-yl)benzonitrile

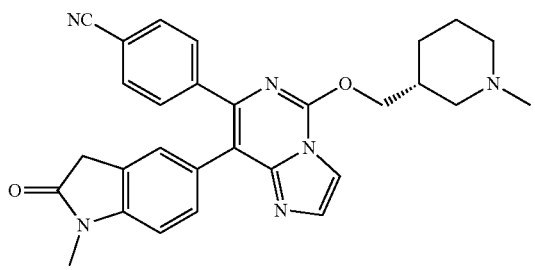

Step 1: 1-methyl-5-(4,4,5,5-tetramethyl-1,3,2-dioxaborolan-2-yl)-1,3-dihydro-2H-indol-2-one

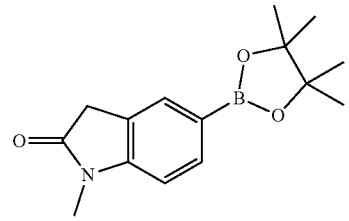 [SMILES: CN1C(=O)Cc2cc(B3OC(C)(C)C(C)(C)O3)ccc21]

A mixture of 5-bromo-1-methyl-1,3-dihydro-2H-indol-2-one (Maybridge, cat #CC63010: 0.30 g, 1.3 mmol), 4,4,5,5,4',4',5',5'-octamethyl-[2,2']bi[[1,3,2]dioxaborolanyl] (500 mg, 2.0 mmol), [1,1'-Bis(diphenylphosphino)ferrocene]dichloropalladium(II) complexed with dichloromethane (1:1) (50 mg, 0.07 mmol) and potassium acetate (390 mg, 4.0 mmol) in 1,4-dioxane (10 mL) was purged with nitrogen then heated at 90° C. overnight. The reaction mixture was cooled to room temperature then concentrated. The residue was purified by flash chromatography on a silica gel column eluting with 0 to 25% EtOAc/Hexanes to give the desired product. LC-MS calculated for $C_{15}H_{21}BNO_3$ (M+H)$^+$: m/z=274.2. found 274.1.

Step 2: 4-(8-(1-methyl-2-oxo-2,3-dihydro-1H-indol-5-yl)-5-{[(3R)-1-methylpiperidin-3-yl]methoxy}imidazo[1,2-c]pyrimidin-7-yl)benzonitrile This compound was prepared using similar procedures as described for Example 1 with 1-methyl-5-(4,4,5,5-tetramethyl-1,3,2-dioxaborolan-2-yl)-1,3-dihydro-2H-indol-2-one (prepared in Step 1) replacing (4-methylphenyl)boronic acid in Step 8. The product was purified by prep-HPLC (pH=2, acetonitrile/water+TFA) to give the desired product as the TFA salt. LC-MS calculated for $C_{29}H_{29}N_6O_2$ (M+H)$^+$: m/z=493.2. found 493.2.

Example 7

4-(8-(3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile

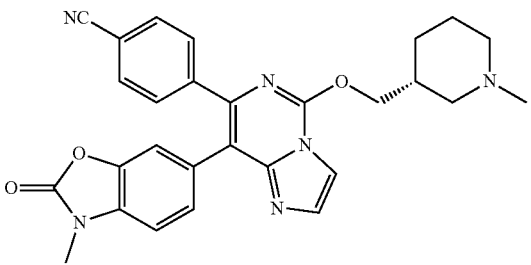 [SMILES: CN1CCC[C@@H](COc2nc(-c3ccc(C#N)cc3)c(-c3ccc4c(c3)oc(=O)n4C)c3nccn23)C1]

Step 1: 6-bromo-3-methyl-1,3-benzoxazol-2(3H)-one

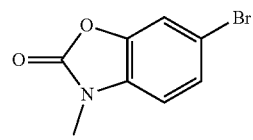

A mixture of 6-bromo-1,3-benzoxazol-2(3H)-one (Aldrich, cat #697036: 0.32 g, 1.5 mmol), methyl iodide (0.28 mL, 4.5 mmol) and potassium carbonate (210 mg, 1.5 mmol) in acetone (3 mL) was heated to 80° C. and stirred for 3 h. The reaction mixture was cooled to room temperature then diluted with water and extracted with EtOAc. The combined extracts were dried over $Na_2SO_4$, filtered and concentrated. The residue was used in the next step without further purification. LC-MS calculated for $C_8H_7BrNO_2$ (M+H)$^+$: m/z=228.0. found 227.9.

Step 2: 3-methyl-6-(4,4,5,5-tetramethyl-1,3,2-dioxaborolan-2-yl)-1,3-benzoxazol-2(3H)-one

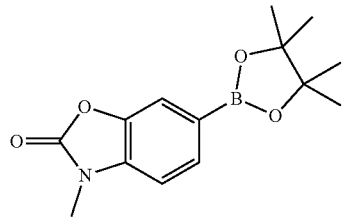 [SMILES: Cn1c(=O)oc2cc(B3OC(C)(C)C(C)(C)O3)ccc21]

A mixture of the crude product from Step 1, 4,4,5,5,4',4',5',5'-octamethyl-[2,2']bi[[1,3,2]dioxaborolanyl] (580 mg, 2.3 mmol), [1,1'-bis(diphenylphosphino)ferrocene]dichloropalladium(II) complexed with dichloromethane (1:1) (60 mg, 0.08 mmol) and potassium acetate (440 mg, 4.5 mmol) in 1,4-dioxane (10 mL) was purged with nitrogen then heated at 90° C. overnight. The reaction mixture was cooled to room temperature then concentrated. The residue was purified by flash chromatography on a silica gel column eluting with 0 to 25% EtOAc/Hexanes to give the desired product. LC-MS calculated for $C_{14}H_{19}BNO_4$ (M+H)$^+$: m/z=276.1. found 276.2.

Step 3: 4-(8-(3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile This compound was prepared using similar procedures as described for Example 1 with 3-methyl-6-(4,4,5,5-tetramethyl-1,3,2-dioxaborolan-2-yl)-1,3-benzoxazol-2(3H)-one (prepared in Step 2) replacing (4-methylphenyl)boronic acid in Step 8. The product was purified by prep-HPLC (pH=2, acetonitrile/water+TFA) to give the desired product as the TFA salt. LC-MS calculated for $C_{28}H_{27}N_6O_3$ (M+H)$^+$: m/z=495.2. found 495.2. $^1$H NMR (500 MHz, DMSO) δ 8.07 (d, J=1.4 Hz, 1H), 7.75 (d, J=8.5 Hz, 2H), 7.71 (d, J=1.4 Hz, 1H), 7.57-7.52 (m, 2H), 7.36 (d, J=1.4 Hz, 1H), 7.21 (d, J=8.1 Hz, 1H), 7.06 (dd, J=8.1, 1.5 Hz, 1H), 4.68-4.62 (m, 1H), 4.59-4.52 (m, 1H), 3.70-3.62 (m, 1H), 3.47-3.40 (m, 1H), 3.35 (s, 3H), 3.00-2.77 (m, 5H), 2.46-2.37 (m, 1H), 1.97-1.85 (m, 2H), 1.82-1.67 (m, 1H), 1.45-1.32 (m, 1H).

Example 8

4-(8-(1-methyl-1H-indazol-5-yl)-5-{[(3R)-1-methylpiperidin-3-yl]methoxy}imidazo[1,2-c]pyrimidin-7-yl)benzonitrile

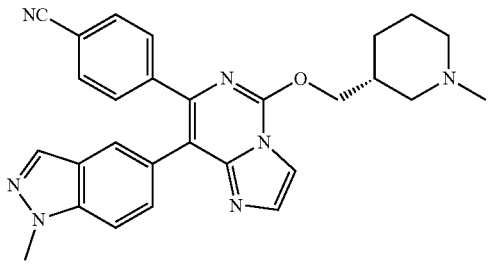 [SMILES: CN1CCC[C@@H](COc2nc(-c3ccc(C#N)cc3)c(-c3ccc4c(cnn4C)c3)c3nccn23)C1]

This compound was prepared using similar procedures as described for Example 1 with 1-methyl-5-(4,4,5,5-tetramethyl-1,3,2-dioxaborolan-2-yl)-1H-indazole (Adv ChemBlocks, cat #C-2063) replacing (4-methylphenyl)boronic acid in Step 8. The product was purified by prep-HPLC (pH=2, acetonitrile/water+TFA) to give the desired product as the TFA salt. LC-MS calculated for $C_{28}H_{28}N_7O$ (M+H)$^+$: m/z=478.2. found 478.2.

Example 9

4-(8-{4-[(4-methylpiperazin-1-yl)methyl]phenyl}-5-{[(3R)-1-methylpiperidin-3-yl]methoxy}imidazo[1,2-c]pyrimidin-7-yl)benzonitrile

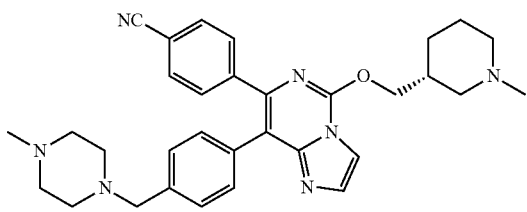

This compound was prepared using similar procedures as described for Example 1 with 1-methyl-4-[4-(4,4,5,5-tetramethyl-1,3,2-dioxaborolan-2-yl)benzyl]piperazine (Combi-Blocks, cat #PN-8801) replacing (4-methylphenyl)boronic acid in Step 8. The reaction mixture was purified by prep-HPLC (pH=10, acetonitrile/water+NH$_4$OH) to give the desired product. LC-MS calculated for $C_{32}H_{38}N_7O$ (M+H)$^+$: m/z=536.3. found 536.3.

Example 10

4-(8-{4-[2-(4-methylpiperazin-1-yl)-2-oxoethyl]phenyl}-5-{[(3R)-1-methylpiperidin-3-yl]methoxy}imidazo[1,2-c]pyrimidin-7-yl)benzonitrile

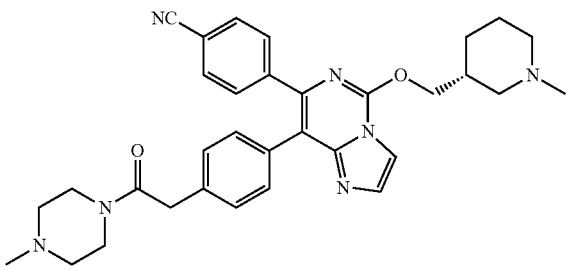

This compound was prepared using similar procedures as described for Example 1 with 1-methyl-4-{[4-(4,4,5,5-tetramethyl-1,3,2-dioxaborolan-2-yl)phenyl]acetyl}piperazine (Combi-Blocks, cat #PN-6945) replacing (4-methylphenyl)boronic acid in Step 8. The reaction mixture was purified by prep-HPLC (pH=10, acetonitrile/water+NH$_4$OH) to give the desired product. LC-MS calculated for $C_{33}H_{38}N_7O_2$ (M+H)$^+$: m/z=564.3. found 564.3.

Example 11

4-{5-{[(3R)-1-methylpiperidin-3-yl]methoxy}-8-[4-(2-morpholin-4-ylethyl)phenyl]imidazo[1,2-c]pyrimidin-7-yl}benzonitrile

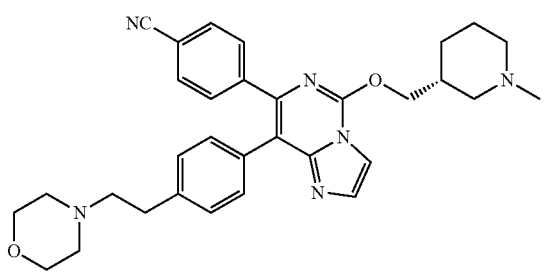 [SMILES: CN1CCC[C@@H](COc2nc(-c3ccc(C#N)cc3)c(-c3ccc(CCN4CCOCC4)cc3)c3nccn23)C1]

This compound was prepared using similar procedures as described for Example 1 with [4-(2-morpholin-4-ylethyl)phenyl]boronic acid (Combi-Blocks, cat #BB-5640) replacing (4-methylphenyl)boronic acid in Step 8. The reaction mixture was purified by prep-HPLC (pH=10, acetonitrile/water+NH$_4$OH) to give the desired product. LC-MS calculated for $C_{32}H_{37}N_6O_2$ (M+H)$^+$: m/z=537.3. found 537.3.

Example 12

4-{5-{[(3R)-1-methylpiperidin-3-yl]methoxy}-8-[4-(morpholin-4-ylmethyl)phenyl]imidazo[1,2-c]pyrimidin-7-yl}benzonitrile

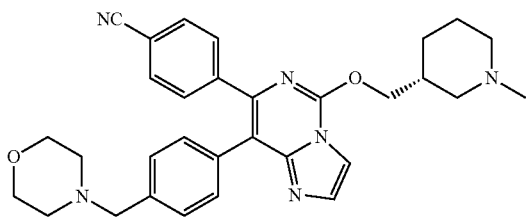 [SMILES: CN1CCC[C@@H](COc2nc(-c3ccc(C#N)cc3)c(-c3ccc(CN4CCOCC4)cc3)c3nccn23)C1]

Step 1: 4-(8-(4-formylphenyl)-5-{[(3R)-1-methylpiperidin-3-yl]methoxy}imidazo[1,2-c]pyrimidin-7-yl)benzonitrile

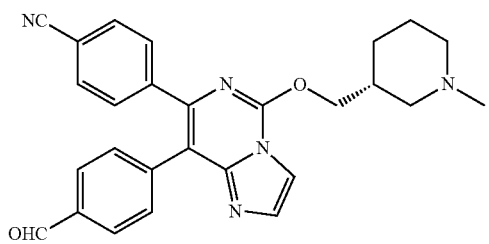 [SMILES: CN1CCC[C@@H](COc2nc(-c3ccc(C#N)cc3)c(-c3ccc(C=O)cc3)c3nccn23)C1]

This compound was prepared using similar procedures as described for Example 1 with (4-formylphenyl)boronic acid (Aldrich, cat #431966) replacing (4-methylphenyl)boronic acid in Step 8. The reaction mixture was purified by flash chromatography on a silica gel column eluting with 0 to 10% MeOH/DCM to give the desired product. LC-MS calculated for $C_{27}H_{26}N_5O_2$ (M+H)$^+$: m/z=452.2. found 452.2.

Step 2: 4-{5-{[(3R)-1-methylpiperidin-3-yl]methoxy}-8-[4-(morpholin-4-ylmethyl)phenyl]imidazo[1,2-c]pyrimidin-7-yl}benzonitrile A mixture of 4-(8-(4-formylphenyl)-5-{[(3R)-1-methylpiperidin-3-yl]methoxy}imidazo[1,2-c]pyrimidin-7-yl)benzonitrile (9.0 mg, 0.020 mmol) and morpholine (20 μL, 0.2 mmol) in methylene chloride (1 mL) was stirred at room temperature for 15 min then sodium triacetoxyborohydride (9.0 mg, 0.043 mmol) was added. The resulting mixture was stirred at room temperature for 2 h then quenched with saturated NaHCO$_3$ solution and extracted with DCM. The combined extracts were dried over Na$_2$SO$_4$ and concentrated. The residue was purified by prep-HPLC (pH=10, acetonitrile/water+NH$_4$OH) to give the desired product. LC-MS calculated for $C_{31}H_{35}N_6O_2$ (M+H)$^+$: m/z=523.3. found 523.2.

Example 13

(3S)-1-[4-(7-(4-cyanophenyl)-5-{[(3R)-1-methylpiperidin-3-yl]methoxy}imidazo[1,2-c]pyrimidin-8-yl)benzyl]pyrrolidine-3-carbonitrile

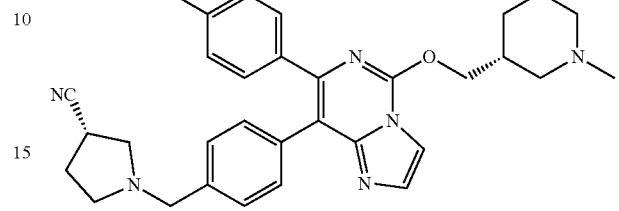

This compound was prepared using similar procedures as described for Example 12 with (3S)-pyrrolidine-3-carbonitrile hydrochloride (Tyger, cat #C90004) replacing morpholine in Step 2. The reaction mixture was purified by prep-HPLC (pH=10, acetonitrile/water+NH$_4$OH) to give the desired product. LC-MS calculated for $C_{32}H_{34}N_7O$ (M+H)$^+$: m/z=532.3. found 532.3.

Example 14

4-(8-(4-methyl-3,4-dihydro-2H-pyrido[3,2-b][1,4]oxazin-7-yl)-5-{[(3R)-1-methylpiperidin-3-yl]methoxy}imidazo[1,2-c]pyrimidin-7-yl)benzonitrile

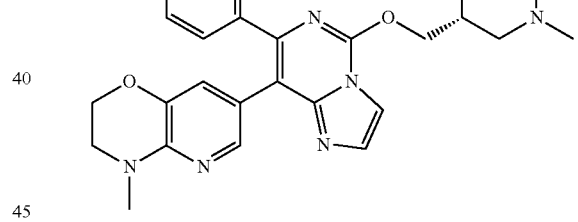

Step 1: 4-methyl-7-(4,4,5,5-tetramethyl-1,3,2-dioxaborolan-2-yl)-3,4-dihydro-2H pyrido[3,2-b][1,4]oxazine

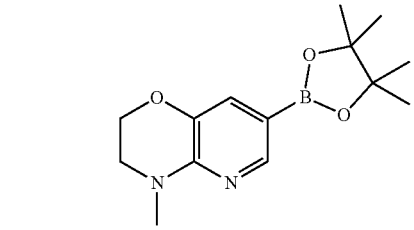 [SMILES: CN1CCOc2cc(B3OC(C)(C)C(C)(C)O3)cnc21]

A mixture of 7-bromo-4-methyl-3,4-dihydro-2H-pyrido[3,2-b][1,4]oxazine (Maybridge, cat #CC62010: 300 mg, 1 mmol), 4,4,5,5,4',4',5',5'-octamethyl-[2,2']bi[[1,3,2]dioxaborolanyl] (660 mg, 2.6 mmol), potassium acetate (380 mg, 3.9 mmol), [1,1'-bis(diphenylphosphino)ferrocene]dichloropalladium(II) complexed with dichloromethane (1:1) (50 mg, 0.06 mmol) in 1,4-dioxane (10 mL, 100 mmol) was purged with nitrogen then heated to 90° C. and stirred overnight. The reaction mixture was cooled to room temperature then concentrated. The residue was purified by flash chromatography on a silica gel column eluting with 0 to 40% EtOAc/DCM to give the desired product. LC-MS calculated for $C_{14}H_{22}BN_2O_3$ (M+H)$^+$: m/z=277.2. found 277.1.

Step 2: 4-(8-(4-methyl-3,4-dihydro-2H pyrido[3,2-b][1,4]oxazin-7-yl)-5-{[(3R)-1-methylpiperidin-3-yl]methoxy}imidazo[1,2-c]pyrimidin-7-yl)benzonitrile This compound was prepared using similar procedures as described for Example 1 with 4-methyl-7-(4,4,5,5-tetramethyl-1,3,2-dioxaborolan-2-yl)-3,4-dihydro-2H-pyrido[3,2-b][1,4]oxazine (prepared in Step 1) replacing (4-methylphenyl)boronic acid in Step 8. The reaction mixture was purified by prep-HPLC (pH=2, acetonitrile/water+TFA) to give the desired product as the TFA salt. LC-MS calculated for $C_{28}H_{30}N_7O_2$ (M+H)$^+$: m/z=496.2; found 496.2.

Example 15

4-(8-(4-methyl-3-oxo-3,4-dihydro-2H-1,4-benzoxazin-7-yl)-5-{[(3R)-1-methylpiperidin-3-yl]methoxy}imidazo[1,2-c]pyrimidin-7-yl)benzonitrile

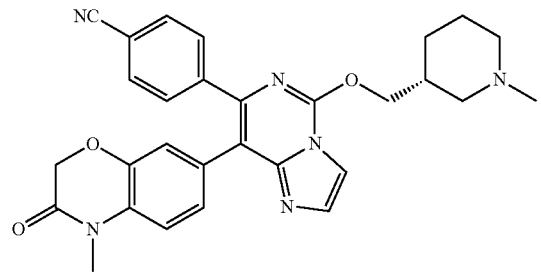 [SMILES: CN1CCC[C@@H](COc2nc(-c3ccc(C#N)cc3)c(-c3ccc4c(c3)OCC(=O)N4C)c3nccn23)C1]

Step 1: 4-methyl-7-(4,4,5,5-tetramethyl-1,3,2-dioxaborolan-2-yl)-2H-1,4-benzoxazin-3(4H)-one

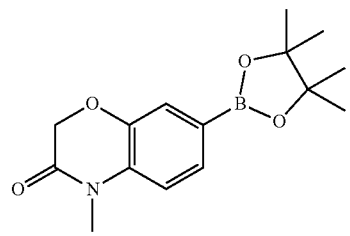 [SMILES: CN1C(=O)COc2cc(B3OC(C)(C)C(C)(C)O3)ccc21]

A mixture of 7-(4,4,5,5-tetramethyl-1,3,2-dioxaborolan-2-yl)-2H-1,4-benzoxazin-3(4H)-one (Combi-Blocks, cat #FM-4852: 0.54 g, 2.0 mmol), methyl iodide (0.18 mL, 2.9 mmol) and potassium carbonate (0.81 g, 5.9 mmol) in N,N-dimethylformamide (8 mL) was stirred at room temperature for 3 h then diluted with water and extracted with EtOAc. The combined extracts were dried over $Na_2SO_4$, filtered and concentrated. The residue was used in the next step without further purification. LC-MS calculated for $C_{15}H_{21}BNO_4$ (M+H)$^+$: m/z=290.2. found 290.1.

Step 2: 4-(8-(4-methyl-3-oxo-3,4-dihydro-2H-1,4-benzoxazin-7-yl)-5-{[(3R)-1-methylpiperidin-3-yl]methoxy}imidazo[1,2-c]pyrimidin-7-yl)benzonitrile This compound was prepared using similar procedures as described for Example 1 with 4-methyl-7-(4,4,5,5-tetramethyl-1,3,2-dioxaborolan-2-yl)-2H-1,4-benzoxazin-3(4H)-one (prepared in Step 1) replacing (4-methylphenyl)boronic acid in Step 8. The reaction mixture was purified by prep-HPLC (pH=2, acetonitrile/water+TFA) to give the desired product as the TFA salt. LC-MS calculated for $C_{29}H_{29}N_6O_3$ (M+H)$^+$: m/z=509.2. found 509.2.

Example 16

4-{5-{[(3R)-1-methylpiperidin-3-yl]methoxy}-8-[6-(2-oxopyrrolidin-1-yl)pyridin-3-yl]imidazo[1,2-c]pyrimidin-7-yl}benzonitrile

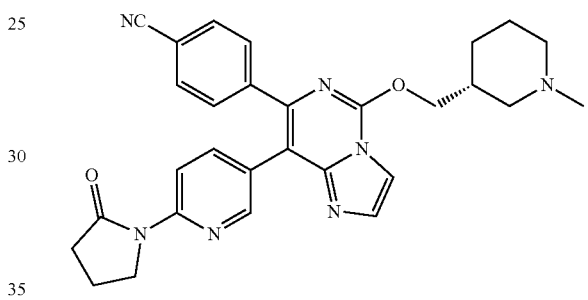

This compound was prepared using similar procedures as described for Example 1 with 1-[5-(4,4,5,5-tetramethyl-1,3,2-dioxaborolan-2-yl)pyridin-2-yl]pyrrolidin-2-one (JPM2 Pharma, cat #JPM2-00-744) replacing (4-methylphenyl)boronic acid in Step 8. The reaction mixture was purified by prep-HPLC (pH=2, acetonitrile/water+TFA) to give the desired product as the TFA salt. LC-MS calculated for $C_{29}H_{30}N_7O_2$ (M+H)$^+$: m/z=508.2. found 508.2.

Example 17

4-(8-(1-methyl-1H-benzimidazol-5-yl)-5-{[(3R)-1-methylpiperidin-3-yl]methoxy}imidazo[1,2-c]pyrimidin-7-yl)benzonitrile

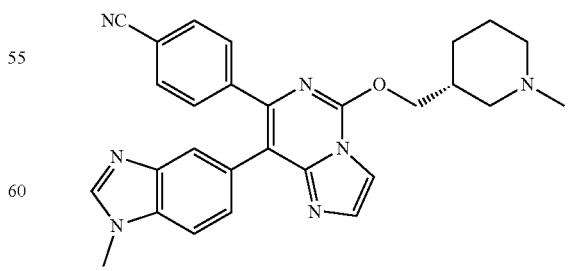

This compound was prepared using similar procedures as described for Example 1 with (1-methyl-1H-benzimidazol-5-yl)boronic acid (Combi-Blocks, cat #FA-4841) replacing (4-methylphenyl)boronic acid in Step 8. The reaction mixture was purified by prep-HPLC (pH=2, acetonitrile/water+TFA) to give the desired product as the TFA salt. LC-MS calculated for $C_{28}H_{28}N_7O$ $(M+H)^+$: m/z=478.2. found 478.2.

Example 18

4-(8-(1-methyl-1H-indazol-6-yl)-5-{[(3R)-1-methylpiperidin-3-yl]methoxy}imidazo[1,2-c]pyrimidin-7-yl)benzonitrile

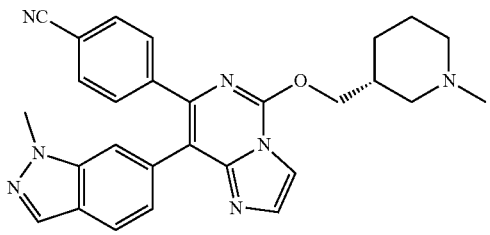 [SMILES: CN1CCC[C@@H](COc2nc(-c3ccc(C#N)cc3)c(-c3ccc4cnn(C)c4c3)c3nccn23)C1]

This compound was prepared using similar procedures as described for Example 1 with (1-methyl-1H-indazol-6-yl) boronic acid (Aldrich, cat #720798) replacing (4-methylphenyl)boronic acid in Step 8. The reaction mixture was purified by prep-HPLC (pH=2, acetonitrile/water+TFA) to give the desired product as the TFA salt. LC-MS calculated for $C_{28}H_{28}N_7O$ $(M+H)^+$: m/z=478.2. found 478.1.

Example 19

4-[5-{[(3R)-1-methylpiperidin-3-yl]methoxy}-8-(1-methyl-1H-pyrrolo[2,3-b]pyridin-5-yl)imidazo[1,2-c]pyrimidin-7-yl]benzonitrile

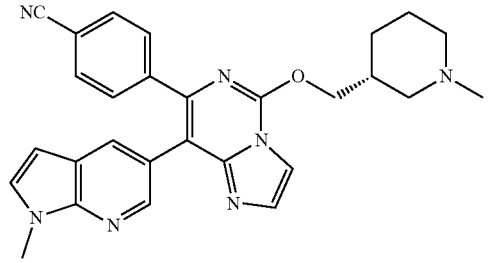 [SMILES: CN1CCC[C@@H](COc2nc(-c3ccc(C#N)cc3)c(-c3cnc4c(ccn4C)c3)c3nccn23)C1]

This compound was prepared using similar procedures as described for Example 1 with 1-methyl-5-(4,4,5,5-tetramethyl-1,3,2-dioxaborolan-2-yl)-1H-pyrrolo[2,3-b]pyridine (AstaTech, cat #37406) replacing (4-methylphenyl)boronic acid in Step 8. The reaction mixture was purified by prep-HPLC (pH=2, acetonitrile/water+TFA) to give the desired product as the TFA salt. LC-MS calculated for $C_{28}H_{28}N_7O$ $(M+H)^+$: m/z=478.2. found 478.4.

Example 20

5-(7-(4-cyanophenyl)-5-{[(3R)-1-methylpiperidin-3-yl]methoxy}imidazo[1,2-c]pyrimidin-8-yl)-N,N-dimethyl-2,3-dihydro-1-benzofuran-2-carboxamide

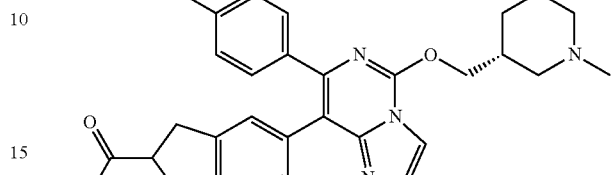

Step 1: 5-bromo-N,N-dimethyl-2,3-dihydro-1-benzofuran-2-carboxamide

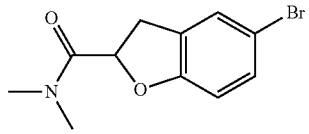

A mixture of 5-bromo-2,3-dihydro-1-benzofuran-2-carboxylic acid (0.50 g, 2.0 mmol), 2.0 M dimethylamine in THF (4 mL, 8 mmol), benzotriazol-1-yloxytris(dimethylamino)phosphonium hexafluorophosphate (1.2 g, 2.7 mmol) in methylene chloride (4 mL) was stirred at room temperature overnight then concentrated. The residue was purified by flash chromatography on a silica gel column eluting with 0 to 40% EtOAc/Hexanes to give the desired product (0.49 g, 88%). LC-MS calculated for $C_{11}H_{13}BrNO_2$ $(M+H)^+$: m/z=270.0. found 270.0.

Step 2: N,N-dimethyl-5-(4,4,5,5-tetramethyl-1,3,2-dioxaborolan-2-yl)-2,3-dihydro-1-benzofuran-2-carboxamide

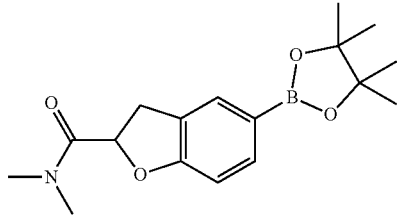

A mixture of 5-bromo-N,N-dimethyl-2,3-dihydro-1-benzofuran-1-carboxamide (0.49 g, 1.8 mmol), 4,4,5,5,4',4',5',5'-Octamethyl-[2,2']bi[[1,3,2]dioxaborolanyl] (0.51 g, 2.0 mmol), potassium acetate (0.44 g, 4.5 mmol) and [1,1'-bis(diphenylphosphino)ferrocene]dichloropalladium(II) complexed with dichloromethane (1:1) (70 mg, 0.09 mmol) and 1,1'-Bis(diphenylphosphino)ferrocene (50 mg, 0.09 mmol) in 1,4-dioxane (9.0 mL) was purged with nitrogen then stirred at 100° C. for 3 h. The reaction mixture was cooled to room temperature and concentrated. The residue was purified by flash chromatography on a silica gel column eluting with 0 to 50% EtOAc/Hexanes to afford the desired product. LC-MS calculated for $C_{17}H_{25}BNO_4$ $(M+H)^+$: m/z=318.2. found 318.1.

Step 3: 5-(7-(4-cyanophenyl)-5-{[(3R)-1-methylpiperidin-3-yl]methoxy}imidazo[1,2-c]pyrimidin-8-yl)-N,N-dimethyl-2,3-dihydro-1-benzofuran-2-carboxamide This compound was prepared using similar procedures as described for Example 1 with N,N-dimethyl-5-(4,4,5,5-tetramethyl-1,3,2-dioxaborolan-2-yl)-2,3-dihydro-1-benzofuran-2-carboxamide (prepared in Step 2) replacing (4-methylphenyl)boronic acid in Step 8. The reaction mixture was purified by prep-HPLC (pH=2, acetonitrile/water+TFA) to give the desired product as the TFA salt. LC-MS calculated for $C_{31}H_{33}N_6O_3$ $(M+H)^+$: m/z=537.3. found 537.3.

Example 21

4-(8-[6-(dimethylamino)pyridin-3-yl]-5-{[(3R)-1-methylpyrrolidin-3-yl]methoxy}imidazo[1,2-c]pyrimidin-7-yl)benzonitrile

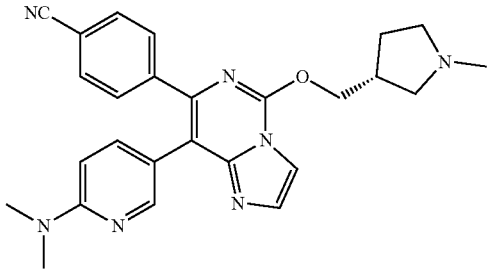

This compound was prepared using similar procedures as described for Example 2 with [6-(dimethylamino)pyridin-3-yl]boronic acid (Combi-Blocks, cat #FA-2296) replacing (4-methylphenyl)boronic acid in Step 2. The reaction mixture was purified by prep-HPLC (pH=10, acetonitrile/water+NH$_4$OH) to give the desired product. LC-MS calculated for $C_{26}H_{28}N_7O$ $(M+H)^+$: m/z=454.2. found 454.2.

Example 22

4-[5-{[(3R)-1-methylpyrrolidin-3-yl]methoxy}-8-(6-pyrrolidin-1-ylpyridin-3-yl)imidazo[1,2-c]pyrimidin-7-yl]benzonitrile

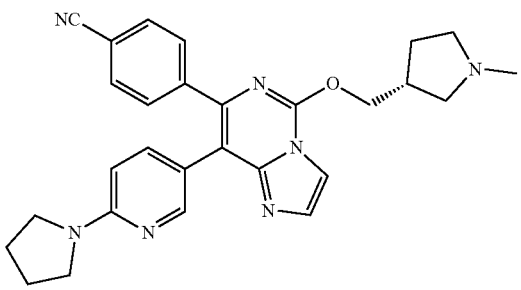 [SMILES: CN1CC[C@@H](COc2nc(-c3ccc(C#N)cc3)c(-c3ccc(N4CCCC4)nc3)c3nccn23)C1]

This compound was prepared using similar procedures as described for Example 2 with 2-pyrrolidin-1-yl-5-(4,4,5,5-tetramethyl-1,3,2-dioxaborolan-2-yl)pyridine (Combi Blocks, cat #PN-8695) replacing (4-methylphenyl)boronic acid in Step 2. The reaction mixture was purified by prep-HPLC (pH=10, acetonitrile/water+NH$_4$OH) to give the desired product. LC-MS calculated for $C_{28}H_{30}N_7O$ $(M+H)^+$: m/z=480.3. found 480.3.

Example 23

4-(8-(1-methyl-2-oxo-2,3-dihydro-1H-indol-5-yl)-5-{[(3R)-1-methylpyrrolidin-3-yl]methoxy}imidazo[1,2-c]pyrimidin-7-yl)benzonitrile

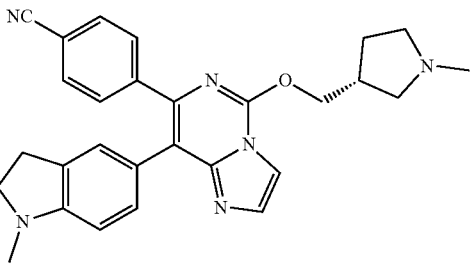

This compound was prepared using similar procedures as described for Example 2 with 1-methyl-5-(4,4,5,5-tetramethyl-1,3,2-dioxaborolan-2-yl)-1,3-dihydro-2H-indol-2-one (Example 6, Step 1) replacing (4-methylphenyl)boronic acid in Step 2. The reaction mixture was purified by prep-HPLC (pH=10, acetonitrile/water+NH$_4$OH) to give the desired product. LC-MS calculated for $C_{28}H_{27}N_6O_2$ $(M+H)^+$: m/z=479.2. found 479.2.

Example 24

4-(8-(4-methyl-3,4-dihydro-2H-pyrido[3,2-b][1,4]oxazin-7-yl)-5-{[(3R)-1-methylpyrrolidin-3-yl]methoxy}imidazo[1,2-c]pyrimidin-7-yl)benzonitrile

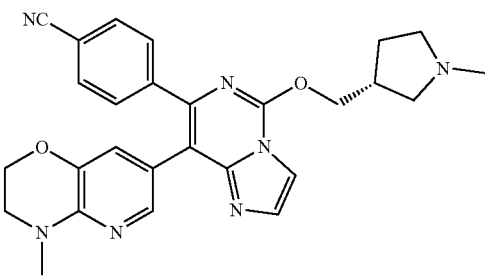 [SMILES: CN1CC[C@@H](COc2nc(-c3ccc(C#N)cc3)c(-c3cnc4c(c3)OCCN4C)c3nccn23)C1]

This compound was prepared using similar procedures as described for Example 2 with 4-methyl-7-(4,4,5,5-tetramethyl-1,3,2-dioxaborolan-2-yl)-3,4-dihydro-2H-pyrido[3,2-b][1,4]oxazine (Example 14, Step 1) replacing (4-methylphenyl)boronic acid in Step 2. The reaction mixture was purified by prep-HPLC (pH=2, acetonitrile/water+TFA) to give the desired product as the TFA salt. LC-MS calculated for $C_{27}H_{28}N_7O_2$ $(M+H)^+$: m/z=482.2; found 482.2.

Example 25

4-(8-(1-methyl-1H-benzimidazol-5-yl)-5-{[(3R)-1-methylpyrrolidin-3-yl]methoxy}imidazo[1,2-c]pyrimidin-7-yl)benzonitrile

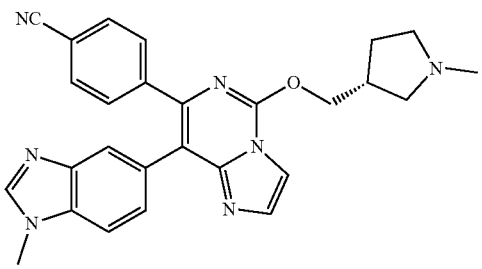 [SMILES: CN1CC[C@@H](COc2nc(-c3ccc(C#N)cc3)c(-c3ccc4c(c3)ncn4C)c3nccn23)C1]

This compound was prepared using similar procedures as described for Example 2 with (1-methyl-1H-benzimidazol-5-yl)boronic acid (Combi-Blocks, cat #FA-4841) replacing (4-methylphenyl)boronic acid in Step 2. The reaction mixture was purified by prep-HPLC (pH=2, acetonitrile/water+TFA) to give the desired product as the TFA salt. LC-MS calculated for $C_{27}H_{26}N_7O$ (M+H)$^+$: m/z=464.2. found 464.2.

Example 26

4-(8-(3-methyl-2-oxo-2,3-dihydro-1,3-benzoxazol-6-yl)-5-{[(3R)-1-methylpyrrolidin-3-yl]methoxy}imidazo[1,2-c]pyrimidin-7-yl)benzonitrile

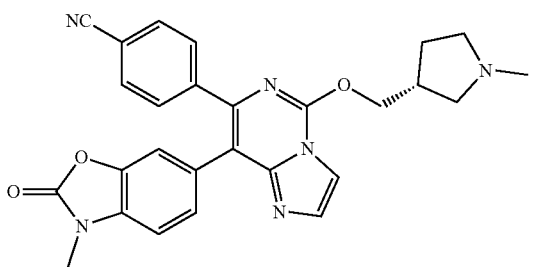 [SMILES: CN1CC[C@@H](COc2nc(-c3ccc(C#N)cc3)c(-c3ccc4c(c3)oc(=O)n4C)c3nccn23)C1]

This compound was prepared using similar procedures as described for Example 2 with 3-methyl-6-(4,4,5,5-tetramethyl-1,3,2-dioxaborolan-2-yl)-1,3-benzoxazol-2(3H)-one (Example 7, Step 2) replacing (4-methylphenyl)boronic acid in Step 2. The reaction mixture was purified by prep-HPLC (pH=10, acetonitrile/water+NH$_4$OH) to give the desired product. LC-MS calculated for $C_{27}H_{25}N_6O_3$ (M+H)$^+$: m/z=481.2. found 481.2.

Example 27

4-(8-(1-methyl-1H-indazol-5-yl)-5-{[(3R)-1-methylpyrrolidin-3-yl]methoxy}imidazo[1,2-c]pyrimidin-7-yl)benzonitrile

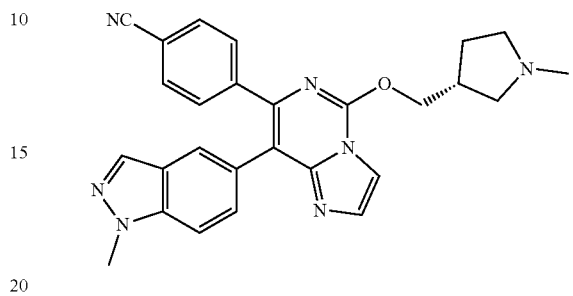

This compound was prepared using similar procedures as described for Example 2 with 1-methyl-5-(4,4,5,5-tetramethyl-1,3,2-dioxaborolan-2-yl)-1H-indazole (Adv Chem-Blocks, cat #C-2063) replacing (4-methylphenyl)boronic acid in Step 2. The reaction mixture was purified by prep-HPLC (pH=10, acetonitrile/water+NH$_4$OH) to give the desired product. LC-MS calculated for $C_{27}H_{26}N_7O$ (M+H)$^+$: m/z=464.2. found 464.3.

Example 28

4-[5-{[(3R)-1-methylpiperidin-3-yl]methoxy}-8-(1-methyl-1H-pyrazolo[3,4-b]pyridin-5-yl)imidazo[1,2-c]pyrimidin-7-yl]benzonitrile

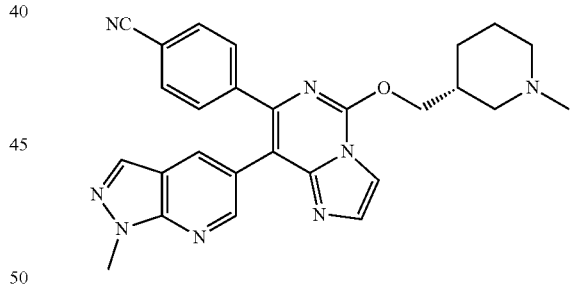

This compound was prepared using similar procedures as described for Example 1 with 1-methyl-5-(4,4,5,5-tetramethyl-1,3,2-dioxaborolan-2-yl)-1H-pyrazolo[3,4-b]pyridine (PharmaBlock, cat #PB02930) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{27}N_8O$ (M+H)$^+$: m/z=479.2. found 479.2. $^1$H NMR (500 MHz, CD$_3$OD) δ 8.38 (d, J=2.1 Hz, 1H), 8.34 (d, J=2.0 Hz, 1H), 8.21 (d, J=1.9 Hz, 1H), 8.14 (s, 1H), 7.86 (d, J=1.8 Hz, 1H), 7.65-7.58 (m, 4H), 4.86-4.83 (m, 1H), 4.77-4.72 (m, 1H), 4.14 (s, 3H), 3.85-3.79 (m, 1H), 3.61-3.55 (m, 1H), 3.08-2.97 (m, 2H), 2.95 (s, 3H), 2.64-2.52 (m, 1H), 2.15-2.05 (m, 2H), 1.96-1.84 (m, 1H), 1.61-1.50 (m, 1H).

Example 29

4-[5-{[(3R)-1-ethylpiperidin-3-yl]methoxy}-8-(1-methyl-1H-pyrazolo[3,4-b]pyridin-5-yl)imidazo[1,2-c]pyrimidin-7-yl]benzonitrile

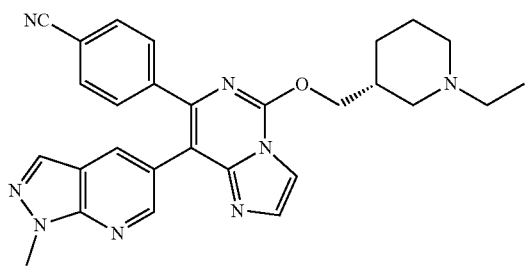 [SMILES: CCN1CCC[C@@H](COc2nc(-c3ccc(C#N)cc3)c(-c3cnc4c(cnn4C)c3)c3nccn23)C1]

Step 1: tert-butyl (3R)-3-({[7-(4-cyanophenyl)-8-(1-methyl-1H-pyrazolo[3,4-b]pyridin-5-yl)imidazo[1,2-c]pyrimidin-5-yl]oxy}methyl)piperidine-1-carboxylate

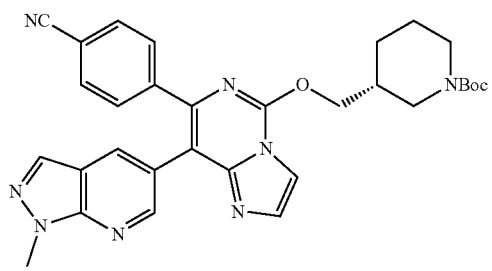 [SMILES: Cn1ncc2cc(-c3c(-c4ccc(C#N)cc4)nc(OC[C@@H]4CCCN(C(=O)OC(C)(C)C)C4)n4ccnc34)cnc21]

A mixture of 1-methyl-5-(4,4,5,5-tetramethyl-1,3,2-dioxaborolan-2-yl)-1H-pyrazolo[3,4-b]pyridine (Pharma-Block, cat #PB02930: 127 mg, 0.492 mmol), tert-butyl (3R)-3-({[8-bromo-7-(4-cyanophenyl)imidazo[1,2-c]pyrimidin-5-yl]oxy}methyl)piperidine-1-carboxylate (prepared in Example 1, Step 5: 126 mg, 0.246 mmol), sodium carbonate (52.1 mg, 0.492 mmol), and dichloro[1,1'-bis(dicyclohexylphosphino)ferrocene]palladium(II) (19 mg, 0.024 mmol) in tert-butyl alcohol (4 mL) and water (2 mL) was first purged with nitrogen, then stirred and heated at 105° C. for 2 h. The reaction mixture was cooled to room temperature then diluted with methylene chloride, washed with saturated NaHCO$_3$, water and brine. The organic layer was dried over Na$_2$SO$_4$, filtered and concentrated. The residue was purified by flash chromatography on a silica gel column eluting with 0 to 10% MeOH in methylene chloride to give the desired product (119 mg, 86%). LCMS calculated for C$_{31}$H$_{33}$N$_8$O$_3$ (M+H)$^+$: m/z=565.3. found 565.2.

Step 2: 4-{8-(1-methyl-1H-pyrazolo[3,4-b]pyridin-5-yl)-5-[(3R) piperidin-3-ylmethoxy]imidazo[1,2-c]pyrimidin-7-yl}benzonitrile

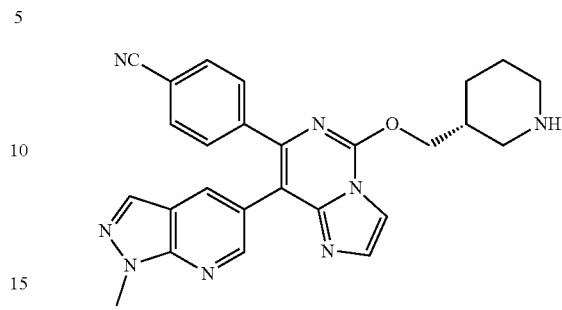

To a solution of tert-butyl (3R)-3-({[7-(4-cyanophenyl)-8-(1-methyl-1H-pyrazolo[3,4-b]pyridin-5-yl)imidazo[1,2-c]pyrimidin-5-yl]oxy}methyl)piperidine-1-carboxylate (29.5 mg, 0.0522 mmol) in methylene chloride (100 μL) was added trifluoroacetic acid (50 μL). The resulting reaction mixture was stirred at room temperature for 30 min then concentrated. The residue was used in the next step without further purification. LC-MS calculated for C$_{26}$H$_{25}$N$_8$O (M+H)$^+$: m/z=465.2. found 465.2.

Step 3: 4-[5-{[(3R)-1-ethylpiperidin-3-yl]methoxy}-8-(1-methyl-1H-pyrazolo[3,4-b]pyridin-5-yl)imidazo[1,2-c]pyrimidin-7-yl]benzonitrile The crude product from Step 2 was dissolved in methylene chloride (0.6 mL) then N,N-diisopropylethylamine (30 μL, 0.2 mmol) was added. The resulting mixture was stirred at room temperature for 10 min then acetaldehyde (17 μL, 0.5 mmol) was added. The resultant reaction mixture was stirred for 30 min then sodium triacetoxyborohydride (30 mg, 0.2 mmol) was added. The reaction mixture was stirred at room temperature for 2 h then diluted with MeOH and purified by prep-HPLC (pH=2, acetonitrile/water+TFA) to give the desired product as the TFA salt. LC-MS calculated for C$_{28}$H$_{29}$N$_8$O (M+H)$^+$: m/z=493.2. found 493.3. $^1$H NMR (500 MHz, CD$_3$OD) δ 8.40-8.35 (m, 3H), 8.15 (s, 1H), 8.01 (d, J=2.1 Hz, 1H), 7.66-7.60 (m, 4H), 4.93-4.88 (m, 1H), 4.83-4.77 (m, 1H), 4.14 (s, 3H), 3.91-3.83 (m, 1H), 3.69-3.60 (m, 1H), 3.30-3.22 (m, 2H), 3.06-2.91 (m, 2H), 2.72-2.59 (m, 1H), 2.17-2.07 (m, 2H), 2.02-1.88 (m, 1H), 1.67-1.55 (m, 1H), 1.39 (t, J=7.3 Hz, 3H).

Example 30

4-(8-[3-fluoro-4-(hydroxymethyl)-5-methylphenyl]-5-{[(3R)-1-methylpiperidin-3-yl]methoxy}imidazo[1,2-c]pyrimidin-7-yl)benzonitrile

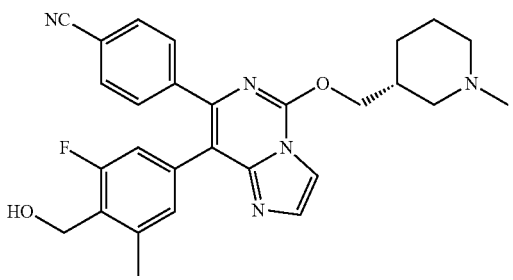 [SMILES: Cc1cc(-c2c(-c3ccc(C#N)cc3)nc(OC[C@@H]3CCCN(C)C3)n3ccnc23)cc(F)c1CO]

Step 1: [2 fluoro-6-methyl-4-(4,4,5,5-tetramethyl-1,3,2-dioxaborolan-2-yl)phenyl]methanol

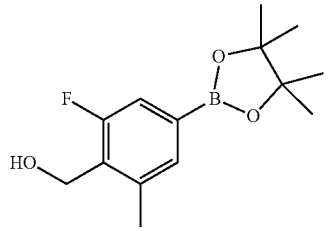 [SMILES: Cc1cc(B2OC(C)(C)C(C)(C)O2)cc(F)c1CO]

This compound was prepared using similar procedures as described for Example 6 with (4-bromo-2-fluoro-6-methylphenyl)methanol (Oxchem, cat #AX8271172) replacing 5-bromo-1-methyl-1,3-dihydro-2H-indol-2-one in Step 1. The reaction mixture was filtered through celite, then concentrated. The crude product was used without further purification. LC-MS calculated for $C_{14}H_{19}BFO_2$ (M+H-H2O)$^+$: m/z=249.1. found 249.1.

Step 2: 4-(8-[3 fluoro-4-(hydroxymethyl)-5-methylphenyl]-5-{[(3R)-1-methylpiperidin-3-yl]methoxy}imidazo[1,2-c]pyrimidin-7-yl)benzonitrile This compound was prepared using similar procedures as described for Example 1 with [2-fluoro-6-methyl-4-(4,4,5,5-tetramethyl-1,3,2-dioxaborolan-2-yl)phenyl]methanol replacing (4-methylphenyl)boronic acid in Step 8. The resulting mixture was purified by prep-HPLC (pH=2, acetonitrile/water+TFA) to give the desired product as the TFA salt. LC-MS calculated for $C_{28}H_{29}FN_5O_2$ (M+H)$^+$: m/z=486.2. found 486.2. $^1$H NMR (400 MHz, CD$_3$OD) δ 8.29 (d, J=2.1 Hz, 1H), 7.95 (d, J=2.1 Hz, 1H), 7.71-7.63 (m, 4H), 7.07 (s, 1H), 6.97 (d, J=9.8 Hz, 1H), 4.86-4.83 (m, 2H, overlapped with H$_2$O peak), 4.76-4.72 (m, 2H), 3.87-3.78 (m, 1H), 3.62-3.52 (m, 1H), 3.09-2.96 (m, 2H), 2.94 (s, 3H), 2.67-2.54 (m, 1H), 2.44 (s, 3H), 2.15-2.03 (m, 2H), 2.02-1.84 (m, 1H), 1.62-1.47 (m, 1H).

Example 31

4-(8-[3-fluoro-4-(hydroxymethyl)phenyl]-5-{[(3R)-1-methylpiperidin-3-yl]methoxy}imidazo[1,2-c]pyrimidin-7-yl)benzonitrile

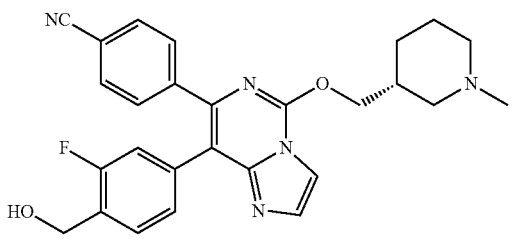 [SMILES: CN1CCC[C@@H](COc2nc(-c3ccc(C#N)cc3)c(-c3ccc(CO)c(F)c3)c3nccn23)C1]

This compound was prepared using similar procedures as described for Example 1 with 3-fluoro-4-hydroxymethylbenzeneboronic acid (Combi-Blocks, cat #FA-4306) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{27}FN_5O_2$ (M+H)$^+$: m/z=472.2. found 472.2.

Example 32

4-(8-[3,5-difluoro-4-(hydroxymethyl)phenyl]-5-{[(3R)-1-methylpiperidin-3-yl]methoxy}imidazo[1,2-c]pyrimidin-7-yl)benzonitrile

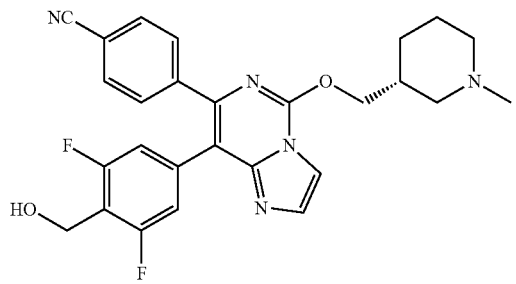

This compound was prepared using similar procedures as described for Example 1 with 3,5-difluoro-4-(hydroxymethyl)phenylboronic acid (Combi-Blocks, cat #BB-8390) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{26}F_2N_5O_2$ (M+H)$^+$: m/z=490.2. found 490.2.

Example 33

4-[5-{[(3R)-1-(2-cyanoethyl)piperidin-3-yl]methoxy}-8-(1-methyl-1H-pyrazolo[3,4-b]pyridin-5-yl)imidazo[1,2-c]pyrimidin-7-yl]benzonitrile

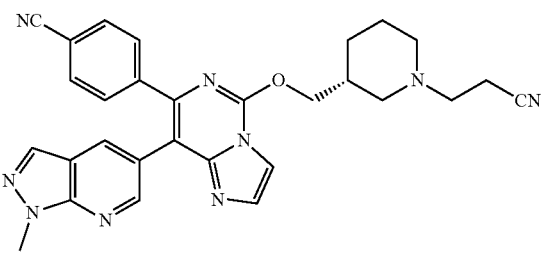 [SMILES: Cn1ncc2cc(-c3c(-c4ccc(C#N)cc4)nc(OC[C@@H]4CCCN(CCC#N)C4)n4ccnc34)cnc21]

To a solution of 2-propenenitrile (2.0 μL, 0.030 mmol) and 4-{8-(1-methyl-1H-pyrazolo[3,4-b]pyridin-5-yl)-5-[(3R)-piperidin-3-ylmethoxy]imidazo[1,2-c]pyrimidin-7-yl}benzonitrile (prepared in Example 29, Step 2: 10 mg, 0.02 mmol) in acetonitrile (0.4 mL) was added 1,8-diazabicyclo[5.4.0]undec-7-ene (9 μL, 0.06 mmol). The reaction mixture was stirred at 80° C. for 3 h. The mixture was cooled to room temperature, diluted with methanol then purified by prep-HPLC (pH=2, acetonitrile/water+TFA) to give the desired product as the TFA salt. LC-MS calculated for $C_{29}H_{28}N_9O$ (M+H)$^+$: m/z=518.2. found 518.1.

Example 34

4-[5-{[(3R)-1-(2-hydroxyethyl)piperidin-3-yl]methoxy}-8-(1-methyl-1H-pyrazolo[3,4-b]pyridin-5-yl)imidazo[1,2-c]pyrimidin-7-yl]benzonitrile

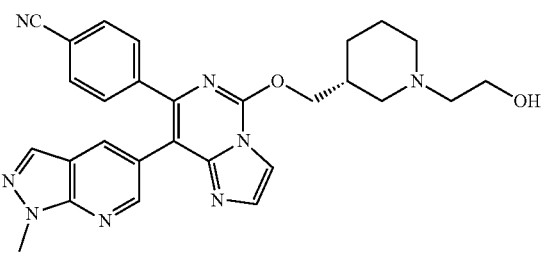 [SMILES: Cn1ncc2cc(-c3c(-c4ccc(C#N)cc4)nc(OC[C@@H]4CCCN(CCO)C4)n4ccnc34)cnc21]

To a solution of 4-{8-(1-methyl-1H-pyrazolo[3,4-b]pyridin-5-yl)-5-[(3R)-piperidin-3-ylmethoxy]imidazo[1,2-c]pyrimidin-7-yl}benzonitrile (prepared in Example 29, Step 2: 10 mg, 0.02 mmol) and 2-bromoethanol (7 µL, 0.1 mmol) in N,N-dimethylformamide (0.4 mL) was added potassium carbonate (30 mg, 0.2 mmol). The reaction mixture was stirred at 45° C. for 2 h. The mixture was cooled to room temperature, filtered and purified by prep-HPLC (pH=2, acetonitrile/water+TFA) to give the desired product as the TFA salt. LC-MS calculated for $C_{28}H_{29}N_8O_2$ (M+H)$^+$: m/z=509.2. found 509.2.

Example 35

4-(8-[4-(hydroxymethyl)-3-methylphenyl]-5-{[(3R)-1-methylpiperidin-3-yl]methoxy}imidazo[1,2-c]pyrimidin-7-yl)benzonitrile

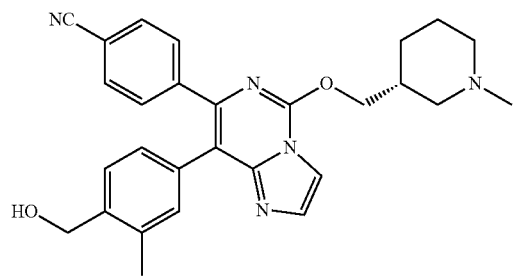

This compound was prepared using similar procedures as described for Example 1 with 4-hydroxymethyl-3-methylphenylboronic acid (Aurum Pharmatech, cat #B-6677) replacing (4-methylphenyl)boronic acid in Step 8. The resulting mixture was purified by prep-HPLC (pH=2, acetonitrile/water+TFA) to give the desired product as the TFA salt. LC-MS calculated for $C_{28}H_{30}N_5O_2$ (M+H)$^+$: m/z=468.2. found 468.2.

Example 36

4-(8-[4-(hydroxymethyl)phenyl]-5-{[(3R)-1-methylpiperidin-3-yl]methoxy}imidazo[1,2-c]pyrimidin-7-yl)benzonitrile

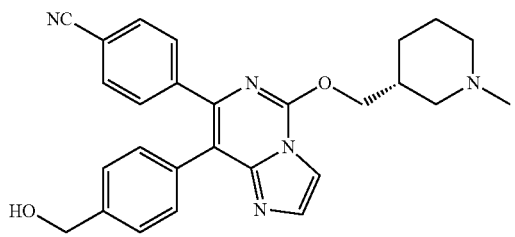 [SMILES: CN1CCC[C@@H](COc2nc(-c3ccc(C#N)cc3)c(-c3ccc(CO)cc3)c3nccn23)C1]

This compound was prepared using similar procedures as described for Example 1 with 4-hydroxymethylbenzeneboronic acid (Combi-Blocks, cat #BB-2317) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{28}N_5O_2$ (M+H)$^+$: m/z=454.2. found 454.2.

Example 37

4-[5-[4-(dimethylamino)piperidin-1-yl]-8-(1-methyl-1H-pyrazolo[3,4-b]pyridin-5-yl)imidazo[1,2-c]pyrimidin-7-yl]benzonitrile

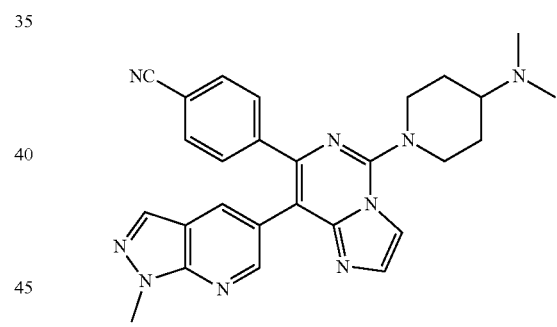

Step 1: 4-{8-bromo-5-[4-(dimethylamino)piperidin-1-yl]imidazo[1,2-c]pyrimidin-7-yl}benzonitrile

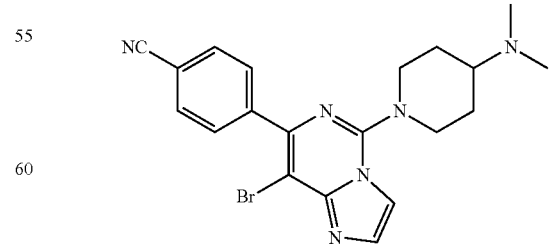

To a mixture of N,N-diisopropylethylamine (0.63 mL, 3.6 mmol) and 4-(8-bromo-5-chloroimidazo[1,2-c]pyrimidin-7-yl)benzonitrile (prepared in Example 1, Step 4: 600, mg, 1.80 mmol) in acetonitrile (10 mL) was added N,N-dimethylpiperidin-4-amine (Alfa Aesar, cat #L20176: 0.51 mL, 3.6 mmol). The resulting reaction mixture was stirred at room temperature for 1 h then water (80 mL) was added. The resulting precipitate was collected via filtration then washed with water and dried to give the desired product (660 mg, 86%), which was used in the next step without further purification. LC-MS calculated for $C_{20}H_{22}BrN_6$ (M+H)$^+$: m/z=425.1; found 425.1.

Step 2: 4-[5-[4-(dimethylamino)piperidin-1-yl]-8-(1-methyl-1H-pyrazolo[3,4-b]pyridin-5-yl)imidazo[1,2-c]pyrimidin-7-yl]benzonitrile A mixture of 1-methyl-5-(4,4,5,5-tetramethyl-1,3,2-dioxaborolan-2-yl)-1H-pyrazolo[3,4-b]pyridine (PharmaBlock, cat #PB02930: 366 mg, 1.41 mmol), 4-{8-bromo-5-[4-(dimethylamino)piperidin-1-yl]imidazo[1,2-c]pyrimidin-7-yl}benzonitrile (300 mg, 0.71 mmol), sodium carbonate (150 mg, 1.41 mmol), and dichloro[1,1'-bis(dicyclohexylphosphino)ferrocene]palladium(II) (53 mg, 0.07 mmol) in tert-butyl alcohol (10 mL) and water (6 mL) was first purged with nitrogen, then heated to 95° C. and stirred for 3 h. The reaction mixture was cooled to room temperature then purified by prep-HPLC (pH=2, acetonitrile/water+TFA) to give the desired product as the TFA salt. LC-MS calculated for $C_{27}H_{28}N_9$ (M+H)$^+$: m/z=478.2. found 478.2. $^1$H NMR (400 MHz, CD$_3$OD) δ 8.38 (d, J=2.0 Hz, 1H), 8.33 (d, J=2.0 Hz, 1H), 8.18 (d, J=2.1 Hz, 1H), 8.15 (s, 1H), 7.97 (d, J=2.1 Hz, 1H), 7.67-7.57 (m, 4H), 4.43-4.33 (m, 2H), 4.14 (s, 3H), 3.69-3.57 (m, 1H), 3.41-3.32 (m, 2H), 2.96 (s, 6H), 2.36-2.26 (m, 2H), 2.19-2.05 (m, 2H).

Example 38

4-[5-[(3R)-3-(dimethylamino)pyrrolidin-1-yl]-8-(1-methyl-1H-pyrazolo[3,4-b]pyridin-5-yl)imidazo[1,2-c]pyrimidin-7-yl]benzonitrile

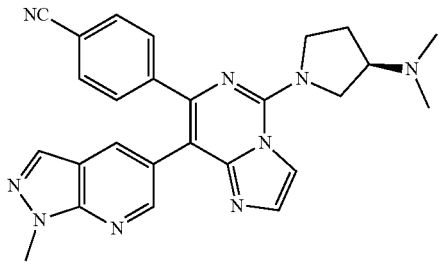 [SMILES: CN(C)[C@@H]1CCN(c2nc(-c3ccc(C#N)cc3)c(-c3cnc4c(cnn4C)c3)c3nccn23)C1]

Step 1: 4-{8-bromo-5-[(3R)-3-(dimethylamino)pyrrolidin-1-yl]imidazo[1,2-c]pyrimidin-7-yl}benzonitrile

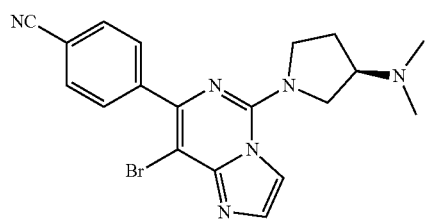 [SMILES: CN(C)[C@@H]1CCN(c2nc(-c3ccc(C#N)cc3)c(Br)c3nccn23)C1]

(3R)—N,N-dimethylpyrrolidin-3-amine (Aldrich, cat #656712: 6.8 mg, 0.060 mmol) was added to a solution of 4-(8-bromo-5-chloroimidazo[1,2-c]pyrimidin-7-yl)benzonitrile (prepared in Example 1, Step 4: 10 mg, 0.03 mmol) in N,N-dimethylformamide (0.2 mL). The reaction mixture was microwaved at 120° C. for 10 min. and then cooled to room temperature and concentrated to dryness. The crude reaction mixture was used in the next step without further purification. LC-MS calculated for $C_{19}H_{20}BrN_6$ (M+H)$^+$: m/z=411.1. found 411.2.

Step 2: 4-[5-[(3R)-3-(dimethylamino)pyrrolidin-1-yl]-8-(1-methyl-1H-pyrazolo[3,4-b]pyridin-5-yl)imidazo[1,2-c]pyrimidin-7-yl]benzonitrile This compound was prepared using similar procedures as described for Example 37 with 4-{8-bromo-5-[(3R)-3-(dimethylamino)pyrrolidin-1-yl]imidazo[1,2-c]pyrimidin-7-yl}benzonitrile replacing 4-{8-bromo-5-[4-(dimethylamino)piperidin-1-yl]imidazo[1,2-c]pyrimidin-7-yl}benzonitrile in Step 2. The resulting mixture was purified by prep-HPLC (pH=2, acetonitrile/water+TFA) to give the desired product as the TFA salt. LC-MS calculated for $C_{26}H_{26}N_9$ (M+H)$^+$: m/z=464.2. found 464.2.

Example 39

4-[5-(7-methyl-2,7-diazaspiro[4.4]non-2-yl)-8-(1-methyl-1H-pyrazolo[3,4-b]pyridin-5-yl)imidazo[1,2-c]pyrimidin-7-yl]benzonitrile

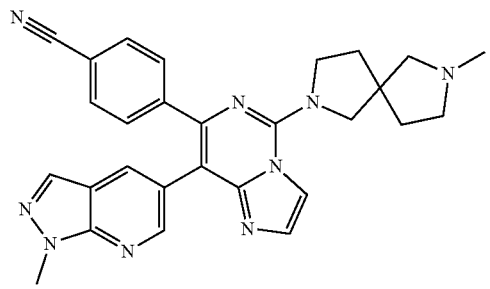 [SMILES: CN1CCC2(CCN(c3nc(-c4ccc(C#N)cc4)c(-c4cnc5c(cnn5C)c4)c4nccn34)C2)C1]

Step 1: tert-butyl 7-[8-bromo-7-(4-cyanophenyl)imidazo[1,2-c]pyrimidin-5-yl]-2,7-diazaspiro[4.4]nonane-2-carboxylate

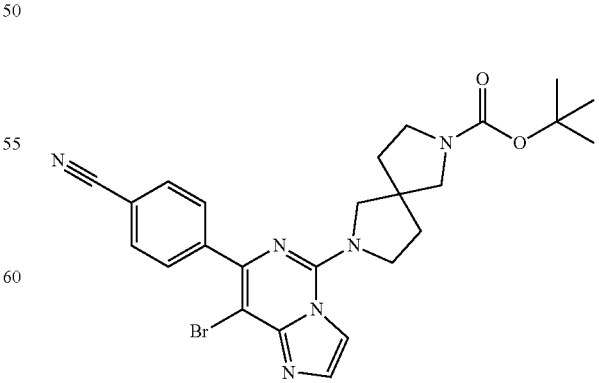

This compound was prepared using similar procedures as described for Example 38 with tert-butyl 2,7-diazaspiro[4.4]

nonane-2-carboxylate (Synthonix, cat #D5983) replacing (3R)—N,N-dimethylpyrrolidin-3-amine in Step 1. The reaction mixture was concentrated and the residue was used in the next step without further purification. LC-MS calculated for $C_{25}H_{28}BrN_6O_2$ (M+H)$^+$: m/z=523.1. found 523.2.

Step 2: tert-butyl 7-[7-(4-cyanophenyl)-8-(1-methyl-1H-pyrazolo[3,4-b]pyridin-5-yl)imidazo[1,2-c]pyrimidin-5-yl]-2,7-diazaspiro[4.4]nonane-2-carboxylate

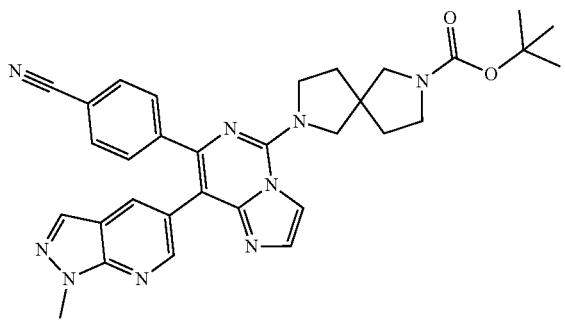 [SMILES: Cn1ncc2cc(-c3c(-c4ccc(C#N)cc4)nc(N4CCC5(CCN(C(=O)OC(C)(C)C)C5)C4)n4ccnc34)cnc21]

This compound was prepared using similar procedures as described for Example 37, Step 2 with tert-butyl 7-[8-bromo-7-(4-cyanophenyl)imidazo[1,2-c]pyrimidin-5-yl]-2,7-diazaspiro[4.4]nonane-2-carboxylate replacing 4-{8-bromo-5-[4-(dimethylamino)piperidin-1-yl]imidazo[1,2-c]pyrimidin-7-yl}benzonitrile. The reaction mixture was diluted with methylene chloride, washed with saturated NaHCO₃, water and brine. The organic layer was dried over Na₂SO₄, filtered and concentrated. The residue was used in the next step without further purification. LC-MS calculated for $C_{32}H_{34}N_9O_2$ (M+H)$^+$: m/z=576.3. found 576.2.

Step 3: 4-[5-(7-methyl-2,7-diazaspiro[4.4]non-2-yl)-8-(1-methyl-1H-pyrazolo[3,4-b]pyridin-5-yl)imidazo[1,2-c]pyrimidin-7-yl]benzonitrile To the solution of tert-butyl 7-[7-(4-cyanophenyl)-8-(1-methyl-1H-pyrazolo[3,4-b]pyridin-5-yl)imidazo[1,2-c]pyrimidin-5-yl]-2,7-diazaspiro[4.4]nonane-2-carboxylate (20 mg) in methylene chloride (0.4 mL) was added trifluoroacetic acid (0.1 mL). The resulting mixture was stirred at room temperature for 1 h then concentrated. The residue was dissolved in acetonitrile (0.4 mL) then N,N-diisopropylethylamine (50 µL, 0.3 mmol) was added, followed by the addition of 7.0 M formaldehyde in water (0.08 mL, 0.6 mmol). The resulting mixture was stirred at room temperature for 30 min then sodium triacetoxyborohydride (60 mg, 0.3 mmol) was added. The reaction mixture was stirred at room temperature for 2 h then quenched with MeOH and purified by prep-HPLC (pH=2, acetonitrile/water+TFA) to give the desired product as the TFA salt. LC-MS calculated for $C_{28}H_{28}N$ (M+H)$^+$: m/z=490.2. found 490.2.

Example 40 methyl [4-(7-(4-cyanophenyl)-5-{[(3R)-1-methylpiperidin-3-yl]methoxy}imidazo[1,2-c]pyrimidin-8-yl)-2-fluorobenzyl]methylcarbamate

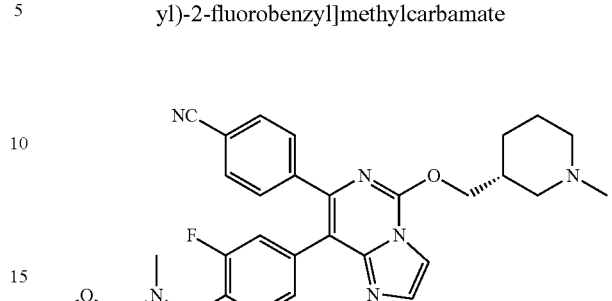

Step 1: 1-[2 fluoro-4-(4,4,5,5-tetramethyl-1,3,2-dioxaborolan-2-yl)phenyl]-N-methylmethanamine

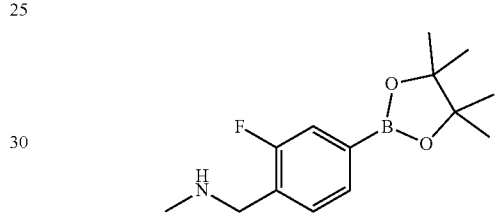

To a solution of 2.0 M methylamine in tetrahydrofuran (3 mL, 6 mmol) was added dropwise a solution of 2-[4-(bromomethyl)-3-fluorophenyl]-4,4,5,5-tetramethyl-1,3,2-dioxaborolane (Combi-Blocks, cat #PN-5654: 200 mg, 0.6 mmol) in tetrahydrofuran (10 mL). The reaction mixture was stirred at room temperature for 2 h, then concentrated. The crude product was used in the next step without further purification.

Step 2: methyl [2 fluoro-4-(4,4,5,5-tetramethyl-1,3,2-dioxaborolan-2-yl)benzyl]methylcarbamate

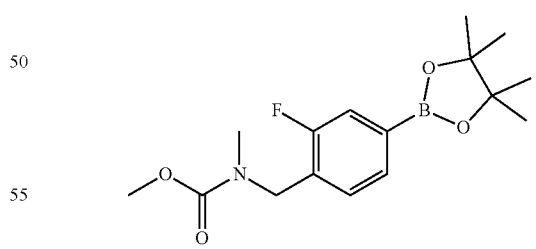

To a solution of 1-[2-fluoro-4-(4,4,5,5-tetramethyl-1,3,2-dioxaborolan-2-yl)phenyl]-N-methylmethanamine (40 mg, 0.2 mmol) and N,N-diisopropylethylamine (0.056 mL, 0.32 mmol) in methylene chloride (2 mL) was added methyl chloroformate (19 µL, 0.24 mmol). The reaction was stirred at room temperature for 2 h, then concentrated. The crude product was used in the next step without further purification. LC-MS calculated for $C_{16}H_{24}BFNO_4$ (M+H)$^+$: m/z=324.2. found 324.2.

Step 3: methyl [4-(7-(4-cyanophenyl)-5-{[(3R)-1-methylpiperidin-3-yl]methoxy}imidazo[1,2-c]pyrimidin-8-yl)-2-fluorobenzyl]methylcarbamate This compound was prepared using similar procedures as described for Example 1 with methyl [2-fluoro-4-(4,4,5,5-tetramethyl-1,3,2-dioxaborolan-2-yl)benzyl]methylcarbamate replacing (4-methylphenyl)boronic acid in Step 8. The resulting mixture was purified by prep-HPLC (pH=2, acetonitrile/water+TFA) to give the desired product as the TFA salt. LC-MS calculated for $C_{30}H_{32}FN_6O_3$ (M+H)+: m/z=543.2. found 543.3.

Example 41

4-[5-{[(3R)-1-(2-methoxyethyl)piperidin-3-yl]methoxy}-8-(1-methyl-1H-pyrazolo[3,4-b]pyridin-5-yl)imidazo[1,2-c]pyrimidin-7-yl]benzonitrile

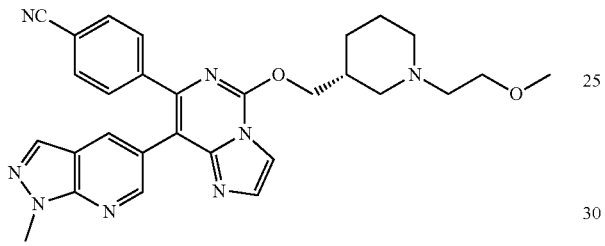

This compound was prepared using similar procedures as described for Example 34 with 1-bromo-2-methoxyethane replacing 2-bromoethanol. The resulting mixture was purified by prep-HPLC (pH=2, acetonitrile/water+TFA) to give the desired product as the TFA salt. LC-MS calculated for $C_{29}H_{32}N_8O_2$ (M+H)+: m/z=523.3. found 523.3.

Example 42

4-(8-(3-amino-1-methyl-1H-indazol-5-yl)-5-{[(3R)-1-methylpiperidin-3-yl]methoxy}imidazo[1,2-c]pyrimidin-7-yl)benzonitrile

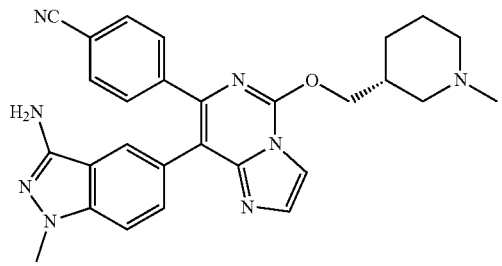 [SMILES: CN1CCC[C@@H](COc2nc(-c3ccc(C#N)cc3)c(-c3ccc4c(c3)c(N)nn4C)c3nccn23)C1]

This compound was prepared using similar procedures as described for Example 1 with 1-methyl-5-(4,4,5,5-tetramethyl-1,3,2-dioxaborolan-2-yl)-1H-indazol-3-amine (Combi Blocks, cat #FF-5931) replacing (4-methylphenyl)boronic acid in Step 8. The resulting mixture was purified by prep-HPLC (pH=2, acetonitrile/water+TFA) to give the desired product as the TFA salt. LC-MS calculated for $C_{28}H_{29}N_8O$ (M+H)+: m/z=493.2. found 493.2.

Example 43

4-(8-(3-methyl-2-oxo-3,4-dihydro-2H-1,3-benzoxazin-7-yl)-5-{[(3R)-1-methylpiperidin-3-yl]methoxy}imidazo[1,2-c]pyrimidin-7-yl)benzonitrile

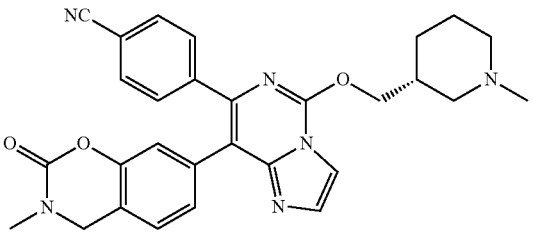

Step 1: 5-bromo-2-[(methylamino)methyl]phenol

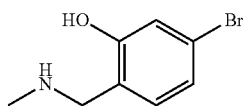

To a solution of 4-bromo-2-hydroxybenzaldehyde (Ark Pharm, cat #AK-24055: 800 mg, 4 mmol) and methylamine (4.0 mL, 30, mmol) in 1,2-dichloroethane (20 mL, 200 mmol) was added sodium triacetoxyborohydride (1.3 g, 6.0 mmol). The reaction mixture was stirred at rt for 2 h. The reaction mixture was then diluted with methylene chloride, washed with saturated NaHCO₃. The aqueous phase was extracted with methylene chloride. The organic layer was dried over Na₂SO₄, filtered and concentrated. The residue was concentrated and used for next step without further purification. LC-MS calculated for $C_8H_{11}BrNO_4$ (M+H)+: m/z=216.1; found 216.1.

Step 2: 7-bromo-3-methyl-3,4-dihydro-2H-1,3-benzoxazin-2-one

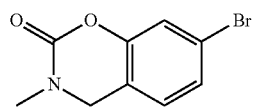

To a solution of 5-bromo-2-[(methylamino)methyl]phenol (crude product from Step 1) and triethylamine (3 mL, 20 mmol) in tetrahydrofuran (30 mL) was added triphosgene (1.4 g, 4.8 mmol) at 0° C. The resulting mixture was stirred for 1 h before 1M NaOH (2 mL) was added. The reaction mixture was allowed to stir for another 1 h, then diluted with methylene chloride, washed with saturated NaHCO₃. The aqueous phase was extracted with methylene chloride. The combined organic layers were dried over Na₂SO₄, filtered and concentrated. The residue was used in the next step without further purification. LC-MS calculated for $C_9H_9BrNO_2$ (M+H)+: m/z=242.1. found 242.1.

Step 3: 3-methyl-7-(4,4,5,5-tetramethyl-1,3,2-dioxaborolan-2-yl)-3,4-dihydro-2H-1,3-benzoxazin-2-one

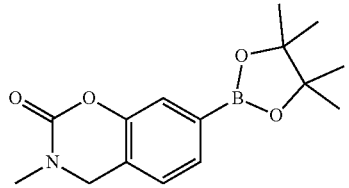 [SMILES: CN1Cc2ccc(B3OC(C)(C)C(C)(C)O3)cc2OC1=O]

This compound was prepared using similar procedures as described for Example 6, Step 1 with 7-bromo-3-methyl-3,4-dihydro-2H-1,3-benzoxazin-2-one (crude product from Step 2) replacing 5-bromo-1-methyl-1,3-dihydro-2H-indol-2-one. After cooling to room temperature, the reaction mixture was concentrated, diluted with methylene chloride, washed over saturated NaHCO$_3$. The aqueous phase was extracted with methylene chloride. The organic layer was dried over Na$_2$SO$_4$, filtered and concentrated. The residue was purified by flash chromatography on a silica gel column eluting with 0 to 25% AcOEt in hexanes to give the desired product. LC-MS calculated for C$_{15}$H$_{21}$BNO$_4$ (M+H)$^+$: m/z=290.2. found 290.1.

Step 4: 4-(8-(3-methyl-2-oxo-3,4-dihydro-2H-1,3-benzoxazin-7-yl)-5-{[(3R)-1-methylpiperidin-3-yl]methoxy}imidazo[1,2-c]pyrimidin-7-yl)benzonitrile This compound was prepared using similar procedures as described for Example 1 with 3-methyl-7-(4,4,5,5-tetramethyl-1,3,2-dioxaborolan-2-yl)-3,4-dihydro-2H-1,3-benzoxazin-2-one replacing (4-methylphenyl)boronic acid in Step 8. The resulting mixture was purified by prep-HPLC (pH=2, acetonitrile/water+TFA) to give the desired product as the TFA salt. LC-MS calculated for C$_{29}$H$_{29}$N$_6$O$_3$ (M+H)$^+$: m/z=509.2. found 509.3.

Example 44

4-(8-(1,3-dimethyl-2-oxo-2,3-dihydro-1H-benzimidazol-5-yl)-5-{[(3R)-1-methylpiperidin-3-yl]methoxy}imidazo[1,2-c]pyrimidin-7-yl)benzonitrile

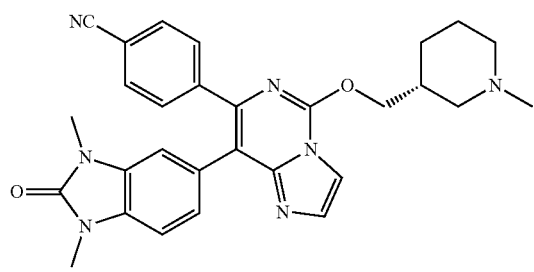 [SMILES: CN1CCC[C@@H](COc2nc(-c3ccc(C#N)cc3)c(-c3ccc4c(c3)n(C)c(=O)n4C)c3nccn23)C1]

Step 1: 1,3-dimethyl-5-(4,4,5,5-tetramethyl-1,3,2-dioxaborolan-2-yl)-1,3-dihydro-2H-benzimidazol-2-one

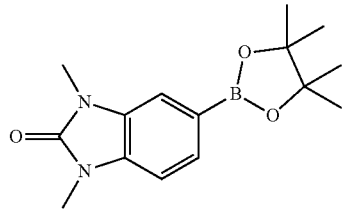 [SMILES: Cn1c(=O)n(C)c2cc(B3OC(C)(C)C(C)(C)O3)ccc21]

This compound was prepared using similar procedures as described for Example 6, Step 1 with 5-bromo-1,3-dimethyl-1,3-dihydro-2H-benzimidazol-2-one (Aurum Pharmatech, cat #NE22745) replacing 5-bromo-1-methyl-1,3-dihydro-2H-indol-2-one. After cooling to room temperature, the reaction mixture was concentrated, diluted with methylene chloride then washed with saturated NaHCO$_3$. The aqueous phase was extracted with methylene chloride. The combined organic layers were dried over Na$_2$SO$_4$, filtered and concentrated. The residue was purified by flash chromatography on a silica gel column eluting with 0 to 4% methanol in methylene chloride to give the desired product. LC-MS calculated for C$_{15}$H$_{22}$BN$_2$O$_3$ (M+H)$^+$: m/z=289.2. found 289.1.

Step 2: 4-(8-(1,3-dimethyl-2-oxo-2,3-dihydro-1H-benzimidazol-5-yl)-5-{[(3R)-1-methylpiperidin-3-yl]methoxy}imidazo[1,2-c]pyrimidin-7-yl)benzonitrile This compound was prepared using similar procedures as described for Example 1 with 1,3-dimethyl-5-(4,4,5,5-tetramethyl-1,3,2-dioxaborolan-2-yl)-1,3-dihydro-2H-benzimidazol-2-one replacing (4-methylphenyl)boronic acid in Step 8. The resulting mixture was purified by prep-HPLC (pH=2, acetonitrile/water+TFA) to give the desired product as the TFA salt. LC-MS calculated for C$_{29}$H$_{30}$N$_7$O$_2$ (M+H)$^+$: m/z=508.2. found 508.3.

Example 45

4-(8-(5-fluoro-3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile

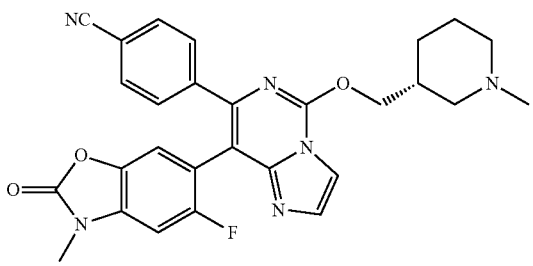 [SMILES: CN1CCC[C@@H](COc2nc(-c3ccc(C#N)cc3)c(-c3cc4oc(=O)n(C)c4cc3F)c3nccn23)C1]

Step 1: 6-bromo-5-fluoro-1,3-benzoxazol-2(3H)-one

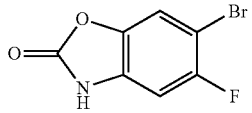

To a mixture of 2-amino-5-bromo-4-fluorophenol (0.3 g, 1 mmol) and triethylamine (1.0 mL, 7.3 mmol) in tetrahydrofuran (20 mL) was added triphosgene (0.52 g, 1.7 mmol) at 0° C. and the resulting reaction mixture was stirred for 1 h before 1M NaOH (2 mL) was added. The reaction mixture was allowed to stir for another 1 h, then diluted with methylene chloride, washed with saturated NaHCO$_3$. The aqueous phase was extracted with methylene chloride. The combined organic layers were dried over Na$_2$SO$_4$, filtered and concentrated. The residue was used for next step without further purification. LC-MS calculated for C$_7$H$_4$BrFNO$_2$ (M+H)$^+$: m/z=231.9. found 231.9.

Step 2: 6-bromo-5-fluoro-3-methyl-1,3-benzoxazol-2(3H)-one

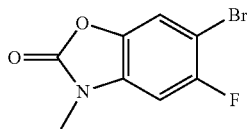

To a mixture of 6-bromo-5-fluoro-1,3-benzoxazol-2(3H)-one (crude product from Step 1) and potassium carbonate (0.4 g, 3 mmol) in acetone (5 mL) was added methyl iodide (0.2 mL, 3 mmol). The reaction mixture was heated at 80° C. overnight then cooled to room temperature and concentrated. The residue was purified by flash chromatography on a silica gel column eluting with 0 to 4% methanol in methylene chloride to give the desired product. LC-MS calculated for C$_8$H$_6$BrFNO$_2$ (M+H)$^+$: m/z=246.0. found 245.9.

Step 3: S fluoro-3-methyl-6-(4,4,5,5-tetramethyl-1,3,2-dioxaborolan-2-yl)-1,3-benzoxazol-2(3H)-one

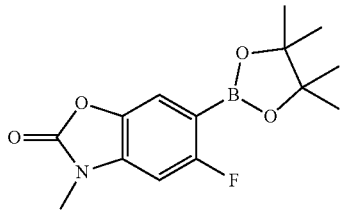 [SMILES: Cn1c(=O)oc2cc(B3OC(C)(C)C(C)(C)O3)c(F)cc21]

This compound was prepared using similar procedures as described for Example 6, Step 1 with 6-bromo-5-fluoro-3-methyl-1,3-benzoxazol-2(3H)-one (product from Step 2) replacing 5-bromo-1-methyl-1,3-dihydro-2H-indol-2-one. After cooling to room temperature, the reaction mixture was concentrated, diluted with methylene chloride, washed over saturated NaHCO$_3$. The aqueous phase was extracted with methylene chloride. The combined organic layers were dried over Na$_2$SO$_4$, filtered and concentrated. The residue was purified by flash chromatography on a silica gel column eluting with 0 to 4% methanol in methylene chloride to give the desired product. LC-MS calculated for C$_{14}$H$_{18}$BFNO$_4$ (M+H)$^+$: m/z=294.1. found 294.1.

Step 4: 4-(8-(5-fluoro-3-methyl-2-oxo-2,3-dihydro-1,3-benzoxazol-6 yl)-5-{[(3R)-1-methylpiperidin-3-yl]methoxy}imidazo[1,2-c]pyrimidin-7-yl)benzonitrile This compound was prepared using similar procedures as described for Example 1 with 5-fluoro-3-methyl-6-(4,4,5,5-tetramethyl-1,3,2-dioxaborolan-2-yl)-1,3-benzoxazol-2 (3H)-one replacing (4-methylphenyl)boronic acid in Step 8. The resulting mixture was purified by prep-HPLC (pH=2, acetonitrile/water+TFA) to give the desired product as the TFA salt. LC-MS calculated for C$_{28}$H$_{26}$FN$_6$O$_3$ (M+H)$^+$: m/z=513.2. found 513.2. $^1$H NMR (400 MHz, MeOD) δ 8.17 (d, J=1.8 Hz, 1H), 7.84 (d, J=1.6 Hz, 1H), 7.70-7.62 (m, 4H), 7.30 (dd, J=5.5, 2.1 Hz, 1H), 7.12 (d, J=8.8 Hz, 1H), 4.84-4.78 (m, 1H), 4.77-4.68 (m, 1H), 3.86-3.76 (m, 1H), 3.63-3.53 (m, 1H), 3.42 (s, 3H), 3.08-2.96 (m, 2H), 2.94 (s, 3H), 2.64-2.50 (m, 1H), 2.15-2.03 (m, 2H), 2.01-1.82 (m, 1H), 1.63-1.47 (m, 1H).

Example 46

4-[5-[4-(dimethylamino)piperidin-1-yl]-8-(1-methyl-1H-indazol-5-yl)imidazo[1,2-c]pyrimidin-7-yl]benzonitrile

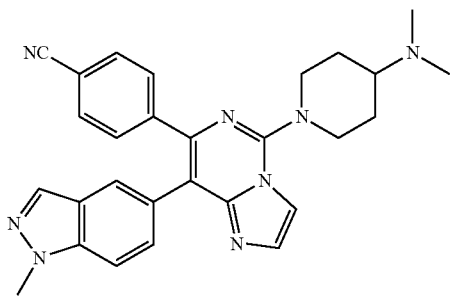 [SMILES: CN(C)C1CCN(c2nc(-c3ccc(C#N)cc3)c(-c3ccc4c(cnn4C)c3)c3nccn23)CC1]

This compound was prepared using similar procedures as described for Example 37 with (1-methyl-1H-indazol-5-yl) boronic acid (Ark Pharm, cat #AK-39590) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for C$_{28}$H$_{29}$N$_8$ (M+H)$^+$: m/z=477.2; found 477.3.

Example 47

4-[5-[4-(dimethylamino)piperidin-1-yl]-8-(3-methyl-2-oxo-2,3-dihydro-1,3-benzoxazol-6-yl)imidazo[1,2-c]pyrimidin-7-yl]benzonitrile

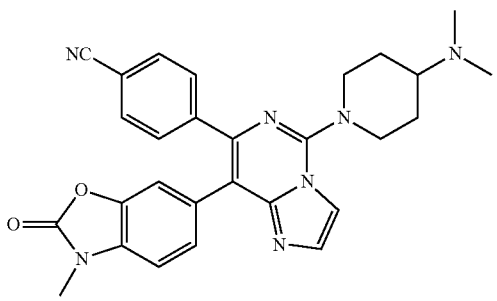 [SMILES: CN(C)C1CCN(c2nc(-c3ccc(C#N)cc3)c(-c3ccc4c(c3)oc(=O)n4C)c3nccn23)CC1]

This compound was prepared using similar procedures as described for Example 37 with 3-methyl-6-(4,4,5,5-tetramethyl-1,3,2-dioxaborolan-2-yl)-1,3-benzoxazol-2(3H)-one (prepared in Example 7, Step 2) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{28}H_{28}N_7O_2$ (M+H)$^+$: m/z=494.2. found 494.2. $^1$H NMR (500 MHz, CD$_3$OD) δ 8.17 (d, J=2.2 Hz, 1H), 7.98 (d, J=2.2 Hz, 1H), 7.66-7.61 (m, 4H), 7.34 (d, J=1.3 Hz, 1H), 7.25 (d, J=8.0 Hz, 1H), 7.16 (dd, J=8.0, 1.6 Hz, 1H), 4.40-4.31 (m, 2H), 3.67-3.56 (m, 1H), 3.44 (s, 3H), 3.39-3.34 (m, 2H), 2.95 (s, 6H), 2.35-2.27 (m, 2H), 2.17-2.05 (m, 2H).

Example 48

4-[5-[4-(dimethylamino)piperidin-1-yl]-8-(6-methoxypyridin-3-yl)imidazo[1,2-c]pyrimidin-7-yl]benzonitrile

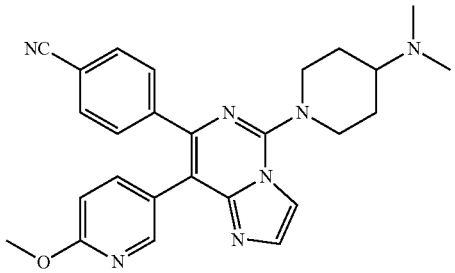

This compound was prepared using similar procedures as described for Example 37 with (6-methoxypyridin-3-yl)boronic acid (Aldrich, cat #637610) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{26}H_{28}N_7O$ (M+H)$^+$: m/z=454.2. found 454.2. $^1$H NMR (500 MHz, CD$_3$OD) δ 8.16 (d, J=2.2 Hz, 1H), 8.11-8.09 (m, 1H), 7.96 (d, J=2.1 Hz, 1H), 7.71-7.68 (m, 2H), 7.66-7.61 (m, 3H), 6.94-6.89 (m, 1H), 4.39-4.31 (m, 2H), 3.96 (s, 3H), 3.66-3.55 (m, 1H), 3.38-3.32 (m, 2H), 2.95 (s, 6H), 2.35-2.25 (m, 2H), 2.17-2.05 (m, 2H).

Example 49

4-[5-[4-(dimethylamino)piperidin-1-yl]-8-(5-fluoro-6-methoxypyridin-3-yl)imidazo[1,2-c]pyrimidin-7-yl]benzonitrile

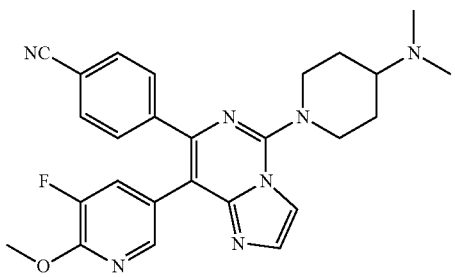

This compound was prepared using similar procedures as described for Example 37 with 3-Fluoro-2-methoxypyridine-5-boronic acid (Combi-Blocks, cat #BB-8460) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{26}H_{27}FN_7O$ (M+H)$^+$: m/z=472.2; found 472.2.

Example 50

4-{5-[4-(dimethylamino)piperidin-1-yl]-8-[6-(2-oxopyrrolidin-1-yl)pyridin-3-yl]imidazo[1,2-c]pyrimidin-7-yl}benzonitrile

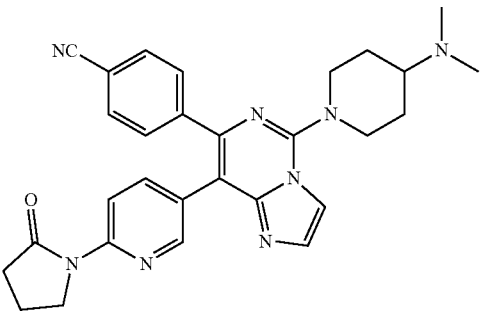 [SMILES: CN(C)C1CCN(c2nc(-c3ccc(C#N)cc3)c(-c3ccc(N4CCCC4=O)nc3)c3nccn23)CC1]

This compound was prepared using similar procedures as described for Example 37 with 1-[5-(4,4,5,5-tetramethyl-1,3,2-dioxaborolan-2-yl)pyridin-2-yl]pyrrolidin-2-one (JPM2 Pharma, cat #JPM2-00-744) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{29}H_{31}N_8O$ (M+H)$^+$: m/z=507.2. found 507.2. $^1$H NMR (400 MHz, CD$_3$OD) δ 8.46 (d, J=8.7 Hz, 1H), 8.28 (d, J=1.7 Hz, 1H), 8.14 (d, J=2.1 Hz, 1H), 7.95 (d, J=2.1 Hz, 1H), 7.80 (dd, J=8.7, 2.4 Hz, 1H), 7.68 (d, J=8.5 Hz, 2H), 7.62 (d, J=8.6 Hz, 2H), 4.42-4.29 (m, 2H), 4.12 (t, J=7.1 Hz, 2H), 3.68-3.54 (m, 1H), 3.38-3.32 (m, 2H), 2.95 (s, 6H), 2.69 (t, J=8.1 Hz, 2H), 2.34-2.25 (m, 2H), 2.23-2.03 (m, 4H).

Example 51

4-[5-[4-(dimethylamino)piperidin-1-yl]-8-(4-methyl-3-oxo-3,4-dihydro-2H-1,4-benzoxazin-7-yl)imidazo[1,2-c]pyrimidin-7-yl]benzonitrile

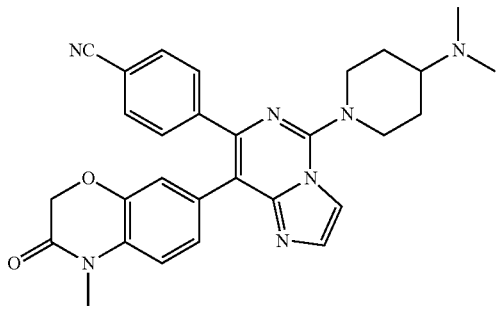 [SMILES: CN1C(=O)COc2cc(-c3c(-c4ccc(C#N)cc4)nc(N4CCC(N(C)C)CC4)n4ccnc34)ccc21]

This compound was prepared using similar procedures as described for Example 37 with 4-methyl-7-(4,4,5,5-tetramethyl-1,3,2-dioxaborolan-2-yl)-2H-1,4-benzoxazin-3 (4H)-one (Prepared in Example 15, Step 1) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{29}H_{30}N_7O_2$ (M+H)+: m/z=508.2. found 508.2. $^1$H NMR (500 MHz, $CD_3OD$) δ 8.17 (d, J=2.2 Hz, 1H), 7.99 (d, J=2.2 Hz, 1H), 7.70-7.64 (m, 4H), 7.24 (d, J=8.3 Hz, 1H), 7.06 (d, J=1.9 Hz, 1H), 7.01 (dd, J=8.3, 2.0 Hz, 1H), 4.68 (s, 2H), 4.39-4.30 (m, 2H), 3.66-3.56 (m, 1H), 3.39 (s, 3H), 3.38-3.32 (m, 2H), 2.95 (s, 6H), 2.34-2.25 (m, 2H), 2.16-2.04 (m, 2H).

Example 52

4-{8-[2-(difluoromethyl)-1-methyl-1H-benzimidazol-5-yl]-5-[4-(dimethylamino)piperidin-1-yl]imidazo[1,2-c]pyrimidin-7-yl}benzonitrile

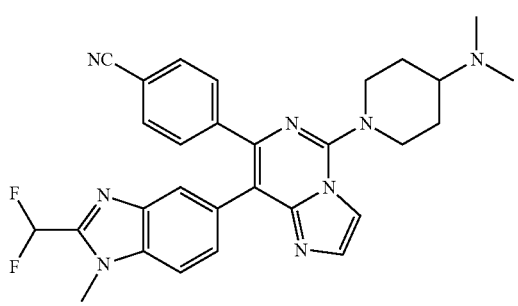 [SMILES: CN(C)C1CCN(c2nc(-c3ccc(C#N)cc3)c(-c3ccc4c(c3)nc(C(F)F)n4C)c3nccn23)CC1]

Step 1: 5-bromo-2-(difluoromethyl)-1-methyl-1H-benzimidazole

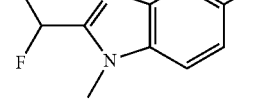

A mixture of 4-bromo-N1-methylbenzene-1,2-diamine (Combi-Blocks, cat #AN-3666: 0.5 g, 2.5 mmol), difluoroacetic acid (0.79 mL) and a few drops of concentrated hydrochloric acid was stirred at 120° C. overnight. After cooling to room temperature, the reaction mixture was concentrated, diluted with EtOAc, washed with saturated $NaHCO_3$. The organic layer was dried over $Na_2SO_4$, filtered and concentrated. The residue was used in the next step without further purification. LC-MS calculated for $C_9H_8BrF_2N_2$ (M+H)+: m/z=261.0. found 261.0.

Step 2: 2-(difluoromethyl)-1-methyl-5-(4,4,5,5-tetramethyl-1,3,2-dioxaborolan-2-yl)-1H-benzimidazole

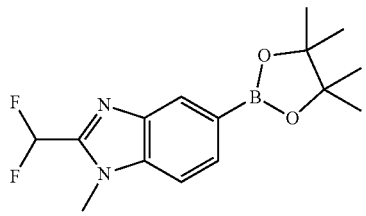 [SMILES: Cn1c(C(F)F)nc2cc(B3OC(C)(C)C(C)(C)O3)ccc21]

A mixture of 5-bromo-2-(difluoromethyl)-1-methyl-1H-benzimidazole (0.59 g, 2.2 mmol), 4,4,5,5,4',4',5',5'-Octamethyl-[2,2']bi[[1,3,2]dioxaborolanyl] (860 mg, 3.4 mmol), [1,1'-bis(diphenylphosphino)ferrocene]dichloropalladium (II) complexed with dichloromethane (1:1) (90 mg, 0.1 mmol) and potassium acetate (660 mg, 6.8 mmol) in 1,4-dioxane (20 mL) was purged with nitrogen then heated at 90° C. overnight. After cooling to room temperature, the reaction mixture was concentrated. The residue was purified by flash chromatography on a silica gel column eluting with 0 to 15% AcOEt in hexanes to give the desired product. LC-MS calculated for $C_{15}H_{20}OBF_2N_2O_2$ (M+H)+: m/z=309.2. found 309.2.

Step 3: 4-{8-[2-(difluoromethyl)-1-methyl-1H-benzimidazol-4-yl]-5-[4-(dimethylamino)piperidin-1-yl]imidazo[1,2-c]pyrimidin-7-yl}benzonitrile This compound was prepared using similar procedures as described for Example 37 with 2-(difluoromethyl)-1-methyl-5-(4,4,5,5-tetramethyl-1,3,2-dioxaborolan-2-yl)-1H-benzimidazole replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{29}H_{29}F_2N_8$ (M+H)+: m/z=527.2. found 527.2. $^1$H NMR (500 MHz, $CD_3OD$) δ 8.18 (d, J=2.2 Hz, 1H), 7.96 (d, J=2.2 Hz, 1H), 7.84-7.80 (m, 1H), 7.76 (d, J=8.5 Hz, 1H), 7.62-7.57 (m, 4H), 7.36 (dd, J=8.5, 1.5 Hz, 1H), 7.17 (t, J=52.3 Hz, 1H), 4.41-4.31 (m, 2H), 4.05 (s, 3H), 3.68-3.56 (m, 1H), 3.40-3.32 (m, 2H), 2.96 (s, 6H), 2.36-2.26 (m, 2H), 2.19-2.06 (m, 2H).

Example 53

4-[5-[4-(dimethylamino)piperidin-1-yl]-8-(6-methoxy-5-methylpyridin-3-yl)imidazo[1,2-c]pyrimidin-7-yl]benzonitrile

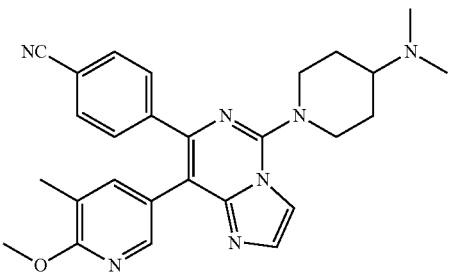

This compound was prepared using similar procedures as described for Example 37 with (6-methoxy-5-methylpyridin-3-yl)boronic acid (Combi-Blocks, cat #BB-6068) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{27}H_{30}N_7O$ (M+H)$^+$: m/z=468.2; found 468.2.

Example 54

4-[5-[4-(dimethylamino)piperidin-1-yl]-8-(5-fluoro-3-methyl-2-oxo-2,3-dihydro-1,3-benzoxazol-6-yl)imidazo[1,2-c]pyrimidin-7-yl]benzonitrile

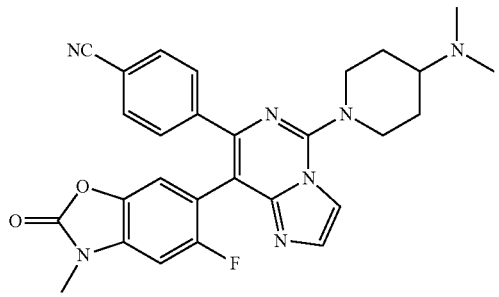 [SMILES: CN(C)C1CCN(c2nc(-c3ccc(C#N)cc3)c(-c3cc4oc(=O)n(C)c4cc3F)c3nccn23)CC1]

This compound was prepared using similar procedures as described for Example 37 with 5-fluoro-3-methyl-6-(4,4,5,5-tetramethyl-1,3,2-dioxaborolan-2-yl)-1,3-benzoxazol-2(3H)-one (Prepared in Example 45, Step 3) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{28}H_{27}FN_7O_2$ (M+H)$^+$: m/z=512.2. found 512.2.

Example 55

4-[5-{[(3R)-1-ethylpiperidin-3-yl]methoxy}-8-(3-methyl-2-oxo-2,3-dihydro-1,3-benzoxazol-6-yl)imidazo[1,2-c]pyrimidin-7-yl]benzonitrile

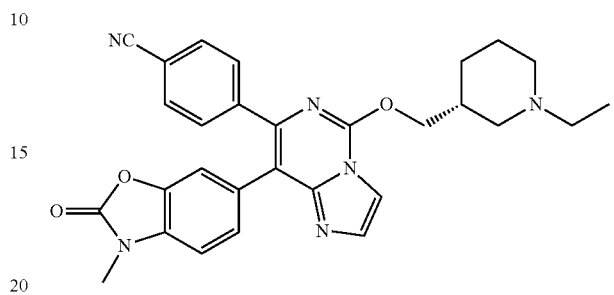

This compound was prepared using similar procedures as described for Example 29 with 3-methyl-6-(4,4,5,5-tetramethyl-1,3,2-dioxaborolan-2-yl)-1,3-benzoxazol-2(3H)-one (prepared in Example 7, Step 2) replacing 1-methyl-5-(4,4,5,5-tetramethyl-1,3,2-dioxaborolan-2-yl)-1H-pyrazolo[3,4-b]pyridine in Step 1. The resulting mixture was purified by prep-HPLC (pH=2, acetonitrile/water+TFA) to give the desired product as the TFA salt. LC-MS calculated for $C_{29}H_{29}N_6O_3$ (M+H)$^+$: m/z=509.2. found 509.3.

Example 56

4-[5-{[(3R)-1-(2-hydroxyethyl)piperidin-3-yl]methoxy}-8-(6-methoxypyridin-3-yl)imidazo[1,2-c]pyrimidin-7-yl]benzonitrile

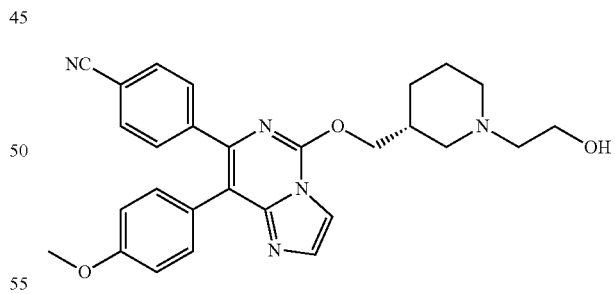

This compound was prepared using similar procedures as described for Example 34 with (6-methoxypyridin-3-yl)boronic acid (Aldrich, cat #637610) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{29}N_6O_3$ (M+H)$^+$: m/z=485.2. found 485.2.

Example 57

4-(8-(5-fluoro-6-methoxypyridin-3-yl)-5-{[(3R)-1-(2-hydroxyethyl)piperidin-3-yl]methoxy}imidazo[1,2-c]pyrimidin-7-yl)benzonitrile

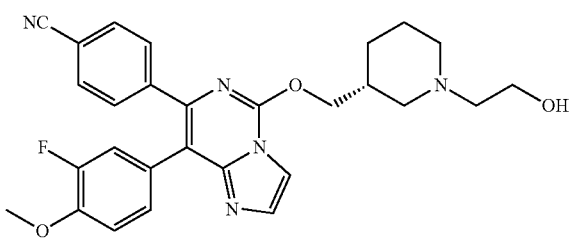 [SMILES: COc1ccc(-c2c(-c3ccc(C#N)cc3)nc(OC[C@@H]3CCCN(CCO)C3)n3ccnc23)cc1F]

This compound was prepared using similar procedures as described for Example 34 with 3-fluoro-2-methoxypyridine-5-boronic acid (Combi-Blocks, cat #BB-8460) replacing 1-methyl-5-(4,4,5,5-tetramethyl-1,3,2-dioxaborolan-2-yl)-1H-pyrazolo[3,4-b]pyridine. The reaction mixture was purified by prep-HPLC (pH=2, acetonitrile/water+TFA) to give the desired product as the TFA salt. LC-MS calculated for $C_{27}H_{28}FN_6O_3$ $(M+H)^+$: m/z=503.2. found 503.2.

Example 58

4-[5-[4-(dimethylamino)piperidin-1-yl]-8-(4-fluoro-3-methyl-2-oxo-2,3-dihydro-1,3-benzoxazol-6-yl)imidazo[1,2-c]pyrimidin-7-yl]benzonitrile

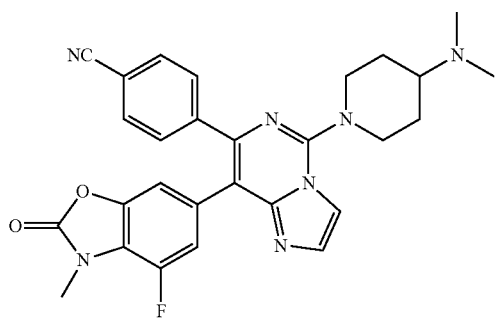 [SMILES: CN(C)C1CCN(c2nc(-c3ccc(C#N)cc3)c(-c3cc(F)c4c(c3)oc(=O)n4C)c3nccn23)CC1]

Step 1: 1-(benzyloxy)-3-fluoro-2-nitrobenzene

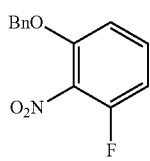

A mixture of 1,3-difluoro-2-nitrobenzene (1 g, 6 mmol), benzyl alcohol (0.81 mL, 7.8 mmol), potassium carbonate (1.79 g, 13.0 mmol) in N,N-dimethylformamide (5 mL) was heated at 60° C. for 18 h. The reaction mixture was cooled to room temperature then diluted with EtOAc and washed with water and brine. The organic layer was dried over $Na_2SO_4$, filtered and concentrated. The residue was purified by flash chromatography on a silica gel column eluting with 0 to 20% EtOAc in Hexanes to give the desired product.

Step 2: 2-(benzyloxy)-6-fluoroaniline

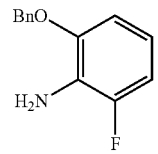 [SMILES: O=[N+]([O-])c1c(F)cccc1OCc1ccccc1]

A mixture of 1-(benzyloxy)-3-fluoro-2-nitrobenzene (2 g, 8 mmol), tin dichloride (4 g, 20 mmol), hydrogen chloride (1M in water, 4.8 mL, 4.8 mmol) in ethanol (25 mL) was refluxed for 18 h. The mixture was cooled to room temperature then concentrated. The residue was dissolved in EtOAc and water then adjusted to basic with NaOH. The precipitate was filtered and the organic phase was separated then dried over $Na_2SO_4$ and concentrated. The residue was purified by flash chromatography on a silica gel column eluting with 0 to 20% EtOAc in Hexanes to give the desired product. LC-MS calculated for $C_{13}H_{13}FNO$ $(M+H)^+$: m/z=218.1. found 218.1.

Step 3: 2-(benzyloxy)-4-bromo-6-fluoroaniline

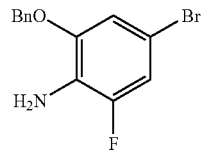

Bromine (0.20 mL, 3.8 mmol) was added to a mixture of 2-(benzyloxy)-6-fluoroaniline (650 mg, 3.0 mmol) in methanol (2.27 mL) and acetic acid (0.76 mL) at 0° C. The mixture was stirred at 0° C. for 4 h then concentrated. The residue was dissolved in EtOAc then washed with 1N NaOH, water and brine. The organic layer was dried over $Na_2SO_4$, filtered and concentrated. The residue was used in the next step without further purification. LC-MS calculated for $C_{13}H_{12}BrFNO$ $(M+H)^+$: m/z=296.0. found 296.0.

Step 4: 2-amino-5-bromo-3-fluorophenol

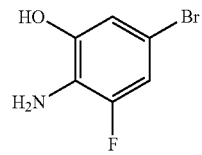

To a solution of 2-(benzyloxy)-4-bromo-6-fluoroaniline (900 mg, 3 mmol) in tetrahydrofuran (6.0 mL) was added platinum dioxide (55 mg, 0.24 mmol). The resulting mixture was purged with H2, then stirred at room temperature overnight under 1 atm of H2. The reaction mixture was filtered then concentrated. The residue was used in the next step without further purification. LC-MS calculated for $C_6H_6BrFNO$ $(M+H)^+$: m/z=206.0. found 206.0.

Step 5: 6-bromo-4 fluoro-1,3-benzoxazol-2(3H)-one

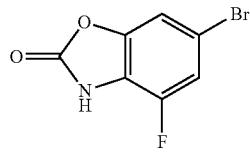 [SMILES: O=c1[nH]c2c(F)cc(Br)cc2o1]

2-Amino-5-bromo-3-fluorophenol (0.2 g, 1 mmol) was dissolved in tetrahydrofuran (10 mL) at 0° C. then triethylamine (0.68 mL, 4.8 mmol) was added, followed by triphosgene (0.34 g, 1.2 mmol). The mixture was stirred at 0° C. for 1 h, then 1.0 M sodium hydroxide in water (1.9 mL, 1.9 mmol) was added. The resulting mixture was stirred at room temperature for 1 h then diluted with EtOAc and washed with water and brine. The organic layer was dried over $Na_2SO_4$ and the solvents were removed under reduced pressure. The residue was used in the next step without further purification.

Step 6: 6-bromo-4 fluoro-3-methyl-1,3-benzoxazol-2(3H)-one

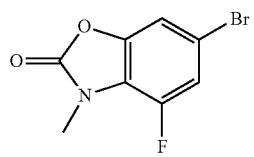

A mixture of 6-bromo-4-fluoro-1,3-benzoxazol-2(3H)-one (crude product from Step 5), potassium carbonate (0.3 g, 2 mmol) and methyl iodide (0.1 mL, 2 mmol) in acetone (3 mL) was heated at 80° C. for overnight. The reaction mixture was cooled to room temperature then concentrated. The residue was purified by flash chromatography on a silica gel column eluting with 0 to 25% EtOAc in Hexanes to give the desired product. LC-MS calculated for $C_8H_6BrFNO$ $(M+H)^+$: m/z=246.0. found 245.9.

Step 7: 4 fluoro-3-methyl-6-(4,4,5,5-tetramethyl-1,3,2-dioxaborolan-2-yl)-1,3-benzoxazol-2(3H)-one

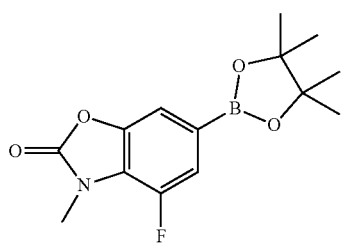 [SMILES: Cn1c(=O)oc2cc(B3OC(C)(C)C(C)(C)O3)cc(F)c21]

A mixture of [1,1'-bis(diphenylphosphino)ferrocene]dichloropalladium(II) complexed with dichloromethane (1:1) (10 mg, 0.02 mmol), 6-bromo-4-fluoro-3-methyl-1,3-benzoxazol-2(3H)-one (90 mg, 0.4 mmol), 4,4,5,5,4',4',5',5'-octamethyl-[2,2']bi[[1,3,2]dioxaborolanyl] (140 mg, 0.55 mmol) and potassium acetate (100 mg, 1 mmol) in 1,4-dioxane (3 mL) was purged with nitrogen then stirred at 90° C. for overnight. The reaction mixture was cooled to room temperature then diluted with EtOAc and washed with water and brine. The organic layer was dried over $Na_2SO_4$, filtered and concentrated. The residue was purified by flash chromatography on a silica gel column eluting with 0 to 25% EtOAc in Hexanes to give the desired product. LC-MS calculated for $C_{14}H_{18}BFNO_4$ $(M+H)^+$: m/z=294.1. found 294.1.

Step 8: 4-[5-[4-(dimethylamino)piperidin-1-yl]-8-(4 fluoro-3-methyl-2-oxo-2,3-dihydro-1,3-benzoxazol-6-yl) imidazo[1,2-c]pyrimidin-7-yl]benzonitrile This compound was prepared using similar procedures as described for Example 37 with 4-fluoro-3-methyl-6-(4,4,5,5-tetramethyl-1,3,2-dioxaborolan-2-yl)-1,3-benzoxazol-2 (3H)-one replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{28}H_{27}FN_7O_2$ $(M+H)^+$: m/z=512.2. found 512.2.

Example 59

4-(8-(4-fluoro-3-methyl-2-oxo-2,3-dihydro-1,3-benzoxazol-6-yl)-5-{[(3R)-1-methylpiperidin-3-yl] methoxy}imidazo[1,2-c]pyrimidin-7-yl)benzonitrile

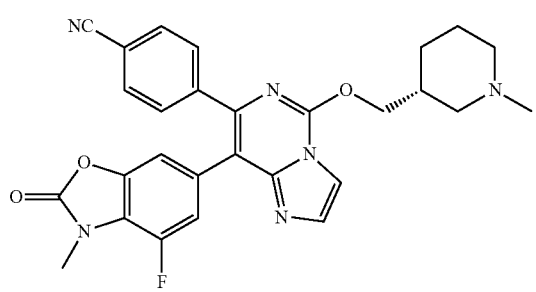 [SMILES: CN1CCC[C@@H](COc2nc(-c3ccc(C#N)cc3)c(-c3cc(F)c4c(c3)oc(=O)n4C)c3nccn23)C1]

This compound was prepared using similar procedures as described for Example 1 with 4-fluoro-3-methyl-6-(4,4,5,5-tetramethyl-1,3,2-dioxaborolan-2-yl)-1,3-benzoxazol-2 (3H)-one (prepared in Example 58, Step 7) replacing (4-methylphenyl)boronic acid in Step 8. The resulting mixture was purified by prep-HPLC (pH=2, acetonitrile/water+ TFA) to give the desired product as the TFA salt. LC-MS calculated for $C_{28}H_{26}FN_6O_3$ $(M+H)^+$: m/z=513.2; found 513.2.

Example 60

4-[5-[4-(dimethylamino)piperidin-1-yl]-8-(3-methyl-2-oxo-2,3-dihydro[1,3]oxazolo[4,5-b]pyridin-6-yl)imidazo[1,2-c]pyrimidin-7-yl]benzonitrile

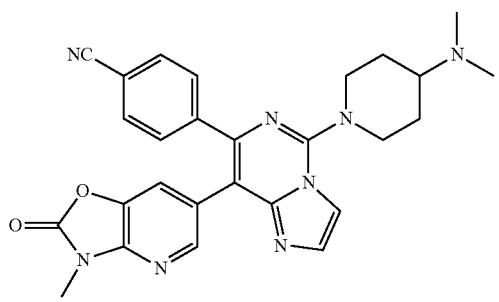 [SMILES: CN(C)C1CCN(c2nc(-c3ccc(C#N)cc3)c(-c3cnc4c(c3)oc(=O)n4C)c3nccn23)CC1]

Step 1: 6-bromo-3-methyl[1,3]oxazolo[4,5-b]pyridin-2(3H)-one

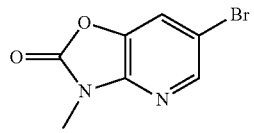

To a solution of 6-bromo[1,3]oxazolo[4,5-b]pyridin-2(3H)-one (Ark Pharm, cat #AK-24539: 0.394 g, 1.83 mmol) in N,N-dimethylformamide (5 mL) at −40° C. was added sodium hydride (60 wt % in mineral oil, 290 mg, 7.3 mmol). The resulting mixture was stirred at −40° C. for 1 hour then methyl iodide (1.14 mL, 18.3 mmol) was added dropwise. The reaction mixture was stirred at −40° C. for another 2 hours, then warmed to 0° C. and quenched by saturated NH$_4$Cl aqueous solution. The mixture was extracted with EtOAc, then DCM/iPrOH (2:1). The combined extracts were dried over Na$_2$SO$_4$, filtered and concentrated. The residue was used in the next step without further purification. LC-MS calculated for C$_7$H$_6$BrN$_2$O$_2$ (M+H)$^+$: m/z=229.0. found 229.0.

Step 2: 3-methyl-6-(4,4,5,5-tetramethyl-1,3,2-dioxaborolan-2-yl)[1,3]oxazolo[4,5-b]pyridin-2(3H)-one

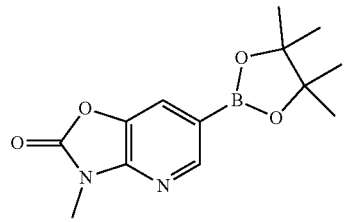 [SMILES: Cn1c(=O)oc2cc(B3OC(C)(C)C(C)(C)O3)cnc21]

A mixture of 6-bromo-3-methyl[1,3]oxazolo[4,5-b]pyridin-2(3H)-one (0.15 g, 0.66 mmol), 4,4,5,5,4',4',5',5'-octamethyl-[2,2']bi[[1,3,2]dioxaborolanyl] (250 mg, 0.98 mmol), [1,1'-bis(diphenylphosphino)ferrocene]dichloropalladium (II) complex with dichloromethane (1:1) (30 mg, 0.03 mmol) and potassium acetate (190 mg, 2.0 mmol) in 1,4-dioxane (6 mL) was purged with nitrogen then heated at 90° C. overnight. After cooling to room temperature, the reaction mixture was concentrated. The crude material was purified by flash chromatography on a silica gel column eluting with 0 to 5% MeOH in DCM to give the desired product. LC-MS calculated for C$_{13}$H$_{18}$BN$_2$O$_4$ (M+H)$^+$: m/z=277.1. found 277.1.

Step 3: 4-[5-[4-(dimethylamino)piperidin-1-yl]-8-(3-methyl-2-oxo-2,3-dihydro[1,3]oxazolo[4,5-b]pyridin-6-yl)imidazo[1,2-c]pyrimidin-7-yl]benzonitrile This compound was prepared using similar procedures as described for Example 37 with 3-methyl-6-(4,4,5,5-tetramethyl-1,3,2-dioxaborolan-2-yl)[1,3]oxazolo[4,5-b]pyridin-2(3H)-one replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for C$_{27}$H$_{27}$N$_8$O$_2$ (M+H)$^+$: m/z=495.2. found 495.2.

Example 61

4-(8-(3-methyl-2-oxo-2,3-dihydro[1,3]oxazolo[4,5-b]pyridin-6-yl)-5-{[(3R)-1-methylpiperidin-3-yl]methoxy}imidazo[1,2-c]pyrimidin-7-yl)benzonitrile

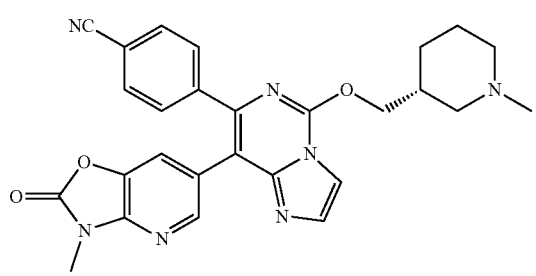

This compound was prepared using similar procedures as described for Example 1 with 3-methyl-6-(4,4,5,5-tetramethyl-1,3,2-dioxaborolan-2-yl) [1,3]oxazolo[4,5-b]pyridin-2(3H)-one (prepared in Example 60, Step 2) replacing (4-methylphenyl)boronic acid in Step 8. The resulting mixture was purified by prep-HPLC (pH=2, acetonitrile/water+TFA) to give the desired product as the TFA salt. LC-MS calculated for C$_{27}$H$_{26}$N$_7$O$_3$ (M+H)$^+$: m/z=496.2; found 496.2.

Example 62

4-[5-[4-(dimethylamino)piperidin-1-yl]-8-(1-methyl-2-oxo-2,3-dihydro-1H-indol-5-yl)imidazo[1,2-c]pyrimidin-7-yl]benzonitrile

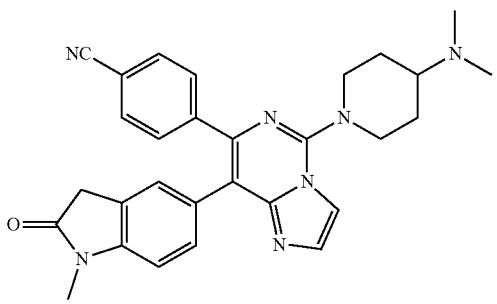 [SMILES: CN1C(=O)Cc2cc(-c3c(-c4ccc(C#N)cc4)nc(N4CCC(N(C)C)CC4)n4ccnc34)ccc21]

This compound was prepared using similar procedures as described for Example 37 with 1-methyl-5-(4,4,5,5-tetramethyl-1,3,2-dioxaborolan-2-yl)-1,3-dihydro-2H-indol-2-one (Example 6, Step 1) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{29}H_{30}N_7O$ (M+H)$^+$: m/z=492.3. found 492.2.

Example 63

4-[5-[4-(dimethylamino)piperidin-1-yl]-8-(1,2-dimethyl-1H-benzimidazol-5-yl)imidazo[1,2-c]pyrimidin-7-yl]benzonitrile

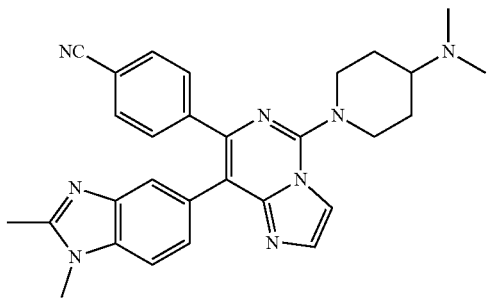

Step 1: 1,2-dimethyl-5-(4,4,5,5-tetramethyl-1,3,2-dioxaborolan-2-yl)-1H-benzimidazole

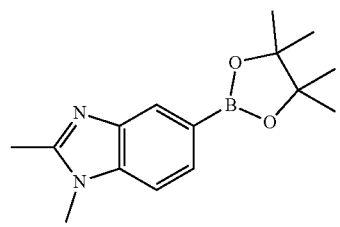

A mixture of [1,1'-bis(diphenylphosphino)ferrocene]dichloropalladium(II) complexed with dichloromethane (1:1) (40 mg, 0.04 mmol), 5-bromo-1,2-dimethyl-1H-benzimidazole (200 mg, 0.9 mmol), 4,4,5,5,4',4',5',5'-octamethyl-[2,2']bi[[1,3,2]dioxaborolanyl] (340 mg, 1.3 mmol) and potassium acetate (300 mg, 3 mmol) in 1,4-dioxane (7 mL) was purged with nitrogen then stirred at 90° C. overnight. The reaction mixture was cooled to room temperature then concentrated. The residue was purified by flash chromatography eluting with 0 to 30% MeOH in DCM to give the desired product. LC-MS calculated for $C_{15}H_{22}BN_2O_2$ (M+H)$^+$: m/z=273.2; found 273.2.

Step 2: 4-[5-[4-(dimethylamino)piperidin-1-yl]-8-(1,2-dimethyl-1H-benzimidazol-5-yl)imidazo[1,2-c]pyrimidin-7-yl]benzonitrile This compound was prepared using similar procedures as described for Example 37 with 1,2-dimethyl-5-(4,4,5,5-tetramethyl-1,3,2-dioxaborolan-2-yl)-1H-benzimidazole replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{29}H_{31}N_8$ (M+H)$^+$: m/z=491.3; found 491.3.

Example 64

4-(8-[2-(difluoromethyl)-1-methyl-1H-benzimidazol-5-yl]-5-{[(3R)-1-methylpiperidin-3-yl]methoxy}imidazo[1,2-c]pyrimidin-7-yl)benzonitrile

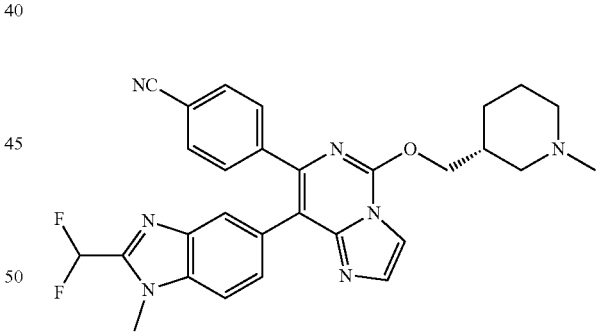

This compound was prepared using similar procedures as described for Example 1 with 2-(difluoromethyl)-1-methyl-5-(4,4,5,5-tetramethyl-1,3,2-dioxaborolan-2-yl)-1H-benzimidazole (prepared in Example 52, Step 2) replacing (4-methylphenyl)boronic acid in Step 8. The resulting mixture was purified by prep-HPLC (pH=2, acetonitrile/water+TFA) to give the desired product as the TFA salt. LC-MS calculated for $C_{29}H_{28}F_2N_7O$ (M+H)$^+$: m/z=528.2; found 528.2.

Example 65

4-(8-(1,2-dimethyl-1H-benzimidazol-5-yl)-5-{[(3R)-1-methylpiperidin-3-yl]methoxy}imidazo[1,2-c]pyrimidin-7-yl)benzonitrile

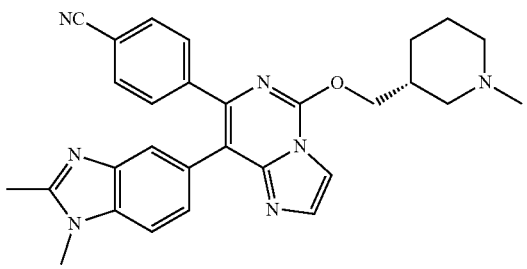

This compound was prepared using similar procedures as described for Example 1 with 1,2-dimethyl-5-(4,4,5,5-tetramethyl-1,3,2-dioxaborolan-2-yl)-1H-benzimidazole (Prepared in Example 63, Step 1) replacing (4-methylphenyl)boronic acid in Step 8. The resulting mixture was purified by prep-HPLC (pH=2, acetonitrile/water+TFA) to give the desired product as the TFA salt. LC-MS calculated for $C_{29}H_{30}N_7O$ (M+H)$^+$: m/z=492.3. found 492.2.

Example 66

5-{7-(4-cyanophenyl)-5-[4-(dimethylamino)piperidin-1-yl]imidazo[1,2-c]pyrimidin-8-yl}-2-methylnicotinonitrile

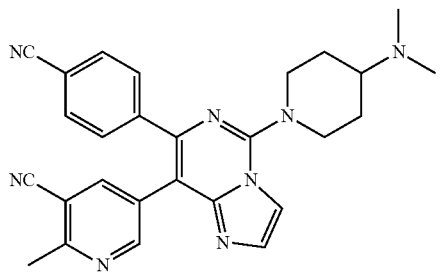

Step 1: 2-methyl-5-(4,4,5,5-tetramethyl-1,3,2-dioxaborolan-2-yl)nicotinonitrile

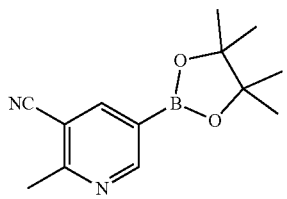

A mixture of 5-bromo-2-methylnicotinonitrile (Combi-Blocks, cat #PY-1861: 100 mg, 0.50 mmol), 4,4,5,5,4',4',5',5'-octamethyl-[2,2']bi[[1,3,2]dioxaborolanyl] (140 mg, 0.55 mmol), [1,1'-bis(diphenylphosphino)ferrocene]dichloropalladium(II) complexed with dichloromethane (1:1) (20 mg, 0.02 mmol) and potassium acetate (150 mg, 1.5 mmol) in 1,4-dioxane (5 mL) was purged with nitrogen then heated at 90° C. overnight. After cooling to room temperature, the reaction mixture was concentrated. The residue was purified by flash chromatography on a silica gel column eluting with 0 to 15% AcOEt in hexanes to give the desired product. LC-MS calculated for $C_{13}H_{18}BN_2O_2$ (M+H)$^+$: m/z=245.2. found 245.2.

Step 2: 5-{7-(4-cyanophenyl)-5-[4-(dimethylamino)piperidin-1-yl]imidazo[1,2-c]pyrimidin-8-yl}-2-methylnicotinonitrile This compound was prepared using similar procedures as described for Example 37 with 2-methyl-5-(4,4,5,5-tetramethyl-1,3,2-dioxaborolan-2-yl)nicotinonitrile replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{27}H_{27}N_8$ (M+H)$^+$: m/z=463.2; found 463.2.

Example 67

Methyl (5-{7-(4-cyanophenyl)-5-[4-(dimethylamino)piperidin-1-yl]imidazo[1,2-c]pyrimidin-8-yl}pyridin-2-yl)methylcarbamate

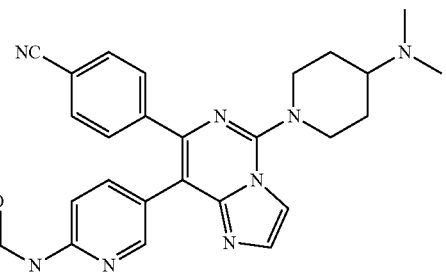

Step 1: methyl (5-bromopyridin-2-yl)methylcarbamate

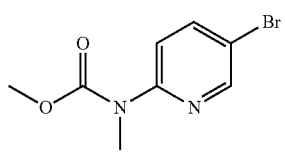

To a solution of 5-bromo-N-methylpyridin-2-amine (Combi-Blocks, cat #PY-1235: 138 mg, 0.738 mmol) in tetrahydrofuran (4 mL) was added cesium carbonate (288 mg, 0.885 mmol) and methyl chloroformate (285 μL, 3.69 mmol). The resulted mixture was heated for 12 h at 50° C., then diluted with ethyl acetate, filtered, and concentrated. The crude product was used without further purification. LC-MS calculated for $C_8H_{10}BrN_2O_2$ (M+H)$^+$: m/z=245.0; found 245.0.

Step 2: methyl methyl[5-(4,4,5,5-tetramethyl-1,3,2-dioxaborolan-2-yl)pyridin-2 yl]carbamate

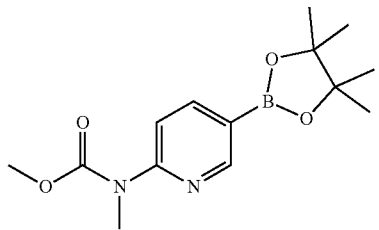

This compound was prepared using similar procedures as described for Example 6, Step 1 with methyl (5-bromopyridin-2-yl)methylcarbamate replacing 5-bromo-1-methyl-1,3-dihydro-2H-indol-2-one. The reaction mixture was filtered through celite, and then concentrated. The crude product was used in the next step without further purification.

Step 3: methyl (5-{7-(4-cyanophenyl)-5-[4-(dimethylamino)piperidin-1-yl]imidazo[1,2-c]pyrimidin-8 yl}pyridin-2-yl)methylcarbamate This compound was prepared using similar procedures as described for Example 37 with methyl methyl [5-(4,4,5,5-tetramethyl-1,3,2-dioxaborolan-2-yl)pyri din-2-yl]carbamate replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{28}H_{31}N_8O_2$ (M+H)$^+$: m/z=511.3; found 511.2.

Example 68

4-[5-[4-(dimethylamino)piperidin-1-yl]-8-(5,6-dimethylpyridin-3-yl)imidazo[1,2-c]pyrimidin-7-yl]benzonitrile

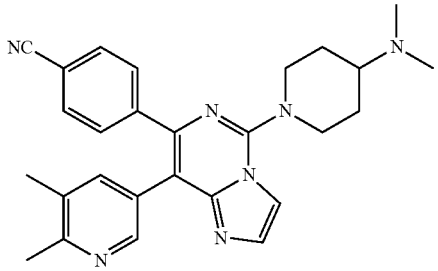

This compound was prepared using similar procedures as described for Example 37 with 2,3-dimethyl-5-(4,4,5,5-tetramethyl-1,3,2-dioxaborolan-2-yl)pyridine (Combi-Blocks, cat #FM-6236) replacing 1-methyl-5-(4,4,5,5-tetramethyl-1,3,2-dioxaborolan-2-yl)-1H-pyrazolo[3,4-b]pyridine in Step 2. The resulting mixture was purified by prep-HPLC (pH=2, acetonitrile/water+TFA) to give the desired product as the TFA salt. LC-MS calculated for $C_{27}H_{30}N_7$ (M+H)$^+$: m/z=452.3. found 452.2.

Example 69

4-(8-(6-methoxy-5-methylpyridin-3-yl)-5-{[(3R)-1-methylpiperidin-3-yl]methoxy}imidazo[1,2-c]pyrimidin-7-yl)benzonitrile

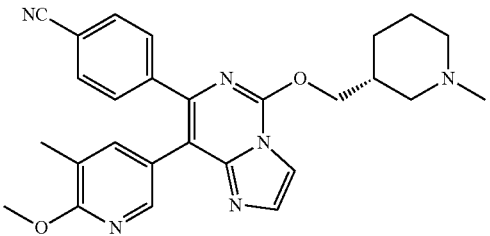

This compound was prepared using similar procedures as described for Example 1 with (6-methoxy-5-methylpyridin-3-yl)boronic acid (Aurum Pharmatech, cat #A-3579) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{29}N_6O_2$ (M+H)$^+$: m/z=469.2. found 469.2.

Example 70

5-(7-(4-cyanophenyl)-5-{[(3R)-1-methylpiperidin-3-yl]methoxy}imidazo[1,2-c]pyrimidin-8-yl)-2-methylnicotinonitrile

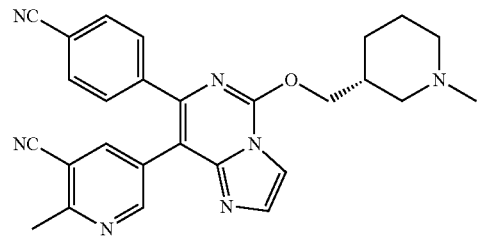

This compound was prepared using similar procedures as described for Example 1 with 2-methyl-5-(4,4,5,5-tetramethyl-1,3,2-dioxaborolan-2-yl)nicotinonitrile (Example 66, Step 1) replacing (4-methylphenyl)boronic acid in Step 8. The resulting mixture was purified by prep-HPLC (pH=2, acetonitrile/water+TFA) to give the desired product as the TFA salt. LC-MS calculated for $C_{27}H_{26}N_7O$ (M+H)$^+$: m/z=464.2. found 464.2.

Example 71

4-(8-[3-(hydroxymethyl)-4-methylphenyl]-5-{[(3R)-1-methylpiperidin-3-yl]methoxy}imidazo[1,2-c]pyrimidin-7-yl)benzonitrile

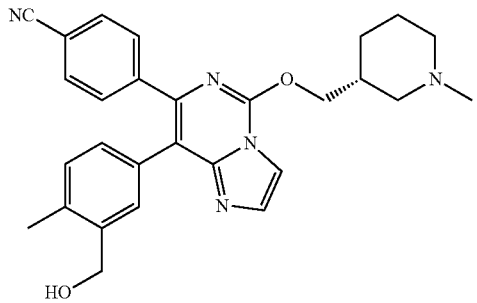

This compound was prepared using similar procedures as described for Example 1 with [2-methyl-5-(4,4,5,5-tetramethyl-1,3,2-dioxaborolan-2-yl)phenyl]methanol (Combi-Blocks, cat #FM-2080) replacing (4-methylphenyl)boronic acid in Step 8. The resulting mixture was purified by prep-HPLC (pH=2, acetonitrile/water+TFA) to give the desired product as the TFA salt. LC-MS calculated for $C_{28}H_{30}N_5O_2$ (M+H)$^+$: m/z=468.2. found 468.2.

Example 72

4-(8-[2-(hydroxymethyl)-4-methylphenyl]-5-{[(3R)-1-methylpiperidin-3-yl]methoxy}imidazo[1,2-c]pyrimidin-7-yl)benzonitrile

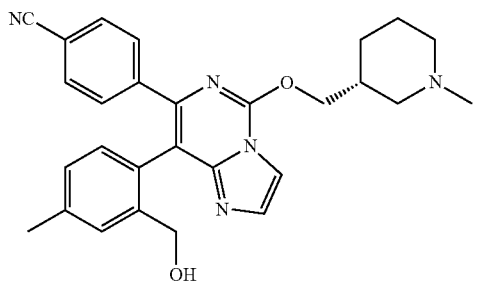

This compound was prepared using similar procedures as described for Example 1 with [2-(hydroxymethyl)-4-methylphenyl]boronic acid (Combi-Blocks, cat #21-2055) replacing (4-methylphenyl)boronic acid in Step 8. The resulting mixture was purified by prep-HPLC (pH=2, acetonitrile/water+TFA) to give the desired product as the TFA salt. LC-MS calculated for $C_{28}H_{30}N_5O_2$ (M+H)$^+$: m/z=468.2. found 468.2.

Example 73

4-[5-{[(3R)-1-methylpiperidin-3-yl]methoxy}-8-(6-methylpyridin-3-yl)imidazo[1,2-c]pyrimidin-7-yl]benzonitrile

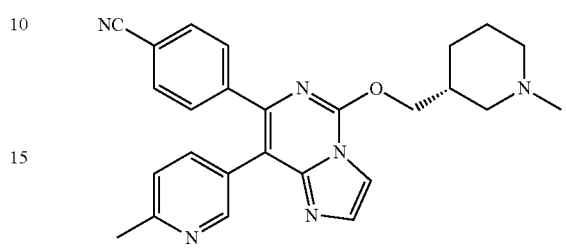

This compound was prepared using similar procedures as described for Example 1 with 2-methyl-5-(4,4,5,5-tetramethyl-1,3,2-dioxaborolan-2-yl)pyridine (Combi-Blocks, cat #PN-5068) replacing (4-methylphenyl)boronic acid in Step 8. The resulting mixture was purified by prep-HPLC (pH=2, acetonitrile/water+TFA) to give the desired product as the TFA salt. LC-MS calculated for $C_{26}H_{27}N_6O$ (M+H)$^+$: m/z=439.2. found 439.2.

Example 74

4-(8-(5-fluoro-6-methylpyridin-3-yl)-5-{[(3R)-1-methylpiperidin-3-yl]methoxy}imidazo[1,2-c]pyrimidin-7-yl)benzonitrile

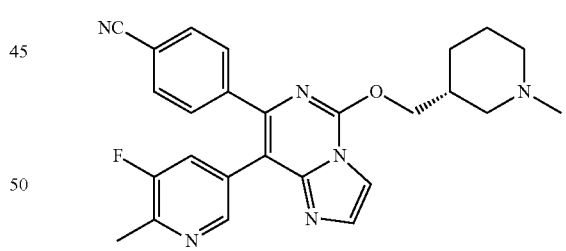

This compound was prepared using similar procedures as described for Example 1 with 3-fluoro-2-methyl-5-(4,4,5,5-tetramethyl-1,3,2-dioxaborolan-2-yl)pyridine (PharmaBlock Inc, cat #PBS07313) replacing (4-methylphenyl)boronic acid in Step 8. The resulting mixture was purified by prep-HPLC (pH=2, acetonitrile/water+TFA) to give the desired product as the TFA salt. LC-MS calculated for $C_{26}H_{26}FN_6O$ (M+H)$^+$: m/z=457.2. found 457.2.

Example 75

Methyl [4-(7-(4-cyanophenyl)-5-{[(3R)-1-methylpiperidin-3-yl]methoxy}imidazo[1,2-c]pyrimidin-8-yl)-2-fluorophenyl]methylcarbamate

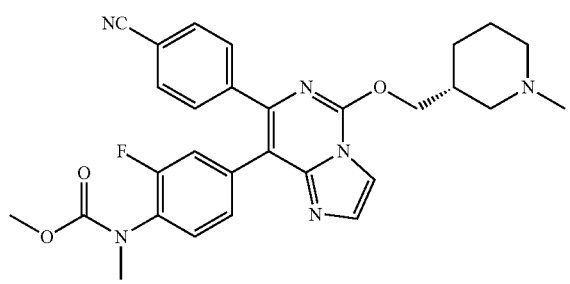

Step 1: methyl (4-bromo-2-fluorophenyl)methylcarbamate

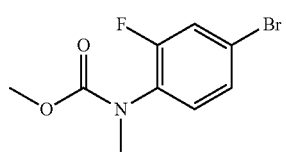

To a solution of 4-bromo-2-fluoro-N-methylaniline hydrochloride (Combi Blocks, cat #HC-3277: 100 mg, 0.4 mmol) and N,N-diisopropylethylamine (220 µL, 1.2 mmol) in methylene chloride (0.3 mL, 5 mmol) was added methyl chloroformate (38 µL, 0.50 mmol). The resultant mixture was stirred at room temperature overnight, then was quenched with saturated NaHCO₃. The aqueous phase was extracted with methylene chloride, and the organic layer was dried over Na₂SO₄, filtered and concentrated. The residue was purified by flash chromatography on a silica gel column eluting with 0 to 40% EtOAc in hexanes to give the desired product.

Step 2: methyl [2 fluoro-4-(4,4,5,5-tetramethyl-1,3,2-dioxaborolan-2-yl)phenyl]methylcarbamate

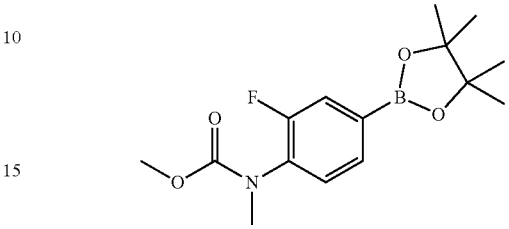

A mixture of methyl (4-bromo-2-fluorophenyl)methylcarbamate (58 mg, 0.22 mmol), 4,4,5,5,4',4',5',5'-octamethyl-[2,2']bi[[1,3,2]dioxaborolanyl] (62 mg, 0.24 mmol), [1,1'-bis(diphenylphosphino)ferrocene]dichloropalladium(II) complexed with dichloromethane (1:1) (9 mg, 0.01 mmol) and potassium acetate (65 mg, 0.66 mmol) in 1,4-dioxane (2 mL) was purged with nitrogen then heated at 90° C. overnight. After cooling to room temperature, the reaction mixture was concentrated. The residue was purified by flash chromatography on a silica gel column eluting with 0 to 15% AcOEt in hexanes to give the desired product. LC-MS calculated for $C_{15}H_{22}BFNO_4$ $(M+H)^+$: m/z=310.2. found 310.2.

Step 3: methyl [4-(7-(4-cyanophenyl)-5-{[(3R)-1-methylpiperidin-3-yl]methoxy}imidazo[1,2-c]pyrimidin-8-yl)-2-fluorophenyl]methylcarbamate This compound was prepared using similar procedures as described for Example 1 with methyl [2-fluoro-4-(4,4,5,5-tetramethyl-1,3,2-dioxaborolan-2-yl)phenyl]methylcarbamate replacing (4-methylphenyl)boronic acid in Step 8. The resulting mixture was purified by prep-HPLC (pH=2, acetonitrile/water+TFA) to give the desired product as the TFA salt. LC-MS calculated for $C_{29}H_{30}FN_6O_3$ $(M+H)^+$: m/z=529.2. found 529.2.

TABLE 2

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 76 | 7-(7-(4-cyanophenyl)-5-{[(3R)-1-methylpiperidin-3-yl]methoxy}imidazo[1,2-c]pyrimidin-8-yl)-N,N-dimethyl-2,3-dihydro-1,4-benzodioxine-2-carboxamide | 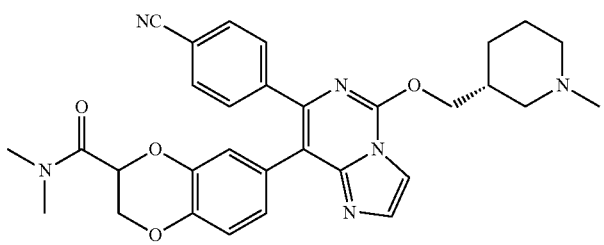 | 553.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 77 | 4-(8-(1-methyl-2,3-dihydro-1H-pyrrolo[2,3-b]pyridin-5-yl)-5-{[(3R)-1-methylpiperidin-3-yl]methoxy}imidazo[1,2-c]pyrimidin-7-yl)benzonitrile | 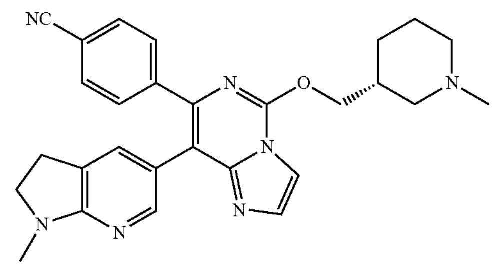 [SMILES: CN1CCC[C@@H](COc2nc(-c3ccc(C#N)cc3)c(-c3cnc4c(c3)CCN4C)c3nccn23)C1] | 480.2 | None |
| 78 | 4-[5-{[(3R)-1-methylpiperidin-3-yl]methoxy}-8-(8-methyl-5,6,7,8-tetrahydro-1,8-naphthyridin-3-yl)imidazo[1,2-c]pyrimidin-7-yl]benzonitrile | 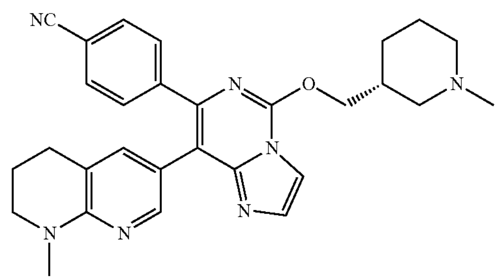 [SMILES: CN1CCC[C@@H](COc2nc(-c3ccc(C#N)cc3)c(-c3cnc4c(c3)CCCN4C)c3nccn23)C1] | 494.3 | TFA |
| 79 | 4-(8-(1-methyl-2-oxo-1,2,3,4-tetrahydroquinolin-7-yl)-5-{[(3R)-1-methylpiperidin-3-yl]methoxy}imidazo[1,2-c]pyrimidin-7-yl)benzonitrile | 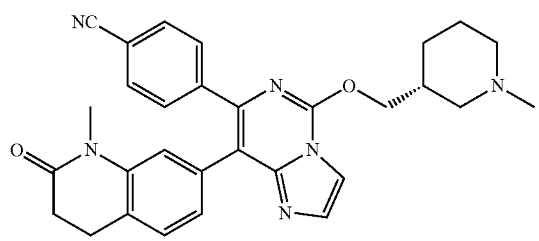 [SMILES: CN1CCC[C@@H](COc2nc(-c3ccc(C#N)cc3)c(-c3ccc4c(c3)N(C)C(=O)CC4)c3nccn23)C1] | 507.2 | TFA |
| 80 | 4-(8-[3-fluoro-4-(morpholin-4-ylmethyl)phenyl]-5-{[(3R)-1-methylpiperidin-3-yl]methoxy}imidazo[1,2-c]pyrimidin-7-yl)benzonitrile | 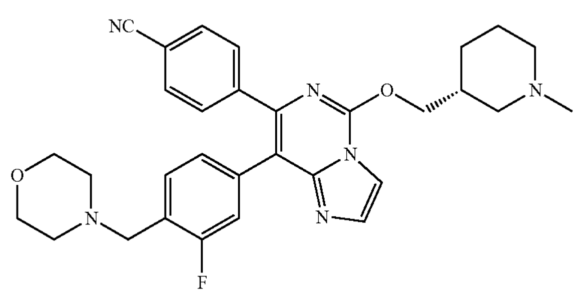 [SMILES: CN1CCC[C@@H](COc2nc(-c3ccc(C#N)cc3)c(-c3ccc(CN4CCOCC4)c(F)c3)c3nccn23)C1] | 541.2 | TFA |
| 81 | 4-[5-{[(3R)-1-(2-cyanoethyl)piperidin-3-yl]mtehoxy}-8-(5-fluoro-6-methoxypyridin-3-yl)imidazo[1,2-c]pyrimidin-7-yl]benzonitrile | 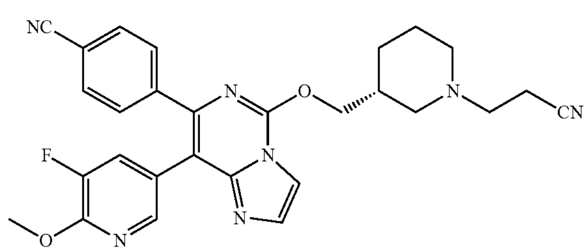 [SMILES: COc1ncc(-c2c(-c3ccc(C#N)cc3)nc(OC[C@@H]3CCCN(CCC#N)C3)n3ccnc23)cc1F] | 512.2 | TFA |

TABLE 2-continued

The compounds in Table 2 were prepared using analogous procedures as in Example 75 using the appropriate Suzuki coupling partners.

| Example | Name/$^1$H NMR | Structure | LCMS (M + H)$^+$ | Salt |
|---|---|---|---|---|
| 82 | 4-{8-[6-(dimethylamino)-5-fluoropyridin-3-yl]-5-[4-(dimethylamino)piperidin-1-yl]imidazo[1,2-c]pyrimidin-7-yl}benzonitrile | 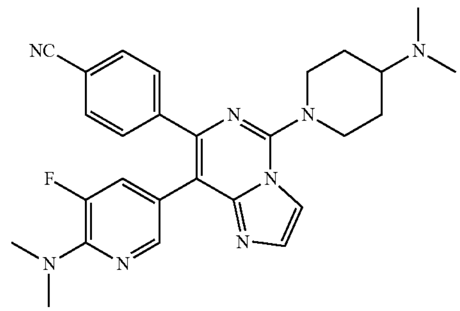 | 485.3 | TFA |
| 83 | 4-[5-{[(3R)-1-(2-cyanoethyl)piperidin-3-yl]methoxy}-8-(3-methyl-2-oxo-2,3-dihydro-1,3-benzoxazol-6-yl)imidazo[1,2-c]pyrimidin-7-yl]benzonitrile | 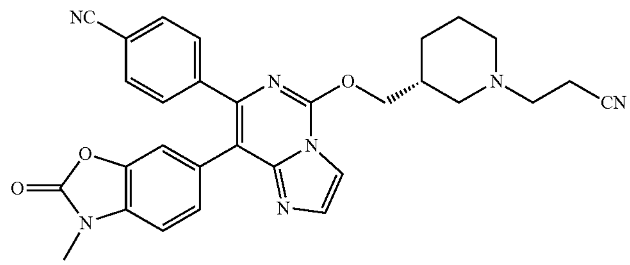 [SMILES: Cn1c(=O)oc2cc(-c3c(-c4ccc(C#N)cc4)nc(OC[C@@H]4CCCN(CCC#N)C4)n4ccnc34)ccc21] | 534.2 | TFA |
| 84 | N-[4-(7-(4-cyanophenyl)-5-{[(3R)-1-methylpiperidin-3-yl]methoxy}imidazo[1,2-c]pyrimidin-8-yl)-2-fluorobenzyl]-N-methylmethanesulfonamide | 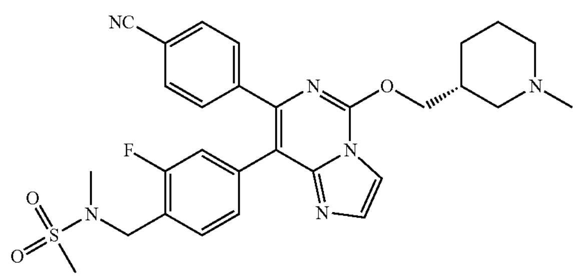 [SMILES: CN1CCC[C@@H](COc2nc(-c3ccc(C#N)cc3)c(-c3ccc(CN(C)S(C)(=O)=O)c(F)c3)c3nccn23)C1] | 563.2 | TFA |
| 85 | N-[4-(7-(4-cyanophenyl)-5-{[(3R)-1-methylpiperidin-3-yl]methoxy}imidazo[1,2-c]pyrimidin-8-yl)-2-fluorobenzyl]-N,N',N'-trimethylurea | 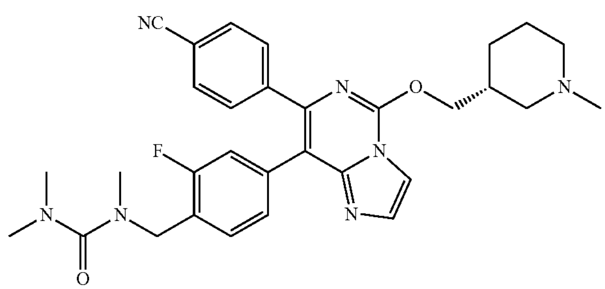 | 556.2 | TFA |
| 86 | N-[4-(7-(4-cyanophenyl)-5-{[(3R)-1-methylpiperidin-3-yl]methoxy}imidazo[1,2-c]pyrimidin-8-yl)benzyl]-N,N',N'-trimethylurea | 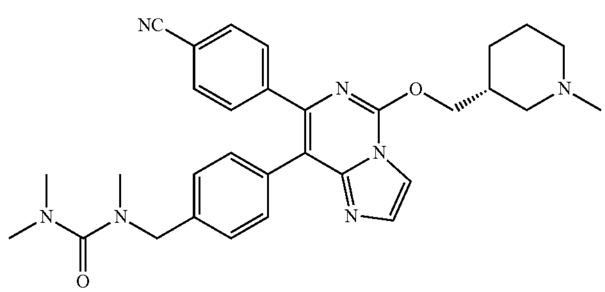 | 538.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---------|-------------|-----------|---------------|------|
| 87 | methyl [4-(7-(4-cyanophenyl)-5-{[(3R)-1-methylpiperidin-3-yl]methoxy}imidazo[1,2-c]pyrimidin-8-yl)benzyl]methylcarbamate | 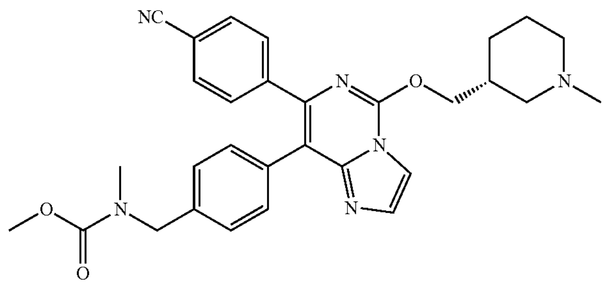 | 525.2 | TFA |
| 88 | 4-(8-(5-chloro-6-methoxypyridin-3-yl)-5-{[(3R)-1-methylpiperidin-3-yl]methoxy}imidazo[1,2-c]pyrimidin-7-yl)benzonitrile | 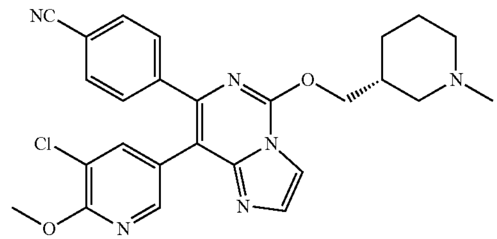 | 489.2 | TFA |
| 89 | 4-{5-[4-(dimethylamino)piperidin-1-yl]-8-[3-fluoro-4-(hydroxymethyl)-5-methylphenyl]imidazo[1,2-c]pyrimidin-7-yl}benzonitrile | 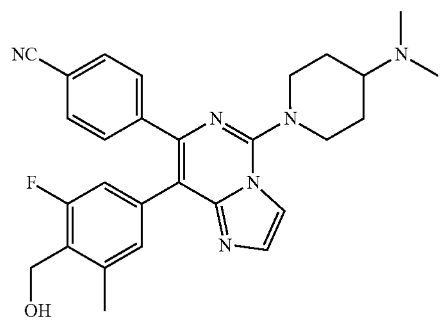 [SMILES: Cc1cc(-c2c(-c3ccc(C#N)cc3)nc(N3CCC(N(C)C)CC3)n3ccnc23)cc(F)c1CO] | 485.2 | TFA |
| 90 | 4-{8-[3,5-difluoro-4-(hydroxymethyl)phenyl]-5-[4-(dimethylamino)piperidin-1-yl]imidazo[1,2-c]pyrimidin-7-yl}benzonitrile | 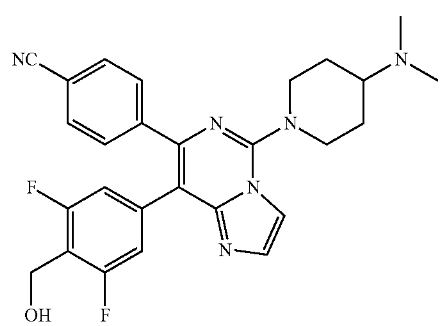 [SMILES: CN(C)C1CCN(c2nc(-c3ccc(C#N)cc3)c(-c3cc(F)c(CO)c(F)c3)c3nccn23)CC1] | 489.2 | TFA |
| 91 | 4-{5-[4-(dimethylamino)piperidin-1-yl]-8-[4-(hydroxymethyl)-3-methylphenyl]imidazo[1,2-c]pyrimidin-7-yl}benzonitrile | 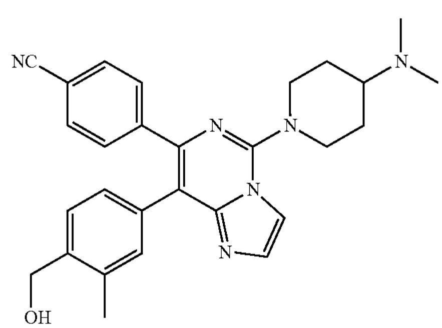 [SMILES: Cc1cc(-c2c(-c3ccc(C#N)cc3)nc(N3CCC(N(C)C)CC3)n3ccnc23)ccc1CO] | 467.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---------|-------------|-----------|---------------|------|
| 92 | 4-(8-(5-chloro-6-methylpyridin-3-yl)-5-{[(3R)-1-methylpiperidin-3-yl]methoxy}imidazo[1,2-c]pyrimidin-7-yl)benzonitrile | 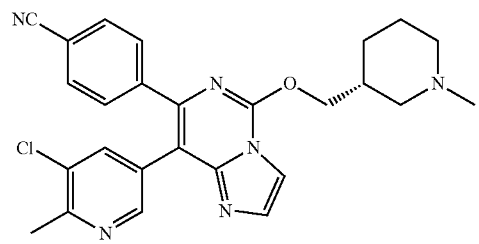 | 473.2 | TFA |
| 93 | 4-(8-[3-(1-hydroxyethyl)-4-methylphenyl]-5-{[(3R)-1-methylpiperidin-3-yl]methoxy}imidazo[1,2-c]pyrimidin-7-yl)benzonitrile | 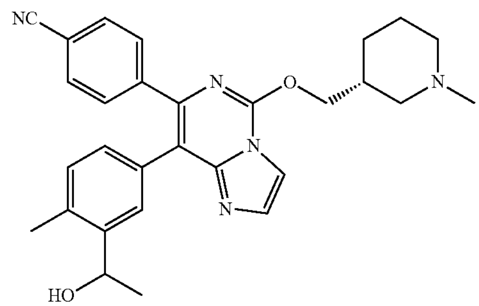 | 482.2 | TFA |
| 94 | 4-(8-[4-(methoxymethyl)phenyl]-5-{[(3R)-1-methylpiperidin-3-yl]methoxy}imidazo[1,2-c]pyrimidin-7-yl)benzonitrile | 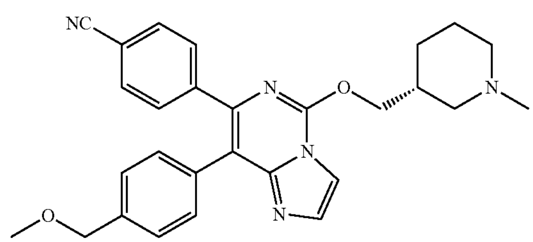 | 468.2 | TFA |
| 95 | 4-(8-[2-fluoro-4-(morpholin-4-ylmethyl)phenyl]-5-{[(3R)-1-methylpiperidin-3-yl]methoxy}imidazo[1,2-c]pyrimidin-7-yl)benzonitrile | 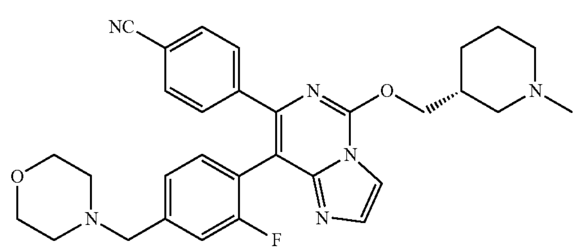 [SMILES: CN1CCC[C@@H](COc2nc(-c3ccc(C#N)cc3)c(-c3ccc(CN4CCOCC4)cc3F)c3nccn23)C1] | 541.3 | None |
| 96 | 5-(7-(4-cyanophenyl)-5-{[(3R)-1-methylpiperidin-3-yl]methoxy}imidazo[1,2-c]pyrimidin-8-yl)-2-methylbenzonitrile | 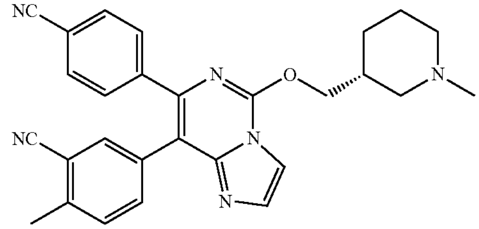 | 463.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 97 | N-(4-{7-(4-cyanophenyl)-5-[4-(dimethylamino)piperidin-1-yl]imidazo[1,2-c]pyrimidin-8-yl}-2-fluorobenzyl)-N,N',N'-trimethylurea | 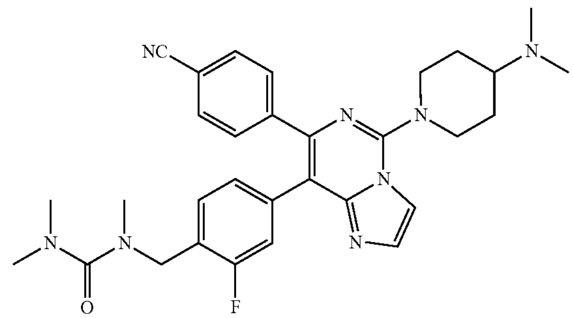 | 555.2 | TFA |
| 98 | 4-{5-[4-(dimethylamino)piperidin-1-yl]-8-[3-fluoro-4-(morpholin-4-ylmethyl)phenyl]imidazo[1,2-c]pyrimidin-7-yl}benzonitrile | 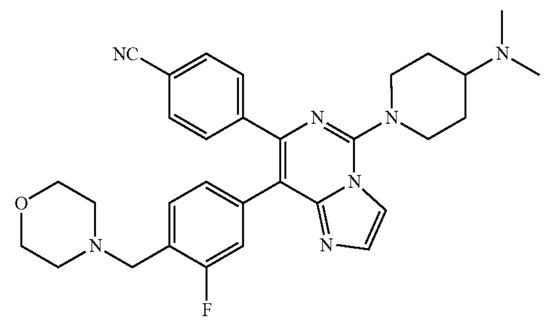 [SMILES: CN(C)C1CCN(c2nc(-c3ccc(C#N)cc3)c(-c3ccc(CN4CCOCC4)c(F)c3)c3nccn23)CC1] | 540.2 | TFA |
| 99 | 4-{5-{[(3R)-1-ethylpiperidin-3-yl]methoxy}-8-[3-(hydroxymethyl)-4-methylphenyl]imidazo[1,2-c]pyrimidin-7-yl}benzonitrile | 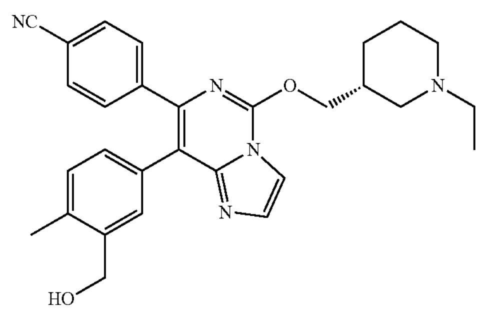 [SMILES: CCN1CCC[C@@H](COc2nc(-c3ccc(C#N)cc3)c(-c3ccc(C)c(CO)c3)c3nccn23)C1] | 482.2 | TFA |
| 100 | 4-{5-[(3R)-3-(dimethylamino)pyrrolidin-1-yl]-8-[3-(hydroxymethyl)-4-methylphenyl]imidazo[1,2-c]pyrimidin-7-yl}benzonitrile | 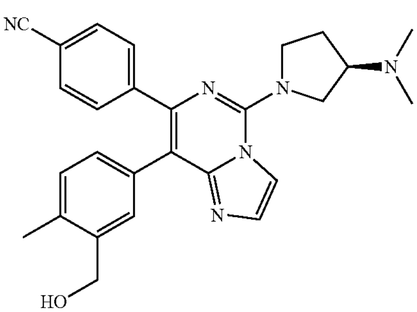 | 453.2 | TFA |
| 101 | 4-(8-[3-chloro-4-(hydroxymethyl)phenyl]-5-{[(3R)-1-methylpiperidin-3-yl]methoxy}imidazo[1,2-c]pyrimidin-7-yl)benzonitrile | 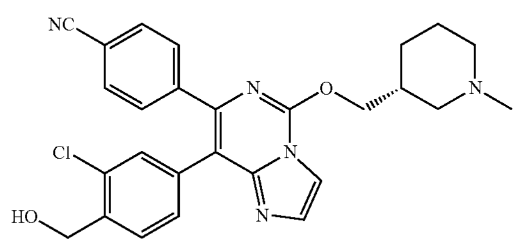 | 488.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---------|-------------|-----------|---------------|------|
| 102 | 4-{5-[4-(dimethylamino)piperidin-1-yl]-8-[3-(hydroxymethyl)-4-methylphenyl]imidazo[1,2-c]pyrimidin-7-yl}benzonitrile | 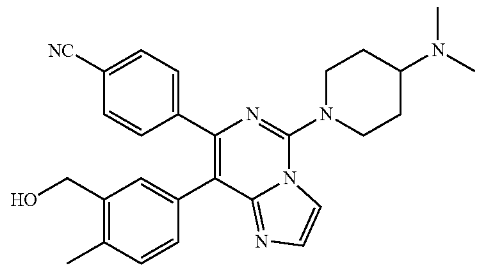 [SMILES: Cc1ccc(-c2c(-c3ccc(C#N)cc3)nc(N3CCC(N(C)C)CC3)n3ccnc23)cc1CO] | 467.2 | TFA |
| 103 | 4-{8-(5-chloro-6-methylpyridin-3-yl)-5-[4-(dimethylamino)piperidin-1-yl]imidazo[1,2-c]pyrimidin-7-yl}benzonitrile | 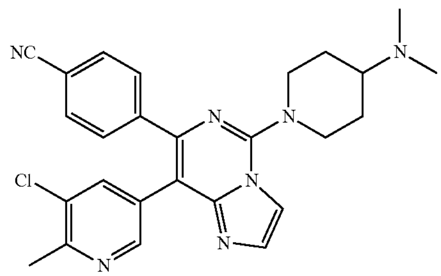 | 472.2 | TFA |
| 104 | 4-{8-(5-chloro-6-methoxypyridin-3-yl)-5-[4-(dimethylamino)piperidin-1-yl]imidazo[1,2-c]pyrimidin-7-yl}benzonitrile | 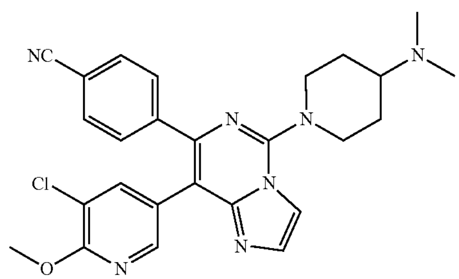 | 488.2 | TFA |
| 105 | 5-{7-(4-cyanophenyl)-5-[4-(dimethylamino)piperidin-1-yl]imidazo[1,2-c]pyrimidin-8-yl}-2-methoxynicotinonitrile | 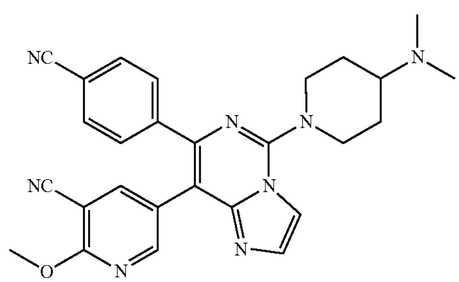 | 479.2 | TFA |
| 106 | methyl [5-(7-(4-cyanophenyl)-5-{[(3R)-1-methylpiperidin-3-yl]methoxy}imidazo[1,2-c]pyrimidin-8-yl)-2-methylphenyl]methylcarbamate | 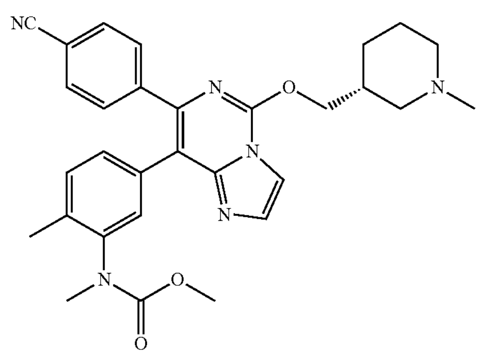 | 525.2 | TFA |

TABLE 2-continued

The compounds in Table 2 were prepared using analogous procedures as in Example 75 using the appropriate Suzuki coupling partners.

| Example | Name/$^1$H NMR | Structure | LCMS (M + H)$^+$ | Salt |
|---|---|---|---|---|
| 107 | 4-(8-(6-ethylpyridin-3-yl)-5-{[(3R)-1-methylpiperidin-3-yl]methoxy}imidazo[1,2-c]pyrimidin-7-yl)benzonitrile | 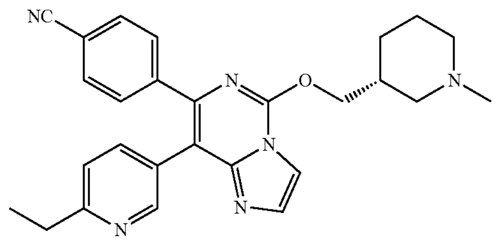 [SMILES: CCc1ccc(-c2c(-c3ccc(C#N)cc3)nc(OC[C@@H]3CCCN(C)C3)n3ccnc23)cn1] | 453.2 | TFA |
| 108 | 4-(8-(6-isopropylpyridin-3-yl)-5-{[(3R)-1-methylpiperidin-3-yl]methoxy}imidazo[1,2-c]pyrimidin-7-yl)benzonitrile | 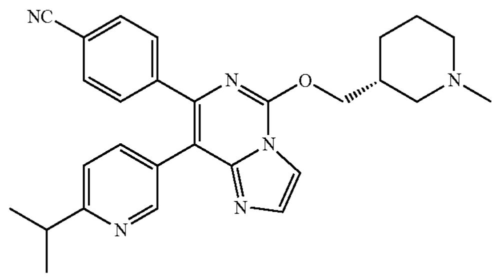 [SMILES: CC(C)c1ccc(-c2c(-c3ccc(C#N)cc3)nc(OC[C@@H]3CCCN(C)C3)n3ccnc23)cn1] | 467.2 | None |
| 109 | 4-{5-{[(3R)-1-ethylpiperidin-3-yl]methoxy}-8-[3-fluoro-4-(hydroxymethyl)-5-methylphenyl]imidazo[1,2-c]pyrimidin-7-yl}benzonitrile | 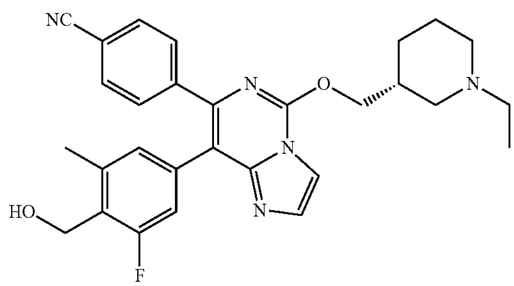 [SMILES: CCN1CCC[C@@H](COc2nc(-c3ccc(C#N)cc3)c(-c3cc(C)c(CO)c(F)c3)c3nccn23)C1] | 500.2 | TFA |
| 110 | 4-{5-[(3R)-3-(dimethylamino)pyrrolidin-1-yl]-8-[3-fluoro-4-(hydroxymethyl)-5-methylphenyl]imidazo[1,2-c]pyrimidin-7-yl}benzonitrile | 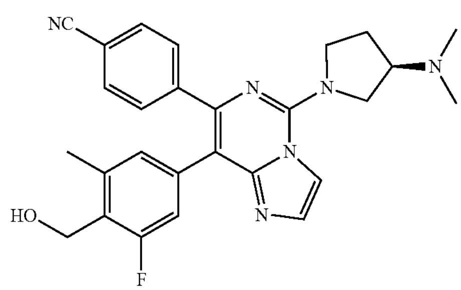 [SMILES: Cc1cc(-c2c(-c3ccc(C#N)cc3)nc(N3CC[C@@H](N(C)C)C3)n3ccnc23)cc(F)c1CO] | 471.2 | TFA |
| 111 | 4-{5-[4-(dimethylamino)piperidin-1-yl]-8-[2-(hydroxymethyl)-4-methylphenyl]imidazo[1,2-c]pyrimidin-7-yl}benzonitrile | 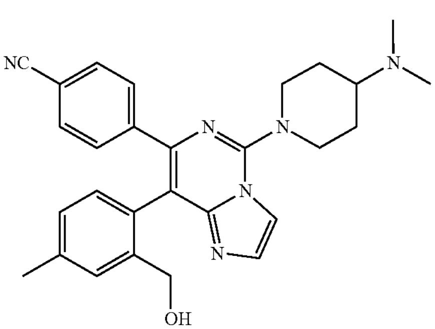 | 467.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 112 | 4-[5-[4-(dimethylamino)piperidin-1-yl]-8-(6-methylpyridin-3-yl)imidazo[1,2-c]pyrimidin-7-yl]benzonitrile | 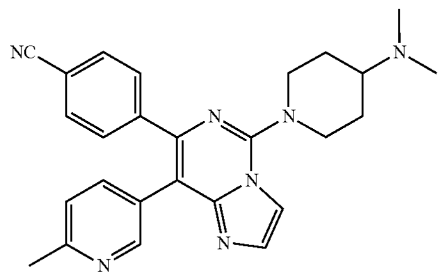 | 438.2 | TFA |
| 113 | 4-[5-[4-(dimethylamino)piperidin-1-yl]-8-(5-fluoro-6-methylpyridin-3-yl)imidazo[1,2-c]pyrimidin-7-yl]benzonitrile ¹H NMR (500 MHz, CD₃OD) δ 8.14 (m, 2H), 7.95 (d, J = 2.0 Hz, 1H), 7.73-7.67 (m, 3H), 7.64-7.58 (m, 2H), 4.37 (d, J = 13.7 Hz, 2H), 3.61 (m, 1H), 3.39-3.31 (m, 2H), 2.95 (s, 6H), 2.57 (d, J = 2.8 Hz, 3H), 2.29 (d, J = 11.1 Hz, 2H), 2.09 (m, 2H). | 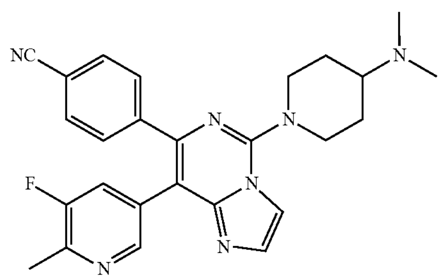 | 456.2 | TFA |
| 114 | methyl (4-{7-(4-cyanophenyl)-5-[4-(dimethylamino)piperidin-1-yl]imidazo[1,2-c]pyrimidin-8-yl}phenyl)methylcarbamate | 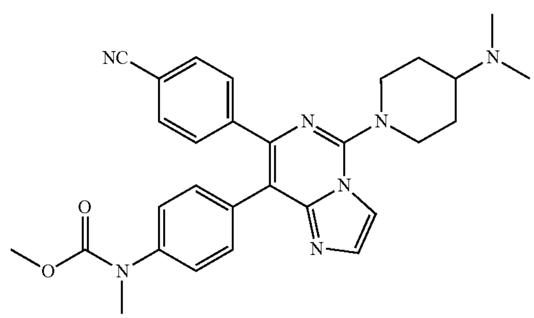 | 510.2 | TFA |
| 115 | N-(5-{7-(4-cyanophenyl)-5-[4-(dimethylamino)piperidin-1-yl]imidazo[1,2-c]pyrimidin-8-yl}pyridin-2-yl)-N-methylmethanesulfonamide | 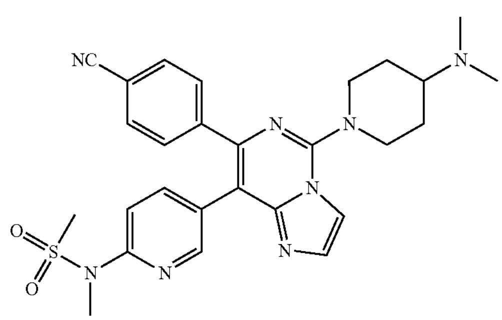 [SMILES: CN(C)C1CCN(c2nc(-c3ccc(C#N)cc3)c(-c3ccc(N(C)S(C)(=O)=O)nc3)c3nccn23)CC1] | 531.2 | TFA |
| 116 | methyl (4-{7-(4-cyanophenyl)-5-[4-(dimethylamino)piperidin-1-yl]imidazo[1,2-c]pyrimidin-8-yl}-2-fluorophenyl)methylcarbamate | 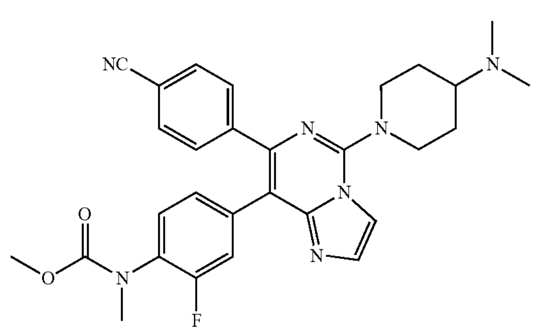 | 528.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 117 | 4-[5-[4-(dimethylamino)piperidin-1-yl]-8-(6-ethoxypyridin-3-yl)imidazo[1,2-c]pyrimidin-7-yl]benzonitrile | 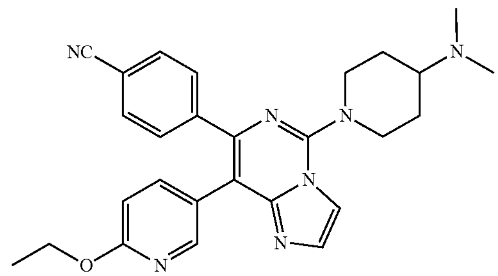 [SMILES: CCOc1ccc(-c2c(-c3ccc(C#N)cc3)nc(N3CCC(N(C)C)CC3)n3ccnc23)cn1] | 468.2 | TFA |
| 118 | 4-[5-[4-(dimethylamino)piperidin-1-yl]-8-(6-isopropylpyridin-3-yl)imidazo[1,2-c]pyrimidin-7-yl]benzonitrile | 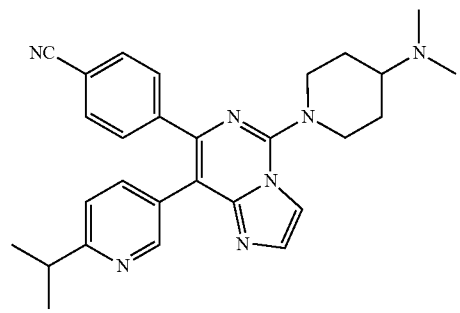 [SMILES: CC(C)c1ccc(-c2c(-c3ccc(C#N)cc3)nc(N3CCC(N(C)C)CC3)n3ccnc23)cn1] | 466.2 | TFA |
| 119 | 4-{5-{[(3R)-1-ethylpiperidin-3-yl]methoxy}-8-[2-(hydroxymethyl)-4-methylphenyl]imidazo[1,2-c]pyrimidin-7-yl}benzonitrile | 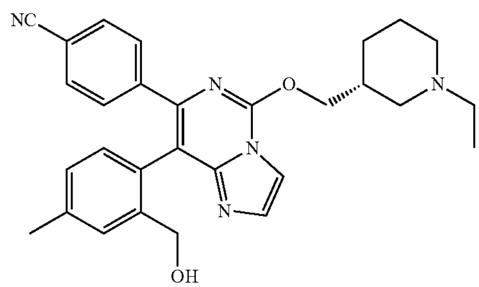 [SMILES: CCN1CCC[C@@H](COc2nc(-c3ccc(C#N)cc3)c(-c3ccc(C)cc3CO)c3nccn23)C1] | 482.2 | TFA |
| 120 | 4-{8-(1,3-benzothiazol-5-yl)-5-[4-(dimethylamino)piperidin-1-yl]imidazo[1,2-c]pyrimidin-7-yl}benzonitrile | 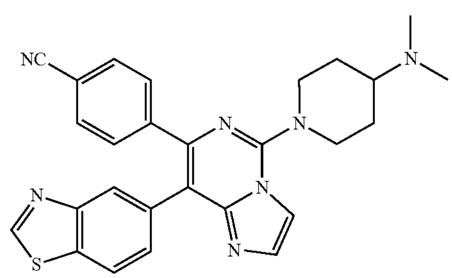 [SMILES: CN(C)C1CCN(c2nc(-c3ccc(C#N)cc3)c(-c3ccc4scnc4c3)c3nccn23)CC1] | 480.1 | TFA |
| 121 | 4-[5-[4-(dimethylamino)piperidin-1-yl]-8-(3-hydroxy-2,3-dihydro-1H-inden-5-yl)imidazo[1,2-c]pyrimidin-7-yl]benzonitrile | 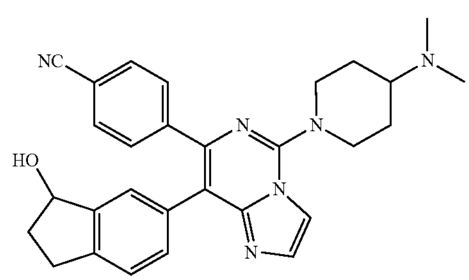 [SMILES: CN(C)C1CCN(c2nc(-c3ccc(C#N)cc3)c(-c3ccc4c(c3)C(O)CC4)c3nccn23)CC1] | 479.3 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 122 | 4-[5-[4-(dimethylamino)piperidin-1-yl]-8-(2-hydroxy-2,3-dihydro-1H-inden-5-yl)imidazo[1,2-c]pyrimidin-7-yl]benzonitrile | 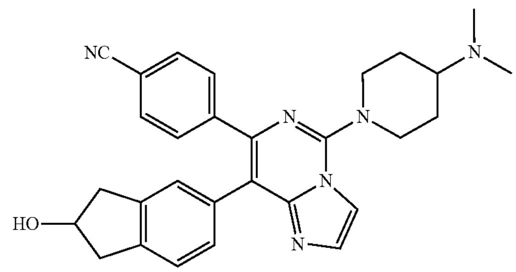 [SMILES: CN(C)C1CCN(c2nc(-c3ccc(C#N)cc3)c(-c3ccc4c(c3)CC(O)C4)c3nccn23)CC1] | 479.2 | TFA |
| 123 | 4-(8-(3-hydroxy-2,3-dihydro-1H-inden-5-yl)-5-{[(3R)-1-methylpiperidin-3-yl]methoxy}imidazo[1,2-c]pyrimidin-7-yl)benzonitrile | 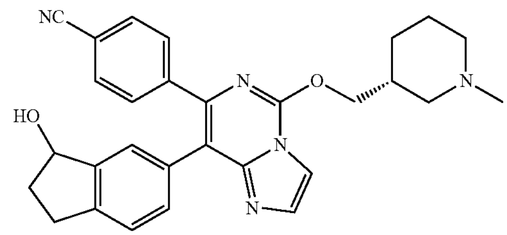 [SMILES: CN1CCC[C@@H](COc2nc(-c3ccc(C#N)cc3)c(-c3ccc4c(c3)C(O)CC4)c3nccn23)C1] | 480.2 | TFA |
| 124 | 4-(8-(2-hydroxy-2,3-dihydro-1H-inden-5-yl)-5-{[(3R)-1-methylpiperidin-3-yl]methoxy}imidazo[1,2-c]pyrimidin-7-yl)benzonitrile | 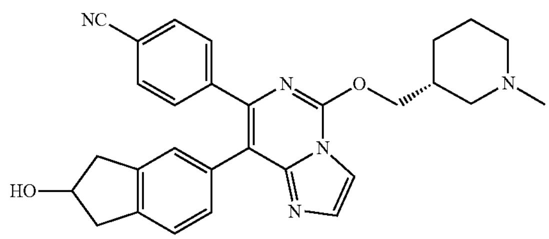 [SMILES: CN1CCC[C@@H](COc2nc(-c3ccc(C#N)cc3)c(-c3ccc4c(c3)CC(O)C4)c3nccn23)C1] | 480.2 | TFA |
| 125 | 4-[5-[4-(dimethylamino)piperidin-1-yl]-8-(1-methyl-1H-pyrrolo[2,3-b]pyridin-5-yl)imidazo[1,2-c]pyrimidin-7-yl]benzonitrile | 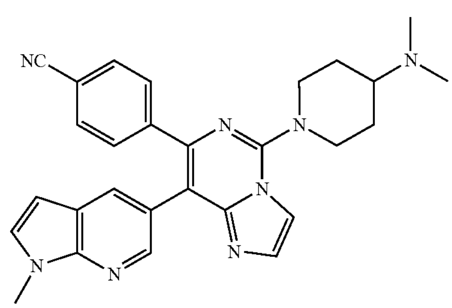 [SMILES: CN(C)C1CCN(c2nc(-c3ccc(C#N)cc3)c(-c3cnc4c(ccn4C)c3)c3nccn23)CC1] | 477.2 | TFA |
| 126 | 4-{5-[4-(dimethylamino)piperidin-1-yl]-8-quinoxalin-6-ylimidazo[1,2-c]pyrimidin-7-yl}benzonitrile | 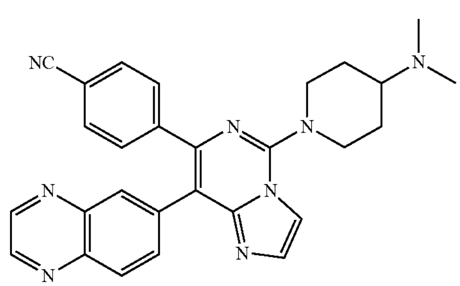 [SMILES: CN(C)C1CCN(c2nc(-c3ccc(C#N)cc3)c(-c3ccc4nccnc4c3)c3nccn23)CC1] | 475.2 | TFA |

TABLE 2-continued

The compounds in Table 2 were prepared using analogous procedures as in Example 75 using the appropriate Suzuki coupling partners.

| Example | Name/$^1$H NMR | Structure | LCMS (M + H)$^+$ | Salt |
|---|---|---|---|---|
| 127 | 4-[5-[4-(dimethylamino)piperidin-1-yl]-8-(4-fluoro-1,3-dimethyl-2-oxo-2,3-dihydro-1H-benzimidazol-5-yl)imidazo[1,2-c]pyrimidin-7-yl]benzonitrile | 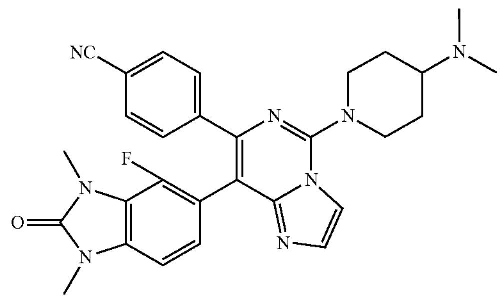 [SMILES: CN(C)C1CCN(c2nc(-c3ccc(C#N)cc3)c(-c3ccc4c(c3F)n(C)c(=O)n4C)c3nccn23)CC1] | 525.2 | TFA |
| 128 | 4-[5-[4-(dimethylamino)piperidin-1-yl]-8-(7-fluoro-1,3-dimethyl-2-oxo-2,3-dihydro-1H-benzimidazol-5-yl)imidazo[1,2-c]pyrimidin-7-yl]benzonitrile | 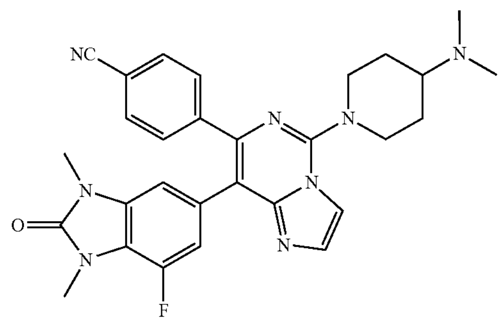 [SMILES: CN(C)C1CCN(c2nc(-c3ccc(C#N)cc3)c(-c3cc(F)c4c(c3)n(C)c(=O)n4C)c3nccn23)CC1] | 525.2 | TFA |
| 129 | 4-[5-[4-(dimethylamino)piperidin-1-yl]-8-(6-fluoro-1,3-dimethyl-2-oxo-2,3-dihydro-1H-benzimidazol-5-yl)imidazo[1,2-c]pyrimidin-7-yl]benzonitrile | 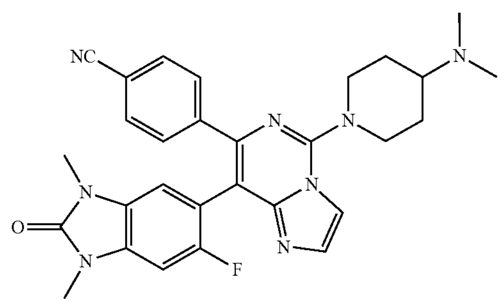 [SMILES: CN(C)C1CCN(c2nc(-c3ccc(C#N)cc3)c(-c3cc4c(cc3F)n(C)c(=O)n4C)c3nccn23)CC1] | 525.2 | TFA |
| 130 | 4-[5-[4-(dimethylamino)piperidin-1-yl]-8-(1-methyl-2-oxo-1,2,3,4-tetrahydroquinolin-6-yl)imidazo[1,2-c]pyrimidin-7-yl]benzonitrile | 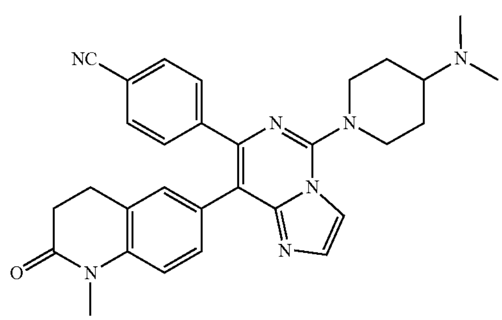 [SMILES: CN1C(=O)CCc2cc(-c3c(-c4ccc(C#N)cc4)nc(N4CCC(N(C)C)CC4)n4ccnc34)ccc21] | 506.2 | TFA |
| 131 | 4-[5-[4-(dimethylamino)piperidin-1-yl]-8-(1-methyl-2-oxo-1,2,3,4-tetrahydroquinolin-7-yl)imidazo[1,2-c]pyrimidin-7-yl]benzonitrile | 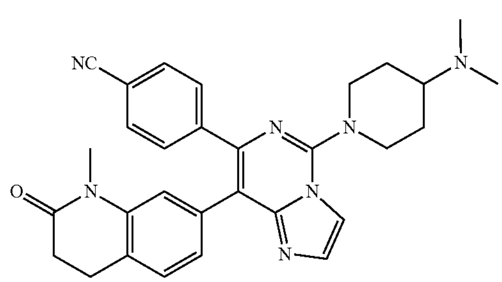 [SMILES: CN1C(=O)CCc2ccc(-c3c(-c4ccc(C#N)cc4)nc(N4CCC(N(C)C)CC4)n4ccnc34)cc21] | 506.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 132 | 4-{8-[5-(difluoromethyl)-6-methylpyridin-3-yl]-5-[4-(dimethylamino)piperidin-1-yl]imidazo[1,2-c]pyrimidin-7-yl}benzonitrile | 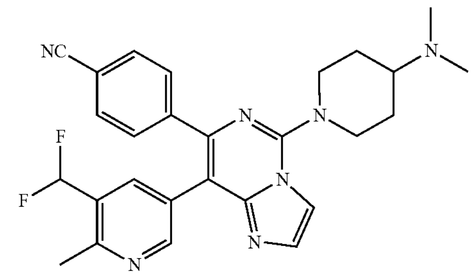 [SMILES: Cc1ncc(-c2c(-c3ccc(C#N)cc3)nc(N3CCC(N(C)C)CC3)n3ccnc23)cc1C(F)F] | 488.2 | TFA |
| 133 | 4-[5-({(3R)-1-[(2R)-2-hydroxypropyl]piperidin-3-yl}methoxy)-8-(3-methyl-2-oxo-2,3-dihydro-1,3-benzoxazol-6-yl)imidazo[1,2-c]pyrimidin-7-yl]benzonitrile | 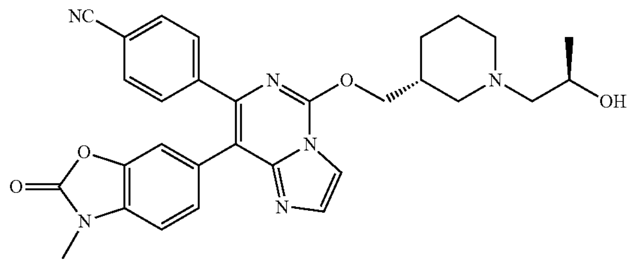 [SMILES: C[C@@H](O)CN1CCC[C@@H](COc2nc(-c3ccc(C#N)cc3)c(-c3ccc4c(c3)oc(=O)n4C)c3nccn23)C1] | 539.2 | TFA |
| 134 | 4-[5-({(3R)-1-[(2S)-2-hydroxypropyl]piperidin-3-yl}methoxy)-8-(3-methyl-2-oxo-2,3-dihydro-1,3-benzoxazol-6-yl)imidazo[1,2-c]pyrimidin-7-yl]benzonitrile | 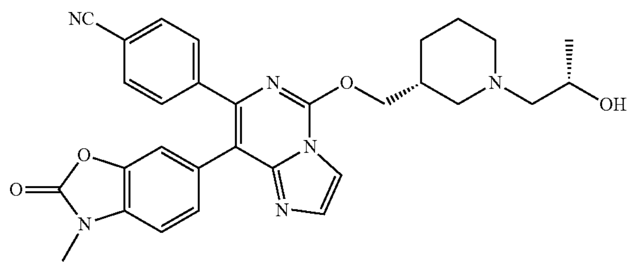 [SMILES: C[C@H](O)CN1CCC[C@@H](COc2nc(-c3ccc(C#N)cc3)c(-c3ccc4c(c3)oc(=O)n4C)c3nccn23)C1] | 539.2 | TFA |
| 135 | 4-[5-{[(3R)-1-(2-hydroxy-2-methylpropyl)piperidin-3-yl]methoxy}-8-(3-methyl-2-oxo-2,3-dihydro-1,3-benzoxazol-6-yl)imidazo[1,2-c]pyrimidin-7-yl]benzonitrile | 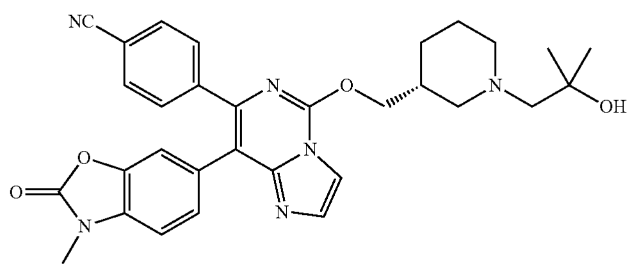 [SMILES: Cn1c(=O)oc2cc(-c3c(-c4ccc(C#N)cc4)nc(OC[C@@H]4CCCN(CC(C)(C)O)C4)n4ccnc34)ccc21] | 553.2 | TFA |
| 136 | 4-[5-({(3R)-1-[(2R)-2-hydroxypropyl]piperidin-3-yl}methoxy)-8-(1-methyl-1H-pyrazolo[3,4-b]pyridin-5-yl)imidazo[1,2-c]pyrimidin-7-yl]benzonitrile | 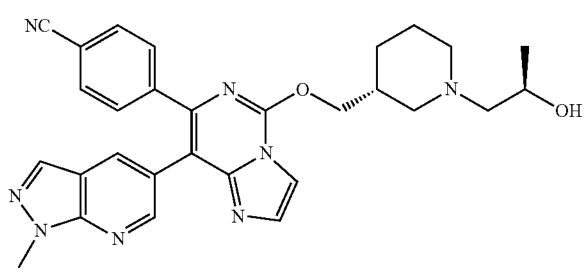 [SMILES: C[C@@H](O)CN1CCC[C@@H](COc2nc(-c3ccc(C#N)cc3)c(-c3cnc4c(cnn4C)c3)c3nccn23)C1] | 523.2 | TFA |

TABLE 2-continued

The compounds in Table 2 were prepared using analogous procedures as in Example 75 using the appropriate Suzuki coupling partners.

| Example | Name/¹H NMR | Structure | LCMS (M + H)⁺ | Salt |
|---|---|---|---|---|
| 137 | 4-[5-({(3R)-1-[(2S)-2-hydroxypropyl]piperidin-3-yl}methoxy)-8-(1-methyl-1H-pyrazolo[3,4-b]pyridin-5-yl)imidazo[1,2-c]pyrimidin-7-yl]benzonitrile | 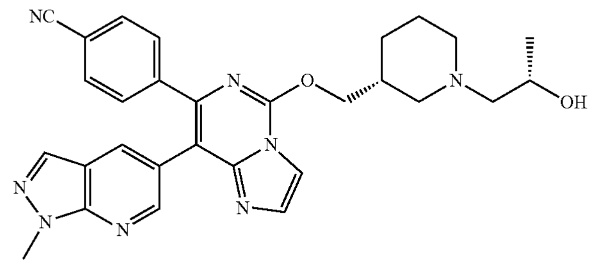 [SMILES: C[C@H](O)CN1CCC[C@@H](COc2nc(-c3ccc(C#N)cc3)c(-c3cnc4c(cnn4C)c3)c3nccn23)C1] | 523.2 | TFA |
| 138 | 4-[5-{[(3R)-1-(2-hydroxy-2-methylpropyl)piperidin-3-yl]methoxy}-8-(1-methyl-1H-pyrazolo[3,4-b]pyridin-5-yl)imidazo[1,2-c]pyrimidin-7-yl]benzonitrile | 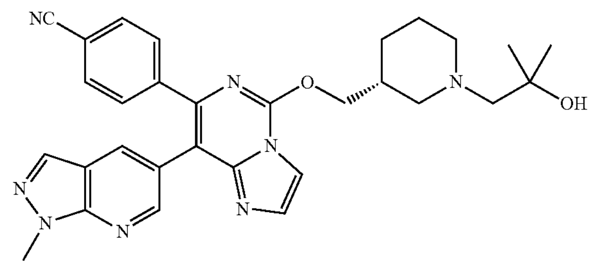 [SMILES: Cn1ncc2cc(-c3c(-c4ccc(C#N)cc4)nc(OC[C@@H]4CCCN(CC(C)(C)O)C4)n4ccnc34)cnc21] | 537.2 | TFA |

Example A: LSD1 Histone Demethylase Biochemical Assay

LANCE LSD1/KDM1A demethylase assay—10 µL of 1 nM LSD-1 enzyme (ENZO BML-SE544-0050) in the assay buffer (50 mM Tris, pH 7.5, 0.01% Tween-20, 25 mM NaCl, 5 mM DTT) were preincubated for 1 hour at 25° C. with 0.8 µL compound/DMSO dotted in black 384 well polystyrene plates. Reactions were started by addition of 10 µL of assay buffer containing 0.4 µM Biotin-labeled Histone H3 peptide substrate: ART-K(Me1)-QTARKSTGGKAPRKQLA-GGK(Biotin) SEQ ID NO:1 (AnaSpec 64355) and incubated for 1 hour at 25° C. Reactions were stopped by addition of 10 µL 1×LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). IC$_{50}$ data for the example compounds is provided in Table 1 (the symbol "+" refers to IC$_{50}$≤50 nM; "++" refers to IC50>50 nM and ≤500 nM; "+++" refers to IC50>500 nM and ≤1000 nM).

TABLE 1

| Example No. | IC$_{50}$ (nM) |
|---|---|
| 1 | + |
| 2 | ++ |
| 3 | + |
| 4 | + |
| 5 | + |
| 6 | ++ |
| 7 | + |
| 8 | + |
| 9 | + |
| 10 | + |

TABLE 1-continued

| Example No. | IC$_{50}$ (nM) |
|---|---|
| 11 | ++ |
| 12 | ++ |
| 13 | + |
| 14 | + |
| 15 | ++ |
| 16 | ++ |
| 17 | + |
| 18 | ++ |
| 19 | + |
| 20 | + |
| 21 | ++ |
| 22 | ++ |
| 23 | ++ |
| 24 | + |
| 25 | ++ |
| 26 | ++ |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | ++ |
| 45 | + |
| 46 | + |
| 47 | + |
| 48 | ++ |
| 49 | + |
| 50 | ++ |
| 51 | + |

TABLE 1-continued

| Example No. | IC$_{50}$ (nM) |
|---|---|
| 52 | + |
| 53 | + |
| 54 | + |
| 55 | + |
| 56 | + |
| 57 | + |
| 58 | + |
| 59 | + |
| 60 | + |
| 61 | ++ |
| 62 | + |
| 63 | + |
| 64 | + |
| 65 | + |
| 66 | ++ |
| 67 | ++ |
| 68 | + |
| 69 | + |
| 70 | + |
| 71 | + |
| 72 | + |
| 73 | ++ |
| 74 | ++ |
| 75 | ++ |
| 76 | + |
| 77 | + |
| 78 | + |
| 79 | ++ |
| 80 | + |
| 81 | ++ |
| 82 | + |
| 83 | + |
| 84 | ++ |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |

TABLE 1-continued

| Example No. | IC$_{50}$ (nM) |
|---|---|
| 100 | + |
| 101 | + |
| 102 | + |
| 103 | + |
| 104 | + |
| 105 | + |
| 106 | + |
| 107 | ++ |
| 108 | ++ |
| 109 | + |
| 110 | + |
| 111 | + |
| 112 | ++ |
| 113 | + |
| 114 | + |
| 115 | + |
| 116 | + |
| 117 | + |
| 118 | ++ |
| 119 | ++ |
| 120 | + |
| 121 | + |
| 122 | + |
| 123 | + |
| 124 | + |
| 125 | + |
| 126 | ++ |
| 127 | + |
| 128 | + |
| 129 | + |
| 130 | + |
| 131 | ++ |
| 132 | ++ |
| 133 | ++ |
| 134 | + |
| 135 | ++ |
| 136 | ++ |
| 137 | + |
| 138 | ++ |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient in need thereof, comprising administering to the patient a compound of Formula I:

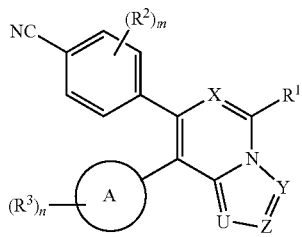

or a pharmaceutically acceptable salt thereof, wherein:
ring A is $C_{6-10}$ aryl, $C_{3-10}$ cycloalkyl, 5-10 membered heteroaryl, or 4-10 membered heterocycloalkyl, wherein the 5-10 membered heteroaryl or 4-10 membered heterocycloalkyl of ring A each has at least one ring-forming carbon atom and 1, 2, 3, or 4 ring-forming heteroatoms selected from N, O, and S, wherein N or S is optionally oxidized; and wherein a ring-forming carbon atom of the $C_{3-10}$ cycloalkyl or 4-10 membered heterocycloalkyl is optionally substituted by oxo to form a carbonyl group;

X is N or $CR^X$, wherein $R^X$ is H, OH, CN, halo, $NH_2$, $C_{1-4}$ alkyl, $C_{1-4}$ alkoxy, $C_{1-4}$ haloalkyl, $C_{1-4}$ haloalkoxy, $NHC_{1-4}$ alkyl, $N(C_{1-4}$ alkyl$)_2$ or $C_{1-4}$ alkylthio;

U is N or $CR^U$, wherein $R^U$ is H, OH, CN, halo, $NH_2$, $C_{1-4}$ alkyl, $C_{1-4}$ alkoxy, $C_{1-4}$ haloalkyl, $C_{1-4}$ haloalkoxy, $NHC_{1-4}$ alkyl, $N(C_{1-4}$ alkyl$)_2$ or $C_{1-4}$ alkylthio;

Y is N or $CR^4$;

Z is N or $CR^5$;

with the proviso that at least one of U, Y, and Z is N;

$R^1$ is H, halo, $C_{1-6}$ alkyl, $C_{2-6}$ alkenyl, $C_{2-6}$ alkynyl, $C_{1-6}$ haloalkyl, $C_{1-6}$haloalkoxy, NHOH, $NHOC_{1-6}$ alkyl, $Cy^1$, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, -$L^1$-$R^6$, or -$L^2$-$NR^7R^8$; wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, OH, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$ $NR^{c1}C(O)R^{b1}$, $NR^{c1}C(O)OR^{a1}$ $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$ $NR^{c1}S(O)R^{b1}$ $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$L^1$ is a bond, —O—, —$NR^9$—, —C(O)NH—, —NHC(O)—, $C_{1-4}$ alkylene; wherein $R^9$ is H, $C_{1-6}$ alkyl, —C(O)$C_{1-6}$ alkyl or —C(O)O$C_{1-6}$ alkyl;

$L^2$ is a bond, —C(O)—, $C_{1-4}$ alkylene, —O—$C_{1-4}$ alkylene-, —$C_{1-4}$ alkylene-O-, —$C_{1-4}$ alkylene-$NR^9$—, or —$NR^9$—$C_{1-4}$ alkylene-;

$R^2$, at each occurrence, is independently selected from H, OH, CN, halo, $NH_2$, $C_{1-4}$ alkyl, $C_{1-4}$ alkoxy, $C_{1-4}$ haloalkyl, $C_{1-4}$ haloalkoxy, $NHC_{1-4}$ alkyl, $N(C_{1-4}$ alkyl$)_2$, and $C_{1-4}$ alkylthio;

$R^3$, at each occurrence, is independently selected from H, $Cy^2$, halo, $C_{1-6}$ alkyl, $C_{2-6}$ alkenyl, $C_{2-6}$ alkynyl, $C_{1-6}$ haloalkyl, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}C(O)R^{b2}$ $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{e2}S(O)R^{b2}$, $NR^{e2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{e2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

or two adjacent $R^3$ substituents on ring A taken together with the atoms to which they are attached form a fused 5- or 6-membered heterocycloalkyl ring, a fused $C_{3-6}$ cycloalkyl ring, or a fused 5- or 6-membered heteroaryl ring, each of which is optionally substituted with 1 or 2 independently selected $R^A$ substituents, wherein a ring carbon of the fused 5- or 6-membered heterocycloalkyl ring or fused $C_{3-6}$ cycloalkyl ring is optionally replaced by a carbonyl group;

alternatively, two $R^A$ substituents attached to the same carbon of the fused 5- or 6-membered heterocycloalkyl ring or fused $C_{3-6}$ cycloalkyl ring taken together form a $C_{3-6}$ cycloalkyl ring or 4- to 7-membered heterocycloalkyl ring;

$R^4$ and $R^5$ are each independently selected from H, $Cy^3$, halo, $C_{1-6}$ alkyl, $C_{2-6}$ alkenyl, $C_{2-6}$ alkynyl, $C_{1-6}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^6$ is 5- to 10-membered heteroaryl, 5- to 10-membered heteroaryl-$C_{1-4}$ alkyl, 4- to 10-membered heterocycloalkyl, or 4- to 10-membered heterocycloalkyl-$C_{1-4}$ alkyl, each of which is optionally substituted with 1, 2, 3 or 4 independently selected $R^A$ substituents;

$R^7$ and $R^8$ together with the nitrogen atom to which they are attached form 4- to 10-membered heterocycloalkyl ring having 0, 1 or 2 heteroatoms selected from N and S in addition to the nitrogen atom connected to $R^7$ and $R^8$, wherein a ring-forming carbon atom of the heterocycloalkyl group is optionally substituted by an oxo group, and wherein the heterocycloalkyl is optionally substituted with 1, 2, 3 or 4 independently selected $R^B$ substituents;

each $R^A$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $Cy^2$, $C_{3-10}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a4}$, $SR^{a4}$, $C(O)$ $R^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said $C_{1-6}$ alkyl, $C_{2-6}$ alkenyl, $C_{2-6}$ alkynyl, Cy$^3$, $C_{3-10}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted by 1, 2, or 3 substituents independently selected from halo, $C_{1-6}$ haloalkyl, $C_{1-6}$ haloalkoxy, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^B$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, Cy$^3$, $C_{3-10}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said $C_{1-6}$ alkyl, $C_{2-6}$ alkenyl, $C_{2-6}$ alkynyl, Cy$^4$, $C_{3-10}$ cycloalkyl-$C_{1-4}$ alkyl, 5-10 membered heteroaryl-$C_{1-4}$ alkyl and 4-10 membered heterocycloalkyl-$C_{1-4}$ alkyl are each optionally substituted by 1, 2, or 3 substituents independently selected from halo, $C_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each Cy$^1$, Cy$^2$, Cy$^3$, and Cy$^4$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from R$^{Cy}$;

each R$^{Cy}$ is independently selected from H, halo, $C_{1-4}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, oxo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said $C_{1-4}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-4}$ alkyl-, $C_{3-7}$ cycloalkyl-$C_{1-4}$ alkyl-, (5-6 membered heteroaryl)-$C_{1-4}$ alkyl-, and (4-7 membered heterocycloalkyl)-$C_{1-4}$ alkyl- are each optionally substituted by 1, 2, or 3 substituents independently selected from $C_{1-6}$ alkyl, $C_{1-4}$ haloalkyl, $C_{1-4}$ cyanoalkyl, halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$) NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^{a1}$, R$^{b1}$, R$^{c1}$, and R$^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$ NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^{a2}$, R$^{b2}$, R$^{c2}$, and R$^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d1}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, phenyl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{3-7}$ cycloalkyl, 4-7 membered heterocycloalkyl, phenyl, and 5-6 membered heteroaryl are each optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, 3, 4, or 5 substituents independently selected from $C_{1-4}$ alkyl, $C_{1-4}$ haloalkyl, $C_{1-4}$ cyanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $N^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl are each optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e1}$, $R^{e2}$, $R^{e3}$, $R^{e4}$, and $R^{e5}$ is independently selected from H, $C_{1-4}$ alkyl, and CN;

the subscript m is 1 or 2; and the subscript n is 1, 2, 3 or 4;

wherein said cancer is selected from myelodysplasia syndrome (MDS), undifferentiated small cell lung cancer, Ewing's sarcoma, primary myelofibrosis (PMF), acute lymphoblastic leukemia (ALL), and acute myelogenous leukemia (AML).

2. The method of claim 1, wherein the compound is a compound of Formula II:

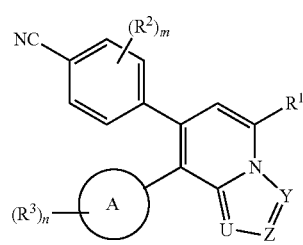

II or a pharmaceutically acceptable salt thereof.

3. The method of claim 1, wherein the compound is a compound of Formula III:

$$\text{III}$$

or a pharmaceutically acceptable salt thereof.

4. The method of claim 1, wherein the compound is a compound of Formula IIIa:

$$\text{IIIa}$$

or a pharmaceutically acceptable salt thereof.

5. The method of claim 1, wherein Y and Z are each CH.

6. The method of claim 1, wherein ring A is phenyl.

7. The method of claim 1, wherein ring A is 5-10 membered heteroaryl.

8. The method of claim 1, wherein ring A is 4-10 membered heterocycloalkyl having at least one ring-forming carbon atom and 1, 2, 3, or 4 ring-forming heteroatoms selected from N, O, and S, wherein N or S is optionally oxidized, and wherein a ring-forming carbon atom is optionally substituted by oxo to form a carbonyl group.

9. The method of claim 1, wherein ring A is phenyl; 2,3-dihydro-1,4-benzodioxine; 2,3-dihydro-1H-pyrrolo[2,3-b]pyridin-5-yl; 5,6,7,8-tetrahydro-1,8-naphthyridin-3-yl; 2-oxo-1,2,3,4-tetrahydroquinolin-7-yl; pyridyl; 2-oxo-2,3-dihydro-1,3-benzoxazolyl; 1,3-benzothiazol-5-yl; 2,3-dihydro-1H-inden-5-yl; 1H-pyrrolo[2,3-b]pyridinyl; 8-quinoxalin-6-yl; 2-oxo-1,2,3,4-tetrahydroquinolin-6-yl; or 1H-pyrazolo[3,4-b]pyridinyl.

10. The method of claim 1, wherein $R^3$, at each occurrence, is independently selected from $Cy^2$, $C_{1-6}$ alkyl, CN, $OR^{a2}$, $C(O)NR^{e2}R^{d2}$, and $NR^{e2}R^{d2}$; wherein the $C_{1-6}$ alkyl is optionally substituted with 1, 2, or 3 substituents independently selected from $Cy^2$, $C(O)R^{b2}$, and $C(O)NR^2R^{d2}$.

11. The method of claim 1, wherein $R^3$ is $C_{1-6}$ alkyl, halo, $C_{1-6}$ hydroxyalkyl, $C_{1-6}$ haloalkyl, CN, $OR^{a2}$, 1-pyrrolidinyl, 2-oxo-1-pyrrolidinyl, $NR^{c2}C(O)OR^{a2}$, —($C_{1-6}$ alkyl)-$NR^{c2}C(O)OR^{a2}$, $C(O)NR^{c2}R^{d2}$, $NR^{c2}R^{d2}$, piperazinylmethyl, 4-methylpiperazinylmethyl, piperidinyl, morpholinyl, 4-methylpiperazinylcarbonylmethyl, morpholinylmethyl, or 3-cyano-1-pyrrolidinyl.

12. The method of claim 1, wherein $R^1$ is -$L^1$-$R^6$ or -$L^2$-$NR^7R^8$.

13. The method of claim 1, wherein $R^1$ is (1-methylpiperidin-3-yl)methoxy, (1-ethylpiperidin-3-yl)methoxy, (2-cyanoethylpiperidin-3-yl)methoxy, 4-dimethylaminopiperidin-1-yl, 3-dimethylaminopyrrolidin-1-yl, (2-hydroxypropylpiperidin-3-yl)methoxy, or 2-hydroxy-2-methylpropyl)piperidin-3-yl]methoxy.

14. The method of claim 1, wherein $R^2$ is H.
15. The method of claim 1, wherein $R^4$ is H.
16. The method of claim 1, wherein $R^5$ is H.
17. The method of claim 1, wherein m is 1.
18. The method of claim 1, wherein n is 1.
19. The method of claim 1, wherein the compound is a compound of Formula V:

$$\text{V}$$

or a pharmaceutically acceptable salt thereof, wherein:
two $R^3$ substituents taken together with the carbon atoms to which they are attached form a fused 5-membered heterocycloalkyl ring or a fused 5-membered heteroaryl ring, each of which is optionally substituted with 1 or 2 independently selected $R^A$ substituents, wherein a ring carbon of the fused 5-membered heterocycloalkyl ring is optionally replaced by a carbonyl group;

$X^1$ is N or CH;

$L^2$ is a bond or O—$C_{1-4}$ alkylene; and $R^7$ and $R^8$ together with the nitrogen atom to which they are attached form 4- to 7-membered heterocycloalkyl ring having 0, 1 or 2 heteroatoms selected from N and S in addition to the nitrogen atom connected to $R^7$ and $R^8$, wherein the heterocycloalkyl is optionally substituted with 1, 2, 3 or 4 independently selected $R^B$ substituents.

20. The method of claim 1, wherein the compound is selected from:
4-(8-(4-methylphenyl)-5-{[(3R)-1-methylpiperidin-3-yl]methoxy}imidazo[1,2-c]pyrimidin-7-yl)benzonitrile,
4-(8-(4-methylphenyl)-5-{[(3R)-1-methylpyrrolidin-3-yl]methoxy}imidazo[1,2-c]pyrimidin-7-yl)benzonitrile,
4-(8-(6-methoxypyridin-3-yl)-5-{[(3R)-1-methylpiperidin-3-yl]methoxy}imidazo[1,2-c]pyrimidin-7-yl)benzonitrile,
4-(8-[6-(dimethylamino)pyridin-3-yl]-5-{[(3R)-1-methylpiperidin-3-yl]methoxy}imidazo[1,2-c]pyrimidin-7-yl)benzonitrile,
4-[5-{[(3R)-1-methylpiperidin-3-yl]methoxy}-8-(6-pyrrolidin-1-ylpyridin-3-yl)imidazo[1,2-c]pyrimidin-7-yl]benzonitrile,
4-(8-(1-methyl-2-oxo-2,3-dihydro-1H-indol-5-yl)-5-{[(3R)-1-methylpiperidin-3-yl]methoxy}imidazo[1,2-c]pyrimidin-7-yl)benzonitrile,
4-(8-(3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile,
4-(8-(1-methyl-1H-indazol-5-yl)-5-{[(3R)-1-methylpiperidin-3-yl]methoxy}imidazo[1,2-c]pyrimidin-7-yl)benzonitrile, 4-(8-{4-[(4-methylpiperazin-1-yl)methyl]phenyl}-5-{[(3R)-1-methylpiperidin-3-yl]methoxy}imidazo[1,2-c]pyrimidin-7-yl)benzonitrile, 4-(8-{4-[2-(4-methylpiperazin-1-yl)-2-oxoethyl]phenyl}-5-{[(3R)-1-methylpiperidin-3-yl]methoxy}imidazo[1,2-c]pyrimidin-7-yl)benzonitrile, 4-{5-{[(3R)-1-methylpiperidin-3-yl]methoxy}-8-[4-(2-morpholin-4-ylethyl)phenyl]imidazo[1,2-c]pyrimidin-7-yl}benzonitrile, 4-{5-{[(3R)-1-methylpiperidin-3-yl]methoxy}-8-[4-(morpholin-4-ylmethyl)phenyl]imidazo[1,2-c]pyrimidin-7-yl}benzonitrile, (3S)-1-[4-(7-(4-cyanophenyl)-5-{[(3R)-1-methylpiperidin-3-yl]methoxy}imidazo[1,2-c]pyrimidin-8-yl)benzyl]pyrrolidine-3-carbonitrile, 4-(8-(4-methyl-3,4-dihydro-2H-pyrido[3,2-b][1,4]oxazin-7-yl)-5-{[(3R)-1-methylpiperidin-3-yl]methoxy}imidazo[1,2-c]pyrimidin-7-yl)benzonitrile, 4-(8-(4-methyl-3-oxo-3,4-dihydro-2H-1,4-benzoxazin-7-yl)-5-{[(3R)-1-methylpiperidin-3-yl]methoxy}imidazo[1,2-c]pyrimidin-7-yl)benzonitrile, 4-{5-{[(3R)-1-methylpiperidin-3-yl]methoxy}-8-[6-(2-oxopyrrolidin-1-yl)pyridin-3-yl]imidazo[1,2-c]pyrimidin-7-yl}benzonitrile, 4-(8-(1-methyl-1H-benzimidazol-5-yl)-5-{[(3R)-1-methylpiperidin-3-yl]methoxy}imidazo[1,2-c]pyrimidin-7-yl)benzonitrile, 4-(8-(1-methyl-1H-indazol-6-yl)-5-{[(3R)-1-methylpiperidin-3-yl]methoxy}imidazo[1,2-c]pyrimidin-7-yl)benzonitrile, 4-[5-{[(3R)-1-methylpiperidin-3-yl]methoxy}-8-(1-methyl-1H-pyrrolo[2,3-b]pyridin-5-yl)imidazo[1,2-c]pyrimidin-7-yl]benzonitrile, 5-(7-(4-cyanophenyl)-5-{[(3R)-1-methylpiperidin-3-yl]methoxy}imidazo[1,2-c]pyrimidin-8-yl)-N,N-dimethyl-2,3-dihydro-1-benzofuran-2-carboxamide, 4-(8-[6-(dimethylamino)pyridin-3-yl]-5-{[(3R)-1-methylpyrrolidin-3-yl]methoxy}imidazo[1,2-c]pyrimidin-7-yl)benzonitrile, 4-[5-{[(3R)-1-methylpyrrolidin-3-yl]methoxy}-8-(6-pyrrolidin-1-ylpyridin-3-yl)imidazo[1,2-c]pyrimidin-7-yl]benzonitrile, 4-(8-(1-methyl-2-oxo-2,3-dihydro-1H-indol-5-yl)-5-{[(3R)-1-methylpyrrolidin-3-yl]methoxy}imidazo[1,2-c]pyrimidin-7-yl)benzonitrile, 4-(8-(4-methyl-3,4-dihydro-2H-pyrido[3,2-b][1,4]oxazin-7-yl)-5-{[(3R)-1-methylpyrrolidin-3-yl]methoxy}imidazo[1,2-c]pyrimidin-7-yl)benzonitrile, 4-(8-(1-methyl-1H-benzimidazol-5-yl)-5-{[(3R)-1-methylpyrrolidin-3-yl]methoxy}imidazo[1,2-c]pyrimidin-7-yl)benzonitrile, 4-(8-(3-methyl-2-oxo-2,3-dihydro-1,3-benzoxazol-6-yl)-5-{[(3R)-1-methylpyrrolidin-3-yl]methoxy}imidazo[1,2-c]pyrimidin-7-yl)benzonitrile, and 4-(8-(1-methyl-1H-indazol-5-yl)-5-{[(3R)-1-methylpyrrolidin-3-yl]methoxy}imidazo[1,2-c]pyrimidin-7-yl)benzonitrile;

or a pharmaceutically acceptable salt thereof.

21. The method of claim 1, wherein the compound is selected from:

4-[5-{[(3R)-1-methylpiperidin-3-yl]methoxy}-8-(1-methyl-1H-pyrazolo[3,4-b]pyridin-5-yl)imidazo[1,2-c]pyrimidin-7-yl]benzonitrile, 4-[5-{[(3R)-1-ethylpiperidin-3-yl]methoxy}-8-(1-methyl-1H-pyrazolo[3,4-b]pyridin-5-yl)imidazo[1,2-c]pyrimidin-7-yl]benzonitrile, 4-(8-[3-fluoro-4-(hydroxymethyl)-5-methylphenyl]-5-{[(3R)-1-methylpiperidin-3-yl]methoxy}imidazo[1,2-c]pyrimidin-7-yl)benzonitrile, 4-(8-[3-fluoro-4-(hydroxymethyl)phenyl]-5-{[(3R)-1-methylpiperidin-3-yl]methoxy}imidazo[1,2-c]pyrimidin-7-yl)benzonitrile, 4-(8-[3,5-difluoro-4-(hydroxymethyl)phenyl]-5-{[(3R)-1-methylpiperidin-3-yl]methoxy}imidazo[1,2-c]pyrimidin-7-yl)benzonitrile, 4-[5-{[(3R)-1-(2-cyanoethyl)piperidin-3-yl]methoxy}-8-(1-methyl-1H-pyrazolo[3,4-b]pyridin-5-yl)imidazo[1,2-c]pyrimidin-7-yl]benzonitrile, 4-[5-{[(3R)-1-(2-hydroxyethyl)piperidin-3-yl]methoxy}-8-(1-methyl-1H-pyrazolo[3,4-b]pyridin-5-yl)imidazo[1,2-c]pyrimidin-7-yl]benzonitrile, 4-(8-[4-(hydroxymethyl)-3-methylphenyl]-5-{[(3R)-1-methylpiperidin-3-yl]methoxy}imidazo[1,2-c]pyrimidin-7-yl)benzonitrile, 4-(8-[4-(hydroxymethyl)phenyl]-5-{[(3R)-1-methylpiperidin-3-yl]methoxy}imidazo[1,2-c]pyrimidin-7-yl)benzonitrile, 4-[5-[4-(dimethylamino)piperidin-1-yl]-8-(1-methyl-1H-pyrazolo[3,4-b]pyridin-5-yl)imidazo[1,2-c]pyrimidin-7-yl]benzonitrile, 4-[5-[(3R)-3-(dimethylamino)pyrrolidin-1-yl]-8-(1-methyl-1H-pyrazolo[3,4-b]pyridin-5-yl)imidazo[1,2-c]pyrimidin-7-yl]benzonitrile, 4-[5-(7-methyl-2,7-diazaspiro[4.4]non-2-yl)-8-(1-methyl-1H-pyrazolo[3,4-b]pyridin-5-yl)imidazo[1,2-c]pyrimidin-7-yl]benzonitrile, methyl [4-(7-(4-cyanophenyl)-5-{[(3R)-1-methylpiperidin-3-yl]methoxy}imidazo[1,2-c]pyrimidin-8-yl)-2-fluorobenzyl]methylcarbamate, 4-[5-{[(3R)-1-(2-methoxyethyl)piperidin-3-yl]methoxy}-8-(1-methyl-1H-pyrazolo[3,4-b]pyridin-5-yl)imidazo[1,2-c]pyrimidin-7-yl]benzonitrile, 4-(8-(3-amino-1-methyl-1H-indazol-5-yl)-5-{[(3R)-1-methylpiperidin-3-yl]methoxy}imidazo[1,2-c]pyrimidin-7-yl)benzonitrile, 4-(8-(3-methyl-2-oxo-3,4-dihydro-2H-1,3-benzoxazin-7-yl)-5-{[(3R)-1-methylpiperidin-3-yl]methoxy}imidazo[1,2-c]pyrimidin-7-yl)benzonitrile, 4-(8-(1,3-dimethyl-2-oxo-2,3-dihydro-1H-benzimidazol-5-yl)-5-{[(3R)-1-methylpiperidin-3-yl]methoxy}imidazo[1,2-c]pyrimidin-7-yl)benzonitrile, 4-(8-(5-fluoro-3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile, 4-[5-[4-(dimethylamino)piperidin-1-yl]-8-(1-methyl-1H-indazol-5-yl)imidazo[1,2-c]pyrimidin-7-yl]benzonitrile, 4-[5-[4-(dimethylamino)piperidin-1-yl]-8-(3-methyl-2-oxo-2,3-dihydro-1,3-benzoxazol-6-yl)imidazo[1,2-c]pyrimidin-7-yl]benzonitrile, 4-[5-[4-(dimethylamino)piperidin-1-yl]-8-(6-methoxypyridin-3-yl)imidazo[1,2-c]pyrimidin-7-yl]benzonitrile, 4-[5-[4-(dimethylamino)piperidin-1-yl]-8-(5-fluoro-6-methoxypyridin-3-yl)imidazo[1,2-c]pyrimidin-7-yl]benzonitrile, 4-{5-[4-(dimethylamino)piperidin-1-yl]-8-[6-(2-oxopyrrolidin-1-yl)pyridin-3-yl]imidazo[1,2-c]pyrimidin-7-yl}benzonitrile, 4-[5-[4-(dimethylamino)piperidin-1-yl]-8-(4-methyl-3-oxo-3,4-dihydro-2H-1,4-benzoxazin-7-yl)imidazo[1,2-c]pyrimidin-7-yl]benzonitrile, 4-{8-[2-(difluoromethyl)-1-methyl-1H-benzimidazol-5-yl]-5-[4-(dimethylamino)piperidin-1-yl]imidazo[1,2-c]pyrimidin-7-yl}benzonitrile, 4-[5-[4-(dimethylamino)piperidin-1-yl]-8-(6-methoxy-5-methylpyridin-3-yl)imidazo[1,2-c]pyrimidin-7-yl]benzonitrile, 4-[5-[4-(dimethylamino)piperidin-1-yl]-8-(5-fluoro-3-methyl-2-oxo-2,3-dihydro-1,3-benzoxazol-6-yl)imidazo[1,2-c]pyrimidin-7-yl]benzonitrile, 4-[5-{[(3R)-1-ethylpiperidin-3-yl]methoxy}-8-(3-methyl-2-oxo-2,3-dihydro-1,3-benzoxazol-6-yl)imidazo[1,2-c]pyrimidin-7-yl]benzonitrile, 4-[5-{[(3R)-1-(2-hydroxyethyl)piperidin-3-yl]methoxy}-8-(6-methoxypyridin-3-yl)imidazo[1,2-c]pyrimidin-7-yl]benzonitrile, 4-(8-(5-fluoro-6-methoxypyridin-3-yl)-5-{[(3R)-1-(2-hydroxyethyl)piperidin-3-yl]methoxy}imidazo[1,2-c]pyrimidin-7-yl)benzonitrile, 4-[5-[4-(dimethylamino)piperidin-1-yl]-8-(4-fluoro-3-methyl-2-oxo-2,3-dihydro-1,3-benzoxazol-6-yl)imidazo[1,2-c]pyrimidin-7-yl]benzonitrile, 4-(8-(4-fluoro-3-methyl-2-oxo-2,3-dihydro-1,3-benzoxazol-6-yl)-5-{[(3R)-1-methylpiperidin-3-yl]methoxy}imidazo[1,2-c]pyrimidin-7-yl)benzonitrile, 4-[5-[4-(dimethylamino)piperidin-1-yl]-8-(3-methyl-2-oxo-2,3-dihydro[1,3]oxazolo[4,5-b]pyridin-6-yl)imidazo[1,2-c]pyrimidin-7-yl]benzonitrile, 4-(8-(3-methyl-2-oxo-2,3-dihydro[1,3]oxazolo[4,5-b]pyridin-6-yl)-5-{[(3R)-1-methylpiperidin-3-yl]methoxy}imidazo[1,2-c]pyrimidin-7-yl)benzonitrile, 4-[5-[4-(dimethylamino)piperidin-1-yl]-8-(1-methyl-2-oxo-2,3-dihydro-1H-indol-5-yl)imidazo[1,2-c]pyrimidin-7-yl]benzonitrile, 4-[5-[4-(dimethylamino)piperidin-1-yl]-8-(1,2-dimethyl-1H-benzimidazol-5-yl)imidazo[1,2-c]pyrimidin-7-yl]benzonitrile, 4-(8-[2-(difluoromethyl)-1-methyl-1H-benzimidazol-5-yl]-5-{[(3R)-1-methylpiperidin-3-yl]methoxy}imidazo[1,2-c]pyrimidin-7-yl)benzonitrile, 4-(8-(1,2-dimethyl-1H-benzimidazol-5-yl)-5-{[(3R)-1-methylpiperidin-3-yl]methoxy}imidazo[1,2-c]pyrimidin-7-yl)benzonitrile, 5-{7-(4-cyanophenyl)-5-[4-(dimethylamino)piperidin-1-yl]imidazo[1,2-c]pyrimidin-8-yl}-2-methylnicotinonitrile, methyl (5-{7-(4-cyanophenyl)-5-[4-(dimethylamino)piperidin-1-yl]imidazo[1,2-c]pyrimidin-8-yl}pyridin-2-yl)methylcarbamate, 4-[5-[4-(dimethylamino)piperidin-1-yl]-8-(5,6-dimethylpyridin-3-yl)imidazo[1,2-c]pyrimidin-7-yl]benzonitrile, 4-(8-(6-methoxy-5-methylpyridin-3-yl)-5-{[(3R)-1-methylpiperidin-3-yl]methoxy}imidazo[1,2-c]pyrimidin-7-yl)benzonitrile, 5-(7-(4-cyanophenyl)-5-{[(3R)-1-methylpiperidin-3-yl]methoxy}imidazo[1,2-c]pyrimidin-8-yl)-2-methylnicotinonitrile, 4-(8-[3-(hydroxymethyl)-4-methylphenyl]-5-{[(3R)-1-methylpiperidin-3-yl]methoxy}imidazo[1,2-c]pyrimidin-7-yl)benzonitrile, 4-(8-[2-(hydroxymethyl)-4-methylphenyl]-5-{[(3R)-1-methylpiperidin-3-yl]methoxy}imidazo[1,2-c]pyrimidin-7-yl)benzonitrile, 4-[5-{[(3R)-1-methylpiperidin-3-yl]methoxy}-8-(6-methylpyridin-3-yl)imidazo[1,2-c]pyrimidin-7-yl]benzonitrile, 4-(8-(5-fluoro-6-methylpyridin-3-yl)-5-{[(3R)-1-methylpiperidin-3-yl]methoxy}imidazo[1,2-c]pyrimidin-7-yl)benzonitrile, and methyl [4-(7-(4-cyanophenyl)-5-{[(3R)-1-methylpiperidin-3-yl]methoxy}imidazo[1,2-c]pyrimidin-8-yl)-2-fluorophenyl]methylcarbamate;

or a pharmaceutically acceptable salt thereof.

22. The method of claim 1, wherein the compound is selected from:

7-(7-(4-cyanophenyl)-5-{[(3R)-1-methylpiperidin-3-yl]methoxy}imidazo[1,2-c]pyrimidin-8-yl)-N,N-dimethyl-2,3-dihydro-1,4-benzodioxine-2-carboxamide, 4-(8-(1-methyl-2,3-dihydro-1H-pyrrolo[2,3-b]pyridin-5-yl)-5-{[(3R)-1-methylpiperidin-3-yl]methoxy}imidazo[1,2-c]pyrimidin-7-yl)benzonitrile, 4-[5-{[(3R)-1-methylpiperidin-3-yl]methoxy}-8-(8-methyl-5,6,7,8-tetrahydro-1,8-naphthyridin-3-yl)imidazo[1,2-c]pyrimidin-7-yl]benzonitrile, 4-(8-(1-methyl-2-oxo-1,2,3,4-tetrahydroquinolin-7-yl)-5-{[(3R)-1-methylpiperidin-3-yl]methoxy}imidazo[1,2-c]pyrimidin-7-yl)benzonitrile, 4-{8-[3-fluoro-4-(morpholin-4-ylmethyl)phenyl]-5-{[(3R)-1-methylpiperidin-3-yl]methoxy}imidazo[1,2-c]pyrimidin-7-yl)benzonitrile, 4-[5-{[(3R)-1-(2-cyanoethyl)piperidin-3-yl]methoxy}-8-(5-fluoro-6-methoxypyridin-3-yl)imidazo[1,2-c]pyrimidin-7-yl]benzonitrile, 4-{8-[6-(dimethylamino)-5-fluoropyridin-3-yl]-5-[4-(dimethylamino)piperidin-1-yl]imidazo[1,2-c]pyrimidin-7-yl}benzonitrile, 4-[5-{[(3R)-1-(2-cyanoethyl)piperidin-3-yl]methoxy}-8-(3-methyl-2-oxo-2,3-dihydro-1,3-benzoxazol-6-yl)imidazo[1,2-c]pyrimidin-7-yl]benzonitrile, N-[4-(7-(4-cyanophenyl)-5-{[(3R)-1-methylpiperidin-3-yl]methoxy}imidazo[1,2-c]pyrimidin-8-yl)-2-fluorobenzyl]-N-methylmethanesulfonamide, N-[4-(7-(4-cyanophenyl)-5-{[(3R)-1-methylpiperidin-3-yl]methoxy}imidazo[1,2-c]pyrimidin-8-yl)-2-fluorobenzyl]-N,N',N'-trimethylurea, N-[4-(7-(4-cyanophenyl)-5-{[(3R)-1-methylpiperidin-3-yl]methoxy}imidazo[1,2-c]pyrimidin-8-yl)benzyl]-N,N',N'-trimethylurea, methyl [4-(7-(4-cyanophenyl)-5-{[(3R)-1-methylpiperidin-3-yl]methoxy}imidazo[1,2-c]pyrimidin-8-yl)benzyl]methylcarbamate, 4-(8-(5-chloro-6-methoxypyridin-3-yl)-5-{[(3R)-1-methylpiperidin-3-yl]methoxy}imidazo[1,2-c]pyrimidin-7-yl)benzonitrile, 4-{5-[4-(dimethylamino)piperidin-1-yl]-8-[3-fluoro-4-(hydroxymethyl)-5-methylphenyl]imidazo[1,2-c]pyrimidin-7-yl}benzonitrile, 4-{8-[3,5-difluoro-4-(hydroxymethyl)phenyl]-5-[4-(dimethylamino)piperidin-1-yl]imidazo[1,2-c]pyrimidin-7-yl}benzonitrile, 4-{5-[4-(dimethylamino)piperidin-1-yl]-8-[4-(hydroxymethyl)-3-methylphenyl]imidazo[1,2-c]pyrimidin-7-yl}benzonitrile, 4-(8-(5-chloro-6-methylpyridin-3-yl)-5-{[(3R)-1-methylpiperidin-3-yl]methoxy}imidazo[1,2-c]pyrimidin-7-yl)benzonitrile, 4-(8-[3-(1-hydroxyethyl)-4-methylphenyl]-5-{[(3R)-1-methylpiperidin-3-yl]methoxy}imidazo[1,2-c]pyrimidin-7-yl)benzonitrile, 4-(8-[4-(methoxymethyl)phenyl]-5-{[(3R)-1-methylpiperidin-3-yl]methoxy}imidazo[1,2-c]pyrimidin-7-yl)benzonitrile, 4-(8-[2-fluoro-4-(morpholin-4-ylmethyl)phenyl]-5-{[(3R)-1-methylpiperidin-3-yl]methoxy}imidazo[1,2-c]pyrimidin-7-yl)benzonitrile,
5-(7-(4-cyanophenyl)-5-{[(3R)-1-methylpiperidin-3-yl]methoxy}imidazo[1,2-c]pyrimidin-8-yl)-2-methylbenzonitrile,
N-(4-{7-(4-cyanophenyl)-5-[4-(dimethylamino)piperidin-1-yl]imidazo[1,2-c]pyrimidin-8-yl}-2-fluorobenzyl)-N,N',N'-trimethylurea,
4-{5-[4-(dimethylamino)piperidin-1-yl]-8-[3-fluoro-4-(morpholin-4-ylmethyl)phenyl]imidazo[1,2-c]pyrimidin-7-yl}benzonitrile,
4-{5-{[(3R)-1-ethylpiperidin-3-yl]methoxy}-8-[3-(hydroxymethyl)-4-methylphenyl]imidazo[1,2-c]pyrimidin-7-yl}benzonitrile,
4-{5-[(3R)-3-(dimethylamino)pyrrolidin-1-yl]-8-[3-(hydroxymethyl)-4-methylphenyl]imidazo[1,2-c]pyrimidin-7-yl}benzonitrile,
4-(8-[3-chloro-4-(hydroxymethyl)phenyl]-5-{[(3R)-1-methylpiperidin-3-yl]methoxy}imidazo[1,2-c]pyrimidin-7-yl)benzonitrile,
4-{5-[4-(dimethylamino)piperidin-1-yl]-8-[3-(hydroxymethyl)-4-methylphenyl]imidazo[1,2-c]pyrimidin-7-yl}benzonitrile,
4-{8-(5-chloro-6-methylpyridin-3-yl)-5-[4-(dimethylamino)piperidin-1-yl]imidazo[1,2-c]pyrimidin-7-yl}benzonitrile,
4-{8-(5-chloro-6-methoxypyridin-3-yl)-5-[4-(dimethylamino)piperidin-1-yl]imidazo[1,2-c]pyrimidin-7-yl}benzonitrile,
5-{7-(4-cyanophenyl)-5-[4-(dimethylamino)piperidin-1-yl]imidazo[1,2-c]pyrimidin-8-yl}-2-methoxynicotinonitrile,
methyl [5-(7-(4-cyanophenyl)-5-{[(3R)-1-methylpiperidin-3-yl]methoxy}imidazo[1,2-c]pyrimidin-8-yl)-2-methylphenyl]methylcarbamate,
4-(8-(6-ethylpyridin-3-yl)-5-{[(3R)-1-methylpiperidin-3-yl]methoxy}imidazo[1,2-c]pyrimidin-7-yl)benzonitrile,
4-(8-(6-isopropylpyridin-3-yl)-5-{[(3R)-1-methylpiperidin-3-yl]methoxy}imidazo[1,2-c]pyrimidin-7-yl)benzonitrile,
4-{5-{[(3R)-1-ethylpiperidin-3-yl]methoxy}-8-[3-fluoro-4-(hydroxymethyl)-5-methylphenyl]imidazo[1,2-c]pyrimidin-7-yl}benzonitrile,
4-{5-[(3R)-3-(dimethylamino)pyrrolidin-1-yl]-8-[3-fluoro-4-(hydroxymethyl)-5-methylphenyl]imidazo[1,2-c]pyrimidin-7-yl}benzonitrile,
4-{5-[4-(dimethylamino)piperidin-1-yl]-8-[2-(hydroxymethyl)-4-methylphenyl]imidazo[1,2-c]pyrimidin-7-yl}benzonitrile,
4-[5-[4-(dimethylamino)piperidin-1-yl]-8-(6-methylpyridin-3-yl)imidazo[1,2-c]pyrimidin-7-yl]benzonitrile,
4-[5-[4-(dimethylamino)piperidin-1-yl]-8-(5-fluoro-6-methylpyridin-3-yl)imidazo[1,2-c]pyrimidin-7-yl]benzonitrile,
methyl (4-{7-(4-cyanophenyl)-5-[4-(dimethylamino)piperidin-1-yl]imidazo[1,2-c]pyrimidin-8-yl}phenyl)methylcarbamate,
N-(5-{7-(4-cyanophenyl)-5-[4-(dimethylamino)piperidin-1-yl]imidazo[1,2-c]pyrimidin-8-yl}pyridin-2-yl)-N-methylmethanesulfonamide,
methyl (4-{7-(4-cyanophenyl)-5-[4-(dimethylamino)piperidin-1-yl]imidazo[1,2-c]pyrimidin-8-yl}-2-fluorophenyl)methylcarbamate,
4-[5-[4-(dimethylamino)piperidin-1-yl]-8-(6-ethoxypyridin-3-yl)imidazo[1,2-c]pyrimidin-7-yl]benzonitrile,
4-[5-[4-(dimethylamino)piperidin-1-yl]-8-(6-isopropylpyridin-3-yl)imidazo[1,2-c]pyrimidin-7-yl]benzonitrile,
4-{5-{[(3R)-1-ethylpiperidin-3-yl]methoxy}-8-[2-(hydroxymethyl)-4-methylphenyl]imidazo[1,2-c]pyrimidin-7-yl}benzonitrile,
4-{8-(1,3-benzothiazol-5-yl)-5-[4-(dimethylamino)piperidin-1-yl]imidazo[1,2-c]pyrimidin-7-yl}benzonitrile,
4-[5-[4-(dimethylamino)piperidin-1-yl]-8-(3-hydroxy-2,3-dihydro-1H-inden-5-yl)imidazo[1,2-c]pyrimidin-7-yl]benzonitrile,
4-[5-[4-(dimethylamino)piperidin-1-yl]-8-(2-hydroxy-2,3-dihydro-1H-inden-5-yl)imidazo[1,2-c]pyrimidin-7-yl]benzonitrile,
4-(8-(3-hydroxy-2,3-dihydro-1H-inden-5-yl)-5-{[(3R)-1-methylpiperidin-3-yl]methoxy}imidazo[1,2-c]pyrimidin-7-yl)benzonitrile,
4-(8-(2-hydroxy-2,3-dihydro-1H-inden-5-yl)-5-{[(3R)-1-methylpiperidin-3-yl]methoxy}imidazo[1,2-c]pyrimidin-7-yl)benzonitrile,
4-[5-[4(dimethylamino)piperidin-1-yl]-8-(1-methyl-1H-pyrrolo[2,3-b]pyridin-5-yl)imidazo[1,2-c]pyrimidin-7-yl]benzonitrile,
4-{5-[4-(dimethylamino)piperidin-1-yl]-8-quinoxalin-6-ylimidazo[1,2-c]pyrimidin-7-yl}benzonitrile,
4-[5-[4-(dimethylamino)piperidin-1-yl]-8-(4-fluoro-1,3-dimethyl-2-oxo-2,3-dihydro-1H-benzimidazol-5-yl)imidazo[1,2-c]pyrimidin-7-yl]benzonitrile,
4-[5-[4-(dimethylamino)piperidin-1-yl]-8-(7-fluoro-1,3-dimethyl-2-oxo-2,3-dihydro-1H-benzimidazol-5-yl)imidazo[1,2-c]pyrimidin-7-yl]benzonitrile,
4-[5-[4-(dimethylamino)piperidin-1-yl]-8-(6-fluoro-1,3-dimethyl-2-oxo-2,3-dihydro-1H-benzimidazol-5-yl)imidazo[1,2-c]pyrimidin-7-yl]benzonitrile,
4-[5-[4-(dimethylamino)piperidin-1-yl]-8-(1-methyl-2-oxo-1,2,3,4-tetrahydroquinolin-6-yl)imidazo[1,2-c]pyrimidin-7-yl]benzonitrile,
4-[5-[4-(dimethylamino)piperidin-1-yl]-8-(1-methyl-2-oxo-1,2,3,4-tetrahydroquinolin-7-yl)imidazo[1,2-c]pyrimidin-7-yl]benzonitrile,
4-{8-[5-(difluoromethyl)-6-methylpyridin-3-yl]-5-[4-(dimethylamino)piperidin-1-yl]imidazo[1,2-c]pyrimidin-7-yl}benzonitrile,
4-[5-({(3R)-1-[(2R)-2-hydroxypropyl]piperidin-3-yl}methoxy)-8-(3-methyl-2-oxo-2,3-dihydro-1,3-benzoxazol-6-yl)imidazo[1,2-c]pyrimidin-7-yl]benzonitrile,
4-[5-({(3R)-1-[(2S)-2-hydroxypropyl]piperidin-3-yl}methoxy)-8-(3-methyl-2-oxo-2,3-dihydro-1,3-benzoxazol-6-yl)imidazo[1,2-c]pyrimidin-7-yl]benzonitrile,
4-[5-{[(3R)-1-(2-hydroxy-2-methylpropyl)piperidin-3-yl]methoxy}-8-(3-methyl-2-oxo-2,3-dihydro-1,3-benzoxazol-6-yl)imidazo[1,2-c]pyrimidin-7-yl]benzonitrile,
4-[5-({(3R)-1-[(2R)-2-hydroxypropyl]piperidin-3-yl}methoxy)-8-(1-methyl-1H-pyrazolo[3,4-b]pyridin-5-yl)imidazo[1,2-c]pyrimidin-7-yl]benzonitrile,
4-[5-({(3R)-1-[(2S)-2-hydroxypropyl]piperidin-3-yl}methoxy)-8-(1-methyl-1H-pyrazolo[3,4-b]pyridin-5-yl)imidazo[1,2-c]pyrimidin-7-yl]benzonitrile, and
4-[5-{[(3R)-1-(2-hydroxy-2-methylpropyl)piperidin-3-yl]methoxy}-8-(1-methyl-1H-pyrazolo[3,4-b]pyridin-5-yl)imidazo[1,2-c]pyrimidin-7-yl]benzonitrile;
or a pharmaceutically acceptable salt thereof.

23. The method of claim 1, wherein the compound is 4-[5-[4-(dimethylamino)piperidin-1-yl]-8-(1-methyl-1H- pyrazolo[3,4-b]pyridin-5-yl)imidazo[1,2-c]pyrimidin-7-yl] benzonitrile, or a pharmaceutically acceptable salt thereof.

24. The method of claim 1, wherein the compound is 4-[5-[(3R)-3-(dimethylamino)pyrrolidin-1-yl]-8-(1-methyl-1H-pyrazolo[3,4-b]pyridin-5-yl)imidazo[1,2-c]pyrimidin-7-yl]benzonitrile, or a pharmaceutically acceptable salt thereof.

25. The method of claim 1, wherein the compound is 4-[5-[4-(dimethylamino)piperidin-1-yl]-8-(1-methyl-1H-pyrrolo[2,3-b]pyridin-5-yl)imidazo[1,2-c]pyrimidin-7-yl] benzonitrile, or a pharmaceutically acceptable salt thereof.

26. The method of claim 1, wherein the cancer is myelodysplasia syndrome (MDS).

27. The method of claim 1, wherein the cancer is undifferentiated small cell lung cancer.

28. The method of claim 1, wherein the cancer is Ewing's sarcoma.

29. The method of claim 1, wherein the cancer is primary myelofibrosis (PMF).

30. The method of claim 1, wherein the cancer is acute lymphoblastic leukemia (ALL).

31. The method of claim 1, wherein the cancer is acute myelogenous leukemia (AML).

\* \* \* \* \*

UNITED STATES PATENT AND TRADEMARK OFFICE
CERTIFICATE OF CORRECTION

PATENT NO. : 11,401,272 B2
APPLICATION NO. : 17/006072
DATED : August 2, 2022
INVENTOR(S) : Chunhong He et al.

It is certified that error appears in the above-identified patent and that said Letters Patent is hereby corrected as shown below:

In the Claims

Column 141, Line 51, Claim 1, delete "$NR^{c1}R^{d1}$" and insert -- $NR^{c1}R^{d1}$, --;

Column 141, Line 52, Claim 1, delete "$NR^{c1}C(O)OR^{a1}$" and insert -- $NR^{c1}C(O)OR^{a1}$, --;

Column 141, Lines 53-54, Claim 1, delete "$NR^{c1}C(=NR^{e1})NR^{c1}R^{d1}\ NR^{c1}S(O)R^{b1}$" and insert -- $NR^{c1}C(=NR^{e1})NR^{c1}R^{d1}$, $NR^{c1}S(O)R^{b1}$, --;

Column 142, Lines 2-3, Claim 1, delete "$NR^{c2}R^{d2}\ NR^{c2}C(O)R^{b2}$" and insert -- $NR^{c2}R^{d2}$, $NR^{c2}C(O)R^{b2}$, --;

Column 142, Line 5, Claim 1, delete "$NR^{e2}S(O)R^{b2}, NR^{e2}S(O)_2R^{b2}$," and insert -- $NR^{e2}S(O)R^{b2}$, $NR^{e2}S(O)_2R^{b2}$, --;

Column 142, Line 13, Claim 1, delete "$NR^{e2}C(O)NR^{c2}R^{d2}$," and insert -- $NR^{e2}C(O)NR^{c2}R^{d2}$, --;

Column 143, Line 2, Claim 1, delete "$NR^{c4}R^{d4}\ NR^{c4}C(O)R^{b4}$" and insert -- $NR^{c4}R^{d4}$, $NR^{c4}C(O)R^{b4}$, --;

Column 144, Line 47, Claim 1, delete "$NR^{c5}S(O)_2R^{b5}$" and insert -- $NR^{c5}S(O)_2R^{b5}$, --;

Column 145, Line 44, Claim 1, delete "$NR^{c5}R^{d1}$," and insert -- $NR^{c5}R^{d5}$, --;

Column 145, Line 46, Claim 1, delete "$NR^{c5}C(=NR^{e5})NR^{c5}R^{d5}$" and insert -- $NR^{c5}C(=NR^{e5})NR^{c5}R^{d5}$, --;

Column 146, Lines 58, Claim 1, delete "$NR^{c5}(=NR^{e5})NR^{c5}R^{d5}$," and insert -- $NR^{c5}C(=NR^{e5})NR^{c5}R^{d5}$, --;

Column 146, Line 25-26, Claim 1, delete "$N^{c5}C(O)NR^{c5}R^{d5}$," and insert -- $NR^{c5}C(O)NR^{c5}R^{d5}$, --.

Signed and Sealed this
Twentieth Day of September, 2022

*Katherine Kelly Vidal*

Katherine Kelly Vidal
*Director of the United States Patent and Trademark Office*

CERTIFICATE OF CORRECTION (continued)
U.S. Pat. No. 11,401,272 B2

Column 147, Line 53, Claim 10, delete "C(O)NR$^{e2}$R$^{d2}$, and NR$^{e2}$R$^{d2}$;" and insert -- C(O)NR$^{c2}$R$^{d2}$, and NR$^{c2}$R$^{d2}$; --;

Column 147, Line 55, Claim 10, delete "C(O)NR$^{2}$R$^{d2}$." and insert -- C(O)NR$^{c2}$R$^{d2}$. --.

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: synthetic peptide
<220> FEATURE:
<221> NAME/KEY: METHYLATION
<222> LOCATION: 4

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Gly Gly Lys
            20
```